(12) United States Patent
Day et al.

(10) Patent No.: US 8,822,177 B2
(45) Date of Patent: Sep. 2, 2014

(54) MODIFIED LIPIDS PRODUCED FROM OIL-BEARING MICROBIAL BIOMASS AND OILS

(71) Applicant: Solazyme, Inc., San Francisco, CA (US)

(72) Inventors: Anthony G. Day, San Francisco, CA (US); Geoffrey Brooks, Reno, NV (US); Scott Franklin, San Diego, CA (US)

(73) Assignee: Solazyme, Inc., South San Francisco, CA (US)

( * ) Notice: Subject to any disclaimer, the term of this patent is extended or adjusted under 35 U.S.C. 154(b) by 0 days.

(21) Appl. No.: 13/889,221

(22) Filed: May 7, 2013

(65) Prior Publication Data

US 2013/0296591 A1 Nov. 7, 2013

Related U.S. Application Data

(60) Continuation of application No. 13/601,928, filed on Aug. 31, 2012, now Pat. No. 8,450,083, which is a continuation of application No. 13/366,198, filed on Feb. 3, 2012, now Pat. No. 8,278,261, which is a division of application No. 12/499,033, filed on Jul. 7, 2009, now Pat. No. 8,119,583, which is a continuation of application No. PCT/US2009/040123, filed on Apr. 9, 2009.

(60) Provisional application No. 61/074,610, filed on Jun. 20, 2008, provisional application No. 61/043,620, filed on Apr. 9, 2008.

(51) Int. Cl.
*C12P 1/00* (2006.01)

(52) U.S. Cl.
USPC .............. 435/41; 435/257.1; 424/195.17

(58) Field of Classification Search
CPC .............. C12P 7/64; Y02E 50/13; C12N 1/12
USPC .............. 435/41, 257.1; 424/195.17
See application file for complete search history.

(56) References Cited

U.S. PATENT DOCUMENTS

| | | | |
|---|---|---|---|
| 3,280,502 A | 10/1966 | Farrow et al. | |
| 3,320,693 A | 5/1967 | Shirota et al. | |
| 3,957,578 A | 5/1976 | Narita et al. | |
| 3,962,466 A | 6/1976 | Nakabayashi | |
| 4,103,039 A | 7/1978 | Mandai et al. | |
| 4,140,805 A * | 2/1979 | Edwards et al. | 426/429 |
| 4,341,038 A | 7/1982 | Bloch et al. | |
| 4,390,561 A | 6/1983 | Blair et al. | |
| 4,519,845 A | 5/1985 | Ou | |
| 4,673,490 A | 6/1987 | Subramanian et al. | |
| 5,001,059 A | 3/1991 | Skatrud et al. | |
| 5,130,242 A | 7/1992 | Barclay | |
| 5,212,087 A | 5/1993 | Fournier et al. | |
| 5,252,198 A | 10/1993 | Harrison et al. | |
| 5,270,177 A | 12/1993 | Ramos Lazcano et al. | |
| 5,338,673 A | 8/1994 | Thepenier et al. | |
| 5,354,878 A | 10/1994 | Connemann et al. | |
| 5,436,394 A | 7/1995 | Willmitzer et al. | |
| 5,492,938 A | 2/1996 | Kyle et al. | |
| 5,518,918 A | 5/1996 | Barclay et al. | |
| 5,547,699 A | 8/1996 | Lizuka et al. | |
| 5,595,965 A | 1/1997 | Wiggins | |
| 5,643,585 A | 7/1997 | Arad et al. | |
| 5,711,983 A | 1/1998 | Kyle et al. | |
| 5,792,631 A | 8/1998 | Running | |
| 5,888,947 A | 3/1999 | Lambert et al. | |
| 5,900,370 A * | 5/1999 | Running | 435/136 |
| 5,968,791 A | 10/1999 | Davies et al. | |
| 6,139,897 A | 10/2000 | Goto et al. | |
| 6,255,505 B1 | 7/2001 | Bijl et al. | |
| 6,338,866 B1 | 1/2002 | Criggall et al. | |
| 6,372,460 B1 | 4/2002 | Gladue et al. | |
| 6,441,208 B2 | 8/2002 | Bijl et al. | |
| 6,620,427 B2 | 9/2003 | Lasekan et al. | |
| 7,053,267 B2 | 5/2006 | Knauf et al. | |
| 7,063,957 B2 | 6/2006 | Chen | |
| 7,879,591 B2 | 2/2011 | Damude et al. | |
| 7,883,882 B2 | 2/2011 | Franklin et al. | |
| 7,935,515 B2 | 5/2011 | Franklin et al. | |
| 7,939,710 B1 | 5/2011 | Apt et al. | |
| 8,029,579 B2 | 10/2011 | Knuth et al. | |

(Continued)

FOREIGN PATENT DOCUMENTS

| | | |
|---|---|---|
| CN | 1940021 A | 4/2007 |
| CN | 101037639 A | 9/2007 |

(Continued)

OTHER PUBLICATIONS

Xu, Han et al. High Quality Biodiesel Production from a Microalga Chlorella protothecoides by Heterotrophic Growth in Fermenters. Journal of Biotechnology 126. Elsevier 2006. pp. 499-507.*
Running, JA. Extracellular Production of Ascorbic Acid by Chlorella protothecoides and mutants of *P. moriformis* during Aerobic Culturing at Low pH. Journal of Industrial Microbiology & Biotechnology 29. 2002. pp. 93-98.*
Guschina, Irina. Lipids and Lipid Metabolism in Eukaryotic Algae. Progess in Lipid Research 45 (2006). pp. 160-186.*
Matsuka, Mitsuo. The Role of Respiration & Photosynthesis in the Chloroplast Regeneration in the Glucose-Bleached Cells of Chlorella Protothecoides. Plant & Cell Physiology. 1966. pp. 149-162.*
Ward, Kerry et al. Effects of Processing & Storage on Chlorophyll Derivatives in Commericially Extracted Canola Oil. JAOCS, vol. 71, No. 8 (Aug. 1994). pp. 811-815.*

(Continued)

*Primary Examiner* — Susan Hanley
*Assistant Examiner* — Nghi Nguyen
(74) *Attorney, Agent, or Firm* — Alston & Bird LLP

(57) ABSTRACT

Provided are methods for preparing chemically modified lipids. The lipids are obtained from heterotrophically cultured microalgae and are subjected to an epoxidation reaction. The microalgae include those from the genus *Parachlorella*, *Prototheca*, *Chlorella*, or strains having at least 85% nucleotide sequence identity in 23S rRNA sequences to a *Parachlorella*, *Prototheca*, or *Chlorella* strain that are cultured in a bioreactor substantially in the absence of light.

15 Claims, 38 Drawing Sheets

(56) References Cited

U.S. PATENT DOCUMENTS

| | | |
|---|---|---|
| 8,119,583 B2 | 2/2012 | Day et al. |
| 8,187,860 B2 | 5/2012 | Franklin et al. |
| 8,222,010 B2 | 7/2012 | Franklin et al. |
| 8,268,610 B2 | 9/2012 | Franklin et al. |
| 8,278,261 B2 | 10/2012 | Day et al. |
| 8,283,483 B2 | 10/2012 | Williams et al. |
| 8,435,767 B2 | 5/2013 | Franklin et al. |
| 8,450,083 B2 | 5/2013 | Day et al. |
| 8,476,059 B2 | 7/2013 | Trimbur et al. |
| 8,497,116 B2 | 7/2013 | Trimbur et al. |
| 8,512,999 B2 | 8/2013 | Trimbur et al. |
| 8,518,689 B2 | 8/2013 | Trimbur et al. |
| 2003/0097686 A1 | 5/2003 | Knauf et al. |
| 2003/0229237 A1 | 12/2003 | Haas et al. |
| 2004/0230085 A1 | 11/2004 | Jakkula et al. |
| 2005/0005333 A1 | 1/2005 | Ruezinsky et al. |
| 2005/0262588 A1 | 11/2005 | Dehesh et al. |
| 2005/0266537 A1 | 12/2005 | Chen |
| 2006/0094089 A1 | 5/2006 | Barclay |
| 2007/0099280 A1 | 5/2007 | Barclay |
| 2007/0118916 A1 | 5/2007 | Puzio et al. |
| 2007/0166266 A1 | 7/2007 | Dillon et al. |
| 2007/0167396 A1 | 7/2007 | Dillon et al. |
| 2007/0261138 A1 | 11/2007 | Graham et al. |
| 2008/0160593 A1 | 7/2008 | Oyler |
| 2008/0206379 A1 | 8/2008 | Fabritius et al. |
| 2008/0283803 A1 | 11/2008 | Rapp et al. |
| 2009/0004715 A1 | 1/2009 | Trimbur et al. |
| 2009/0011480 A1 | 1/2009 | Trimbur et al. |
| 2009/0047721 A1 | 2/2009 | Trimbur et al. |
| 2009/0061493 A1 | 3/2009 | Trimbur et al. |
| 2009/0099260 A1 | 4/2009 | Namal Senanayake et al. |
| 2009/0148918 A1 | 6/2009 | Trimbur et al. |
| 2009/0211150 A1 | 8/2009 | Wu et al. |
| 2009/0234146 A1 | 9/2009 | Cooney et al. |
| 2009/0274736 A1 | 11/2009 | Dillon et al. |
| 2009/0298159 A1 | 12/2009 | Wu et al. |
| 2010/0021912 A1 | 1/2010 | Farese et al. |
| 2010/0058651 A1 | 3/2010 | Knuth et al. |
| 2010/0120643 A1 | 5/2010 | Brown et al. |
| 2010/0151112 A1 | 6/2010 | Franklin et al. |
| 2010/0151538 A1 | 6/2010 | Franklin et al. |
| 2010/0170144 A1 | 7/2010 | Day et al. |
| 2010/0186117 A1 | 7/2010 | Fabijanski et al. |
| 2010/0196575 A1 | 8/2010 | Sanchez et al. |
| 2010/0228068 A1 | 9/2010 | O'Connor et al. |
| 2010/0239712 A1 | 9/2010 | Brooks et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323414 A1 | 12/2010 | Trimbur et al. |
| 2011/0014665 A1 | 1/2011 | Trimbur et al. |
| 2011/0047863 A1 | 3/2011 | Trimbur et al. |
| 2011/0072714 A1 | 3/2011 | Gaertner et al. |
| 2011/0190522 A1 | 8/2011 | Trimbur et al. |
| 2011/0203168 A1 | 8/2011 | Franklin et al. |
| 2012/0028319 A1 | 2/2012 | Trimbur et al. |
| 2012/0034662 A1 | 2/2012 | Hu et al. |
| 2012/0128851 A1 | 5/2012 | Brooks et al. |
| 2012/0164701 A1 | 6/2012 | Trimbur et al. |
| 2012/0277453 A1 | 11/2012 | Franklin et al. |
| 2012/0288930 A1 | 11/2012 | Trimbur et al. |
| 2013/0006006 A1 | 1/2013 | Day et al. |
| 2013/0031678 A1 | 1/2013 | Zheng et al. |
| 2013/0078709 A1 | 3/2013 | Franklin et al. |
| 2013/0089916 A1 | 4/2013 | Franklin et al. |
| 2013/0165677 A1 | 6/2013 | Franklin et al. |
| 2013/0273621 A1 | 10/2013 | Franklin et al. |
| 2013/0295268 A1 | 11/2013 | Day et al. |
| 2013/0330790 A1 | 12/2013 | Trimbur et al. |

FOREIGN PATENT DOCUMENTS

| | | |
|---|---|---|
| CN | 101130513 A | 2/2008 |
| EP | 0562504 B1 | 11/1995 |
| EP | 1681337 A1 | 7/2006 |
| EP | 1741767 A1 | 1/2007 |
| GB | 824151 A | 11/1959 |
| JP | 06-253872 A | 9/1994 |
| JP | 07-008217 | 1/1995 |
| JP | 07-075557 | 3/1995 |
| JP | 2002-12501 | 5/2002 |
| WO | WO 94/10288 A2 | 5/1994 |
| WO | WO 99/37166 A1 | 7/1999 |
| WO | WO 00/61740 A1 | 10/2000 |
| WO | WO 02/08403 A2 | 1/2002 |
| WO | WO 2006/122299 A2 | 11/2006 |
| WO | WO 2007/027669 A1 | 3/2007 |
| WO | WO 2007/117511 A2 | 10/2007 |
| WO | WO 2007/134294 A2 | 11/2007 |
| WO | WO 2008/002643 A2 | 1/2008 |
| WO | WO 2008/083352 A1 | 7/2008 |
| WO | WO 2008/130372 A2 | 10/2008 |
| WO | WO 2008/134836 A2 | 11/2008 |
| WO | WO 2008/151149 A2 | 12/2008 |
| WO | WO 2009/126843 A2 | 10/2009 |
| WO | WO 2010/019813 A2 | 2/2010 |
| WO | WO 2010/045368 A2 | 4/2010 |
| WO | Wo 2010/063031 A2 | 6/2010 |
| WO | WO 2010/063032 A2 | 6/2010 |
| WO | WO 2010/111698 A2 | 9/2010 |
| WO | WO 2010/120923 A1 | 10/2010 |
| WO | WO 2010/120939 A2 | 10/2010 |
| WO | WO 2011/090730 A1 | 7/2011 |

OTHER PUBLICATIONS

Gunstone, Frank. Enzymes as biocatalysts in the modification of natural lipids. Journal of the Science of Food & Agriculture 79 (1999). pp. 1535-1549.*

Shi, Xian. High-Yield Production of Lutein by the Green Microalga *Chlorella* protothecoides in Heterotrophic Fed-Batch Culture. Biotechnology Prog. 2002, 18. pp. 723-727.*

"Soybean Oil Innovations, 3rd Edition," United Soybean Board, www.soyconnection.com, 8 pages, (2009). [Available from the Internet on Jan. 15, 2009: <URL: http://www.soyconnection.com/sites/default/files/soy-oil-solutions.pdf>].

"Codex Standard for Named Vegetable Oils," CODEX Alimentarius, CODEX STAN 210-1999, pp. 1-16, (1999).

"The research on the lipid content and composition of microalgae and their impact factors," Marine Science, 12(33)122-128, (2009). (English translation of first two pages).

Abate et al., "Production of ethanol by a flocculent *Saccharomyces* sp. in a continuous upflow reactor using sucrose, sugar-cane juice, and molasses as the carbon source," Mircen Journal, 3:401-409, (1987).

Aggelis et al., "Enhancement of single cell oil production by *Yarrowia lipolytica* growing in the presence of *Teucrium polium* L. aqueous extract," Biotechnology Letters, 21:747-749, (1999).

Andersen, "Biology and Systematics of Heterokont and Haptophyte Algae," American Journal of Botany, 91(10):1508-1522, (2004).

Barnes et al., "Contribution of 5'- and 3'-untranslated regions of plastid mRNAs to the expression of *Chlamydomonas reinhardtii* chloroplast genes," Mol Genet Genomics, 274(6):625-636, (2005).

Barton et al., "Chapter 27: Pylogenetic Reconstruction," Evolution, Online Chapter, Cold Spring Harbor Laboratory Press, pp. 1-55, (2007). [Retrieved from the Internet Jul. 10, 2013: <URL: http://evolution-textbook.org/content/free/contents/Chapter_27_Web.pdf>].

Becker et al., "Micro-algae as a source of protein," Biotechnology Advances, 25:207-210, (2007).

Belasco, "Algae Burgers for a Hungry World? The Rise and Fall of *Chlorella* Cuisine," Technology and Culture, 38(3):608-634, (1997).

Bigogno et al., "Biosynthesis of arachidonic acid in the oleaginous

(56) References Cited

OTHER PUBLICATIONS microalga *Parietochloris incisa* (Cholorphyceae): Radiolabeling studies," Lipids 37(2):209-216 (2002); Abstract Only.
Blowers et al., "Studies on *Chlamydomonas* chloroplast transformation: foreign DNA can be stably maintained in the chromosome," Plant Cell, 1(1):123-132, (1989).
Bonaventure et al., "Distruption of the FATB Gene in *Arabidopsis* Dethonstrates an Essential Role of Saturated Fatty Acids in Plant Growth," The Plant Cell 15:1020-1033, (2003).
Bornscheuer et al. (ed), "Enzymes in Lipid Modification," Wiley-VCH Verlag Gmbh & Co. KGaA, 1st Edition, ISBN: 3-527-30176-3, Sections 1-11, 231 pages, (2000). (part 1 of 2 of book).
Bornscheuer et al. (ed), "Enzymes in Lipid Modification," Wiley-VCH Verlag Gmbh & Co. KGaA, 1st Edition, ISBN: 3-527-30176-3, Sections 12-18, 133 pages, (2000). (part 2 of 2 of book).
Borza et al., "Multiple Metabolic Roles for the Nonphotosynthetic Plastid of the Green Alga *Prototheca wickerhamii*," Eukaryotic Cell, 4(2):253-261, (2005).
Broun et al., "Accumulation of Ricinoleic, Lesquerolic, and Densipolic Acids in Seeds of Transgenic *Arabidopsis* Plants That Express a Fatty Acyl Hydroxylase cDNA from Castor Bean," Plant, Physiol., 113:933-942, (1997).
Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Cartens et al,. "Eicosapentaenoic Acid (20:5n-3) from the Marine Microalga *Phaeodactylum tricornutum*," Journal of the American Oil Chemists' Society, 73(8):1025-1031, (1996).
Chen et al., "Heterotrophic Growth of *Chlamydomonas reinhardtii* on Acetate in Chemostat Culture," Process Biochemistry, 31(6):601-604, (1996).
Chen et al., "High cell density culture of microalgae in heterotrophic growth," Trends in Biotechnology, 14:421-426, (1996).
Ciferri, "Thiamine-deficiency of *Prototheca*, a Yeast-like Achloric Alga," Nature, 178:1475-1476, (1956).
Cognato, "Standard Percent DNA Sequence Difference for Insects Does Not Predict Species Boundaries," Journal of Economic Entomology, 99(4):1037-1045, (2006). Abstract only. [Retrieved from the Internet Jul. 10, 2013: <URL: http://www.bioone.org/doi/abs/10.1603/0022-0493-99.4.1037?journalCode=ecen>].
Courchesne et al., "Enhancement of Lipid Production Using Biochemical, Genetic and Transcription Factor Engineering Approaches," J Biotechnol. Epub, 141(1-2):31-41, (2009).
Dai et al., "Biodiesel generation from oleaginous yeast *Rhodotorula glutinis* with xylose assimilating capacity," African Journal of Biotechnology, 6(18):2130-2134, (2007).
Davies et al.,"Expression of the Arylsulfatase Gene from the Beta 2-Tubulin Promoter in *Chlamydomonas reinhardtii*," Nucleic Acids Research, 20(12):2959-2965, (1992).
Debuchy et al., "The argininosuccinate lyase gene of *Chlamydomonas reinhardtii*: an important tool for nuclear transformation and for correlating the genetic and molecular maps of the ARG7 locus," Embo J., 8(10):2803-2809, (1989).
Decatur et al., "rRNA modifications and ribosome function," Trends in Biochemical Sciences, 27(7):344-351, (2002).
Dehesh et al., "KAS IV: a 3-ketoacyl-ACP synthase from *Cuphea* sp. is a medium chain specific condensing enzyme," The Plant Journal, 15:383-390, (1998).
Dehesh et al., "Production of high levels of 8:0 and 10:0 fatty acids in transgenic canola by overexpression of Ch FatB2, a thioesterase cDNA from *Cuphea hookeriana*," The Plant Journal, 9(2):167-172, (1996).
Deng et al., "Ionic Liquid as a Green Catalytic Reaction Medium for Esterifications," J. Mol. Catalysis A: Chemical, 165:33-36, (2001).
Deshnium et al., "Transformation of *Synechococcus* with a gene for choline oxidase enhances tolerance to salt stress," Plant Mol Biol, 29(5):897-907, (1995).
Dewhirst et al., "Discordant 16S and 23S rRNA Gene Phylogenies for the Genus Helicobacter: Implications for Phylogenetic Inference and Systematics," Journal of Bacteriology, American Society of Microbiology, 187(17):6106-6118, (2005).
Dunahay et al., "Genetic Engineering of Microalgae for Fuel Production," Applied Biochemistry and Biotechnology, 34/35:331-339 (1992).
Dunahay et al., "Manipulation of Microalgal Lipid Production Using Genetic Engineering," Applied Biochemistry and Biotechnology, 57/58:223-231, (1996).
El-Fadaly et al., "Single Cell Oil Production by an Oleaginous Yeast Strain in a Low Cost Cultivation Medium," Research Journal of Microbiology, 4(8):301-313, (2009).
El-Sheekh et al., "Variation of Some Nutritional Constituents and Fatty Acid Profiles of *Chlorella vulgaris* Beijerinck Grown under Auto and Heterotrophic Conditions," International Journal of Botany, 5(2):153-159, (2009).
Epo Supplementary European Search Report and European Search Opinion for application EP09729658 mailed Jan. 3, 2013.
Erhan, "Vegetable Oils as Lubricants, Hydraulic Fluids, and Inks," Bailey's Industrial Oil and Fat Products, 6:259-278, (2005).
European Search Report and European Search Opinion for application EP08769988 mailed Jul. 1, 2011.
European Search Report and European Search Opinion for application EP11158642 mailed Jul. 1, 2011.
Evans et al., "A comparison of the oleaginous yeast, *Candida curvata*, grown on different carbon sources in continuous and batch culture," Lipids, 18(09):623-629, (1983).
Fall et al., "Bioconversion of Xylan to Triglycerides by Oil-Rich Yeasts," Applied and Environmental Microbiology, 47(5):1130-1134, (1984).
Ferrentino, "Microalgal oil extraction and in situ transesterification," University of New Hampshire, Pub. No. MT 1447885, 93 pages, (2007).
Ferrentino, et al., "Microalgal Oil Extraction and In-situ Transesterification," AIChE Annual Mtg, San Francisco, CA, Nov. 11-13, 2006. Abstract.
Florencio et al., "A factorial approach for a sugarcane juice-based low cost culture medium: increasing the astaxanthin production by the red yeast *Phaffia rhodozyma*," Bioprocess Engineering, 19:161-164, (1998).
Forster et al., "Critic acid production from sucrose using a recombinant strain of the yeast *Yarrowia lipolyticae*," Appl Microbiol Biotechnol, 75:1409-1417 , (2007).
Franzen et al., "Chloroplast transit peptides from the green alga *Chlamydomonas reinhardtii* share features with both mitochondrial and higher plant chloroplast presequences," FEBS Letters, 260(2):165-168, (1990).
Frazer et al., "Cross-Species Sequence Comparisons: A Review of Methods and Available Resources," Genome Res., 13:1-12, (2003).
Frenz et al., "Hydrocarbon recovery by extraction with a biocompatible solvent from free and immobilized cultures of *Botryococcus braunii*," Enzyme Microb Technol, 11(11):717-724, (1989).
Frohns et al., "Potassium ion channels of *Chlorella* viruses cause rapid depolarization of host cells during infection," J Virol, 80(5):2437-2444, (2006).
Fukuda et al., "Biodiesel Fuel Production by Transesterification of Oils," J. Biosci. Bioeng., 92(5):405-416, (2001).
Funes et al., "The typically mitochondrial DNA-encoded ATP6 subunit of the F1F0-ATPase is encoded by a nuclear gene in *Chlamydomonas reinhardtii*," J Biol Chem, 277(8):6051-6058, (2002).
Gill et al., "Lipid Accumulation in an Oleaginous Yeast (Candida 107) Growing on Glucose in Single-Stage Continuous Culture," Applied and Environmental Microbiology, 33(02):231-239, (1977).
Gonzalez et al., "Optimization of Fatty Add Extraction from *Phaeodactylum tricornutum* UTEX 640 Biomass," JAOCS, 75(12):1735-1740, (1998).
Graves et al., "Hyaluronan synthesis in virus PBCV-1-infected *Chlorella*-like green algae," Virology, 257(1):15-23, (1999).
Gul et al., "Sterols and the Phytosterol Content in Oilseed Rape (*Brassica napus* L.)," Journal of Cell and Molecular Biology, 5:71-79 (2006).

(56) References Cited

OTHER PUBLICATIONS

Haas et al., "The General Applicability of in Situ Transesterification for the Production of Fatty Acid Esters from a Variety of Feedstocks," J Am Oil Chem Soc, 84:963-970, (2007).
Hall et al., "Expression of a foreign gene in *Chlamydomonas reinhardtii*," Gene, 124(1):75-81, (1993).
Hall et al., "Lipid Accumulation in an Oleaginous Yeast (Candida 107) Growing on Glucose Under Various Conditions in a One- and Two-Stage Continuous Culture," Applied and Environmental Microbiology, 33(3):577-584, (1977).
Hase et al., "Nutritional Control of Cell Pigmentation in *Chlorella* Protothecoides With Special Reference to the Degeneration of Chloroplast Induced by Glucose," Plant and Cell Physiology, 5(2):227-240 (1964), [online abstract], Retrieved on Jun. 3, 2010 from http://pcp.oxfordjounals.org/cgi/content/abstract/5/2/227.
Heise et al., "Factors Controlling Medium-Chain Fatty Acid Synthesis in Plastids From Cuphea Embryos," Prog. Lipid Res., 33(1/2):87-95, (1994).
Henderson et al., "Lipid Composition and Biosynthesis in the Marine Dinoflagellate *Crypthecodznzum cohnii*," Phytochem. 27(6):1679-1683 (1988).
Heredia et al., "Simultaneous utilization of glucose and xylose by *Candida curvata* D in continuous culture," Biotechnology Letters, 10(01):25-30, (1988).
Hillen et al., "Hydrocracking of the Oils of *Botryococcus braunii* to Transport Fuels," Biotechnology and Bioengineering, 24(1):193-205 (1982).
Hiramatsu et al., "Expression of a chitinase gene and lysis of the host cell wall during *Chlorella* virus CVK2 infection," Virology, 260(2):308-315, (1999).
Hitz et al.,"Cloning of a Higher-Plant Plastid Omega-6 Fatty Acid Desaturase cDNA and Its Expression in a Cyanobacterium," Plant Physiology, 105(2):635-641, (1994).
Hossain et al., "The effect of the sugar source on citric acid production by *Aspergillus niger*," Appl Microbiol Biotechnol , 19:393-397, (1984).
Hu et al., "Microalgal Triacylglycerols as Feedstocks for Biofuel Production: Perspectives and Advances," The Plant Journal 54:621-639, (2008).
Huang et al., "Expression of Mercuric Reductase From *Bacillus megaterium* MB1 in Eukaryotic Microalga *Chlorella* sp. DT: An Approach for Mercury Phytoremediation," Appl. Microbiol. Biotechnol., 72:197-205, (2006).
Huber et al., "Production of Liquid Alkanes by Aqueous-Phase Processing of Biomass-Derived Carbohydrates," Science, 308:1446-1450, (2005).
Huber et al., "Synthesis of Transportation Fuels from Biomass: Chemistry, Catalysts, and Engineering," Chem. Rev., 106: 4044-4098, (2006).
Husic et al., "Effect of Osmotic Stress on Carbon Metabolism in *Chlangdomonas reinhardtii*," Plant Physioi., 82:594-596, (1986).
Inoue et al., "Analysis of oil derived from liquefaction of *Botryococcus Braunii*," Biomass and Bioenergy, 6(4):269-274, (1994).
Jakobiak et al., "The Bacterial Paromomycin Resistance Gene, aphH, as a Dominant Selectable Marker in *Volvox carteri*," Protist, 55: 381-393, (2004).
Jaworski et al., "Industrial oils from transgenic plants," Current Opinion in Plant Biology, 6:178-184, (2003).
Jiang et al., "The actin gene promoter-driven bar as a dominant selectable marker for nuclear transformation of *Dunaliella salina*," Yi Chuan Xue Bao 32(4):424-433, (2005).
Kamiya, "Effects of Blue Light and Ammonia on Nitrogen Metabolism in a Colorless Mutant of *Chlorella*," Plant Cell Physiol., 30(4):513-521, (1989).
Kang et al., "Genetic diversity in *Chlorella* viruses flanking kcv, a gene that encodes a potassium ion channel protein." Virology, 326(1):150-159, (2004).
Kang et al., "The regulation activity of *Chlorella* virus gene 5' upstream sequence in *Escherichia coli* and eucaryotic alage," Institute of Microbiology, Chinese Academy of Sciences, Beijing, 16(4):443-6, (2000). Abstract only.
Katayama et al., "Alpha-Linolenate and Photosynethetic Activity in *Chlorella* Protothecoides," Plant Physiol., 42:308-313, (1967).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kenyon, "Fatty Acid Composition of Unicellular Strains of Blue-Green Algae," J. Bacteriology 109(2):827-834 (1972).
Kessler et al., "Physiological and Biochemical Contributions to the Taxonomy of the Genus Prototheca III. Utilization of Organic Carbon and Nitrogen Compounds," Arch Microbiol, 132:103-106, (1982).
Kindle, "High-Frequency Nuclear Transformation of *Chlamydomonas reinhardtii*," Proc Natl Acad Sci, 87(3):1228-1232, (1990).
Kong et al., "Microbial production of lipids by cofermentation of glucose and xylose with *Lipomyces starkeyi* 2#," Chinese Journal of Bioprocess Engineering, 05(02):36, (2007).
Krinsky et al., "The Appearance of Neoxanthin during the Regreening of Dark-grown *Euglena*," Plant Physiol. 39(4441-445 (1964).
La Scala et al., "The effect of fatty acid composition on the acrylation kinetics of epoxidized triacylglycerols," Journal of the American Oil Chemists' Society, 79(1):59-63, (2002).
Lapidot et al., "Stable Chloroplast Transformation of the Unicellular Red Alga *Porphyridium* Species," Plant Physiol, 129:7-12, (2002).
Lawford et al., "Performance Testing of *Zymomonas mobilis* Metabolically Engeineered for Confermation of Glucose, Xylose, and Arabinose," Appl Biochem Biotechnol., 98-100:429-48, (2002).
Leon-Banares et al., "Transgenic microalgae as green cell-factories," Trends in Biotechnology, 22(1):45-52, (2004).
Li et al., "Large-scale biodiesel production from microalga *Chlorella* protothecoides through heterotrophic cultivation in bioreactors," Biotechnology and Bioengineering, 98(04):764-771, (2007).
Li et al., "High-density cultivation of oleaginous yeast *Rhodosporidium toruloides* Y4 in fed-batch culture," Enzyme and Microbial Technology, 41:312-317, (2007).
Li et al., "Isolation and Purification of Lutein from the Microalga *Chlorella vulgaris* by Extraction after Saponification," J. Agric. Food Chem., 50(5):1070-1072, (2002).
Li et al., "Perspectives of microbial oils for biodiesel production," Appl Microbiol Biotechnol., 80(5):749-756, (2008). Abstract only.
Li et al., "Screening of oleaginous yeasts for broad-spectrum carbohydrates assimilating capacity," China Biotechnology, 25(12):39-44 (2005), and machine translation.
Lindley, "The impact of food processing antioxidants in vegetable oils, fruits, and vegetables," Trends in Food Science & Technology. 9:336-340, (1998).
List et al., "Melting properties of some structured lipids native to high stearic acid soybean oil," Grasas y Aceites, 55(Fasc. 2):135-137, (2004).
Lubitz, "The Protein Quality, Digestibility, and Composition of Algae, *Chlorella* 71105," J. Food Sci. 28(2):229-232 (1963).
Manuell et al., "Robust expression of a bioactive mammalian protein in *Chlamydomonas* chloroplast," Plant Biotech J, 5(3):402-412, (2007).
Mayfield et al., "Expression and Assembly of a Fully Active Antibody in Algae," Proc Natl Acad Sci, 100(2):438-442, (2003).
Meesters et al., "High-cell-density cultivation of the lipid accumulating yeast *Cryptococcus curvatus* using glycerol as a carbon source," Applied Microbiology and Biotechnology, 45:575-579, (1996).
Mendes et al., "Supercritical Carbon Dioxide Extraction of Compounds With Pharmaceutical Importance from Microalgae," Inorganica Chimica Acta, 356:328-334, (2003).
Meng et al., "Biodiesel production from oleaginous microorganisms," Renewable Energy, 34:1-5, (2009).
Metzger et al., "*Botryococcus braunii*: A Rich Source for Hydrocarbons and Related Ether Lipids," Applied Microbiology and Biotechnology, 66(5):486-496, (2005).
Miao et al., "Biodiesel Production From Heterotrophic Microalgal Oil," Biosource Technology, 97(06):841-846, (2006).

(56) References Cited

OTHER PUBLICATIONS

Miao et al., "High Yield Bio-Oil Production from Fast Pyrolysis by Metabolic Controlling of *Chlorella* Protothecoides," J. Biotech., 110:85-93, (2004).
Minowa et al., "Oil Production from Algal Cells of *Dunaliella tertiolecta* by Direct Thermochemical Liquefaction," Fuel, 74(12):1735-1738, (1995).
Mitra et al., "A *Chlorella* Virus Gene Promoter Functions as a Strong Promoter Both in Plants and Bacteria," Biochemical and Biophysical Research Communications, 204(1):189-194, (1994).
Mitra et al., "The *Chlorella* Virus Adenine Methyltransferase Gene Promoter is a Strong Promoter in Plants," Plant Molecular Biology, 26(1):85-93, (1994).
Morris, "Effect of Growth Temperature on the Cryopreservation of Prototheca," Journal of General Microbiology, 94:395-399, (1976).
Murakami et al., "Lipid Composition of Commercial Bakers' Yeasts Having Different Freeze-tolerance in Frozen Dough," Biosci. Biotechnol. Biochem., 60(11)1874-1876, (1996).
Murakami et al., "Lipids and Fatty Acid Custipvsi lions of *Chlorella*," Nihon Yuka gakkai-shi, 46(4):423-427, (1997).
Neish et al., "Carbohydrate Nutrition of *Cholorella vulgaris*," Canadian Journal of Botany, 29:68-78, (1951).
Otles et al., "Fatty Acid Composition of *Chlorella* and Spirulina Microalgae Species," Journal of AOAC International, 84(6):1708-1714, (2001).
Papanikolaou et al., "Lipid production by *Yarrowia lipolytica* growing on industrial glycerol in a single-stage continuous culture," Bioresource Technology, 82:43-49, (2002).
Patil et al., "Fatty acid composition of 12 microalgae for possible use in aquaculture feed," Aquacult Int , 15:1-9, (2007).
PCT International Preliminary Report on Patentability (Chapter I) of May 31, 2011 for application PCT/US09/066142.
PCT International Preliminary Report on Patentability (Chapter I) of Aug. 13, 2012 for application PCT/US11/38463.
PCT International Preliminary Report on Patentability (Chapter I) of Dec. 7, 2009 for application PCT/US08/65563.
PCT International Preliminary Report on Patentability for application PCT/US2011/059224 mailed May 16, 2013.
PCT International Search Report and Written Opinion of the International Searching Authority for application PCT/US2013/037261 mailed Aug. 23, 2013.
PCT International Search Report for application PCT/US2011/032582 mailed Aug. 9, 2011.
PCT International Search Report for application PCT/US2011/038463 mailed Jan. 18, 2012.
PCT International Search Report for application PCT/US2011/059224 mailed Jun. 27, 2012.
PCT International Search Report for application PCT/US2012/023696 mailed May 23, 2012.
PCT International Search Report for application PCT/US2012/036690 mailed Aug. 30, 2012.
PCT International Search Report of Aug. 20, 2010 for application PCT/US2009/066142.
PCT International Search Report of Nov. 5, 2010 for application PCT/US2009/066141.
PCT International Search Report of Nov. 6, 2008 for application PCT/US2008/065563.
PCT Written Opinion of the International Search Authority of Aug. 20, 2010 for application PCT/US2009/066142.
PCT Written Opinion of the International Searching Authority for application PCT/US2011/032582 mailed Aug. 9, 2011.
PCT Written Opinion of the International Searching Authority for application PCT/US2011/038463 mailed Jan. 18, 2012.
PCT Written Opinion of the International Searching Authority for application PCT/US2012/023696 mailed May 23, 2012.
PCT Written Opinion of the International Searching Authority for application PCT/US2012/036690 mailed Aug. 30, 2012.
PCT Written Opinion of the International Searching Authority of Nov. 5, 2010 for application PCT/US2009/066141.
PCT Written Opinion of the International Searching Authority of Nov. 6, 2008 for application PCT/US2008/065563.
Petkov et al., "Which are fatty acids of the green alga *Chlorella*?," Biochemical Systematics and Ecology, 35:281-285, (2007).
Powell et al., "Algae Feeding in Humans," J. Nutrition, 75:7-12, (1961).
Proschold et al., "Portrait of a Species: *Chlamydomonas reinhardtii*," Genetics, 170(4):1601-1610, (2005).
Qingyu et al., "Fine Cell Structure and Biochemical Compositions of *Chlorella* Protothecoides after Transferring from Autotrophic to Heterotrophic Metabolism," Journal of Nanjing University, Natural Sciences Edition, 29(4):622-630, (1993). Abstract.
Randolph-Anderson et al., "Further characterization of the respiratory deficient dum-1 mutation of *Chlamydomonas reinhardtii* and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-1050, (2002).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Roy et al., "Production of Intracellular Fat by the Yeast *Lipomyces starkeyi*," Indian Journal of Experimental Biology, 16(4):511-512, (1978).
Sakuradani, "Studies of Metabolic Engineering of Useful Lipid-producing Microorganisms," NISR Research Grant, (2004).
Salou et al., "Growth and Energetics of *Leuconostoc oenos* during Cometabolism of Glucose with Citrate or Fructose," Applied and Environmental Microbiology, 60(5):1459-1466, (1994).
Sansawa et al., "Production of Intracellular Phytochemicals in *Chlorella* under Heterotrophic Conditions," Journal of Bioscience and Bioengineering, 98(6):437-444, (2004).
Sawayama et al., "Possibility of renewable energy production and $CO_2$ mitigation by thermochemical liquefaction of microalgae," Biomass and Bioenergy, 17(1):33-39, (1999).
Schreier et al., "The use of nuclear-encoded sequences to direct the light-regulated synthesis and transport of a foreign protein into plant chloroplasts," Embo J, 4(1):25-32, (1985).
Shao et al., "Cloning and expression of metallothionein mutant α-KKS-α in *Anabaena* sp. PCC 7120," Marine Pollution Bulletin, 45(1012):163-167, (2002).
Smith et al., "Production of hydroxy fatty acids in the seeds of *Arabidopsis thaliana*," Biochemical Society Transactions, 28(6):947-950, (2000).
Sorger et al., "Triacylglycerol biosynthesis in yeast," AppL Microbiol Biotechnol, 61:289-299, (2003).
Spolaore et al., "Commercial Applications of Microalgae," J. Biosci. Bioeng. 101(2):87-96 (2006).
Stackebrandt et al., "Taxonomic Note: A Place for DNA-DNA Reassociation and 16S rRNA Sequence Analysis in the Present Species Definition in Bacteriology," International Journal of Systematic Bacteriology, 44(4):846-849, (1994).
Sud et al., "Lipid Composition and Sensitivity of *Prototheca wickerhamii* to Membrane-Active Antimicrobial Agents," Antimicrobial Agents and Chemotherapy, 16:486-490, (1979).
Suda, et al., "Evidence for a novel *Chlorella* virus-encoded alginate lyase," FEMS Microbiology Letters, 180(1):45-53, (1999).
Suh et al., "What limits production of unusual monoenoic fatty acids in transgenic plants?," Planta, 215:584-595, (2002).
Sun et al., "Characterization of two chitinase genes and one chitosanase gene encoded by *Chlorella* virus PBCV-1," Virology, 263(2):376-387, (1999).
Swern et al. "Fractionation of tallow fatty acids:Preparation of purified oleic acid and an inedible olive oil substitute," Oil & Soap, 22(11):302-304 (1945).
Takashima et al., "Further Notes on the Growth and Chlorophyll Formation of *Chlorella* Protothecoides," Plant & Cell Physiol., 5:321-332, (1964).
Talbot et al., "Formulation and Production of Confectionery Fats," OFI Middle East 2007 Conference and Exhibition, 378 pages, (2007).

(56) References Cited

OTHER PUBLICATIONS

Tang et al., "Insertion mutagenesis of *Chlamydomonas reinhardtii* by electroporation and heterologous DNA," Biochem Mol Biol Int, 36(5)1025-1035, (1995).
Taylor et al., "Continuous Fermentation and Stripping of Ethanol," Biotechnol Prog., 11(6):693-698, (1995).
Thavarungkul et al., "Batch injection analysis for the determination of sucrose in sugar cane juice using immobilized invertase and thermometric detection," Biosensors & Bioelectronics , 14:19-25, (1999).
Tornabene et al., "Lipid composition of the nitrogen starved green alga *Neochloris oleoabundans*," Enzyme Microb. Technol., 5:435-440, (1983).
U.S. Appl. No. 12/131,766, Advisory Action mailed Oct. 13, 2011.
U.S. Appl. No. 12/131,766, Non-Final Office Action mailed Aug. 1, 2011.
U.S. Appl. No. 12/131,766, Non-Final Office Action mailed Nov. 23, 2010.
U.S. Appl. No. 12/131,766, Non-Final Office Action mailed Dec. 10, 2009.
U.S. Appl. No. 12/131,766, Requirement for Restriction/Election mailed Aug. 5, 2009.
U.S. Appl. No. 12/131,766, Requirement for Restriction/Election mailed Aug. 17, 2010.
U.S. Appl. No. 12/131,773, Final Office Action mailed Mar. 21, 2011.
U.S. Appl. No. 12/131,773, Final Office Action mailed Oct. 15, 2013.
U.S. Appl. No. 12/131,773, Non-Final Office Action mailed Jun. 5, 2013.
U.S. Appl. No. 12/131,773, Non-Final Office Action mailed Jun. 25, 2010.
U.S. Appl. No. 12/131,773, Non-Final Office Action mailed Dec. 15, 2009.
U.S. Appl. No. 12/131,773, Requirement for Restriction/Election mailed Aug. 6, 2009.
U.S. Appl. No. 12/131,783, Final Office Action mailed Jan. 12, 2012.
U.S. Appl. No. 12/131,783, Final Office Action mailed Dec. 13, 2013.
U.S. Appl. No. 12/131,783, Non-Final Office Action mailed Jun. 6, 2011.
U.S. Appl. No. 12/131,783, Non-Final Office Action mailed Jul. 18, 2013.
U.S. Appl. No. 12/131,783, Requirement for Restriction/Election mailed Apr. 19, 2011.
U.S. Appl. No. 12/131,793, Non-Final Office Action mailed Apr. 3, 2013.
U.S. Appl. No. 12/131,793, Non-Final Office Action mailed Nov. 13, 2012.
U.S. Appl. No. 12/131,793, Notice of Allowance mailed Apr. 3, 2013.
U.S. Appl. No. 12/131,804, Final Office Action mailed Feb. 2, 2011.
U.S. Appl. No. 12/131,804, Non-Final Office Action mailed Oct. 26, 2012.
U.S. Appl. No. 12/131,804, Non-Final Office Action mailed Mar. 3, 2010.
U.S. Appl. No. 12/131,804, Non-Final Office Action mailed Jun. 7, 2012.
U.S. Appl. No. 12/131,804, Requirement for Restriction/Election mailed Sep. 17, 2009.
U.S. Appl. No. 12/131,804, Requirement for Restriction/Election mailed Nov. 18, 2009.
U.S. Appl. No. 12/194,389, Final Office Action mailed Jan. 5, 2011.
U.S. Appl. No. 12/194,389, Non-Final Office Action mailed Feb. 4, 2010.
U.S. Appl. No. 12/194,389, Requirement for Restriction/Election mailed Oct. 5, 2010.
U.S. Appl. No. 12/194,389, Requirement for Restriction/Election mailed Nov. 2, 2009.
U.S. Appl. No. 12/628,140, Final Office Action mailed Mar. 15, 2013.
U.S. Appl. No. 12/628,140, Final Office Action mailed Sep. 12, 2013.
U.S. Appl. No. 12/628,140, Non-Final Office Action mailed Oct. 30, 2012.
U.S. Appl. No. 12/628,144, Final Office Action mailed Nov. 16, 2010.
U.S. Appl. No. 12/628,144, Final Office Action mailed Dec. 5, 2011.
U.S. Appl. No. 12/628,144, Non-Final Office Action mailed Jun. 7, 2011.
U.S. Appl. No. 12/628,144, Non-Final Office Action mailed Jul. 8, 2010.
U.S. Appl. No. 12/628,149, Non-Final Office Action mailed Jun. 25, 2010.
U.S. Appl. No. 12/628,149, Non-Final Office Action mailed Sep. 16, 2010.
U.S. Appl. No. 12/628,149, Notice of Allowance mailed Dec. 15, 2010.
U.S. Appl. No. 12/628,150, Non-Final Office Action mailed Apr. 29, 2010.
U.S. Appl. No. 12/628,150, Non-Final Office Action mailed Oct. 13, 2010.
U.S. Appl. No. 12/628,150, Notice of Allowance mailed Mar. 21, 2011.
U.S. Appl. No. 12/642,487, Non-Final Office Action mailed Jan. 4, 2013.
U.S. Appl. No. 12/642,487, Requirement for Restriction/Election mailed Jun. 18, 2012.
U.S. Appl. No. 12/642,487, Requirement for Restriction/Election mailed Nov. 8, 2012.
U.S. Appl. No. 12/772,164, Final Office Action mailed May 24, 2012.
U.S. Appl. No. 12/772,164, Non-Final Office Action mailed Oct. 12, 2011.
U.S. Appl. No. 12/772,164, Requirement for Restriction/Election mailed Jul. 20, 2011.
U.S. Appl. No. 12/772,170, Final Office Action mailed Feb. 21, 2012.
U.S. Appl. No. 12/772,170, Non-Final Office Action mailed Sep. 13, 2011.
U.S. Appl. No. 12/772,170, Non-Final Office Action mailed Dec. 17, 2013.
U.S. Appl. No. 12/772,170, Requirement for Restriction/Election mailed Jul. 13, 2011.
U.S. Appl. No. 12/960,388, Notice of Allowance mailed May 28, 2013.
U.S. Appl. No. 12/960,388, Requirement for Restriction/Election mailed Apr. 1, 2013.
U.S. Appl. No. 12/981,409, Non-Final Office Action mailed Jan. 6, 2012.
U.S. Appl. No. 12/981,409, Notice of Allowance mailed May 29, 2012.
U.S. Appl. No. 12/981,409, Requirement for Restriction/Election mailed Apr. 19, 2012.
U.S. Appl. No. 12/981,409, Requirement for Restriction/Election mailed Oct. 28, 2011.
U.S. Appl. No. 13/029,061, Requirement for Restriction/Election mailed Nov. 29, 2011.
U.S. Appl. No. 13/045,500, Non-Final Office Action mailed Mar. 9, 2012.
U.S. Appl. No. 13/045.500, Final Office Action mailed Sep. 26, 2012.
U.S. Appl. No. 13/073,757, Non-Final Office Action mailed Aug. 15, 2011.
U.S. Appl. No. 13/073,757, Non-Final Office Action mailed Dec. 29, 2011.
U.S. Appl. No. 13/073,757, Notice of Allowance mailed Apr. 17, 2012.
U.S. Appl. No. 13/087,311, Final Office Action mailed Dec. 16, 2013.
U.S. Appl. No. 13/087,311, Non-Final Office Action mailed Apr. 23, 2013.
U.S. Appl. No. 13/118,365, Final Office Action mailed Jul. 22, 2013
U.S. Appl. No. 13/118,365, Non-Final Office Action mailed Feb. 11, 2013.
U.S. Appl. No. 13/118,365, Requirement for Restriction/Election mailed Oct. 11, 2012.
U.S. Appl. No. 13/273,179, Requirement for Restriction/Election mailed Nov. 14, 2013.
U.S. Appl. No. 13/406,417, Non-Final Office Action mailed Nov. 5, 2012.

(56) References Cited

OTHER PUBLICATIONS

U.S. Appl. No. 13/406,417, Requirement for Restriction/Election mailed Apr. 30, 2012.
U.S. Appl. No. 13/464,948, Requirement for Restriction/Election mailed Aug. 21, 2013.
U.S. Appl. No. 13/479,200, Non-Final Office Action mailed Apr. 10, 2013.
U.S. Appl. No. 13/479,200, Non-Final Office Action mailed Sep. 9, 2013.
U.S. Appl. No. 13/479,200, Notice of Allowance mailed Nov. 25, 2013.
U.S. Appl. No. 13/479,200,Requirement for Restriction/Election mailed Jan. 15, 2013.
U.S. Appl. No. 13/527,480, Non-Final Office Action mailed Jun. 26, 2013.
U.S. Appl. No. 13/527,480, Requirement for Restriction/Election mailed May 3, 2013.
U.S. Appl. No. 13/543,666, Non-Final Office Action mailed Sep. 5, 2013.
U.S. Appl. No. 13/543,666, Requirement for Restriction/Election mailed Jan. 3, 2013.
U.S. App. No. 13/547,457, Non-Final Office Action mailed Jul. 8, 2013.
U.S. Appl. No. 13/55,8252, Notice of Allowance mailed Oct. 23, 2013.
U.S. Appl. No. 13/550,412, Non-Final Office Action mailed Oct. 29, 2012.
U.S. Appl. No. 13/550,412, Notice of Allowance mailed Feb. 21, 2013.
U.S. Appl. No. 13/558,252, Final Office Action mailed Jul. 9, 2013.
U.S. Appl. No. 13/558,252, Non-Final Office Action mailed Jan. 18, 2013.
U.S. Appl. No. 13/601,928, Non-Final Office Action mailed Jan. 31, 2013.
U.S. Appl. No. 13/601,928, Notice of Allowance mailed Feb. 26, 2013.
U.S. Appl. No. 13/601,937, Final Office Action mailed Nov. 22, 2013.
U.S. Appl. No. 13/601,937, Non-Final Office Action mailed Jun. 10, 2013.
U.S. Appl. No. 13/601,937, Requirement for Restriction/Election mailed Feb. 27, 2013.
U.S. Appl. No. 13/650,018, Non-Final Office Action mailed Dec. 23, 2013.
U.S. Appl. No. 13/650,018, Requirement for Restriction/Election mailed Aug. 22, 2013.
U.S. Appl. No. 13/650,024, Non-Final Office Action mailed Jul. 2, 2013.
U.S. Appl. No. 13/650,024, Notice of Allowance mailed Oct. 17, 2013.
U.S. Appl. No. 13/889,214, Non-Final Office Action mailed Sep. 18, 2013.
U.S. Appl. No. 13/941,357, Requirement for Restriction/Election mailed Jan. 7, 2014.
Urano, et al., "Effect of Osmotic Stabilizers on Protoplast Generation of *Chlorella ellipsoidea* Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2):155-159, (2003).
Vazquez-Bermudez et al., "Uptake of 2-Oxoglutarate in *Synechococcus* Strains Transformed with the *Escherichia coli* kgtP Gene," Journal of Bacteriology, 182(1):211-215, (2000).
Walker et al., "Characterization of the *Dunaliella tertiolecta* RbcS Genes and Their Promoter Activity in *Chlamydomonas reinhardtii*," Plant Cell Rep, 23(10-11):727-735, (2005).
Warner et al., "Analysis of Tocopherols and Phytosterols in Vegetable Oils by HPLC with Evaporative Light-Scattering Detection," JAOCS, 67(11):827-831 (1990).
Westphal, et al., "Vipp1 Deletion Mutant of Synechocystis: A Connection Between Bacterial Phage Shock and Thylakoid Biogenesis," Proc Natl Acad Sci U S A., 98(.7):4243-4248, (2001).
Wiberg et al., "The distribution of caprylate, caprate and laurate in lipids from developing and mature seeds of transgenic *Brassica napus* L.," Planta, 212:33-40, (2000).
Wu et al., "A Comparative Study of Gases Generated from Simulant Thermal Degradation of Autotrophic and Heterotrophic *Chlorella*," Progress in Natural Science, 2(4):311-318, (1992).
Wu et al., "Comparative study on Liposoluble Compounds in Autotrophic and Heterotrophic *Chlorella* Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (1994).
Xiong et al., "High-density fermentation of microalga *Chlorella* protothecoides in bioreactor for microbio-diesel production," Appl. Microbiol. Biotechnol., 78:29-36, (2008).
Yamada et al, "Alternative expression of a chitosanase gene produces two different proteins in cells infected with *Chlorella* virus CVK2," Virology, 230(2):361-368, (1997).
Yamada et al., "*Chlorella* viruses," Adv Virus Res, 66:293-336, (2006).
Zarowska et al., "Production of Citric Acid on Sugar Beet Molasses by Single and Mixed Cultures of *Yarrowia lipolytica*," Electronic Journal of Polish Agricultural Universities, 4(2):1-7, (2001). [Retrieved from the Internet Oct. 3, 2011: <URL: http://www.ejpau.media.pl/volume4/issue2/biotechnology/art-01.html>].
Zhang et al., "Malic enzyme: the controlling activity for lipid production? Overexpression of malic enzyme in *Mucor circinelloides* leads to a 2.5-fold increase in lipid accumulation," Microbiology, 153(7):2013-2025, (2007).
Zhao et al., "Medium optimization for lipid production through co-fermentation of glucose and xylose by the oleaginous yeast *Lipomyces starkeyi*," Eur. J. Lipid Sci. Technol., 110:405-412, (2008).
Zurawski et al., "Nucleotide sequence of the gene for the Mr 32,000 thylakoid membrane protein from *Spinacia oleracea* and *Nicotiana debneyi* predicts a totally conserved primary translation product of Mr 38,950," Proc Natl Acad Sci, 79(24):7699-7703, (1982).

* cited by examiner

| Diversity of Lipid Chains in Microalgal Species | | | | | | | | | |
|---|---|---|---|---|---|---|---|---|---|
| Strain # From Table 8 | C:14:0 | C:16:0 | C:16:1 | C:18:0 | C:18:1 | C:18:2 | C:18:3 | C:20:0 | C:20:1 |
| 1 | 0.57 | 10.30 | 0 | 3.77 | 70.52 | 14.24 | 1.45 | 0.27 | 0 |
| 2 | 0.61 | 8.70 | 0.30 | 2.42 | 71.98 | 14.21 | 1.15 | 0.20 | 0.24 |
| 4 | 0.68 | 9.82 | 0 | 2.83 | 65.78 | 12.94 | 1.46 | 0 | 0 |
| 5 | 1.47 | 21.96 | 0 | 4.35 | 22.64 | 9.58 | 5.2 | 3.88 | 3.3 |
| 10 | 0 | 12.01 | 0 | 0 | 50.33 | 17.14 | 0 | 0 | 0 |
| 11 | 1.41 | 29.44 | 0.70 | 3.05 | 57.72 | 12.37 | 0.97 | 0.33 | 0 |
| 12 | 1.09 | 25.77 | 0 | 2.75 | 54.01 | 11.90 | 2.44 | 0 | 0 |

```
SEQUENCE LISTING

<160> NUMBER OF SEQ ID NOS: 29

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgttgaagaa tgagccggcg ac                                              22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtgagcta ttacgcactc                                                 20

<210> SEQ ID NO 3
<211> LENGTH: 546
<212> TYPE: DNA
<213> ORGANISM: Chlorella protothecoides

<400> SEQUENCE: 3
tgttgaagaa tgagccggcg acttagaaaa cgtggcaagg ttaaggaaac gtatccggag    60
```

-continued

```
ccgaagcgaa agcaagtctg aacagggcga ttaagtcatt ttttctagac ccgaacccgg      120
gtgatctaac catgaccagg atgaagcttg ggtgacacca agtgaaggtc cgaaccgacc      180
gatgttgaaa atcggcgga tgagttgtgg ttagcggtga aataccagtc gaactcggag       240
ctagctggtt ctccccgaaa tgcgttgagg cgcagcggtt cataaggctg tctagggta       300
aagcactgtt tcggtgcggg ctgcgaaagc ggtaccaaat cgtggcaaac tctgaatact      360
agatatgcta tttatgggcc agtgagacgg tgggggataa gcttcatcgt cgagagggaa      420
acagcccaga tcactagcta aggccccaaa atgatcgtta agtgacaaag gaggtgagaa      480
tgcagaaaca accaggaggt ttgcttagaa gcagccaccc tttaaagagt gcgtaatagc      540
tcactg                                                                 546

<210> SEQ ID NO 4
<211> LENGTH: 565
<212> TYPE: DNA
<213> ORGANISM: Chlorella protothecoides

<400> SEQUENCE: 4
tgttgaagaa tgagccggcg acttagaaaa agtggcgtgg ttaaggaaaa attccgaagc       60
cttagcgaaa gcgagtctga ataggcgat caaatatttt aatatttaca atttagtcat      120
tttttctaga cccgaacccg ggtgatctaa ccatgaccag gatgaaactt gggtgatacc      180
aagtgaaggt ccgaaccgac cgatgttgaa aaatcggcgg atgagttgtg gttagcggtg      240
aaataccagt cgaacccgga gctagctggt tctccccgaa atgcgttgag gcgcagcagt      300
acatctagtc tatctagggg taaagcactg tttcggtgcg ggctgtgaaa acggtaccaa      360
atcgtggcaa actctgaata ctagaaatga cggtgtagta gtgagactgt gggggataag      420
ctccattgtc aagagggaaa cagcccagac caccagctaa ggccccaaaa tggtaatgta      480
gtgacaaagg aggtgaaaat gcaaacacaa ccaggaggtt ggcttagaag cagccatcct      540
ttaaagagtg cgtaatagct cactg                                            565

<210> SEQ ID NO 5
<211> LENGTH: 565
<212> TYPE: DNA
<213> ORGANISM: Prototheca moriformis

<400> SEQUENCE: 5
tgttgaagaa tgagccggcg acttagaaaa ggtggcatgg ttaaggaaat attccgaagc       60
cgtagcaaaa gcgagtctga ataggcgat aaaatatatt aatatttaga atctagtcat      120
tttttctaga cccgaacccg ggtgatctaa ccatgaccag gatgaagctt gggtgatacc      180
aagtgaaggt ccgaaccgac cgatgttgaa aaatcggcgg atgagttgtg gttagcggtg      240
aaataccagt cgaacccgga gctagctggt tctccccgaa atgcgttgag gcgcagcagt      300
acatctagtc tatctagggg taaagcactg tttcggtgcg ggctgtgaga acggtaccaa      360
atcgtggcaa actctgaata ctagaaatga cgatgtagta gtgagactgt gggggataag      420
ctccattgtc aagagggaaa cagcccagac caccagctaa ggccccaaaa tggtaatgta      480
gtgacaaagg aggtgaaaat gcaaatacaa ccaggaggtt ggcttagaag cagccatcct      540
ttaaagagtg cgtaatagct cactg                                            565

<210> SEQ ID NO 6
<211> LENGTH: 573
<212> TYPE: DNA
<213> ORGANISM: Prototheca moriformis
```

<400> SEQUENCE: 6

```
tgttgaagaa tgagccggcg acttaaaata aatggcaggc taagagaatt aataactcga      60
aacctaagcg aaagcaagtc ttaatagggc gctaatttaa caaaacatta ataaaaatct     120
aaagtcattt attttagacc cgaacctgag tgatctaacc atggtcagga tgaaacttgg     180
gtgacaccaa gtggaagtcc gaaccgaccg atgttgaaaa atcggcggat gaactgtggt     240
tagtggtgaa ataccagtcg aactcagagc tagctggttc tccccgaaat gcgttgaggc     300
gcagcaatat atctcgtcta tctagggta aagcactgtt tcggtgcggg ctatgaaaat     360
ggtaccaaat cgtggcaaac tctgaatact agaaatgacg atatattagt gagactatgg     420
gggataagct ccatagtcga gagggaaaca gcccagacca ccagttaagg ccccaaaatg     480
ataatgaagt ggtaaaggag gtgaaaatgc aaatacaacc aggaggttgg cttagaagca     540
gccatccttt aaagagtgcg taatagctca ctg                                   573
```

<210> SEQ ID NO 7
<211> LENGTH: 565
<212> TYPE: DNA
<213> ORGANISM: Chlorella protothecoides

<400> SEQUENCE: 7

```
tgttgaagaa tgagccggcg acttagaaaa agtggcgtgg ttaaggaaaa attccgaagc      60
cttagcgaaa gcgagtctga atagggcgat caaatatttt aatatttaca atttagtcat     120
tttttctaga cccgaacccg ggtgatctaa ccatgaccag gatgaaactt gggtgatacc     180
aagtgaaggt ccgaaccgac cgatgttgaa aaatcggcgg atgagttgtg gttagcggtg     240
aaataccagt cgaaccccga gctagctggt tctccccgaa atgcgttgag gcgcagcagt     300
acatctagtc tatctagggg taaagcactg tttcggtgcg ggctgtgaaa acggtaccaa     360
atcgtggcaa actctgaata ctagaaatga cggtgtagta gtgagactgt gggggataag     420
ctccattgtc aagagggaaa cagcccagac caccagctaa ggccccaaaa tggtaatgta     480
gtgacaaagg aggtgaaaat gcaaacacaa ccaggaggtt ggcttagaag cagccatcct     540
ttaaagagtg cgtaatagct cactg                                             565
```

<210> SEQ ID NO 8
<211> LENGTH: 546
<212> TYPE: DNA
<213> ORGANISM: Chlorella protothecoides

<400> SEQUENCE: 8

```
tgttgaagaa tgagccggcg acttagaaaa cgtggcaagg ttaaggaaac gtatccggag      60
ccgaagcgaa agcaagtctg aacagggcga ttaagtcatt ttttctagac ccgaacccgg     120
gtgatctaac catgaccagg atgaagcttg gtgacaccaa agtgaaggtc cgaaccgacc     180
gatgttgaaa atcggcgga tgagttgtgg ttagcggtga ataccagtc gaactcggag      240
ctagctggtt ctccccgaaa tgcgttgagg cgcagcggtt cataaggctg tctagggta     300
aagcactgtt tcggtgcggg ctgcgaaagc ggtaccaaat cgtggcaaac tctgaatact     360
agatatgcta tttatgggcc agtgagacgg tgggggataa gcttcatcgt cgagagggaa     420
acagcccaga tcactagcta aggccccaaa atgatcgtta agtgacaaag gaggtgagaa     480
tgcagaaaca accaggaggt ttgcttagaa gcagccaccc tttaaagagt gcgtaatagc     540
tcactg                                                                  546
```

<210> SEQ ID NO 9
<211> LENGTH: 565
<212> TYPE: DNA
<213> ORGANISM: Chlorella protothecoides

<400> SEQUENCE: 9

```
tgttgaagaa tgagccggcg acttagaaaa agtggcgtgg ttaaggaaaa attccgaagc    60
cttagcgaaa gcgagtctga atagggcgat caaatatttt aatatttaca atttagtcat   120
tttttctaga cccgaacccg ggtgatctaa ccatgaccag gatgaaactt gggtgatacc   180
aagtgaaggt ccgaaccgac cgatgttgaa aaatcggcgg atgagttgtg gttagcggtg   240
aaataccagt cgaacccgga gctagctggt tctccccgaa atgcgttgag gcgcagcagt   300
acatctagtc tatctagggg taaagcactg tttcggtgcg ggctgtgaaa acggtaccaa   360
atcgtggcaa actctgaata ctagaaatga cggtgtagta gtgagactgt gggggataag   420
ctccattgtc aagagggaaa cagcccagac caccagctaa ggccccaaaa tggtaatgta   480
gtgacaaagg aggtgaaaat gcaaacacaa ccaggaggtt ggcttagaag cagccatcct   540
ttaaagagtg cgtaatagct cactg                                         565
```

<210> SEQ ID NO 10
<211> LENGTH: 565
<212> TYPE: DNA
<213> ORGANISM: Chlorella kessleri

<400> SEQUENCE: 10

```
tgttgaagaa tgagccggcg acttagaaaa agtggcgtgg ttaaggaaaa attccgaagc    60
cttagcgaaa gcgagtctga atagggcgat caaatatttt aatatttaca atttagtcat   120
tttttctaga cccgaacccg ggtgatctaa ccatgaccag gatgaaactt gggtgatacc   180
aagtgaaggt ccgaaccgac cgatgttgaa aaatcggcgg atgagttgtg gttagcggtg   240
aaataccagt cgaacccgga gctagctggt tctccccgaa atgcgttgag gcgcagcagt   300
acatctagtc tatctagggg taaagcactg tttcggtgcg ggctgtgaaa acggtaccaa   360
atcgtggcaa actctgaata ctagaaatga cggtgtagta gtgagactgt gggggataag   420
ctccattgtc aagagggaaa cagcccagac caccagctaa ggccccaaaa tggtaatgta   480
gtgacaaagg aggtgaaaat gcaaacacaa ccaggaggtt ggcttagaag cagccatcct   540
ttaaagagtg cgtaatagct cactg                                         565
```

<210> SEQ ID NO 11
<211> LENGTH: 548
<212> TYPE: DNA
<213> ORGANISM: Chlorella kessleri

<400> SEQUENCE: 11

```
tgttgaagaa tgagccggcg acttagaaga agtggcttgg ttaaggataa ctatccggag    60
ccagagcgaa agcaagtctg aatagggcgc ttaaaggtca cttttttctag acccgaaccc   120
gggtgatcta accatgacca ggatgaagct tgggtaacac cacgtgaagg tccgaaccga   180
ccgatgttga aaaatcggcg gatgagttgt ggttagcggt gaaataccaa tcgaactcgg   240
agctagctgg ttctccccga aatgcgttga ggcgcagcgg tttatgaggc tgtctagggg   300
taaagcactg tttcggtgcg ggctgcgaaa gcggtaccaa atcgtggcaa actctgaata   360
ctagatatgc tattcatgag ccagtgagac ggtgggggat aagcttcatc gtcaagaggg   420
aaacagccca gatcaccagc taaggcccca aaatggtcgt taagtggcaa aggaggtgag   480
```

```
aatgctgaaa caaccaggag gtttgcttag aagcagccac cctttaaaga gtgcgtaata    540
gctcactg                                                             548

<210> SEQ ID NO 12
<211> LENGTH: 548
<212> TYPE: DNA
<213> ORGANISM: Chlorella kessleri

<400> SEQUENCE: 12
tgttgaagaa tgagccggcg acttagaaga agtggcttgg ttaaggataa ctatccggag     60
ccagagcgaa agcaagtctg aatagggcgc ttaaaggtca cttttctag acccgaaccc    120 gggtgatcta accatgacca ggatgaagct tgggtaacac cacgtgaagg tccgaaccga    180
ccgatgttga aaaatcggcg gatgagttgt ggttagcggt gaaataccaa tcgaactcgg    240
agctagctgg ttctccccga aatgcgttga ggcgcagcgg tttatgaggc tgtctagggg    300
taaagcactg tttcggtgcg ggctgcgaaa gcggtaccaa atcgtggcaa actctgaata    360
ctagatatgc tattcatgag ccagtgagac ggtgggggat aagcttcatc gtcaagaggg    420
aaacagccca gatcaccagc taaggcccca aaatggtcgt taagtggcaa aggaggtgag    480
aatgctgaaa caaccaggag gtttgcttag aagcagccac cctttaaaga gtgcgtaata    540
gctcactg                                                             548

<210> SEQ ID NO 13
<211> LENGTH: 548
<212> TYPE: DNA
<213> ORGANISM: Parachlorella kessleri

<400> SEQUENCE: 13
tgttgaagaa tgagccggcg acttagaaga agtggcttgg ttaaggataa ctatccggag     60
ccagagcgaa agcaagtctg aatagggcgc ttaaaggtca cttttctag acccgaaccc    120 gggtgatcta accatgacca ggatgaagct tgggtaacac cacgtgaagg tccgaaccga    180
ccgatgttga aaaatcggcg gatgagttgt ggttagcggt gaaataccaa tcgaactcgg    240
agctagctgg ttctccccga aatgcgttga ggcgcagcgg tttatgaggc tgtctagggg    300
taaagcactg tttcggtgcg ggctgcgaaa gcggtaccaa atcgtggcaa actctgaata    360
ctagatatgc tattcatgag ccagtgagac ggtgggggat aagcttcatc gtcaagaggg    420
aaacagccca gatcaccagc taaggcccca aaatggtcgt taagtggcaa aggaggtgag    480
aatgctgaaa caaccaggag gtttgcttag aagcagccac cctttaaaga gtgcgtaata    540
gctcactg                                                             548

<210> SEQ ID NO 14
<211> LENGTH: 548
<212> TYPE: DNA
<213> ORGANISM: Parachlorella kessleri

<400> SEQUENCE: 14
tgttgaagaa tgagccggcg acttagaaga agtggcttgg ttaaggataa ctatccggag     60
ccagagcgaa agcaagtctg aatagggcgc ttaaaggtca cttttctag acccgaaccc    120 gggtgatcta accatgacca ggatgaagct tgggtaacac cacgtgaagg tccgaaccga    180
ccgatgttga aaaatcggcg gatgagttgt ggttagcggt gaaataccaa tcgaactcgg    240
agctagctgg ttctccccga aatgcgttga ggcgcagcgg tttatgaggc tgtctagggg    300
```

```
taaagcactg tttcggtgcg ggctgcgaaa gcggtaccaa atcgtggcaa actctgaata      360
ctagatatgc tattcatgag ccagtgagac ggtgggggat aagcttcatc gtcaagaggg      420
aaacagccca gatcaccagc taaggcccca aaatggtcgt taagtggcaa aggaggtgag      480
aatgctgaaa caaccaggag gtttgcttag aagcagccac cctttaaaga gtgcgtaata      540
gctcactg                                                              548
```

```
<210> SEQ ID NO 15
<211> LENGTH: 565
<212> TYPE: DNA
<213> ORGANISM: Parachlorella kessleri

<400> SEQUENCE: 15
tgttgaagaa tgagccggcg acttagaaaa agtggcgtgg ttaaggaaaa attccgaagc       60
cttagcgaaa gcgagtctga atagggcgat caaatatttt aatatttaca atttagtcat      120
tttttctaga cccgaacccg ggtgatctaa ccatgaccag gatgaaactt gggtgatacc      180
aagtgaaggt ccgaaccgac cgatgttgaa aaatcggcgg atgagttgtg gttagcggtg      240
aaataccagt cgaacccgga gctagctggt tctccccgaa atgcgttgag gcgcagcagt      300
acatctagtc tatctagggg taaagcactg tttcggtgcg ggctgtgaaa acggtaccaa      360
atcgtggcaa actctgaata ctagaaatga cggtgtagta gtgagactgt gggggataag      420
ctccattgtc aagagggaaa cagcccagac caccagctaa ggccccaaaa tggtaatgta      480
gtgacaaagg aggtgaaaat gcaaacacaa ccaggaggtt ggcttagaag cagccatcct      540
ttaaagagtg cgtaatagct cactg                                           565
```

```
<210> SEQ ID NO 16
<211> LENGTH: 541
<212> TYPE: DNA
<213> ORGANISM: Prototheca stagnora

<400> SEQUENCE: 16
tgttgaagaa tgagccggcg agttaaaaaa aatggcatgg ttaaagatat ttctctgaag       60
ccatagcgaa agcaagtttt acaagctata gtcattttt ttagacccga aaccgagtga      120
tctacccatg atcagggtga agtgttggtc aaataacatg gaggcccgaa ccgactaatg      180
gtgaaaaatt agcggatgaa ttgtgggtag gggcgaaaaa ccaatcgaac tcggagttag      240
ctggttctcc ccgaaatgcg tttaggcgca gcagtagcaa cacaaataga ggggtaaagc      300 actgttctt ttgtgggctt cgaaagttgt acctcaaagt ggcaaactct gaatactcta      360
tttagatatc tactagtgag accttggggg ataagctcct tggtcaaaag ggaaacagcc      420
cagatcacca gttaaggccc caaaatgaaa atgatagtga ctaaggacgt gagtatgtca      480
aaacctccag caggttagct tagaagcagc aatcctttca agagtgcgta atagctcact      540
g                                                                     541
```

```
<210> SEQ ID NO 17
<211> LENGTH: 573
<212> TYPE: DNA
<213> ORGANISM: Prototheca moriformis

<400> SEQUENCE: 17
tgttgaagaa tgagccggcg acttaaaata aatggcaggc taagagaatt aataactcga       60
aacctaagcg aaagcaagtc ttaatagggc gctaatttaa caaaacatta aataaaatct      120
aaagtcattt attttagacc cgaacctgag tgatctaacc atggtcagga tgaaacttgg      180
```

```
gtgacaccaa gtggaagtcc gaaccgaccg atgttgaaaa atcggcggat gaactgtggt      240
tagtggtgaa ataccagtcg aactcagagc tagctggttc tccccgaaat gcgttgaggc      300
gcagcaatat atctcgtcta tctaggggta aagcactgtt tcggtgcggg ctatgaaaat      360
ggtaccaaat cgtggcaaac tctgaatact agaaatgacg atatattagt gagactatgg      420
gggataagct ccatagtcga gagggaaaca gcccagacca ccagttaagg ccccaaaatg      480
ataatgaagt ggtaaaggag gtgaaaatgc aaatacaacc aggaggttgg cttagaagca      540
gccatccttt aaagagtgcg taatagctca ctg                                    573

<210> SEQ ID NO 18
<211> LENGTH: 573
<212> TYPE: DNA
<213> ORGANISM: Prototheca moriformis

<400> SEQUENCE: 18
tgttgaagaa tgagccggcg acttaaaata aatggcaggc taagagaatt aataactcga       60
aacctaagcg aaagcaagtc ttaatagggc gctaatttaa caaaacatta aataaaatct      120
aaagtcattt attttagacc cgaacctgag tgatctaacc atggtcagga tgaaacttgg      180
gtgacaccaa gtggaagtcc gaaccgaccg atgttgaaaa atcggcggat gaactgtggt      240
tagtggtgaa ataccagtcg aactcagagc tagctggttc tccccgaaat gcgttgaggc      300
gcagcaatat atctcgtcta tctaggggta aagcactgtt tcggtgcggg ctatgaaaat      360
ggtaccaaat cgtggcaaac tctgaatact agaaatgacg atatattagt gagactatgg      420
gggataagct ccatagtcga gagggaaaca gcccagacca ccagttaagg ccccaaaatg      480
ataatgaagt ggtaaaggag gtgaaaatgc aaatacaacc aggaggttgg cttagaagca      540
gccatccttt aaagagtgcg taatagctca ctg                                    573

<210> SEQ ID NO 19
<211> LENGTH: 565
<212> TYPE: DNA
<213> ORGANISM: Chlorella minutissima

<400> SEQUENCE: 19
tgttgaagaa tgagccggcg acttagaaaa agtggcgtgg ttaaggaaaa attccgaagc       60
cttagcgaaa gcgagtctga atagggcgat caaatatttt aatatttaca atttagtcat      120
tttttctaga cccgaacccg ggtgatctaa ccatgaccag gatgaaactt gggtgatacc      180
aagtgaaggt ccgaaccgac cgatgttgaa aaatcggcgg atgagttgtg gttagcggtg      240
aaataccagt cgaacccgga gctagctggt tctccccgaa atgcgttgag gcgcagcagt      300
acatctagtc tatctagggg taaagcactg tttcggtgcg gctgtgaaa cggtaccaa       360 atcgtggcaa actctgaata ctagaaatga cggtgtagta gtgagactgt ggggataag      420 ctccattgtc aagagggaaa cagcccagac caccagctaa ggccccaaaa tggtaatgta      480
gtgacaaagg aggtgaaaat gcaaacacaa ccaggaggtt ggcttagaag cagccatcct      540
ttaaagagtg cgtaatagct cactg                                            565

<210> SEQ ID NO 20
<211> LENGTH: 565
<212> TYPE: DNA
<213> ORGANISM: Chlorella sp.

<400> SEQUENCE: 20
```

| | |
|---|---|
| tgttgaagaa tgagccggcg acttagaaaa agtggcgtgg ttaaggaaaa attccgaagc | 60 |
| cttagcgaaa gcgagtctga atagggcgat caaatatttt aatatttaca atttagtcat | 120 |
| tttttctaga cccgaacccg ggtgatctaa ccatgaccag gatgaaactt gggtgatacc | 180 |
| aagtgaaggt ccgaaccgac cgatgttgaa aaatcggcgg atgagttgtg gttagcggtg | 240 |
| aaataccagt cgaacccgga gctagctggt tctccccgaa atgcgttgag cgcagcagt | 300 |
| acatctagtc tatctagggg taaagcactg tttcggtgcg ggctgtgaaa acggtaccaa | 360 |
| atcgtggcaa actctgaata ctagaaatga cggtgtagta gtgagactgt gggggataag | 420 |
| ctccattgtc aagagggaaa cagcccgac caccagctaa ggccccaaaa tggtaatgta | 480 |
| gtgacaaagg aggtgaaaat gcaaacacaa ccaggaggtt ggcttagaag cagccatcct | 540 |
| ttaaagagtg cgtaatagct cactg | 565 |

<210> SEQ ID NO 21
<211> LENGTH: 546
<212> TYPE: DNA
<213> ORGANISM: Chlorella sp.

<400> SEQUENCE: 21

| | |
|---|---|
| tgttgaagaa tgagccggcg acttagaaaa cgtggcaagg ttaaggacat gtatccggag | 60 |
| ccgaagcgaa agcaagtctg aatagggcgc ctaagtcatt ttttctagac ccgaacccgg | 120 |
| gtgatctaac catgaccagg atgaagcttg ggtgacacca agtgaaggtc cgaaccgacc | 180 |
| gatgttgaaa aatcggcgga tgagttgtgg ttagcggtga ataccagtc gaactcggag | 240 |
| ctagctggtt ctccccgaaa tgcgttgagg cgcagcggtt cataaggctg tctagggta | 300 |
| aagcactgtt tcggtgcggg ctgcgaaagc ggtaccaaat cgtggcaaac tctgaatact | 360 |
| agatatgcta tttatgagcc agtgagacgg tgggggataa gcttcatcgt cgagagggaa | 420 |
| acagcccaga tcactagcta aggcccctaa atgatcgtta agtgacaaag gaggtgagaa | 480 |
| tgcagaaaca accaggaggt tgcttagaa gcagccaccc tttaaagagt gcgtaatagc | 540 |
| tcactg | 546 |

<210> SEQ ID NO 22
<211> LENGTH: 550
<212> TYPE: DNA
<213> ORGANISM: Chlorella sorokiniana

<400> SEQUENCE: 22

| | |
|---|---|
| tgttgaagaa tgagccggcg acttatagga agtggcaggg ttaaggaaga atctccggag | 60 |
| cccaagcgaa agcgagtctg aaaagggcga tttggtcact tcttatggac ccgaacctgg | 120 |
| atgatctaat catggccaag ttgaagcatg ggtaacacta tgtcgaggac tgaacccacc | 180 |
| gatgttgaaa aatcggggga tgagctgtga ttagcggtga aattccaatc gaattcagag | 240 |
| ctagctggat ctccccgaaa tgcgttgagg cgcagcggcg acgatgtcct gtctaagggt | 300 |
| agagcgactg tttcggtgcg ggctgcgaaa gcggtaccaa gtcgtggcaa actccgaata | 360 |
| ttaggcaaag gattccgtga gccagtgaga ctgtggggga taagcttcat agtcaagagg | 420 |
| gaaacagccc agaccatcag ctaaggcccc taaatggctg ctaagtggaa aaggatgtga | 480 |
| gaatgctgaa acaaccagga ggttcgctta gaagcagcta ttccttgaaa gagtgcgtaa | 540 |
| tagctcactg | 550 |

<210> SEQ ID NO 23
<211> LENGTH: 548

```
<212> TYPE: DNA
<213> ORGANISM: Parachlorella beijerinkii

<400> SEQUENCE: 23
tgttgaagaa tgagccggcg acttagaaga agtggcttgg ttaaggataa ctatccggag      60
ccagagcgaa agcaagtctg aatagggcgc ttaaaggtca cttttttctag acccgaaccc     120 gggtgatcta accatgacca ggatgaagct tgggtaacac cacgtgaagg tccgaaccga     180
ccgatgttga aaaatcggcg gatgagttgt ggttagcggt gaaataccaa tcgaactcgg     240
agctagctgg ttctccccga aatgcgttga ggcgcagcgg tttatgaggc tgtctagggg     300
taaagcactg tttcggtgcg ggctgcgaaa gcggtaccaa atcgtggcaa actctgaata     360
ctagatatgc tattcatgag ccagtgagac ggtgggggat aagcttcatc gtcaagaggg     420
aaacagccca gatcaccagc taaggcccca aaatggtcgt taagtggcaa aggaggtgag     480
aatgctgaaa caaccaggag gtttgcttag aagcagccac cctttaaaga gtgcgtaata     540
gctcactg                                                             548

<210> SEQ ID NO 24
<211> LENGTH: 556
<212> TYPE: DNA
<213> ORGANISM: Chlorella luteoviridis

<400> SEQUENCE: 24
tgttgaagaa tgagccggcg acttataggg ggtggcgtgg ttaaggaagt aatccgaagc      60
caaagcgaaa gcaagttttc aatagagcga ttttgtcacc ccttatggac ccgaacccgg     120
gtgatctaac cttgaccagg atgaagcttg gtaacacca agtgaaggtc cgaactcatc     180
gatcttgaaa aatcgtggga tgagttgggg ttagttggtt aaatgctaat cgaactcgga     240
gctagctggt tctccccgaa atgtgttgag gcgcagcgat taacgaaata ttttgtacgg     300
tttaggggta agcactgtt tcggtgcggg ctgcgaaagc ggtaccaaat cgtggcaaac     360
tctgaatact aagcctgtat accgttagtc agtgagagta tagggataa gctctatact     420 caagagggaa acagcccaga tcaccagcta aggccccaaa atgacagcta agtggcaaag     480
gaggtgaaag tgcagaaaca accaggaggt tcgcttagaa gcagcaaccc tttaaagagt     540
gcgtaatagc tcactg                                                   556

<210> SEQ ID NO 25
<211> LENGTH: 548
<212> TYPE: DNA
<213> ORGANISM: Chlorella vulgaris

<400> SEQUENCE: 25
tgttgaagaa tgagccggcg acttagaaga agtggcttgg ttaaggataa ctatccggag      60
ccagagcgaa agcaagtctg aatagggcgc ttaaaggtca cttttttctag acccgaaccc     120 gggtgatcta accatgacca ggatgaagct tgggtaacac cacgtgaagg tccgaaccga     180
ccgatgttga aaaatcggcg gatgagttgt ggttagcggt gaaataccaa tcgaactcgg     240
agctagctgg ttctccccga aatgcgttga ggcgcagcgg tttatgaggc tgtctagggg     300
taaagcactg tttcggtgcg ggctgcgaaa gcggtaccaa atcgtggcaa actctgaata     360
ctagatatgc tattcatgag ccagtgagac ggtgggggat aagcttcatc gtcaagaggg     420
aaacagccca gatcaccagc taaggcccca aaatggtcgt taagtggcaa aggaggtgag     480
aatgctgaaa caaccaggag gtttgcttag aagcagccac cctttaaaga gtgcgtaata     540
```

```
gctcactg                                                              548

<210> SEQ ID NO 26
<211> LENGTH: 565
<212> TYPE: DNA
<213> ORGANISM: Chlorella reisiglii

<400> SEQUENCE: 26
tgttgaagaa tgagccggcg acttagaaaa agtggcgtgg ttaaggaaaa attccgaagc      60
cttagcgaaa gcgagtctga atagggcgat caaatatttt aatatttaca atttagtcat     120
tttttctaga cccgaacccg ggtgatctaa ccatgaccag gatgaaactt gggtgatacc     180
aagtgaaggt ccgaaccgac cgatgttgaa aaatcggcgg atgagttgtg gttagcggtg     240
aaataccagt cgaacccgga gctagctggt tctccccgaa atgcgttgag gcgcagcagt     300
acatctagtc tatctagggg taaagcactg tttcggtgcg ggctgtgaaa acggtaccaa     360
atcgtggcaa actctgaata ctagaaatga cggtgtagta gtgagactgt ggggataag     420 ctccattgtc aagagggaaa cagcccagac caccagctaa ggccccaaaa tggtaatgta     480
gtgacaaagg aggtgaaaat gcaaacacaa ccaggaggtt ggcttagaag cagccatcct     540
ttaaagagtg cgtaatagct cactg                                           565

<210> SEQ ID NO 27
<211> LENGTH: 573
<212> TYPE: DNA
<213> ORGANISM: Chlorella ellipsoidea

<400> SEQUENCE: 27
tgttgaagaa tgagccggcg acttataggg ggtggcttgg ttaaggacta caatccgaag      60
cccaagcgaa agcaagtttg aagtgtacac acattgtgtg tctagagcga ttttgtcact     120
ccttatggac ccgaacccgg gtgatctatt catggccagg atgaagcttg ggtaacacca     180
agtgaaggtc cgaactcatc gatgttgaaa aatcgtggga tgagttgtga ataggggtga     240
aatgccaatc gaactcggag ctagctggtt ctccccgaaa tgtgttgagg cgcagcgatt     300
cacgatctaa agtacggttt aggggtaaag cactgttttcg gtgcgggctg ttaacgcggt     360
accaaatcgt ggcaaactaa gaatactaaa cttgtatgcc gtgaatcagt gagactaaga     420
gggataagct tcttagtcaa gagggaaaca gcccagatca ccagctaagg ccccaaaatg     480
acagctaagt ggcaaaggag gtgagagtgc agaaacaacc aggaggtttg cttagaagca     540
gccatccttt aaagagtgcg taatagctca ctg                                  573

<210> SEQ ID NO 28
<211> LENGTH: 573
<212> TYPE: DNA
<213> ORGANISM: Chlorella saccharophila

<400> SEQUENCE: 28
tgttgaagaa tgagccggcg acttataggg ggtggcttgg ttaaggacta caatccgaag      60
cccaagcgaa agcaagtttg aagtgtacac acgttgtgtg tctagagcga ttttgtcact     120
ccttatggac ccgaacccgg gtgatctatt catggccagg atgaagcttg ggtaacacca     180
agtgaaggtc cgaactcatc gatgttgaaa aatcgtggga tgagttgtga ataggggtga     240
aatgccaatc gaactcggag ctagctggtt ctccccgaaa tgtgttgagg cgcagcgatt     300
cacgatctaa agtacggttt aggggtaaag cactgttttcg gtgcgggctg ttaacgcggt     360
accaaatcgt ggcaaactaa gaatactaaa cttgtatgcc gtgaatcagt gagactaaga     420
```

```
gggataagct tcttagtcaa gagggaaaca gcccagatca ccagctaagg ccccaaaatg      480
acagctaagt ggcaaaggag gtgagagtgc agaaacaacc aggaggtttg cttagaagca      540
gccatccttt aaagagtgcg taatagctca ctg                                   573

<210> SEQ ID NO 29
<211> LENGTH: 573
<212> TYPE: DNA
<213> ORGANISM: Chlorella saccharophila

<400> SEQUENCE: 29
tgttgaagaa tgagccggcg acttataggg ggtggcttgg ttaaggacta caatccgaag       60
cccaagcgaa agcaagtttg aagtgtacac acattgtgtg tctagagcga ttttgtcact      120
ccttatggac ccgaacccgg gtgatctatt catggccagg atgaagcttg ggtaacacca      180
agtgaaggtc cgaactcatc gatgttgaaa aatcgtggga tgagttgtga atagggtga      240 aatgccaatc gaactcggag ctagctggtt ctccccgaaa tgtgttgagg cgcagcgatt      300
cacgatctaa agtacggttt aggggtaaag cactgtttcg gtgcgggctg ttaacgcggt      360
accaaatcgt ggcaaactaa gaatactaaa cttgtatgcc gtgaatcagt gagactaaga      420
gggataagct tcttagtcaa gagggaaaca gcccagatca ccagctaagg ccccaaaatg      480
acagctaagt ggcaaaggag gtgagagtgc agaaacaacc aggaggtttg cttagaagca      540
gccatccttt aaagagtgcg taatagctca ctg                                   573
```

MODIFIED LIPIDS PRODUCED FROM OIL-BEARING MICROBIAL BIOMASS AND OILS

CROSS-REFERENCE TO RELATED APPLICATIONS

This application is a continuation of U.S. application Ser. No. 13/601,928, filed Aug. 31, 2012, now U.S. Pat. No. 8,450,083, which is a continuation of U.S. application Ser. No. 13/366,198, filed Feb. 3, 2012, now U.S. Pat. No. 8,278,261, which is a divisional of U.S. application Ser. No. 12/499,033, filed Jul. 7, 2009, now US Pat. No. 8,119,583, which is a continuation of international application Ser. No. PCT/US2009/040123, filed Apr. 9, 2009, which claims the benefit under 35 U.S.C. 119(e) of U.S. Provisional Patent Application No. 61/043,620, filed Apr 9, 2008 and U.S. Provisional Patent Application No. 61/074,610, filed Jun. 20, 2008. Each of these applications is incorporated herein by reference in its entirety for all purposes.

REFERENCE TO A SEQUENCE LISTING

This application includes an electronic sequence listing in a file named "433106-Sequence.txt", created on May 7, 2013 and containing 24,025 bytes, which is hereby incorporated by reference in its entirety for all purposes.

FIELD OF THE INVENTION

The invention resides in the fields of genetic engineering, aquaculture, and the chemical modification of lipid-containing microbial biomass.

BACKGROUND OF THE INVENTION

Increased demand for energy by the global economy has placed increasing pressure on the cost of fossil fuels. This, along with increasing interest in reducing air pollution, has spurred the development of domestic energy supplies and triggered the development of non-petroleum fuels for internal combustion engines. For compression ignition (diesel) engines, it has been shown that the simple alcohol esters of fatty acids (biodiesel) are acceptable as an alternative diesel fuel. Biodiesel has a higher oxygen content than diesel derived from fossil fuels, and therefore reduces emissions of particulate matter, hydrocarbons, and carbon monoxide, while also reducing sulfur emissions due to a low sulfur content (Sheehan, J., et al., Life Cycle Inventory of Biodiesel and Petroleum Diesel for Use in an Urban Bus, National Renewable Energy Laboratory, Report NREL/SR-580-24089, Golden, Colo. (1998); Graboski, M. S., and R. L. McCormick, Prog. Energy Combust. Sci., 24:125-164 (1998)).

Initial efforts at the production, testing, and use of biodiesel employed refined edible vegetable oils (expelled or recovered by solvent extraction of oilseeds) and animal fats (e.g., beef tallow) as feedstocks for fuel synthesis (see, e.g., Krawczyk, T., INFORM, 7: 800-815 (1996); and Peterson, C. L., et al., Applied Engineering in Agriculture, 13: 71-79 (1997). Further refinement of the methods has enabled production of fatty acid methyl esters (FAME) from cheaper, less highly refined lipid feedstocks such as spent restaurant grease and soybean soapstock (see, e.g., Mittelbach, M., and P. Tritthart, J. Am Oil Chem. Soc., 65(7):1185-1187 (1988); Graboski, M. S., et al., The Effect of Biodiesel Composition on Engine Emissions from a DDC Series 60 Diesel Engine, Final Report to USDOE/National Renewable Energy Laboratory, Contract No. ACG-8-17106-02 (2000).

For decades, photoautotrophic growth of algae has been proposed as an attractive method of manufacturing biodiesel from algae; see A Look Back at the U.S. Department of Energy's Aquatic Species Program: Biodiesel from Algae, NREL/TP-580-24190, John Sheehan, Terri Dunahay, John Benemann and Paul Roessler (1998). Many researchers believe that because sunlight is a "free" resource, photoautotrophic growth of algae is the most desirable method of culturing microalgae as a feedstock for biofuel production (see, for example Chisti, Biotechnol Adv. 2007 May-Jun; 25(3):294-306: "heterotrophic production is not as efficient as using photosynthetic microalgae . . . because the renewable organic carbon sources required for growing heterotrophic microorganisms are produced ultimately by photosynthesis, usually in crop plants"). Other research has not only assumed that photoautotrophic growth is the best way to grow microalgae for biofuels, but also that there is no need to transesterify any material from microalgal biomass before introduction into a diesel engine (see Screagg et al., Enzyme and Microbial Technology, Vol. 33:7, 2003, Pages 884-889).

Photosynthetic growth methods have been the focus of considerable research over the past several decades, spurred in part by the U.S. Department of Energy's Office of Fuels Development, which funded a program to develop renewable transportation fuels from algae during the period spanning 1978 to 1996. The principal production design was centered around a series of shallow outdoor sunlight-driven ponds designed as "raceways" in which algae, water and nutrients were circulated around a circular pond in proximity to a source of waste $CO_2$ (e.g., a fossil fuel powered electricity generating plant).

Transesterification of extracted/refined plant oils is conventionally performed by reacting a triacylglycerol ("TAG") with a lower-alkyl alcohol (e.g., methanol) in the presence of a catalyst (e.g., a strong acid or strong base) to yield fatty acid alkyl esters (e.g., fatty acid methyl esters or "FAME") and glycerol.

As described above, traditional biodiesel production has relied on extracted and/or refined oils (expelled or recovered by solvent extraction of oilseeds) as a feedstock for the transesterification process. Oil sources, including soy, palm, coconut, and canola, are commonly used, and extraction is performed by drying the plant material and pretreating the material (e.g., by flaking) to facilitate penetration of the plant structure by a solvent, such as hexane. Extraction of these oils for use as a starting material contributes significantly to the cost of traditional biodiesel production.

Similar to the solvent extraction processes utilized to extract oils from dried plant materials, solvent extraction of oils from microbial biomass is carried out in the presence of an organic solvent. Solvent extraction in this context requires the use of a solvent that is essentially immiscible in water, such as hexane, to produce a solvent phase, in which the oil is soluble, and an aqueous phase, which retains the largely non-lipid portion of the biomass. Unfortunately, in an industrial scale production, the volume of volatile, potentially carcinogenic, and flammable organic solvent that must be used for efficient extraction creates hazardous operating conditions having both environmental and worker safety aspects. Moreover, the solvent extraction process generates a substantial solvent waste stream that requires proper disposal, thereby increasing overall production costs.

Alternatively, "solventless" extraction processes have been reported; these employ an aqueous solvent comprising no more than about 5% organic solvent for extracting lipids from microorganisms for use as a feedstock in a transesterification process for the production of biodiesel. Briefly, the "solventless" extraction process includes contacting a lysed cell mixture with an aqueous solvent containing no more than about 5% organic solvent (e.g., hexane) to produce a phase separated mixture. The mixture comprises a heavier aqueous layer and a lighter layer comprising emulsified lipids. The extraction process is repeatedly performed on the lighter lipid layer until a non-emulsified lipid layer is obtained. Unfortunately, the repeated isolation and washing of the lipid layer makes the "solventless" process particularly laborious.

There remains a need for cheaper, more efficient methods for extracting valuable biomolecules derived from lipids produced by microorganisms. The present invention meets this need.

SUMMARY OF THE INVENTION

In a first aspect, the present invention relates to the discovery that direct chemical modification of lipid-containing microbial biomass can dramatically increase the efficiency and decrease the cost of obtaining valuable materials derived from those lipids. Thus, in a first embodiment, then invention provides a method of chemically modifying lipid-containing microbial biomass including the steps of culturing a population of microbes, harvesting microbial biomass that contains at least 5% lipid by dry cell weight (DCW), and subjecting the biomass to a chemical reaction that covalently modifies at least 1% of the lipid. In some embodiments, the method further includes separating the covalently modified lipid from other components of the biomass.

In various embodiments, the ratio of the covalently modified lipid to the biomass from which it is separated is between 10% lipid and 90% biomass and 90% biomass and 10% lipid by dry weight. In some embodiments, the step of separating the lipid from other components of the biomass includes a phase separation step in which the covalently modified lipids form a lighter non-aqueous phase and components of the biomass form one or more heavier phases. In some embodiments, the biomass is subjected to the chemical reaction without a step of prior enrichment that increases the ratio of the lipids to the non-lipid material by more than 50% by weight. In other embodiments, the biomass is subjected to the chemical reaction with a step of prior enrichment that increases the ratio of the lipids to the dry weight of the microbes. In some embodiments, the harvested biomass is not subjected to any treatment other than the removal of water and/or lysis of the cells before the chemical reaction. In some embodiments, the biomass subjected to the chemical reaction contains components other than water in the same relative proportions as the cell culture. In some embodiments, the lipid content of the biomass is less than 90% of the biomass subjected to the chemical reaction.

In one embodiment, chemical modification of the lipid-containing microbial biomass comprises transesterifying the biomass to generate a lipophilic phase containing fatty acid alkyl esters and a hydrophilic phase containing cell material and glycerol. In some embodiments, the method further comprises removing water from the biomass prior to subjecting the biomass to the transesterifying chemical reaction. In other embodiments, the method further comprises removing water from the biomass after the disrupting of the biomass. In some embodiments, removing water from the biomass is performed using a method selected from the group consisting of lyophilization, drum drying, and oven drying the biomass.

In some embodiments, in which the chemical modification of the lipid-containing microbial biomass comprises transesterifying the biomass, the method further comprises disrupting the biomass prior to transesterifying the biomass. In some embodiments, water is removed from the biomass prior to the disrupting of the biomass. In some embodiments, disrupting the biomass comprises heating the biomass to generate a lysate. In other embodiments, disrupting the biomass comprises contacting the biomass with an acid or base sufficient to generate a lysate. In still other embodiments, disrupting the biomass comprises contacting the biomass with one or more enzymes to generate a lysate. In some embodiments, the biomass is contacted with at least one protease and at least one polysaccharide-degrading enzyme. In some embodiments, disrupting the biomass comprises mechanically lysing the population of microbes to generate a lysate. In other embodiments, disrupting the biomass comprises subjecting the biomass to osmotic shock to generate a lysate. In still other embodiments, disrupting the biomass comprises infecting the population of microbes with a lytic virus to generate a lysate. In other embodiments, disrupting the biomass comprises inducing the expression of a lytic gene within the population of microbes to promote autolysis and generation of a lysate.

In some embodiments of the chemical modification method in which the chemical reaction comprises transesterification, the fatty acid alkyl esters are fatty acid methyl esters or fatty acid ethyl esters. In some embodiments, transesterifying the biomass comprises contacting the biomass with an alcohol and a base. In some embodiments, the alcohol is selected from methanol, ethanol, propanol, isopropanol, and mixtures thereof. In some embodiments, the base is selected from NaOH, KOH, and mixtures thereof. In one embodiment, the alcohol is methanol and the base is NaOH. In some embodiments, transesterifying the biomass comprises contacting the biomass with an alcohol and a lipase. In some embodiments, the lipase is expressed from an exogenous lipase gene within the population of microbes. In some embodiments, expression of the exogenous lipase gene is induced by contacting the biomass with a stimulus to activate an inducible promoter controlling expression of the exogenous lipase gene.

In various embodiments, the amount of calcium and magnesium, combined, by weight in the lipophilic phase is no greater than 5 parts per million. In some embodiments, the amount of phosphorous in the lipophilic phase is no greater than 0.001%, by mass. In some embodiments, the amount of sulfur in the lipophilic phase is no greater than 15 parts per million. In some embodiments, the amount of potassium and sodium, combined, by weight in the lipophilic phase is no greater than 5 parts per million. In some embodiments, the total carotenoid content of the lipophilic phase is no greater than 100 micrograms of carotenoid per gram. In some embodiments, the total chlorophyll content in the lipophilic phase is no greater than 0.1 mg/kg.

In some embodiments, subjecting the biomass to a chemical reaction includes contacting the biomass with an enzyme to catalyze the chemical reaction. In some embodiments, the enzyme is a lipase. In one embodiment, the method further comprises separating a lipophilic phase containing the covalently modified lipids from hydrophilic cell material of the biomass.

In various embodiments of the present invention, the microbes and the resulting microbial biomass are selected from the group consisting of bacteria, cyanobacteria, eukaryotic microalgae, oleaginous yeast, and fungi. In some embodiments, the microbes are selected from the group consisting of the eukaryotic microalgae listed in Table 1. In some embodiments, the microbes are a species of the genus *Chlorella*, and in various embodiments, the species is selected from the group consisting of *Chlorella fusca, Chlorella protothecoides, Chlorella pyrenoidosa, Chlorella kessleri, Chlorella vulgaris, Chlorella saccharophila, Chlorella sorokiniana* and *Chlorella ellipsoidea*. In one embodiment, the species is *Chlorella protothecoides*. In some embodiments, the microbes is a species of the genus *Prototheca*, or the species is selected from the group consisting of *Prototheca wickerhamii, Prototheca stagnora, Prototheca portoricensis, Prototheca moriformis,* and *Prototheca zopfii*. In some embodiments, the microbes are selected from the group consisting of the oleaginous yeast listed in Table 2, and in other embodiments, the microbes are selected from the group consisting of the fungi listed in Table 3. In some embodiments, the microbial biomass comprises a mixture of biomass from two distinct strains or species of microbes that have been separately cultured. In one embodiment, at least two of the distinct strains or species of microbes have different glycerolipid profiles. In some embodiments, the species has a high degree of taxonomic similarity to members of the *Chlorella* or *Prototheca* genera, such as at least 95% nucleotide identity at the 23S rRNA level, as disclosed in the examples.

In various embodiments of the present invention, the harvested biomass comprises a lipid content of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% by DCW. In some embodiments, at least 20% of the lipid is C18. In some embodiments, at least 30% of the lipid is C18. In some embodiments, at least 40% of the lipid is C18. In some embodiments, at least 50% of the lipid is C18. In some embodiments, at least 50% of the lipid is C16 or longer chain lengths. In some embodiments, at least 10% of the lipid is C14 or shorter chain lengths. In some embodiments, at least 20% of the lipid is C14 or shorter chain lengths.

In some embodiments of the present invention, the population of microbes expresses an exogenous sucrose utilization gene. In some embodiments, the gene is a sucrose invertase. In some embodiments, the population of microbes expresses an exogenous lipid pathway enzyme. In some embodiments, the lipid pathway enzyme comprises an acyl-ACP thioesterase. In some embodiments, the population of microbes further expresses an exogenous "naturally co-expressed" acyl carrier protein that is co-expressed with the acyl-ACP thioesterase. In some embodiments, the lipid pathway enzyme has a specificity for acting on a substrate having a specified number of carbon atoms in a chain.

In some embodiments, chemical modification of the lipid-containing microbial biomass comprises hydrogenating the biomass to saturate at least a subset of unsaturated bonds in the lipid. In some embodiments, chemical modification of the lipid-containing microbial biomass comprises interesterifying the biomass to generate a mixture of glycerolipids having a modified arrangement of fatty acid constituents relative to the glycerolipids in the harvested biomass. In some embodiments, chemical modification of the lipid-containing microbial biomass comprises hydroxylating the biomass to generate hydroxylated lipids. In some embodiments, at least a portion of the hydroxylated lipids are esterified to generate estolides. In some embodiments, chemical modification of the lipid-containing microbial biomass comprises hydrolyzing the biomass to generate free fatty acids from the lipid. In some embodiments, the free fatty acids are subjected to further chemical modification. In one embodiment, chemical modification of the lipid-containing microbial biomass comprises deoxygenation at elevated temperature in the presence of hydrogen and a catalyst, isomerization in the presence of hydrogen and a catalyst, and removal of gases and naphtha compounds.

In another embodiment, chemical modification of the lipid-containing microbial biomass comprises saponifying the biomass to generate fatty acid salts from the lipid. In one embodiment, the biomass is derived from a microalgae of the genus *Prototheca*. In some embodiments, saponifying the biomass comprises contacting the biomass with a base sufficient to convert at least a portion of the glycerolipid and/or fatty acid ester components of the lipid to fatty acid salts. In some embodiments, the base is an alkali metal hydroxide, such as NaOH or KOH. In some embodiments, the method further comprises contacting the biomass with a salt to precipitate the fatty acid salts from solution. In some embodiments, the salt comprises a water-soluble alkali metal halide, such as NaCl or KCl.

In some embodiments, two distinct strains or species of microbes are separately cultured, and biomass from both cultures is mixed prior to subjecting the biomass to a chemical reaction that modifies at least 1% of the lipid. In some embodiments, at least two of the distinct strains of microbes have different glycerolipid profiles.

In one aspect, the present invention is directed to a saponification method for making a soap. In some embodiments, the method includes culturing a population of microbes, harvesting microbial biomass that contains at least 5% lipid by DCW, including glycerolipids or fatty acid esters, and subjecting the biomass to an alkaline hydrolysis reaction to produce a soap from the chemical conversion of at least a portion of the glycerolipids or fatty acid esters to fatty acid salts. In some embodiments, the alkaline hydrolysis reaction includes contacting the biomass with a base and optionally heating the biomass. In some embodiments, the base is an alkali metal hydroxide such as NaOH or KOH. In some embodiments, less than 100% of the glycerolipids and fatty acid esters in the biomass are converted to fatty acid salts. In some embodiments, less than 1% of the glycerolipids and fatty acid esters in the biomass are converted to fatty acid salts.

In some embodiments of the saponification method, the method further comprises substantially separating the fatty acid salts from other components of the biomass. Some methods of the invention further comprise boiling the separated fatty acid salts in water and re-precipitating the fatty acid salts by introducing a salt into the aqueous solution to produce a purified soap. In some embodiments, the salt is a water-soluble alkali metal halide, such as NaCl or KCl.

Some saponification methods of the invention further comprise combining the purified soap or saponified oil composition with one or more additives selected from the group consisting of essential oils, fragrance oils, flavor oils, botanicals, extracts, $CO_2$ extracts, clays, colorants, titanium dioxide, micas, tinting herbs, glitters, exfoliants, fruit seeds, fibers, grain powders, nut meals, seed meals, oil beads, wax beads, herbs, hydrosols, vitamins, milk powders, preservatives, antioxidants, tocopherols, salts, sugars, vegetable oils, waxes, glycerin, sea vegetables, nutritive oils, moisturizing oils, vegetable butters, propylene glycol, parabens, honey, bees wax, aloe, polysorbate, cornstarch, cocoa powder, coral powder, humectants, gums, emulsifying agents, and thickeners. In one embodiment, the mixture is packaged as a cosmetics product. In another embodiment, the cosmetic product comprises a facial cleanser.

In some embodiments of the saponification method, the ratio of fatty acid salts to the biomass from which they are separated is between 10% fatty acid salts to 90% biomass and 90% fatty acid salts to 10% biomass by dry weight. In some methods, the biomass is subjected to the alkaline hydrolysis reaction without a step of prior enrichment that increases a ratio of lipid to non-lipid material in the biomass by more than 50% by weight. In some methods, the harvested biomass is not subjected to treatments other than lysis before the alkaline hydrolysis reaction. In other methods, the biomass is subjected to the alkaline hydrolysis reaction with a step of prior enrichment that increases the ratio of lipid to non-lipid material in the biomass as compared to the ratio at harvesting. In some embodiments, the biomass subjected to the alkaline hydrolysis reaction contains components other than water in the same relative proportions as the biomass at harvesting. In some embodiments, lipid comprises no more than 90% of the biomass subjected to the alkaline hydrolysis reaction.

In some embodiments of the saponification method, the harvested biomass comprises a lipid content of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% by DCW. In some embodiments, the lipid comprises at least 50%, at least 60%, at least 70%, at least 80%, at least 90%, or at least 95% saturated fatty acid constituents.

In some embodiments, the saponification method further comprises disrupting the biomass prior to subjecting the biomass to the alkaline hydrolysis reaction. In some embodiments, disrupting the biomass comprises mechanically lysing the population of microbes to generate a lysate. In some embodiments, the oil is extracted from the biomass before saponification. In some embodiments, the extracted oil is substantially free of color or pigments.

In another aspect, the present invention is directed to a composition comprising a lighter phase containing fatty acid alkyl esters, and at least one heavier phase containing microbial biomass.

In various embodiments of the composition, at least 20% of the fatty acid alkyl esters are C18. In some embodiments, at least 30% of the fatty acid alkyl esters are C18. In some embodiments, at least 40% of the fatty acid alkyl esters are C18. In some embodiments, at least 50% of the fatty acid alkyl esters are C18. In some embodiments, at least 50% of the fatty acid alkyl esters are C16 or longer chain lengths. In some embodiments, at least 10% of the fatty acid alkyl esters are C14 or shorter chain lengths. In some embodiments, at least 20% of the fatty acid alkyl esters are C14 or shorter chain lengths.

In another aspect, the present invention is directed to a composition comprising a lighter phase containing completely saturated lipids and at least one heavier phase containing microbial biomass. In another aspect, the present invention is directed to a composition comprising a lighter phase containing lipids and at least one heavier phase containing microbial biomass from more than one species or strain. In another aspect, the present invention is directed to a composition comprising a lighter phase containing hydroxylated lipids, and at least one heavier phase containing microbial biomass. In another aspect, the present invention is directed to a composition comprising a lighter phase containing free fatty acids and at least one heavier phase containing microbial biomass.

In another aspect, the present invention is directed to a composition comprising saponified oil derived from the alkaline hydrolysis of biomass produced by culturing a population of microbes. In some embodiments, the composition further comprises at least one and optionally more than one oil selected from the group of oils consisting of soy, rapeseed, canola, palm, palm kernel, coconut, corn, waste vegetable, Chinese tallow, olive, sunflower, cotton seed, chicken fat, beef tallow, porcine tallow, microalgae, macroalgae, *Cuphea*, flax, peanut, choice white grease, lard, *Camelina sativa*, mustard seed, cashew nut, oats, lupine, kenaf, *calendula*, hemp, coffee, linseed (flax), hazelnut, *euphorbia*, pumpkin seed, coriander, camellia, sesame, safflower, rice, tung oil tree, cocoa, copra, opium poppy, castor beans, pecan, jojoba, jatropha, *macadamia*, Brazil nuts, avocado, a fossil oil or a distillate fraction thereof.

In various embodiments, the saponified oil composition can be a solid (including a powder), or a liquid. In some embodiments, the composition further comprises carotenoids derived from the biomass, and/or unsaponified glycerolipids derived from the biomass, and/or polysaccharides derived from the biomass. In some embodiments, the saponified oil comprises at least 50% of the composition's total mass. In some embodiments, the saponified oil comprises at least 75% of the composition's total mass. In other embodiments, the saponified oil comprises less than 50% of the composition's total mass. In other embodiments, the saponified oil comprises less than 25% of the composition's total mass. In some embodiments, components derived from the biomass constitute at least 50% of the composition's total mass. In some embodiments, components derived from the biomass constitute no more than 50% of the composition's total mass.

In another aspect, the present invention is directed to a kit comprising a saponified oil composition as described herein and an oral supplement. In some embodiments, the oral supplement comprises a vitamin or an herb.

BRIEF DESCRIPTION OF THE DRAWINGS

FIG. 11(*b*) shows lipid as a percent of DCW of *Navicula pelliculosa* when cultured in the presence of various types of glycerol and in the presence of combinations of glycerol and glucose.

FIG. 12(*b*) shows DCW per liter of *Scenedesmus armatus* when cultured in the presence of various types of glycerol and in the presence of a combination of biodiesel byproduct glycerol and glucose.

DETAILED DESCRIPTION OF THE INVENTION

I. Definitions

Figure 1:
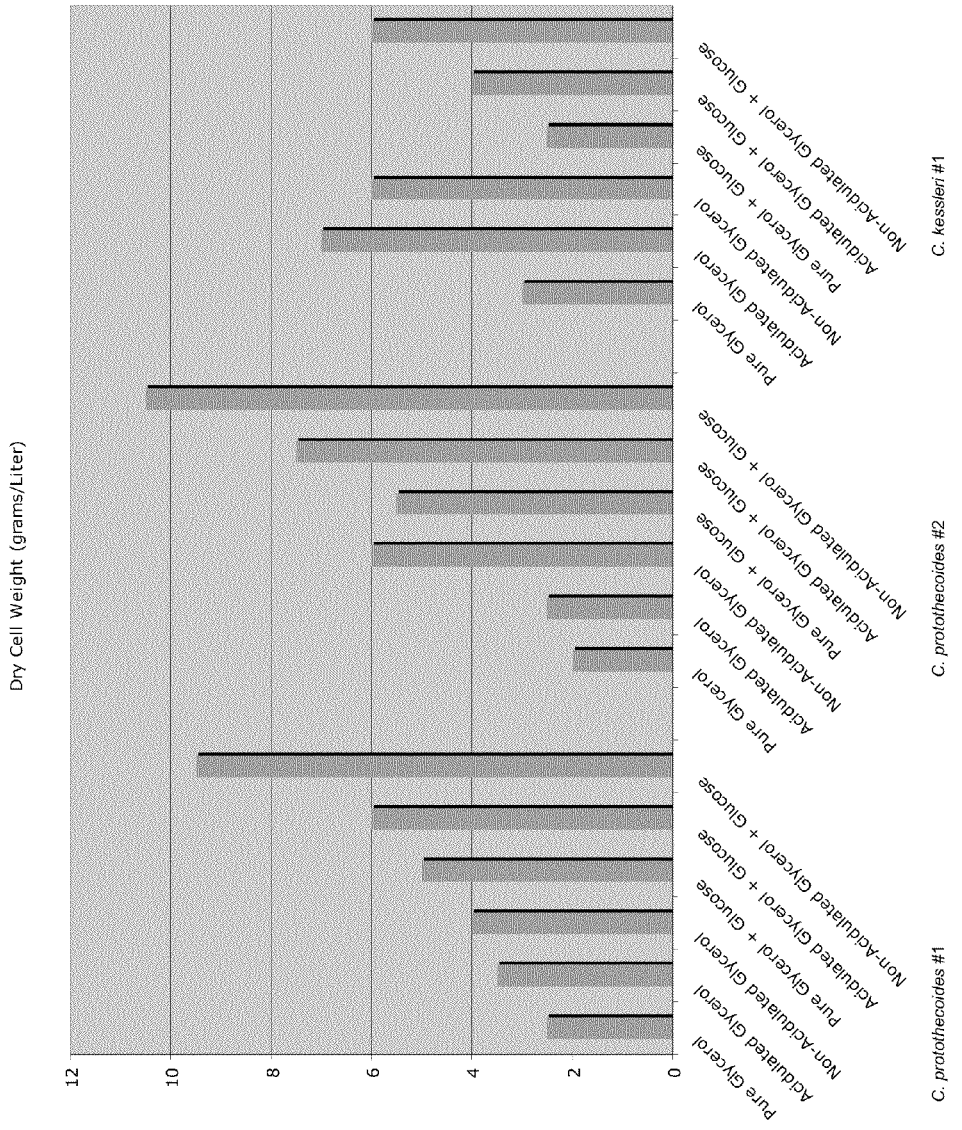
FIG. 1 shows DCW per liter of multiple species and strains of *Chlorella* when cultured in the presence of various types of glycerol with and without additional glucose.

Definitions of certain terms used herein are provided below for the convenience of the reader.

"Active in microalgae," with reference to a nucleic acid, refers to a nucleic acid that is functional in microalgae. For example, a promoter that has been used to drive an antibiotic resistance gene to impart antibiotic resistance to a transgenic microalgae is active in microalgae. Examples of promoters active in microalgae include promoters endogenous to certain algae species and promoters found in plant viruses.

"Acyl carrier protein" or "ACP" is a protein that binds a growing acyl chain during fatty acid synthesis as a thiol ester at the distal thiol of the 4'-phosphopantetheine moiety and comprises a component of the fatty acid synthase complex. The phrase "naturally co-expressed" with reference to an acyl carrier protein in conjunction with a fatty acyl-ACP thioesterase means that the ACP and the thioesterase are co-expressed naturally (in nature) in a tissue or organism from which they are derived, e.g., because the genes encoding the two enzymes are under the control of a common regulatory sequence or because they are expressed in response to the same stimulus.

"Acyl-CoA molecule" or "acyl-CoA" is a molecule comprising an acyl moiety covalently attached to coenzyme A through a thiol ester linkage at the distal thiol of the 4'-phosphopantetheine moiety of coenzyme A.

"Axenic" means a culture of an organism that is free from contamination by other living organisms.

"Biodiesel" refers to a fatty acid ester produced from the transesterification of lipid. The ester can be a methyl ester, ethyl ester, or other ester depending on the components of the transesterification reaction.

"Biomass" refers to material produced by growth and/or propagation of cells. Biomass may contain cells and/or intracellular contents as well as extracellular material. Extracellular material includes, but is not limited to, compounds secreted by a cell.

"Bioreactor" means an enclosure or partial enclosure in which cells, e.g., microorganisms, are cultured, optionally in suspension.

"Catalyst" refers to an agent, such as a molecule or macromolecular complex, capable of facilitating or promoting a chemical reaction of a reactant to a product without becoming a part of the product. A catalyst thus increases the rate of a reaction, after which, the catalyst may act on another reactant to form the product. A catalyst generally lowers the overall activation energy required for the reaction such that the reaction proceeds more quickly or at a lower temperature and/or a reaction equilibrium may be more quickly attained. Examples of catalysts include enzymes, which are biological catalysts, and heat, which is a non-biological catalyst.

"Cellulosic material" means the products of digestion of cellulose, such as glucose, xylose, arabinose, disaccharides, oligosaccharides, lignin, furfurals and other molecules.

"Co-culture", and variants thereof such as "co-cultivate", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or propagation of one cell type, or a subset of the cell types, of the two or more cell types while maintaining cellular growth for the remainder.

"Cofactor" is used herein to refer to any molecule, other than the substrate, that is required for an enzyme to carry out its enzymatic activity.

"Complementary DNA" ("cDNA") is a DNA copy of an mRNA, which can be obtained, for example, by reverse transcription of messenger RNA (mRNA) or amplification (e.g., via polymerase chain reaction ("PCR")).

"Cultivated" and variants thereof refer to the intentional fostering of growth (increases in cell size, cellular contents, and/or cellular activity) and/or propagation (increases in cell numbers via mitosis) of one or more cells by use of appropriate culture conditions. The combination of both growth and propagation may be termed proliferation. The one or more cells may be those of a microorganism, such as microalgae. Examples of appropriate conditions include the use of a defined medium (with known characteristics such as pH, ionic strength, and carbon source), specified temperature, oxygen tension, and carbon dioxide levels in a bioreactor. The term does not refer to the growth or propagation of microorganisms in nature or otherwise without direct human intervention, such as natural growth of an organism that ultimately becomes fossilized to produce geological crude oil.

"Exogenous gene" refers to a nucleic acid transformed (introduced) into a cell. A transformed cell may be referred to as a recombinant cell, into which additional exogenous gene(s) may be introduced. The exogenous gene may be from a different species (and so heterologous) or from the same species (and so homologous) relative to the cell being transformed. In the case of a homologous gene, the introduced gene occupies a different location in the genome of the cell relative to the endogenous copy of the gene or is under different regulatory controls of the endogenous gene it replaces or both. The exogenous gene may be present in more than one copy in the cell. The exogenous gene may be maintained in a cell as an insertion into the genome or as an episomal molecule.

"Exogenously provided" describes a molecule provided to the culture media of a cell culture.

"Extracted" refers to oil or lipid separated from aqueous biomass with or without the use of solvents.

"Fatty acyl-ACP thioesterase" is an enzyme that catalyzes the cleavage of a fatty acid from an acyl carrier protein (ACP) during lipid synthesis.

"Fixed carbon source" means molecule(s) containing carbon, typically organic molecules, that are present at ambient temperature and pressure in solid or liquid form.

"Fungus," as used herein, means heterotrophic organisms characterized by a chitinous cell wall from the kingdom of fungi.

"Heteroatom" means an atom other than carbon or hydrogen. Examples of heteroatoms are magnesium, calcium, potassium, sodium, sulfur, phosphorus, iron, and copper.

"Homogenate" means biomass that has been physically disrupted.

"Hydrophobic fraction" refers to the portion, or fraction, of a material that is more soluble in a hydrophobic phase than in an aqueous phase. A hydrophobic fraction is substantially immiscible with water and usually non-polar.

"Increased lipid yield" refers to an increase in the lipid productivity of a microbial culture, which can be achieved by, for example, increasing dry weight of cells per liter of culture, increasing the percentage of cells that constitute lipid, or increasing the overall amount of lipid per liter of culture volume per unit time.

"Inducible promoter" is a promoter that mediates transcription of an operably linked gene in response to a particular stimulus.

"In operable linkage" refers to a functional linkage between two nucleic acid sequences, such as a control sequence (typically a promoter) and the linked sequence. A promoter is in operable linkage with an exogenous gene if it can mediate transcription of the gene.

"In situ" means "in place" or "in its original position". For example, a culture may contain a first microorganism, such as a microalgae, secreting a catalyst and a second microorganism secreting a substrate, wherein the first and second microorganisms produce the components necessary for a particular chemical reaction to occur in situ in the co-culture without requiring further separation or processing of the materials.

"Lipase" is an enzyme that catalyzes the hydrolysis of ester bonds in lipid substrates. Lipases catalyze the hydrolysis of lipids into glycerols and fatty acids, and can function to catalyze the transesterification of TAGs to fatty acid alkyl esters.

"Lipids" are lipophilic molecules that can be obtained from microorganisms. The main biological functions of lipids include storing energy, acting as structural components of cell membranes, and serving as signaling molecules, although they perform other functions as well. Lipids are soluble in nonpolar solvents (such as ether and chloroform) and are relatively insoluble in water. Lipids consist largely of long, hydrophobic hydrocarbon "tails." Examples of lipids include fatty acids (saturated and unsaturated); glycerides or glycerolipids (such as monoglycerides, diglycerides, triglycerides (including TAGs) or neutral fats, and phosphoglycerides or glycerophospholipids); nonglycerides (sphingolipids, sterol lipids including cholesterol and steroid hormones, prenol lipids including terpenoids, waxes, and polyketides); and complex lipid derivatives (sugar-linked lipids, or glycolipids, and protein-linked lipids). Other examples of lipids include free fatty acids; esters of fatty acids; sterols; pigments (e.g., carotenoids and oxycarotenoids), xanthophylls, phytosterols, ergothionine, lipoic acid, antioxidants including beta-carotene and tocopherol. Also included are polyunsaturated fatty acids such as arachidonic acid, stearidonic acid, cholesterol, desmesterol, astaxanthin, canthaxanthin, and n-6 and n-3 highly unsaturated fatty acids such as eicosapentaenoic acid (EPA), docosapentaenoic acid and docosahexaenoic acid (DHA).

A "lipid pathway enzyme" is an enzyme involved in lipid metabolism, i.e., either lipid synthesis, modification, or degradation, and includes, without limitation, lipases, fatty acyl-ACP thioesterases, and acyl carrier proteins.

A "limiting concentration of a nutrient" is a nutrient concentration in a culture that limits the propagation of a cultured organism. A "non-limiting concentration of a nutrient" is a nutrient concentration that can support maximal propagation during a given culture period. Thus, the number of cells produced during a given culture period is lower in the presence of a limiting concentration of a nutrient than when the nutrient is non-limiting. A nutrient is said to be "in excess" in a culture when the nutrient is present at a concentration greater than that which supports maximal propagation.

"Glycerolipid profile" refers to the distribution of different carbon chain lengths and saturation levels of glycerolipids in a particular sample of biomass. For example, a sample could contain glycerolipids in which approximately 60% of the glycerolipid is C18:1, 20% is C18:0, 15% is C16:0, and 5% is C14:0. Where a carbon length is referenced without regard to saturation, as in "C18", such reference can include any amount of saturation; for example, microbial biomass that contains 20% lipid as C18 can include C18:0, C18:1, C18:2, etc., in equal or varying amounts, the sum of which constitute 20% of the microbial biomass.

"Lysate" refers to a solution containing the contents of lysed cells. "Lysing" refers to disrupting the cellular membrane and optionally cell wall of a cell sufficient to release at least some intracellular contents. "Lysis" refers to the breakage of the plasma membrane and optionally the cell wall of a biological organism sufficient to release at least some intracellular contents, often by mechanical, viral or osmotic mechanisms that compromise its integrity.

"Microalgae" means a microbial organism that is either (a) eukaryotic and contains a chloroplast or chloroplast remnant, or (b) a cyanobacteria. Microalgae include obligate photoautotrophs, which cannot metabolize a fixed carbon source as energy, as well as heterotrophs, which can live solely off of a fixed carbon source. Microalgae can refer to unicellular organisms that separate from sister cells shortly after cell division, such as *Chlamydomonas*, as well as to microbes such as, for example, *Volvox*, which is a simple multicellular photosynthetic microbe of two distinct cell types. "Microalgae" also includes other microbial photosynthetic organisms that exhibit cell-cell adhesion, such as *Agmenellum*, *Anabaena*, and *Pyrobotrys*, as well as organisms that contain chloroplast-like structures that are no longer capable of performing photosynthesis, such as microalgae of the genus *Prototheca* and some dinoflagellates.

"Microorganism" and "microbe" are used interchangeably herein to refer to microscopic unicellular organisms.

"Oil" means a hydrophobic, lipophilic, nonpolar carbon-containing substance including but not limited to geologically-derived crude oil, distillate fractions of geologically-derived crude oil, vegetable oil, algal oil, and microbial lipids.

"Oleaginous yeast," as used herein, means yeast that can accumulate more than 10% of DCW as lipid. Oleaginous yeast includes yeasts such as *Yarrowia lipolytica*, as well as engineered strains of yeast such as *Saccharomyces cerevisiae* that have been engineered to accumulate more than 10% of the DCW as lipid.

"Osmotic shock" refers to the rupture of bacterial, algal, or other cells in a solution following a sudden reduction in osmotic pressure. Osmotic shock is sometimes induced to release cellular components into a solution.

"Photobioreactor" refers to a container, at least part of which is at least partially transparent or partially open, thereby allowing light to pass through, in which one or more microalgae cells are cultured. Photobioreactors may be closed, as in the instance of a polyethylene bag or Erlenmeyer flask, or may be open to the environment, as in the instance of an outdoor pond.

A "polysaccharide-degrading enzyme" refers to an enzyme capable of catalyzing the hydrolysis, or depolymerization, of any polysaccharide. For example, cellulases are polysaccharide degrading enzymes that catalyze the hydrolysis of cellulose.

"Polysaccharides" (or "glycans") are carbohydrates made up of monosaccharides joined together by glycosidic linkages. Cellulose is an example of a polysaccharide that makes up certain plant cell walls. Cellulose can be depolymerized by enzymes to yield monosaccharides such as xylose and glucose, as well as larger disaccharides and oligosaccharides.

"Port," in the context of a bioreactor, refers to an opening in the bioreactor that allows influx or efflux of materials such as gases, liquids, and cells. Ports are usually connected to tubing leading from the photobioreactor.

"Recombinant," when used with reference, e.g., to a cell, or nucleic acid, protein, or vector, indicates that the cell, nucleic acid, protein, or vector, has been modified by the introduction of a heterologous nucleic acid or protein or the alteration of a native (naturally occurring) nucleic acid or protein, or that the cell is derived from a cell so modified. Thus, e.g., recombinant cells express non-native genes, genes not found in the native (non-recombinant) form of the cell, or express native genes differently than does the non-recombinant cell, i.e., the native gene is over-expressed, under-expressed or not expressed at all, relative to gene expression in the non-recombinant cell. "Recombinant nucleic acid" refers to a nucleic acid, typically formed in vitro by the manipulation of nucleic acid, e.g., using polymerases and endonucleases, in a form not found in nature (and can include purified preparations of naturally occurring nucleic acids). Thus, an isolated nucleic acid, in a linear form, or an expression vector formed in vitro by ligating DNA molecules that are not normally joined (for example to place two different nucleic acids in operable linkage with one another), are recombinant. Once a recombinant nucleic acid is introduced into a host cell or organism, it may replicate non-recombinantly, i.e., using the in vivo cellular machinery of the host cell; however, such nucleic acids, produced recombinantly and subsequently replicated non-recombinantly, are still considered recombinant. Similarly, a "recombinant protein" is a protein made using recombinant techniques, i.e., through the expression of a recombinant nucleic acid.

"Saponified oil" refers to the carboxylic acid salts and associated compounds that are created during saponification of fatty acid esters from microbial sources. Fatty acid esters can be derived from the triacylgylcerols (TAGs) produced by microorganims. Compounds associated with oils from microbial sources include carotenoids, tocopherols, tocotrienols, and other compounds of biological origin.

"Sonication" refers to a process of disrupting biologic materials, such as a cell, by use of sound wave energy.

"Stover" refers to the dried stalks and leaves of a crop remaining after a grain has been harvested.

A "sucrose utilization gene" is a gene that, when expressed, aids the ability of a cell to utilize sucrose as an energy source. Sucrose transporters, sucrose invertases, and hexokinases such as glucokinases and fructokinases are examples of sucrose utilization genes.

II. General

Certain microorganisms can be used to produce lipids in large quantities for use in the transportation fuel and petrochemical industries, among other applications. The present invention provides methods that significantly decrease the cost and increase the efficiency of obtaining lipids and valuable lipid-derived compounds form microorganisms. Suitable microorganisms for use in the methods of the invention include microalgae, oleaginous yeast, fungi, bacteria, and cyanobacteria. A genus of microalgae for use in the invention is the lipid-producing microalgae *Chlorella*. The present invention also provides methods for the in situ transesterification of triacylglycerols (TAGs) to fatty acid alkyl esters, which are useful as biodiesel fuels and/or for other applications, as well as other methods for chemical modification of the lipids in microbial biomass.

The present invention also provides methods of making fatty acid alkyl esters (e.g., fatty acid methyl esters (FAME)) by culturing a population of microbes that generate at least 5% of their DCW as lipid, such as triglycerides. In this method, the microbial biomass is harvested from the culture and optionally dried to remove water. Transesterification is then accomplished by the addition of a lower-alkyl alcohol and a catalyst (e.g., NaOH) to generate a lipophilic phase containing the fatty acid alkyl esters and a hydrophilic phase containing hydrophilic cell material. The lipophilic phase can be readily separated from the hydrophilic phase.

The direct transesterification of the biomass, without an intervening separation process step in which the lipophilic components are extracted from the biomass prior to transesterification, permits production of biodiesel at greatly reduced costs, as compared to methods which employ traditional extraction and refining steps prior to transesterification.

The methods of the present invention provide further advantages in the generation of biodiesel via the in situ transesterification of glycerolipids to fatty acid alkyl esters. In particular, the microbes of the present invention can be cultured under conditions which permit modulation of the glycerolipid content of the cells. Surprisingly, it has been discovered that a greater proportion of total glycerolipids can be converted to fatty acid alkyl esters in cells which comprise increasingly higher oil:non-oil ratios as a function of DCW. Moreover, these higher oil:non-oil ratios also lead to another unexpected advantage: fatty acid alkyl esters generated from cells that comprise increasingly higher oil:non-oil ratios have a lower concentration of heteroatoms than those produced from cells with lower oil:non-oil ratios. The methods provided contrast markedly with current dogma in the field, namely that photoautotrophic growth of microalgae is the best method of microalgae cultivation for biofuel production (see for example, Rodolfi, et al., *Biotechnology & Bioengineering* 102(1):100-112 (2008) for discussion on screening microalgal strains for their biomass productivity and lipid content for growth in an outdoor photobioreactor). It was also discovered that the higher the oil content of the biomass, the higher quality of the resulting product after direct chemical modification. The present invention provides heterotrophic methods of culturing microbes (e.g., microalgae) to achieve higher oil content for direct chemical modification for the production of higher quality chemical products.

The present invention also provides other methods of chemically modifying lipid-containing microbial biomass, including without limitation, hydrogenation, interesterification, hydroxylation, hydrolysis, and saponification. These methods can be used with the various microorganisms and culturing conditions set forth herein to produce a wide variety of chemical products for a multitude of applications.

The present invention also provides useful compositions, including: a composition comprising a lighter phase containing fatty acid alkyl esters and at least one heavier phase containing microbial biomass; a composition comprising a lighter phase containing completely saturated lipids and at least one heavier phase containing microbial biomass; a composition comprising a lighter phase containing lipids and at least one heavier phase containing microbial biomass from more than one species or strain; a composition comprising a lighter phase containing hydroxylated lipids and at least one heavier phase containing microbial biomass; and a composition comprising a lighter phase containing free fatty acids and at least one heavier phase containing microbial biomass. The present invention also provides compositions comprising saponified oil derived from the alkaline hydrolysis of biomass produced by culturing a population of microorganisms.

III. Microorganisms

Microorganisms useful in the invention produce lipids suitable for chemical modification for biodiesel production and for production of fatty acid esters for other purposes such as industrial chemical feedstocks and edible oils, as well as the production of other chemical entities. Suitable lipids for biodiesel and chemicals production include TAGs containing fatty acid molecules. In some embodiments, suitable fatty acids contain at least 8, at least 10, at least 12, at least 14, at least 16, at least 18, at least 20, at least 22, at least 24, at least 26, at least 28, at least 30, at least 32, or at least 34 carbon atoms or more. Preferred fatty acids for biodiesel generally contain 16 and 18 carbon atoms. In certain embodiments, the above fatty acids are saturated (with no carbon-carbon double or triple bonds); mono unsaturated (single double bond); polyunsaturated (two or more double bonds); are linear (not cyclic); and/or have little or no branching in their structures.

In some embodiments, culturing microorganisms useful in the in situ transesterification and modification methods of the present invention yields a biomass that, when dry, comprises an oil content of at least 5%, at least 10%, at least 15%, at least 20%, or at least 25%. In other embodiments, the dried biomass comprises an oil content of at least 30%, at least 35%, at least 40%, at least 45%, at least 50%, at least 55%, at least 60%, at least 65%, at least 70%, at least 75%, at least 80%, at least 85%, or at least 90%. "Dry" or "dried," as used in this context, refers to the absence of substantially all water. Biomass can also be chemically modified without being dried; for example, biomass includes a centrifuged cell paste.

In some embodiments, culturing microorganisms useful in the in situ transesterification and other chemical modification methods of the invention yields a biomass in which at least 10% of the lipid is C18, at least 15% of the lipid is C18, at least 20% of the lipid is C18, or at least 25% of the lipid is C18. In other embodiments, the biomass comprises a lipid constituent which is at least 30% C18, at least 35% C18, at least 40% C18, at least 45% C18, or at least 50% C18. In still other embodiments, the biomass can comprise a lipid component that is at least 10%, at least 15%, at least 20%, at least 25%, at least 30%, at least 35%, at least 40%, at least 45%, or at least 50% C14 and/or C16, or longer chain lengths. Alternatively, the biomass can comprise a lipid component that is at least 10% or at least 20% C14, or shorter chain lengths.

The microorganims useful in the methods of the present invention can be naturally occurring or genetically engineered to increase lipid yield, to generate TAGs comprising higher proportions of desirable carbon chain length (e.g., C18) fatty acids, or to use particular feedstocks (e.g., molasses) as an energy and carbon source. Such genetic engineering modifications are described below under the header "Lipid Pathway Engineering."

Any species of microorganism that produces suitable lipid can be used in the methods of the invention, although microorganisms that naturally produce high levels of suitable lipid are typically preferred. In addition, microorganisms that can produce high levels of lipid as a percentage of DCW when subjected to specific fermentation conditions are also preferred. Microalgae can be used in the methods of the invention, and nonlimiting examples of microalgae, both genus and species, that can be used in the methods of the present invention are listed in Table 1.

TABLE 1

Examples of microalgae.

*Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia hooglandii, Borodinella* sp., *Botryococcus braunii, Botryococcus sudeticus, Carteria, Chaetoceros gracilis, Chaetoceros muelleri, Chaetoceros muelleri subsalsum, Chaetoceros* sp., *Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri,*

TABLE 1-continued

Examples of microalgae.

*Chlorella lobophora* (strain SAG 37.88), *Chlorella luteoviridis*, *Chlorella luteoviridis* var. *aureoviridis*, *Chlorella luteoviridis* var. *lutescens*, *Chlorella miniata*, *Chlorella minutissima*, *Chlorella mutabilis*, *Chlorella nocturna*, *Chlorella parva*, *Chlorella photophila*, *Chlorella pringsheimii*, *Chlorella protothecoides* (including any of UTEX strains 1806, 411, 264, 256, 255, 250, 249, 31, 29, 25), *Chlorella protothecoides* var. *acidicola*, *Chlorella regularis*, *Chlorella regularis* var. *minima*, *Chlorella regularis* var. *umbricata*, *Chlorella reisiglii*, *Chlorella saccharophila*, *Chlorella saccharophila* var. *ellipsoidea*, *Chlorella salina*, *Chlorella simplex*, *Chlorella sorokiniana*, *Chlorella* sp., *Chlorella sphaerica*, *Chlorella stigmatophora*, *Chlorella vanniellii*, *Chlorella vulgaris*, *Chlorella vulgaris*, *Chlorella vulgaris f. tertia*, *Chlorella vulgaris* var. *autotrophica*, *Chlorella vulgaris* var. *viridis*, *Chlorella vulgaris* var. *vulgaris*, *Chlorella vulgaris* var. *vulgaris f. tertia*, *Chlorella vulgaris* var. *vulgaris f. viridis*, *Chlorella xanthella*, *Chlorella zofingiensis*, *Chlorella trebouxioides*, *Chlorella vulgaris*, *Chlorococcum infusionum*, *Chlorococcum* sp., *Chlorogonium*, *Chroomonas* sp., *Chrysosphaera* sp., *Cricosphaera* sp., *Crypthecodinium cohnii*, *Cryptomonas* sp., *Cyclotella cryptica*, *Cyclotella meneghiniana*, *Cyclotella* sp., *Dunaliella* sp., *Dunaliella bardawil*, *Dunaliella bioculata*, *Dunaliella granulate*, *Dunaliella maritime*, *Dunaliella minuta*, *Dunaliella parva*, *Dunaliella peircei*, *Dunaliella primolecta*, *Dunaliella salina*, *Dunaliella terricola*, *Dunaliella tertiolecta*, *Dunaliella viridis*, *Dunaliella tertiolecta*, *Eremosphaera viridis*, *Eremosphaera* sp., *Ellipsoidon* sp., *Euglena*, *Franceia* sp., *Fragilaria crotonensis*, *Fragilaria* sp., *Gleocapsa* sp., *Gloeothamnion* sp., *Hymenomonas* sp., *Isochrysis aff. galbana*, *Isochrysis galbana*, *Lepocinclis*, *Micractinium*, *Micractinium* (UTEX LB 2614), *Monoraphidium minutum*, *Monoraphidium* sp., *Nannochloris* sp., *Nannochloropsis salina*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrina*, *Nitzschia communis*, *Nitzschia dissipata*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Pascheria acidophila*, *Pavlova* sp., *Phagus*, *Phormidium*, *Platymonas* sp., *Pleurochrysis carterae*, *Pleurochrysis dentate*, *Pleurochrysis* sp., *Prototheca wickerhamii*, *Prototheca stagnora*, *Prototheca portoricensis*, *Prototheca moriformis*, *Prototheca zopfii*, *Pyramimonas* sp., *Pyrobotrys*, *Sarcinoid chrysophyte*, *Scenedesmus armatus*, *Schizochytrium*, *Spirogyra*, *Spirulina platensis*, *Stichococcus* sp., *Synechococcus* sp., *Tetraedron*, *Tetraselmis* sp., *Tetraselmis suecica*, *Thalassiosira weissflogii*, and *Viridiella fridericiana*

Nonlimiting examples of oleaginous yeast that can be used in the methods of the present invention are listed in Table 2.

TABLE 2

Examples of oleaginous yeast.

*Cryptococcus curvatus*, *Cryptococcus terricolus*, *Candida* sp., *Lipomyces starkeyi*, *Lipomyces lipofer*, *Endomycopsis vernalis*, *Rhodotorula glutinis*, *Rhodotorula gracilis*, and *Yarrowia lipolytica*

Nonlimiting examples of fungi that can be used in the methods of the present invention are listed in Table 3.

TABLE 3

Examples of fungi.

*Mortierella*, *Mortierrla vinacea*, *Mortierella alpine*, *Pythium debaryanum*, *Mucor circinelloides*, *Aspergillus ochraceus*, *Aspergillus terreus*, *Pennicillium iilacinum*, *Hensenulo*, *Chaetomium*, *Cladosporium*, *Malbranchea*, *Rhizopus*, and *Pythium*

Considerations affecting the selection of a microorganism for use in the invention include, in addition to production of suitable lipids for biodiesel production: (1) high lipid content as a percentage of cell weight; (2) ease of growth; and (3) ease of processing. Preferred microorganisms grow heterotrophically (on sugar in the absence of light) or have been engineered to do so using, for example methods disclosed in U.S. Patent Application Nos. 60/941,581 (filed Jun. 1, 2007), 60/959,174 (filed Jul. 10, 2007), 60/968,291 (filed Aug. 27, 2007) and 61/024,069 (filed Jan. 28, 2008).

Processing considerations can include, for example, the availability of effective means for lysing the cells. Bacteria can also be used in the methods of the invention invention, particularly oleaginous bacteria such as species of the genus *Rhodococcus*, such as *Rhodococcus opacus* and *Rhodococcus* sp.

Species of microalgae for use in the methods of the invention can be identified by amplification of certain target regions of the genome of a test microalgae. For example, identification of a specific species or strain of microalgae can be achieved through amplification and sequencing of nuclear and/or chloroplast DNA using primers and methodology using any region of the genome (see, e.g., Wu et al., *Bot. Bull. Acad. Sin.* (2001) 42:115-121 "Identification of *Chlorella* spp. Isolates using ribosomal DNA sequences"). Well established methods of phylogenetic analysis, such as amplification and sequencing of ribosomal internal transcribed spacer (ITS1 and ITS2 rDNA), 23S rRNA, 18s rRNA, and other conserved genomic regions can be used to identify species of microalgal and other hydrocarbon and lipid producing organisms that can be used in the methods disclosed herein. For examples of methods of identification and classification of algae, see also, e.g., *Genetics*, 2005 August; 170(4):1601-10 and *RNA*, 2005 April, 11(4):361-4.

Genomic DNA comparisons can also be used to identify suitable species of microalgae for use in the methods of the present invention. Regions of conserved DNA, including, but not limited to, DNA encoding 23S rRNA, can be amplified from microalgal species and compared to consensus sequences to screen for microalgal species that are taxonomically related to a microalgae used in a method of the present invention. Examples of such DNA sequence comparison for species within the *Chlorella* and *Prototheca* genus are shown below in the Examples.

In some embodiments, microalgae for use in the methods of the present invention have genomic DNA sequences encoding 23S rRNA that have at least 99%, at least 98%, at least 97%, at least 96%, at least 95%, at least 94%, at least 93%, at least 92%, at least 91%, at least 90%, at least 89%, at least 88%, at least 87%, or at least 86% nucleotide identity to at least one of the sequences listed in SEQ ID NOs:3-6. In other embodiments, microalgae for use in the methods of the present invention have genomic DNA sequences encoding 23S rRNA that have at least 85%, at least 80%, at least 75%, at least 70%, at least 65% or at least 60% nucleotide identity to at least one of the sequences listed in SEQ ID NOs:3-29.

*Chlorella* is a genus of single-celled green algae, belonging to the phylum Chlorophyta, that can be used in the methods of the present invention. *Chlorella* is spherical in shape, about 2 to 10 μm in diameter, and is without flagella. Some species of *Chlorella* are naturally heterotrophic. *Chlorella*, particularly *Chlorella protothecoides*, is a preferred microorganism for use in the invention because of its high composition of lipid, particularly long-chain lipid suitable for biodiesel and chemical modification into other molecules. In addition, this microalgae grows heterotrophically.

*Prototheca* is a genus of single-cell microalgae thought to be a non-photosynthetic mutant of *Chlorella* that is useful in the methods of the present invention. While *Chlorella* can obtain its energy through photosynthesis, species of the genus *Prototheca* are obligate heterotrophs. *Prototheca* are spherical in shape, about 2 to 15 micrometers in diameter, and without flagella. *Prototheca*, particularly *Prototheca moriformis*, is a preferred microorganism for use in the invention because of its lipid composition, particularly saturated lipids suitable for saponification. In addition, the lipid extracted from this microalgae has very few colorant contaminants, further making it suitable for saponification.

As with both plants and animals, algae and other microbes store excess energy in the form of lipids for use when other sources of energy (e.g., sunlight) are unavailable. Moreover, modulation of oil content allows algae living in an aqueous environment to float and thereby optimize access to sunlight to carry out photosynthetic processes. The ability to modify buoyancy via modulation of oil content has led to microalgal cells that can generate high cellular oil concentrations as compared to higher plants. The characteristic of high oil content is advantageous for in situ chemical modification of oil-bearing biomass, because, as demonstrated herein, high-oil biomass yields higher purity TAG derivatives compared to low-oil biomass, particularly photosynthetically-derived low-oil biomass. Accordingly, microorganisms that can be used to generate high-oil biomass are preferred for use in the methods of the present invention.

A. Growth Methods

Microrganisms can be cultured both for purposes of conducting optional genetic manipulations and for the production of lipids. The former type of culture is conducted on a small scale and, at least initially, under conditions in which the starting microorganism can grow. For example, if the starting microorganism is a photoautotroph, the initial culture is conducted in the presence of light. The culture conditions can be changed if the microorganism is evolved or engineered to grow independently of light. Culture for purposes of lipid production is usually conducted on a large scale.

1. Photosynthetic Growth Methods

Photosynthetic microorganisms, such as microalgae, can be grown in the presence of light in a liquid culture medium that may be contained, for example, in a photobioreactor. The number of photons striking a culture of microalgae cells can be manipulated, as well as other parameters, such as the wavelength spectrum and ratio of dark:light hours per day. Microalgae can also be cultured in natural light, as well as simultaneous and/or alternating combinations of natural light and artificial light. For example, microalgae of the genus *Chlorella* can be cultured under natural light during daylight hours and under artificial light during night hours.

The gas content of a photobioreactor to grow microorganisms such as microalgae can be manipulated. Part of the volume of a photobioreactor can contain gas rather than liquid. Gas inlets can be used to pump gases into the photobioreactor. Any gas can be pumped into a photobioreactor, including air, air/$CO_2$ mixtures, noble gases such as argon and other gases. The rate of entry of gas into a photobioreactor can also be manipulated. Increasing gas flow into a photobioreactor increases the turbidity of a culture of microalgae. The placement of ports conveying gases into a photobioreactor can also affect the turbidity of a culture at a given gas flow rate. Air/$CO_2$ mixtures can be modulated to generate optimal amounts of $CO_2$ for maximal growth by a particular organism. Microalgae grow significantly faster in the light under, for example, 3% $CO_2$/97% air than in 100% air. 3% $CO_2$/97% air has approximately 100-fold more $CO_2$ than air. For example, air:$CO_2$ mixtures of about 99.75% air:0.25% $CO_2$, about 99.5% air:0.5% $CO_2$, about 99.0% air:1.00% $CO_2$, about 98.0% air:2.0% $CO_2$, about 97.0% air:3.0% $CO_2$, about 96.0% air:4.0% $CO_2$, and about 95.00% air:5.0% $CO_2$ can be infused into a bioreactor or photobioreactor in accordance with the present methods. A 5% $CO_2$:95% air mixture infused into a photobioreactor containing *Botryococcus* cells is reported in *J Agric Food Chem.* 2006 Jun. 28; 54(13):4593-9; *J Biosci Bioeng.* 1999; 87(6):811-5; and *J Nat Prod.* 2003 June; 66(6):772-8).

Microalgae can be grown and maintained in closed photobioreactors made of any of a variety of different types of transparent or semitransparent material. Such material includes Plexiglas® enclosures, glass enclosures, bags made from substances such as polyethylene, transparent or semitransparent pipes, and other materials. Microalgae can also be grown and maintained in open photobioreactors such as raceway ponds, settling ponds, and other non-enclosed containers.

"Algal shading" refers to the inability of a light source to penetrate and reach all cells of a photosynthetic culture. Cells nearest the light source will "shade" (by virtue of their physical presence and absorption of photons in the chloroplasts) those cells further from the light source and thereby limit the exposure of those other cells to the energy needed to convert a carbon feedstock into lipids or other materials necessary for cell growth and reproduction. By mixing the culture, one can provide a mechanism to expose all cells to the light source, but "shading" nevertheless impacts the total duration of exposure, leading to slower growth and lower oil content as a percentage of DCW. As a result, longer growth periods may be required to achieve high densities of cells and/or high oil content. Even after extended periods of growth, cells grown on light as a sole energy source rarely contain more than 15% oil as a percentage of DCW. In addition, photosynthetic growth of microalgae results in high levels of chlorophyll in the biomass, leading to much higher quantities of magnesium in directly transesterified biomass, because magnesium is a component of chlorophyll, and chlorophyll is a highly hydrophobic compound that accumulates in the lipophilic phase. In addition, higher carotenoid levels accumulate in algae grown photosynthetically than in algae grown heterotrophically.

2. Heterotrophic Growth Methods for Lipid Production

In contrast to photosynthetic growth methods, microalgae can be cultured in liquid media with the culture contained in a bioreactor that does not allow light to enter. Heterotrophic culture methods such as these rely on the use of a fixed carbon source (e.g., glucose, glycerol, cellulosics, etc.) to provide energy for growth and lipid production. Culture condition parameters can be manipulated to optimize total lipid production.

Microalgal culture media typically contain components such as a fixed nitrogen source, trace elements, optionally a buffer for pH maintenance, and phosphate. Other components can include a fixed carbon source such as acetate or glucose and salts such as sodium chloride, particularly for seawater microalgae. Examples of trace elements include zinc, boron, cobalt, copper, manganese, and molybdenum in, for example, their respective forms of $ZnCl_2$, $H_3BO_3$, $CoCl_2.6H_2O$, $CuCl_2.2H_2O$, $MnCl_2.4H_2O$ and $(NH_4)_6Mo_7O_{24}.4H_2O$. These and other culture parameters, such as the pH of the culture media, the identity and concentration of trace elements and other media constituents, can also be manipulated in the methods of the invention to achieve a desired production result.

For organisms able to grow on a fixed carbon source, the fixed carbon source can be, for example, glucose, fructose, sucrose, galactose, xylose, mannose, rhamnose, glycerol, cellulosic sources, and/or floridoside. The one or more carbon source(s) can be supplied at a concentration of at least about 50 μM, at least about 100 μM, at least about 500 μM, at least about 5 mM, at least about 50 mM, and at least about 500 mM, of one or more exogenously provided fixed carbon source(s). For multiple species of *Chlorella*, for example, heterotrophic growth results in high production of biomass and accumulation of high lipid content in cells.

For lipid production, cells, including recombinant cells, are typically cultured or fermented in large quantities. The culturing may take place in large liquid volumes, such as in suspension cultures as an example. Other examples include starting with a small culture of cells that is expanded into a large biomass by cell growth and propagation concurrently with lipid production. Bioreactors or steel fermentors can be used to accommodate large culture volumes. A fermentor similar those used in the production of beer and/or wine is suitable, as are the very large fermentors used in the production of ethanol.

Appropriate nutrient sources for culture in a fermentor are provided. These include raw materials such as one or more of the following: a fixed carbon source such as glucose, corn starch, depolymerized cellulose, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Gaseous components, like oxygen or nitrogen, can be bubbled through a liquid culture.

A fermentor can be used to allow cells to undergo the various phases of their growth cycle. As an example, an inoculum of lipid-producing cells can be introduced into a medium followed by a lag period (lag phase) before the cells begin growth. Following the lag period, the growth rate increases steadily and enters the log, or exponential, phase. The exponential phase is typically followed by a slowing or complete cessation of cell division due to decreases in nutrients, nitrogen in particular. After slowing, growth stops, and the cells enter a steady state of converting a fixed carbon feedstock into a desired product, such as a TAG. Maintaining the steady state for a longer period of time results in a higher percentage of DCW being the desired product, such as lipid in the case of the microorganisms described herein. In some instances, it is desirable to maintain the microbial cells in a steady state in which the cells convert a carbohydrate such as glucose into lipid while not undergoing cell division for an extended period of time to generate microbial biomass with more than 30%, more than 40%, more than 50%, or more than 60% lipid as a percentage of the dry weight of the cells. Nitrogen limitation is generally sufficient to prevent cells from undergoing cell division.

Microorganisms grown using conditions described herein and known in the art can comprise at least 20% lipid by weight, preferably at least 40% lipid by weight, more preferably at least 50% lipid by weight, more preferably at least 60% lipid by weight, more preferably at least 70% lipid by weight, and most preferably at least 80% lipid by weight. In some embodiments, microorganisms are cultured using conditions described herein to attain a lipid component of at least 20% by weight within a culture period of no more than 1 week. In some embodiments, the culture period is no more than 14 days, no more than 13 days, no more than 12 days, no more than 11 days, no more than 10 days, no more than 9 days, no more than 8 days, no more than 6 days, no more than 5 days, no more than 4 days, or no more than 3 days. In any one of the foregoing culture periods, the microorganisms may yield at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% lipid by DCW. In some embodiments, microorganisms are cultured using conditions described herein to attain a lipid component of at least 20% by weight within a culture period of at least 2 days. In some embodiments, the culture period is at least 3 days, at least 4 days, at least 5 days, at least 6 days, at least 7 days or at least 8 days. In any one of the foregoing culture periods, the microorganisms may yield at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% lipid by DCW.

Process conditions can be adjusted to increase the yield of lipids suitable for use as biodiesel or other target molecules and/or to reduce production cost. For example, in certain embodiments, a microbe (e.g., a microalgae) is cultured in the presence of a limiting concentration of one or more nutrients, such as, for example, nitrogen. This condition tends to increase microbial lipid yield over microbial lipid yield in a culture in which nitrogen is provided in excess. In particular embodiments, the increase in lipid yield is at least about: 10%, 20%, 30%, 40%, 50%, 75%, 100%, 200%, 300%, 400%, or 500%. The microbe can be cultured in the presence of a limiting amount of the nutrient for a portion of the total culture period or for the entire period. In particular embodiments, the nutrient concentration is cycled between a limiting concentration and a non-limiting concentration at least twice during the total culture period. In addition and as shown in the Figures, certain fixed carbon feedstocks such as glycerol can be employed to increase the percentage of cell weight that is lipid compared to comparable quantities of other fixed carbon feedstocks.

To increase lipid yield, acetic acid can be employed in the feedstock for a lipid-producing microbe (e.g., a microalgae). Acetic acid feeds directly into the point of metabolism that initiates fatty acid synthesis (i.e., acetyl-CoA); thus, providing acetic acid in the culture can increase fatty acid production. Generally, in this embodiment, the microbe is cultured in the presence of a sufficient amount of acetic acid to increase microbial lipid yield, and/or microbial fatty acid yield, specifically, over microbial lipid (e.g., fatty acid) yield in the absence of acetic acid.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, in this embodiment, the concentration of the cofactor(s) is sufficient to increase microbial lipid (e.g., fatty acid) yield over microbial lipid yield in the absence of the cofactor(s). In a particular embodiment, the cofactor(s) is provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include any vitamin required by a lipid pathway enzyme, such as, for example, biotin or pantothenate. Genes encoding cofactors suitable for use in the invention or that participate in the synthesis of such cofactors are well known and can be introduced into microbes (e.g., microalgae) using constructs and techniques known to those in the art.

Microalgal biomass with a high percentage of oil/lipid accumulation by dry weight has been generated using a variety of different methods of culture known in the art. Microalgal biomass with a higher percentage of accumulated oil/lipid is useful in accordance with the present invention. Li et al. describe *Chlorella vulgaris* cultures with up to 56.6% lipid by DCW in stationary cultures grown under autotrophic conditions (i.e., photosynthetic growth conditions) using high iron concentrations (Li et al., *Bioresource Technology* 99(11):4717-22 (2008)). Rodolfi et al. describe *Nanochloropsis* sp. and *Chaetoceros calcitrans* cultures with 60% lipid DCW and 39.8% lipid DCW, respectively, grown in a photobioreactor under nitrogen starvation conditions (Rodolfi et al., *Biotechnology & Bioengineering* 102(1):100-112 (2008)). Solovchenko et al. describe *Parietochloris incise* cultures with approximately 30% lipid accumulation (DCW) when grown phototrophically and under low nitrogen conditions (Solovchenko et al., *Journal of Applied Phcology* 20:245-251 (2008)). *Chlorella protothecoides* can produce up to 55% lipid (DCW) grown under certain heterotrophic conditions with nitrogen starvation (Miao and Wu, *Bioresource Technology* 97:841-846 (2006)). Other *Chlorella* species including *Chlorella emersonii*, *Chlorella sorokiniana*, and *Chlorella minutissima* have been described to have accumulated up to 63% oil (DCW) when grown in stirred tank bioreactors under low-nitrogen media conditions (Illman et al., *Enzyme and Microbial Technology* 27:631-635 (2000)). Still higher percent lipid accumulation by DCW has been reported, including 70% lipid (DCW) accumulation in *Dumaliella tertiolecta* cultures grown in increased NaCl conditions (Takagi et al., *Journal of Bioscience and Bioengineering* 101(3): 223-226 (2006)) and 75% lipid accumulation in *Botryococcus braunii* cultures (Banerjee et al., *Critical Reviews in Biotechnology* 22(3): 245-279 (2002)). These and similar methods can be used for photosynthetic and heterotrophic growth of microalgae to produce oil.

Microalgal biomass generated by the culture methods described herein and useful in accordance with the present invention comprises at least 10% microalgal oil by dry weight. In some embodiments, the microalgal biomass comprises at least 15%, at least 25%, at least 35%, at least 45%, at least 50%, at least 55%, or at least 60% microalgal oil by dry weight. In some embodiments, the microalgal biomass contains from 10-90% microalgal oil, from 25-75% microalgal oil, from 40-75% microalgal oil, or from 50-70% microalgal oil by dry weight.

In various embodiments, the microalgal biomass comprises at least 25% at least 26%, at least 27%, at least 28%, at least 29%, at least 30%, at least 31%, at least 32%, at least 33%, at least 34%, at least 35%, at least 36%, at least 37%, at least 38%, at least 38%, at least 40%, at least 41%, at least 42%, at least 43%, at least 44%, at least 45%, at least 46%, at least 47%, at least 48%, at least 49%, or at least 50% microalgal oil by dry weight. In other embodiments, the microalgal biomass comprises at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, or at least 90% microalgal oil by dry weight.

a. Use of Non-Traditional Carbon Sources

Microorganism can naturally grow on, or engineered to grow on, non-traditional carbon sources, such as sucrose, xylose, cellulosic materials, *sorghum* syrup and waste materials. Suitable cellulosic materials include residues from herbaceous and woody energy crops, as well as agricultural crops, i.e., the plant parts, primarily stalks and leaves, that are not the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill waste (wood chips, sawdust) and pulp mill waste; urban wastes such as paper fractions of municipal solid waste, urban wood waste, and urban green waste such as municipal grass clippings; and wood construction waste. Additional cellulosics include dedicated cellulosic crops such as switchgrass, hybrid poplar wood, and miscanthus, fiber cane, and fiber *sorghum*. Five-carbon sugars that are produced from such materials include xylose.

In another heterotrophic growth method, microalgal species can utilize mixed carbon sources such as *sorghum* syrup or pure *sorghum*. *Sorghum* syrup is produced from the juice of sweet *sorghum* cane. Its sugar profile consists of mainly glucose (dextrose), fructose, and sucrose. Microalgal strains can be screened for the capability to utilize *sorghum* as the sole carbon source. As non-limiting examples, microalgae from several strains of *Chlorella protothecoides*, *Chlorella luteovirdis*, *Prototheca moriformis*, *Chlorella kessleri*, *Parachlorella kessleri*, and *Prototheca stagnora* can utilize *sorghum* syrup in heterotrophic conditions, as described in the Examples below.

Some microorganisms naturally grow on or can be engineered to grow on a fixed carbon source that is a heterogeneous source of compounds, such as municipal waste, secondarily treated sewage, wastewater, and other sources of fixed carbon and other nutrients such as sulfates, phosphates, and nitrates. The sewage component serves as a nutrient source in the production of lipids, and the culture provides an inexpensive source of lipids for in situ transesterification and the production of biodiesel or for other chemical modification in accordance with the methods of the invention.

To reduce the cost of producing biodiesel or other chemically-modified lipids, crude, partially purified, or purified glycerol produced as a byproduct of lipid transesterification can be employed as a feedstock for fermenting, for example, lipid-producing microbial cultures. Thus, the invention provides methods involving the steps of culturing a microbe (e.g., a microalgae) in a first microbial culture; subjecting the microbial biomass to transesterification to produce fatty acid ester(s) and glycerol, as described below; and adding the glycerol to a second microbial culture as a feedstock. The first and second microbial cultures can, but need not, be cultures of the same microbe. If desired, a continuous system can be implemented in accordance with the invention whereby glycerol produced from the lipid recovered from a culture can be fed back into the same culture.

Improved culture parameters incorporating the use of glycerol for fermentation of multiple genera of both eukaryotic and prokaryotic microbes, including microbes of the genera *Chlorella, Navicula, Scenedesmus,* and *Spirulina,* are described herein. As the examples demonstrate, microbes of extremely divergent evolutionary lineage, including *Chlorella, Navicula, Scenedesmus,* and *Spirulina* as well as cultures of multiple distinct *Chlorella* species grow very well on not only purified reagent-grade glycerol, but also acidulated and non-acidulated glycerol byproduct from biodiesel transesterification. In some instances microalgae, such as *Chlorella* strains, undergo cell division faster in the presence of glycerol than in the presence of glucose.

The methods of the present invention can utilize microorganisms, for example, cultured via two-stage growth processes in which cells are first fed glycerol to increase cell density rapidly, and are then fed glucose to accumulate lipids. This can provide significant economic benefits in that the glycerol byproduct of the transesterification process is put back into the production process. Other feeding methods are provided as well, such as methods in which mixtures of glycerol and glucose are fed, and methods in which glucose is fed during the growth phase and glycerol is fed during the lipid production phase. Feeding such mixtures can provide economic benefit. In addition, the methods of the invention include methods in which microorganisms are fed alternative sugars such as sucrose in various combinations with glycerol. These alternatives have been demonstrated with microbes from extremely divergent evolutionary lineage, including both prokaryotes and eukaryotes, demonstrating the feasibility of these alternative culture conditions for microbial fermentation in accordance with the methods of the present invention.

Multiple *Chlorella* species, and multiple strains within a species of *Chlorella,* perform better in the presence of glycerol byproduct from transesterification than in an equivalent amount of reagent grade glycerol. Glycerol byproduct from transesterification usually contains residual methanol and other contaminants in addition to glycerol. For example, FIGS. 1-6 demonstrate that strains of *Chlorella protothecoides* and *Chlorella kessleri* exhibit better productivity on acidulated and non-acidulated glycerol byproduct from biodiesel transesterification than when grown on pure reagent grade glycerol. Other microbes, such as *Scenedesmus* and *Navicula* microalgae, can also perform better in the presence of glycerol byproduct from transesterification than in an equivalent amount of reagent grade glycerol.

Figure 2:
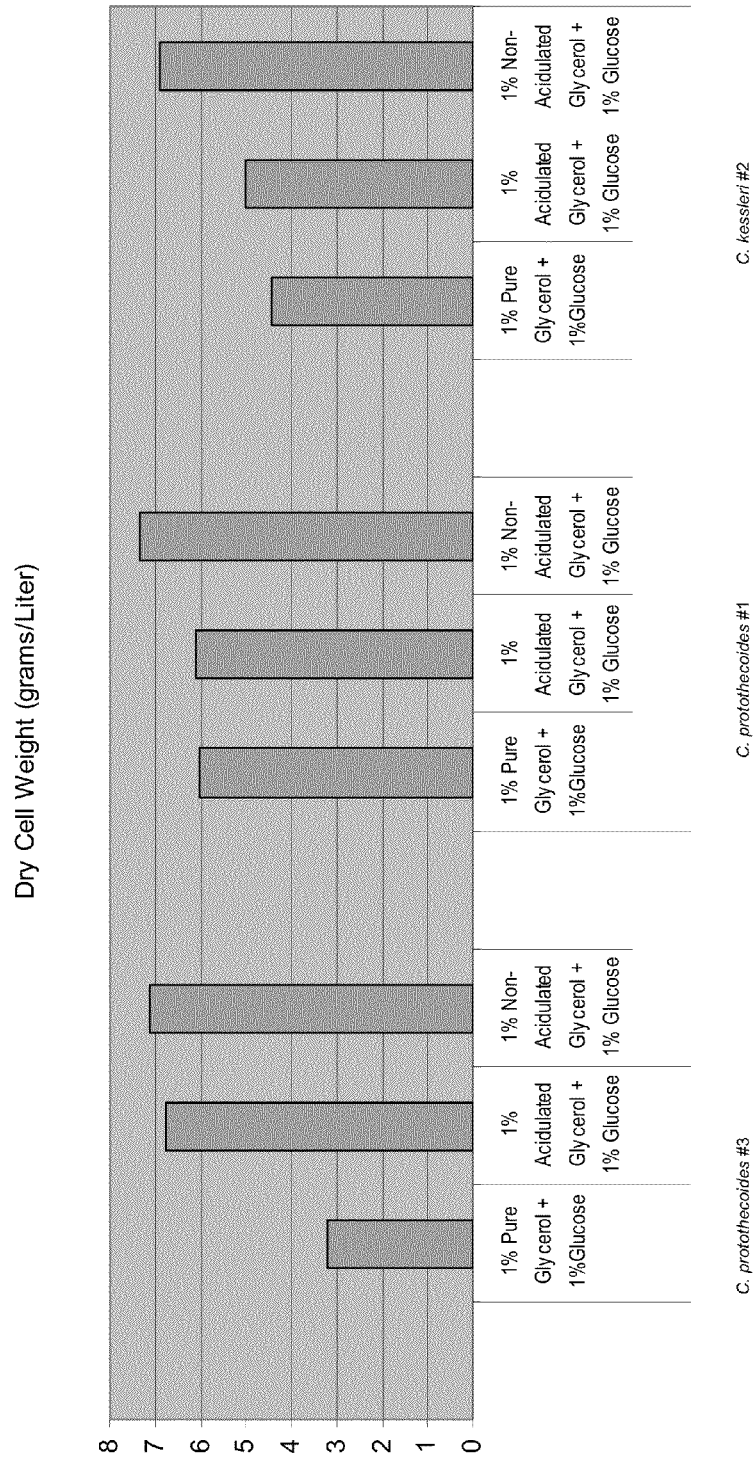
FIG. 2 shows DCW per liter of multiple species and strains of *Chlorella* when cultured in the presence of various types of glycerol with additional glucose.
Figure 12:
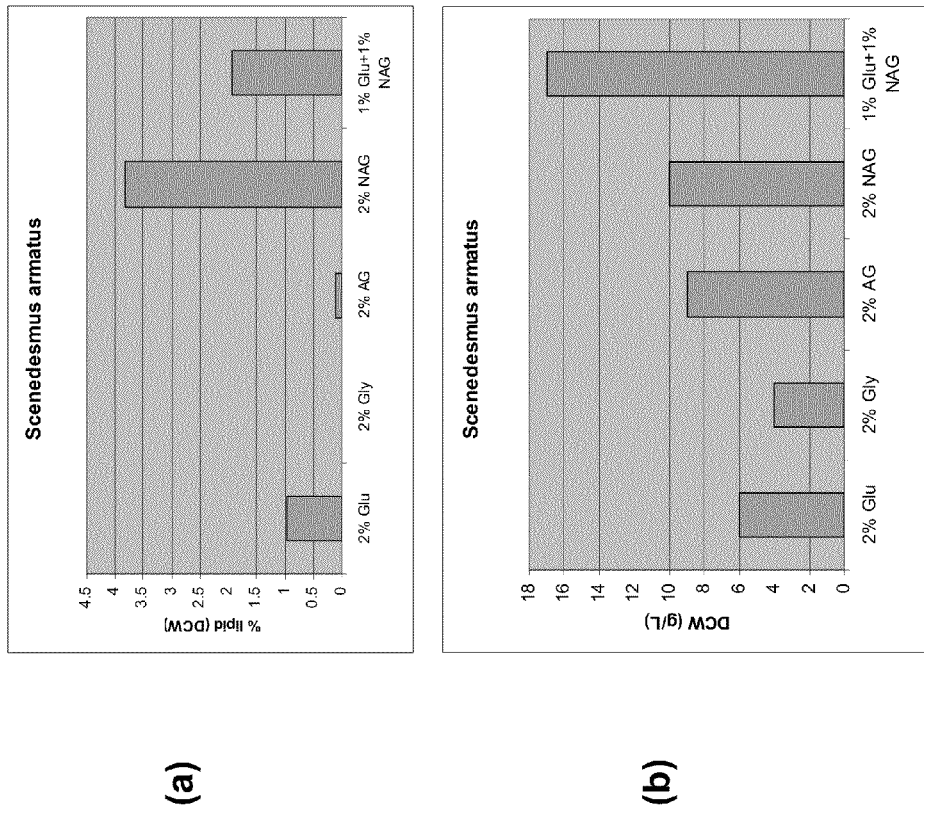
FIG. 12(*a*) shows lipid as a percent of DCW of *Scenedesmus armatus* when cultured in the presence of various types of glycerol and in the presence of a combination of glycerol and glucose.
Figure 13:
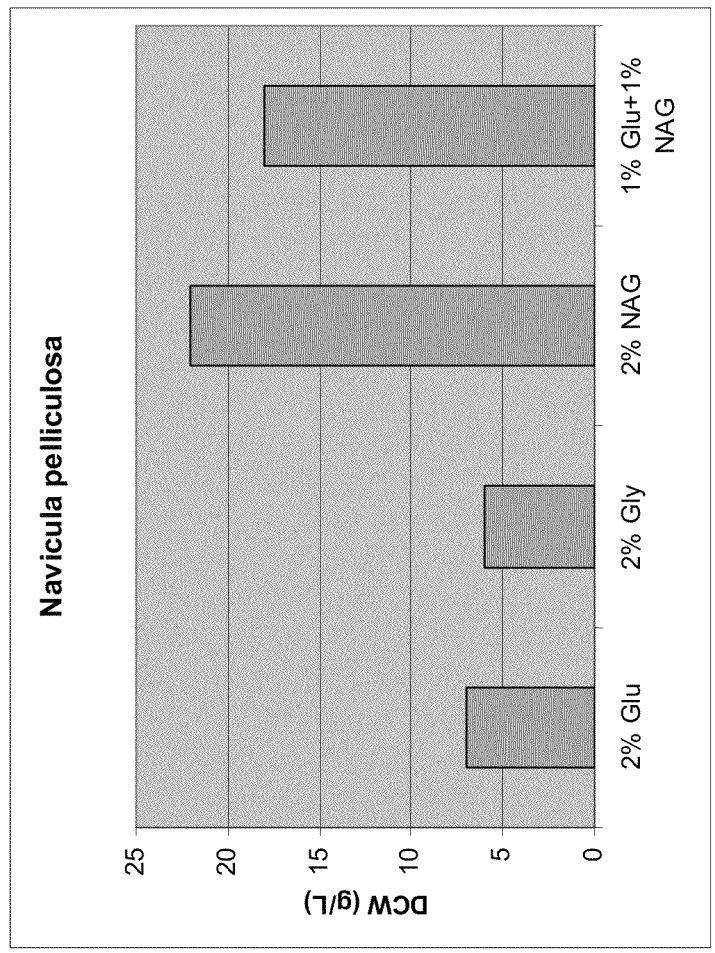
FIG. 13 shows DCW per liter of *Navicula pelliculosa* when cultured in the presence of various types of glycerol and in the presence of a combination of non-acidulated biodiesel byproduct glycerol and glucose.

FIG. 1 demonstrates that dry cell weight per liter (DCW per L) was higher on biodiesel glycerol byproduct than on pure glycerol, and this trend held true when the cells were grown in glycerol by itself or in combination with glucose. FIG. 2 shows the same trends with additional strains of *Chlorella*. FIG. 12(*b*) demonstrates that DCW per L of *Scenedesmus armatus* is higher on acidulated and non-acidulated biodiesel byproducts glycerol than on pure reagent grade glycerol. FIG. 13 demonstrates that DCW per L of *Navicula pelliculosa* is higher on non-acidulated biodiesel byproduct glycerol than on pure reagent grade glycerol.

Figure 3:
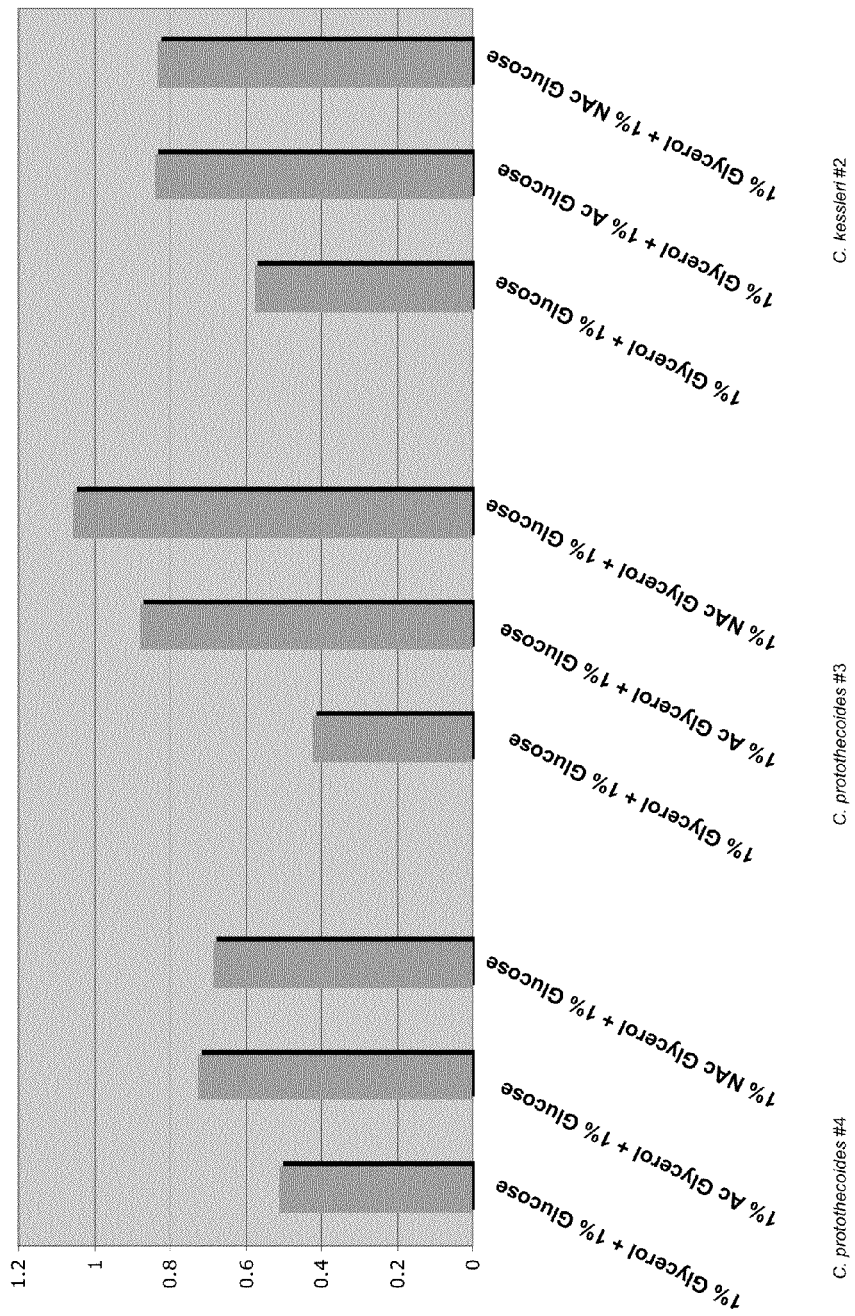
FIG. 3 shows relative lipid concentration of cultures of multiple species and strains of *Chlorella* when cultured in the presence of various types of glycerol with additional glucose.
Figure 4:
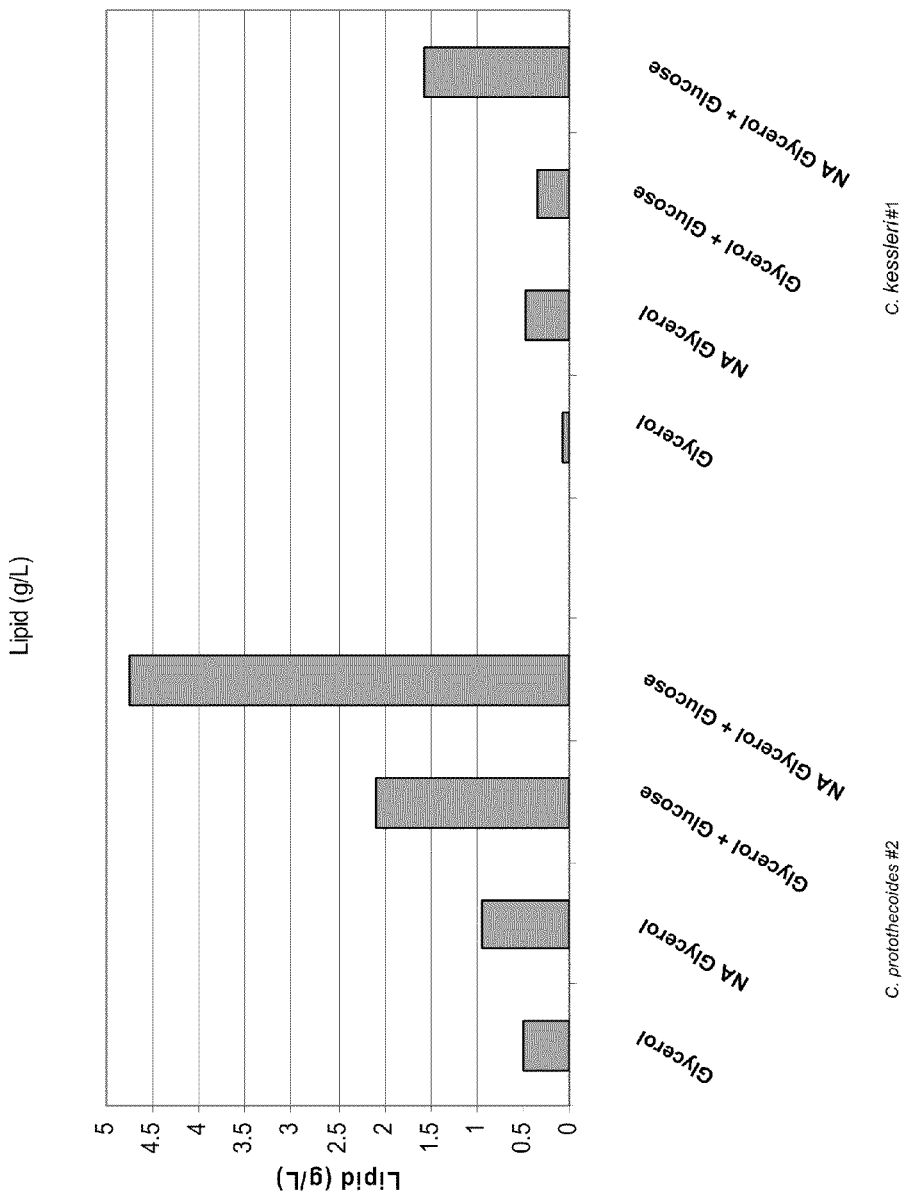
FIG. 4 shows lipid concentration of cultures of multiple species and strains of *Chlorella* when cultured in the presence of various types of glycerol with and without additional glucose.

FIGS. 3 and 4 demonstrate that, with multiple species of *Chlorella* and multiple strains within a species of *Chlorella*, lipid levels (or lipid content) per liter are higher when the cells are cultured in the presence of biodiesel glycerol byproduct than when cultured in the presence of equivalent concentrations of pure reagent grade glycerol.

Figure 5:
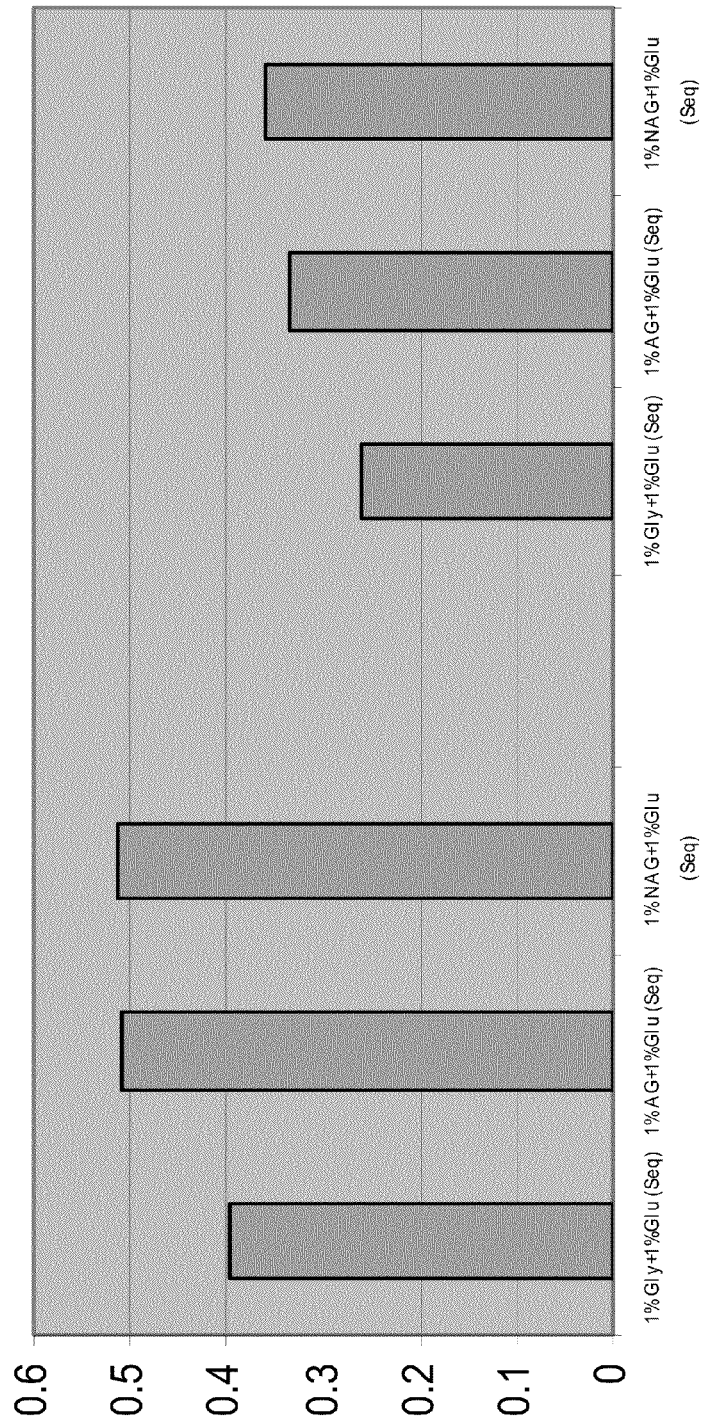
FIG. 5 shows lipid as a percent of DCW of two species and strains of *Chlorella* when cultured in the presence of various types of glycerol with additional glucose, wherein glycerol is added sequentially after glucose.
Figure 6:
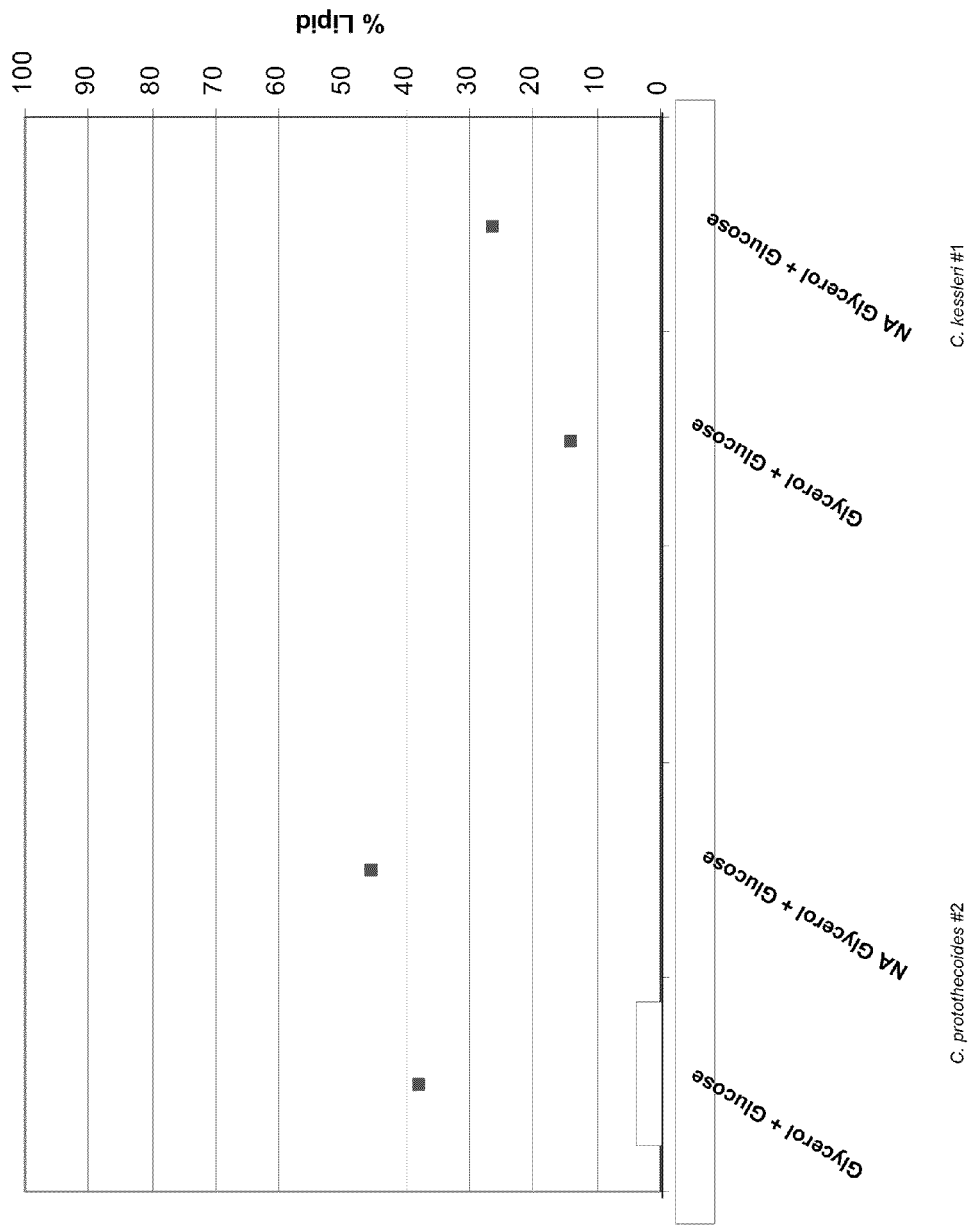
FIG. 6 shows lipid as a percent of DCW of two species and strains of *Chlorella* when cultured in the presence of various types of glycerol with additional glucose.
Figure 11:
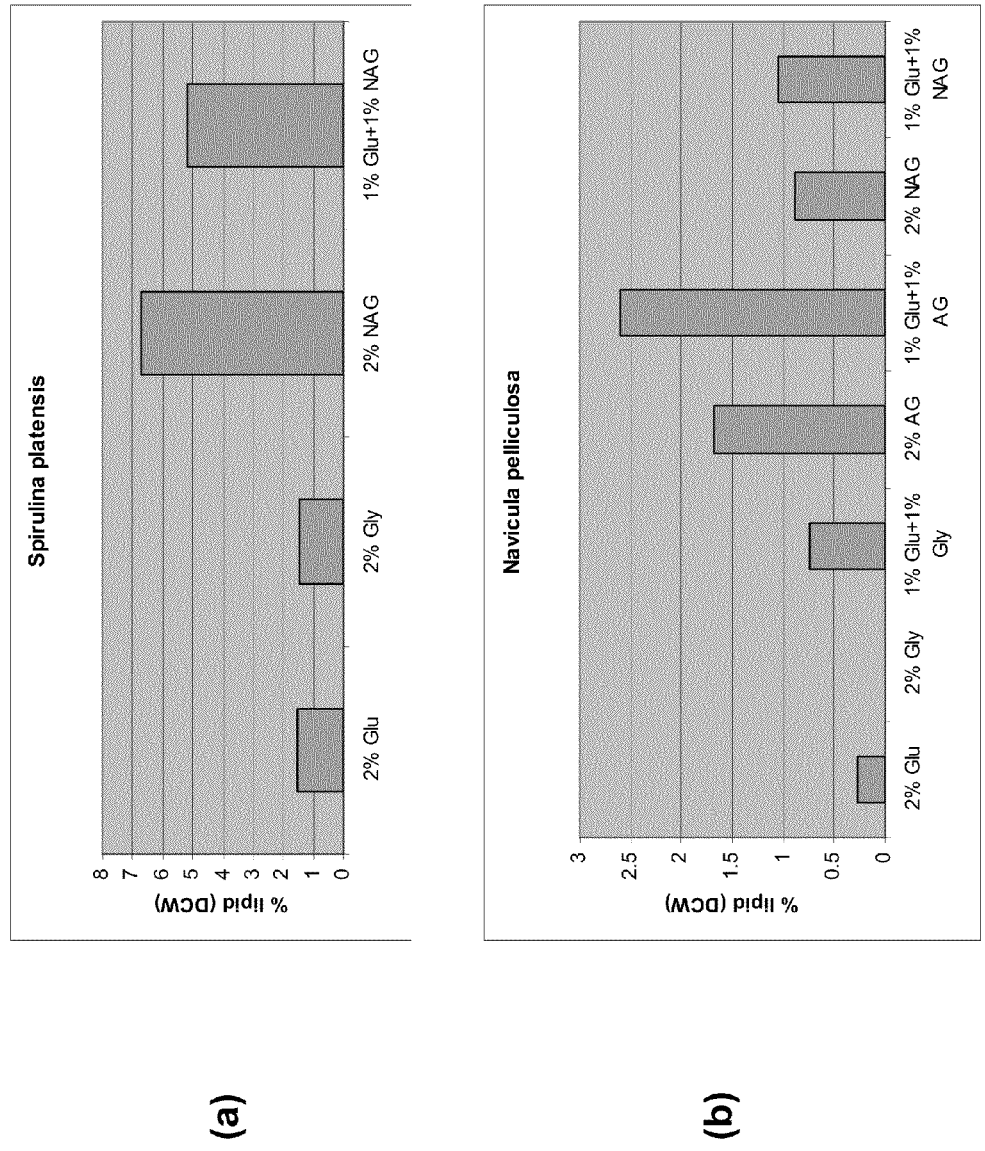
FIG. 11(*a*) shows lipid as a percent of DCW of *Spirulina platensis* when cultured in the presence of glucose, reagent grade glycerol, non-acidulated biodiesel byproduct glycerol, and a combination of glycerol and glucose.

FIGS. 5 and 6 demonstrate that multiple species of *Chlorella* and multiple strains within a species of *Chlorella* accumulate a higher percentage of DCW as lipid (Lipid as a Percentage of Cell Weight) when cultured in the presence of biodiesel glycerol byproduct than when cultured in the presence of equivalent concentrations of pure reagent grade glycerol. FIG. 11 demonstrates that both *Spirulina platensis* and *Navicula pelliculosa* can accumulate a higher percentage of DCW as lipid when cultured in the presence of biodiesel glycerol byproduct than when cultured in the presence of equivalent concentrations of pure reagent grade glycerol. FIG. 12(*a*) demonstrates that *Scenedesmus armatus* can accumulate a higher percentage of DCW as lipid when cultured in the presence of biodiesel glycerol byproduct than when cultured in the presence of equivalent concentrations of pure reagent grade glycerol.

Moreover, multiple species of microbes, including microalgae such as *Chlorella, Scenedesmus, Navicula,* and *Spirulina* exhibit better characteristics as biodiesel producers in the presence of mixtures of glycerol and glucose than in the presence of only glucose. Thus, FIG. 7 demonstrates that *Chlorella* can accumulate higher lipid levels (content) per liter of culture in the presence of 1% glycerol/1% glucose than in the presence of 2% glucose. FIG. 12(*b*) demonstrates that DCW per L of *Scenedesmus armatus* is higher when cultured in the presence of 1% biodiesel byproduct glycerol/1% glucose than in the presence of 2% glucose. FIG. 13 demonstrates that DCW per L of *Navicula pelliculosa* is higher when cultured in the presence of 1% biodiesel byproduct glycerol/1% glucose than in the presence of 2% glucose.

Figure 8:
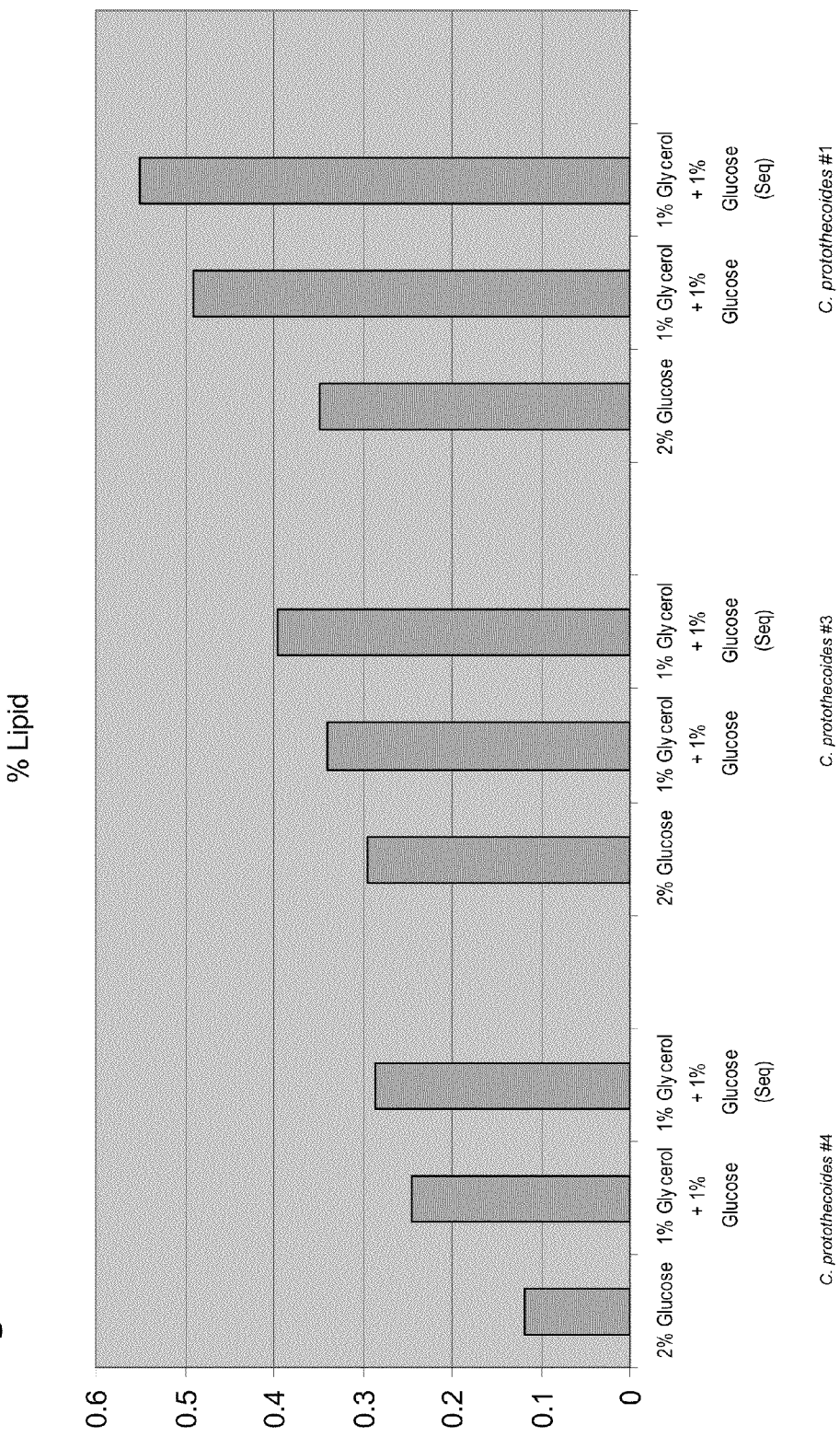
FIG. 8 shows lipid as a percent of DCW of multiple species and strains of *Chlorella* when cultured in the presence of glucose with and without reagent grade glycerol, wherein glycerol is added sequentially or in combination with glucose.

FIG. 8 demonstrates that *Chlorella* can accumulate a higher percentage of DCW as lipid when cultured in the presence of an equal concentration (weight percent) mixture of glycerol and glucose than when cultured in the presence of only glucose. FIG. 11(*a*) demonstrates that *Spirulina platensis* can accumulate a higher percentage of DCW as lipid when cultured in the presence of an equal concentration (weight percent) mixture of biodiesel byproduct glycerol and glucose than when cultured in the presence of only glucose. FIG. 11(*b*) demonstrates that *Navicula pelliculosa* can accumulate a higher percentage of DCW as lipid when cultured in the presence of an equal concentration (weight percent) mixture of reagent grade glycerol and glucose, as well as biodiesel byproduct glycerol and glucose, than when cultured in the presence of only glucose. FIG. 12(*b*) demonstrates that *Scenedesmus armatus* can accumulate a higher percentage of DCW as lipid when cultured in the presence of an equal concentration (weight percent) mixture of biodiesel byproduct glycerol and glucose than when cultured in the presence of only glucose. Such methods of increasing the lipid as a percentage of DCW are useful in generating biomass that yields a lower amount of heteroatoms in biodiesel than lower percentage lipid biomass when the biomass is subjected to direct transesterification.

It has further been discovered that, by adding glycerol and glucose to microbes, including microalgae such as *Chlorella, Scenedesmus,* and *Navicula* sequentially, rather than as a single batch mixture of glycerol and glucose, can generate additional yield gains. This attribute of multiple species of *Chlorella* and multiple strains within a species of *Chlorella* was tested in the presence of both biodiesel glycerol byproduct and reagent grade glycerol.

Figure 9:
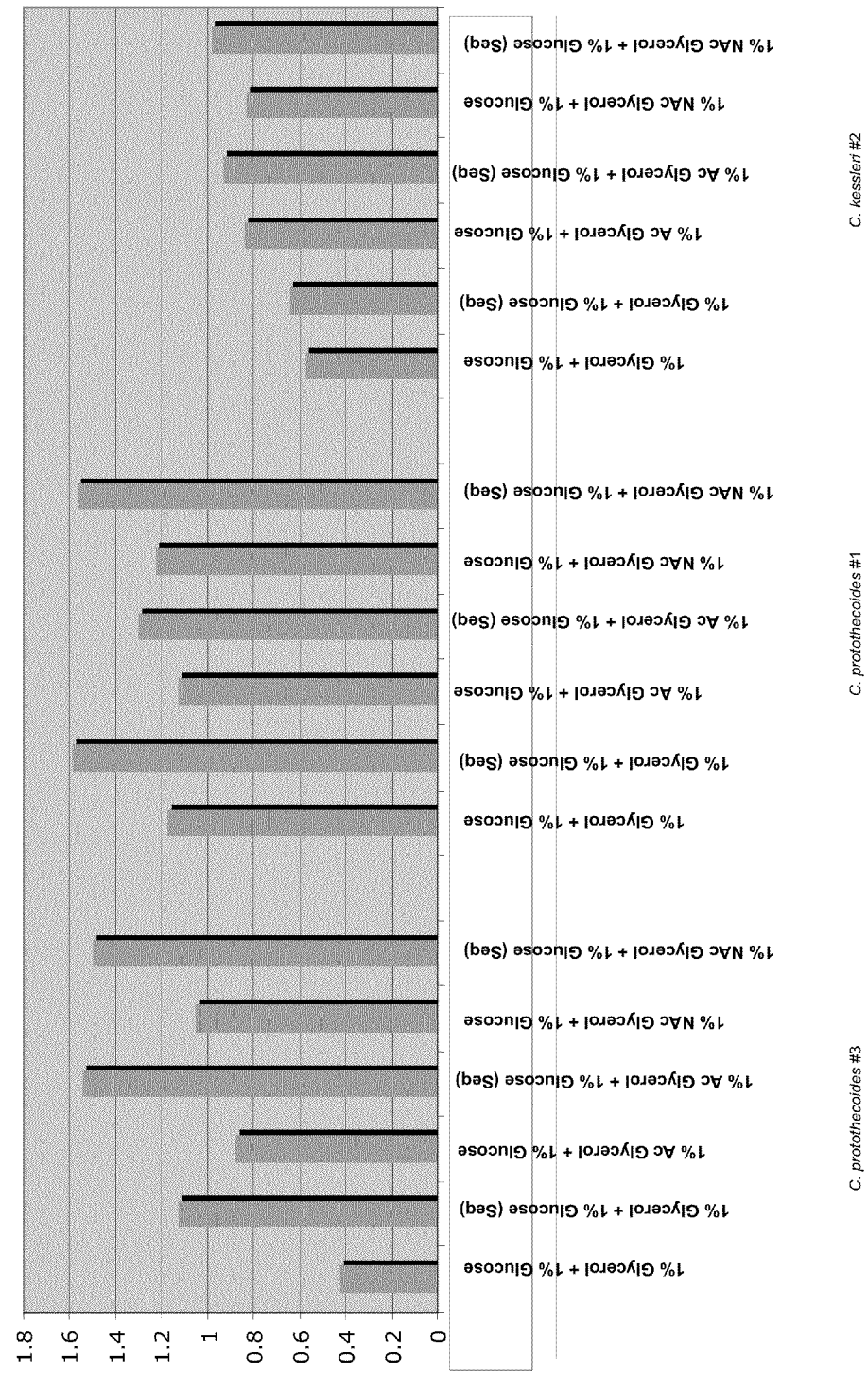
FIG. 9 shows relative lipid concentration of cultures of multiple species and strains of *Chlorella* when cultured in the presence of various types of glycerol with additional glucose, wherein glycerol is added sequentially or in combination with glucose.

Thus, FIG. 8 demonstrates that *Chlorella* can accumulate a higher percentage of DCW as lipid when glycerol is added to a culture for a first period of time, followed by addition of glucose and continued culturing for a second period of time, than when the same quantities of glycerol and glucose are added together at the beginning of the experiment. Such methods of increasing the lipid as a percentage of DCW are useful in generating biomass that yields a lower amount of heteroatoms in biodiesel or other products than lower percentage lipid biomass when the biomass is subjected to direct transesterification or other methods of chemical modification. FIG. 9 shows *Chlorella* exhibit higher lipid levels (content) per liter of culture when glycerol and glucose are added sequentially than when the same quantities of glycerol and glucose are added together at the beginning of the culture. This trend was observed when acidulated biodiesel byproduct glycerol, non-acidulated biodiesel byproduct glycerol, or reagent grade glycerol was used.

Figure 10:
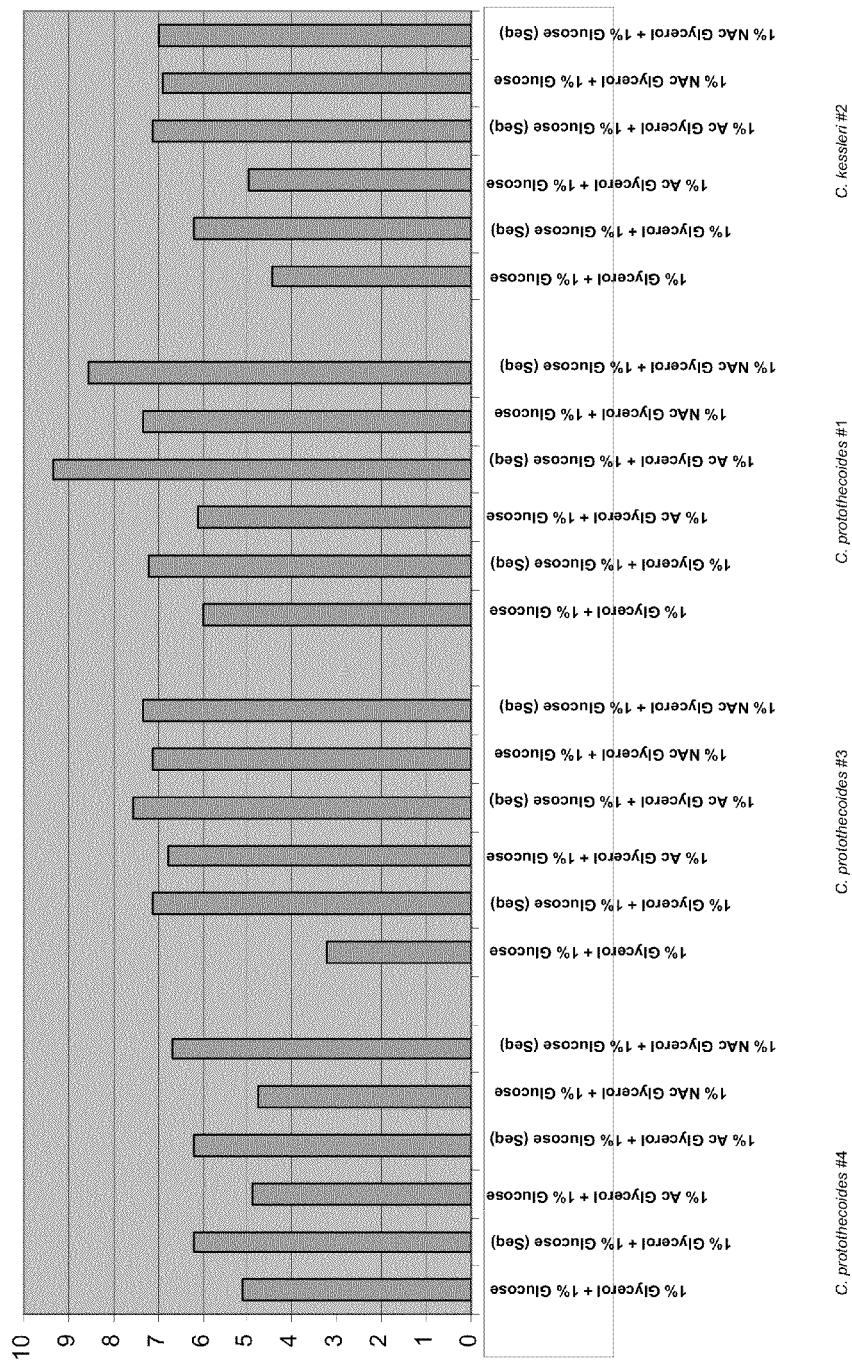
FIG. 10 shows DCW per liter of multiple species and strains of *Chlorella* when cultured in the presence of various types of glycerol with additional glucose, wherein glycerol is added sequentially or in combination with glucose.

FIG. 10 demonstrates four different strains of *Chlorella* of two different species accumulating higher DCW per L of culture when glycerol and glucose are added sequentially than when the same quantities of glycerol and glucose are added together at the beginning of the experiment. This trend was observed when acidulated biodiesel byproduct glycerol, non-acidulated biodiesel byproduct glycerol, or reagent grade glycerol was used. FIG. 14(a) and (b) demonstrate that both *Scenedesmus armatus* and *Navicula pelliculosa* can exhibit increases in DCW per L when biodiesel byproduct glycerol only is added to a culture for a first period of time, followed later by addition of glucose, compared to adding identical amounts of glycerol and glucose at the beginning of the fermentation.

Thus, three different markers of productivity (DCW per L, grams per L of lipid, and percentage of DCW as lipid) in microbial lipid production are improved by the use of biodiesel byproduct and temporal separation of carbon sources.

The cost of producing biodiesel or other chemically-modified lipids can also be reduced by using cellulosic biomass as a feedstock. Cellulosic biomass (e.g., stover, such as corn stover) is inexpensive and readily available; however, attempts to use this material as a feedstock for yeast have failed. In particular, such feedstocks have been found to be inhibitory to yeast growth, and yeast cannot use the 5-carbon sugars produced from cellulosic materials (e.g., xylose from hemi-cellulose). By contrast, microalgae can grow on processed cellulosic material. Accordingly, the invention provides a method of culturing a microalgae in the presence of a cellulosic material and/or a 5-carbon sugar for the production of lipids that can be transesterified according to the methods described herein. Cellulosic materials generally include cellulose (40-60% dry weight); hemicellulose (20-40% dry weight); and lignin (10-30% dry weight).

Figure 15:
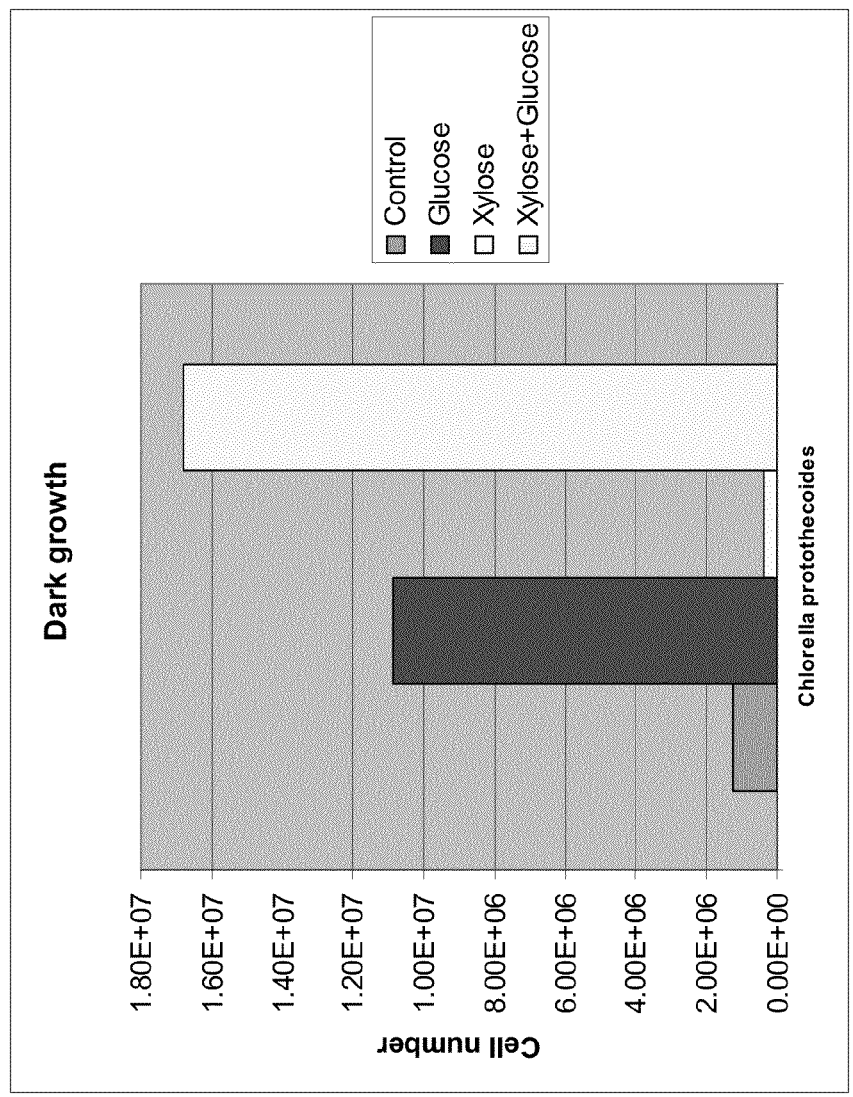
FIG. 15 shows a synergistic effect of a combination of xylose and glucose on growth of *Chlorella* compared to xylose or glucose alone.

Surprisingly, *Chlorella protothecoides* can exhibit higher levels of productivity when cultured on a combination of glucose and xylose than when cultured on either glucose or xylose alone. This synergistic effect provides a significant advantage in that it allows cultivation of *Chlorella* on combinations of xylose and glucose, such as cellulosic material, as shown in FIG. 15.

The specific examples of process conditions to increase the yield of lipids suitable for use as biodiesel and/or to reduce production cost can be used individually, as described above, or in combination. In addition, the invention includes the selection and/or genetic engineering of microbes, such as microalgae, to produce microbes that are even more suitable for use in the above-described methods. For example, the use of microbes having a greater ability to utilize any of the above-described feedstocks for increased proliferation and/or lipid production are within the scope of the methods of the invention.

The cost of producing biodiesel or other chemically-modified lipids can also be reduced by using sucrose as a feedstock, including sucrose produced, for example, from sugar cane. The methods of the invention include the use of engineered species of *Chlorella* that can utilize sucrose as a carbon source. For example, expression of a sucrose transporter and a sucrose invertase allows *Chlorella* to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters include those described under Genbank accession numbers CAD91334, CAB92307, and CAA53390. Examples of suitable sucrose invertases include those described under Genbank accession numbers CAB95010, NP_012104 and CAA06839. Examples of suitable fructokinases include those described under Genbank accession numbers P26984, P26420 and CAA43322. Vectors for transformation of microalgae, including *Chlorella*, encoding one or more of such genes can be designed as described in, for example, international publication number WO2008/151149.

Secretion of a sucrose invertase can obviate the need for expression of a transporter that can transport sucrose into the cell. This is because a secreted invertase catalyzes the conversion of a molecule of sucrose into a molecule of glucose and a molecule of fructose, both of which can be transported and utilized by microbes disclosed herein. Expression of a sucrose invertase with a secretion signal generates invertase activity outside the cell. See Hawkins et al., *Current Microbiology* Vol. 38 (1999), pp. 335-341, for examples of secretion signals active in *Chlorella*. Expression of such a protein allows cells already capable of utilizing extracellular glucose as an energy source to utilize sucrose as an extracellular energy source. In cells such as *Chlorella protothecoides*, which as demonstrated herein can use both extracellular fructose and extracellular glucose as an energy source, secretion of an invertase can provide the sole catalytic activity necessary for use of sucrose as an efficient, inexpensive energy source.

Figure 19:
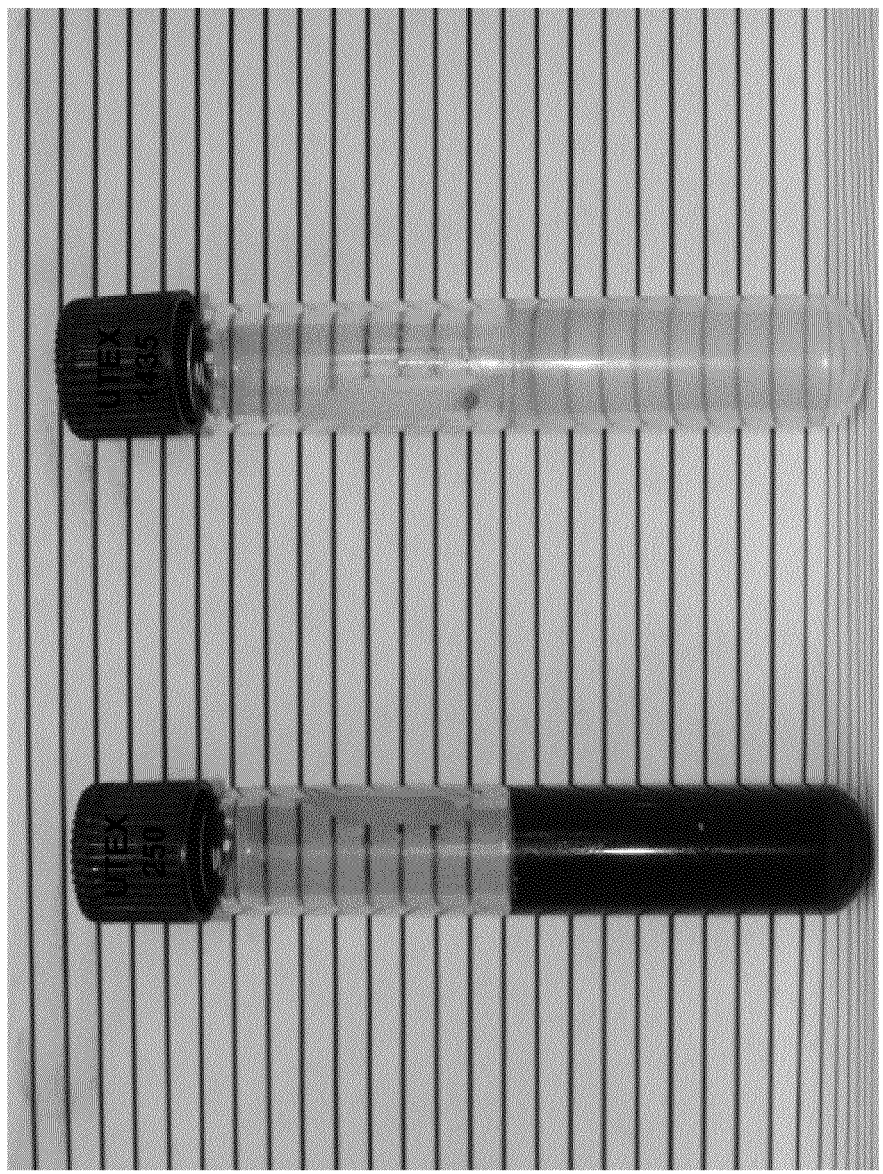
FIG. 19 shows a visual comparison of oil that was hexane extracted from strain UTEX 1435 compared to oil extracted from UTEX 250.
Figure 20:
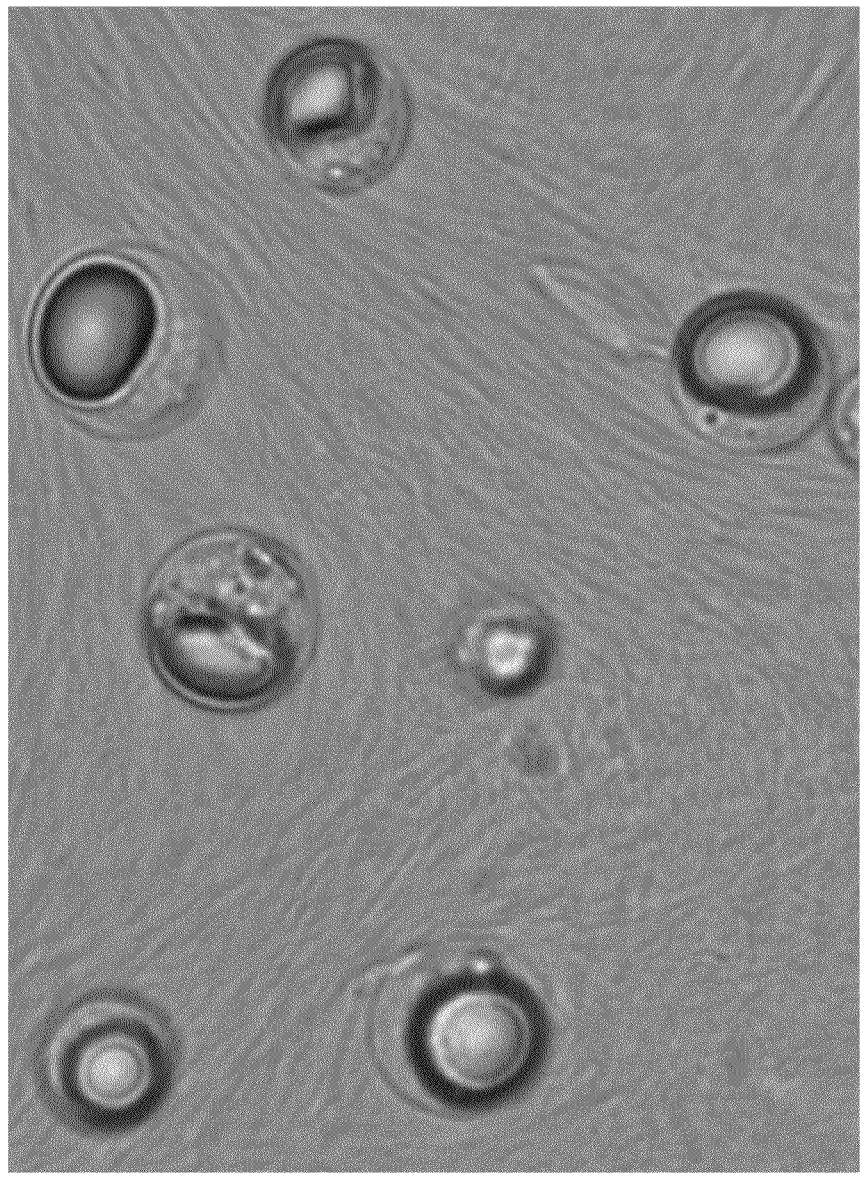
FIG. 20 shows high oil algae cells embedded in soap.

The growth potential of microorganisms expressing an exogenous secretable sucrose invertase is illustrated by the addition of an invertase to the culture medium of *Chlorella protothecoides*. Addition of the invertase permits cells to be fermented on a sugar source containing lignin (e.g., molasses). Algae or other microorganisms can be engineered as described herein to grow as well on molasses as they do on pure glucose, and the use of this low-value waste product of sugar cane processing can provide significant cost savings in the production of hydrocarbons. FIGS. 19-20 show the growth of cells on three sources of molasses (designated BS1, BS2 and HTM), as compared to growth on glucose or sucrose in the presence or absence of an extracellular sucrose invertase.

A sucrose invertase can also be expressed intracellularly in cells that express a sucrose transporter, as well as in cells that express any carbohydrate transporter that allows sucrose to enter the cell.

B. Lipid Pathway Engineering

As described herein, microorganisms useful in accordance with the methods of the present invention can optionally be engineered to express particular genes that can be beneficial in culturing the microorganisms (e.g., expression of a sucrose invertase gene to facilitate the utilization of a sucrose feedstock) or in performing the direct chemical modification methods of the invention (e.g., expression of a lytic gene to facilitate biomass disruption, and/or expression of a lipase gene to catalyze transesterification). In addition, optional genetic engineering can be used advantageously to engineer a microorganism's lipid pathway. This pathway can be modified to alter the properties and/or proportions of lipids produced and/or to increase carbon flux into lipids.

1. Alteration of Properties and/or Proportions of Lipids Produced

In the case of microalgae, some wild-type cells already have good growth characteristics but do not produce the desired types or quantities of lipids. Examples include *Pyrobotrys, Phormidium, Agmenellum, Carteria, Lepocinclis, Pyrobotrys, Nitzschia, Lepocinclis, Anabaena, Euglena, Spirogyra, Chlorococcum, Tetraedron, Oscillatoria, Phagus*, and *Chlorogonium*, which have the desirable growth characteristic of growing in municipal sewage or wastewater. Such cells can be engineered to have improved lipid production characteristics. Desired characteristics include optimizing lipid yield per unit volume and/or per unit time, carbon chain length (e.g., for biodiesel production or for industrial applications requiring hydrocarbon feedstock), reducing the number of double or triple bonds, optionally to zero, removing or eliminating rings and cyclic structures, and increasing the hydrogen:carbon ratio of a particular species of lipid or of a population of distinct lipids. In addition, microalgae that produce desirable lipids can also be engineered to have even more advantageous outputs. Examples of such microalgae include species of the genus *Chlorella*.

In particular embodiments, one or more key enzymes that control branch points in metabolism to fatty acid synthesis can be up-regulated or down-regulated to improve lipid production. Up-regulation can be achieved, for example, by transforming cells with expression constructs in which a gene encoding the enzyme of interest is expressed, e.g., using a strong promoter and/or enhancer elements that increase transcription. Such constructs can include a selectable marker such that the transformants can be subjected to selection, which can result in amplification of the construct and an increase in the expression level of the encoded enzyme. Examples of enzymes suitable for up-regulation according to the methods of the invention include pyruvate dehydrogenase, which plays a role in converting pyruvate to acetyl-CoA (examples, some from microalgae, include those described under Genbank accession numbers NP_415392; AAA53047; Q1XDM1; and CAF05587). Up-regulation of pyruvate dehydrogenase can increase production of acetyl-CoA, and thereby increase fatty acid synthesis. Acetyl-CoA carboxylase catalyzes the initial step in fatty acid synthesis. Accordingly, this enzyme can be up-regulated to increase production of fatty acids (examples, some from microalgae, include those described under Genbank accession numbers BAA94752; AAA75528; AAA81471; YP_537052; YP_536879; NP_045833; and BAA57908). Fatty acid production can also be increased by up-regulation of acyl carrier protein (ACP), which carries the growing acyl chains during fatty acid synthesis (examples, some from microalgae, include those described under Genbank accession numbers A0T0F8; P51280; NP_849041; YP_874433). Glycerol-3-phosphate acyltransferase catalyzes the rate-limiting step of fatty acid synthesis. Up-regulation of this enzyme can increase fatty acid production (examples, some from microalgae, include those described under Genbank accession numbers AAA74319; AAA33122; AAA37647; P44857; and ABO94442). The preceding proteins are candidates for expression in microalge, including species of the genus *Chlorella*.

Down-regulation of an enzyme of interest can achieved using, e.g., antisense, catalytic RNA/DNA, RNA interference (RNA$_i$), "knock-out," "knock-down," or other mutagenesis techniques. Enzyme expression/function can also be inhibited using intrabodies. Examples of enzymes suitable for down-regulation according to the methods of the invention include citrate synthase, which consumes acetyl-CoA as part of the tricarboxylic acid (TCA) cycle. Down-regulation of citrate synthase can force more acetyl-CoA into the fatty acid synthetic pathway.

Global regulators modulate the expression of the genes of the fatty acid biosynthetic pathways. Accordingly, one or more global regulators of fatty acid synthesis can be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples, see Genbank those described under accession numbers NP_035610 and Q9WTN3). Global regulators can be up- or down-regulated, as described above with respect to regulation of control point enzymes.

The methods of the invention can also be practiced using microbes (e.g., microalgae, oleaginous yeast, bacteri or fungi) that have been genetically engineered to express one or more exogenous genes encoding lipid pathway enzymes such as, for example, a fatty acyl-ACP thioesterase (see examples in Table 4 with accession numbers) or an acyl carrier protein (ACP), which can failitate the cleavage of fatty acids having desirable carbon chain lengths from the acyl carrier protein during lipid synthesis. The fatty acyl-ACP thioesterase can be chosen based on its specificity for a fatty acid having a particular carbon chain length. In some embodiments, the fatty acyl-ACP thioesterase can be expressed from a gene operably linked to an inducible promoter, and/or can be expressed in an intracellular compartment. In some embodiments, genes encoding a fatty acyl-ACP thioesterase and a naturally co-expressed ACP may be transformed into a cell, optionally with one or more genes encoding other lipid pathway enzymes, as described above. In other embodiments, the ACP and the fatty acyl-ACP thioesterase may have an affinity for one another that imparts an advantage when the two are used together in the microbes and methods of the present invention, irrespective of whether they are or are not naturally co-expressed in a particular tissue or organism. Thus, the methods of the present invention can be practiced with cells expressing both naturally co-expressed pairs of such enzymes as well as with pairs that share an affinity for interacting with one another to facilitate cleavage of a length-specific carbon chain from the ACP.

Examples of further modifications suitable for use in the present invention are described in now abandoned U.S. Provisional Application No. 60/837,839, filed 15 Aug. 2006, and U.S. patent application Ser. No. 11/893,364, filed 15 Aug. 2007, each of which is incorporated herein by reference. This application discloses genetically engineering strains of microalgae to express two or more exogenous genes, one encoding a transporter of a fixed carbon source (such as sucrose) and a second encoding a sucrose invertase enzyme. The resulting fermentable organisms produce lipids at lower manufacturing cost than what has been obtainable by previously known methods of production. This co-pending application also teaches that the insertion of the two exogenous genes described above can be combined with the disruption of polysaccharide biosynthesis through directed and/or random mutagenesis, which steers ever greater carbon flux into lipid production. Individually and in combination, trophic conversion, engineering to alter lipid production and treatment with exogenous enzymes alter the lipid composition produced by a microorganism. The alteration can be a change in the amount of lipids produced, the amount of one or more lipid species produced relative to other lipids, and/or the types of lipid species produced in the microorganism. For example, microalgae can be engineered to produce a higher amount and/or percentage of TAGs, or TAGs with higher proportions of particular carbon length fatty acid molecules.

Fatty acyl-ACP thioesterases suitable for use with the microbes and methods of the invention include, without limitation, those listed in Table 4.

TABLE 4

Fatty acyl-ACP thioesterases and GenBank accession numbers.

*Umbellularia californica* fatty acyl-ACP thioesterase (GenBank #AAC49001)
*Cinnamomum camphora* fatty acyl-ACP thioesterase (GenBank #Q39473)
*Umbellularia californica* fatty acyl-ACP thioesterase (GenBank #Q41635)
*Myristica fragrans* fatty acyl-ACP thioesterase (GenBank #AAB71729)
*Myristica fragrans* fatty acyl-ACP thioesterase (GenBank #AAB71730)
*Elaeis guineensis* fatty acyl-ACP thioesterase (GenBank #ABD83939)
*Elaeis guineensis* fatty acyl-ACP thioesterase (GenBank #AAD42220)
*Populus tomentosa* fatty acyl-ACP thioesterase (GenBank #ABC47311)
*Arabidopsis thaliana* fatty acyl-ACP thioesterase (GenBank #NP_172327)
*Arabidopsis thaliana* fatty acyl-ACP thioesterase (GenBank #CAA85387)
*Arabidopsis thaliana* fatty acyl-ACP thioesterase (GenBank #CAA85388)
*Gossypium hirsutum* fatty acyl-ACP thioesterase (GenBank #Q9SQI3)
*Cuphea lanceolata* fatty acyl-ACP thioesterase (GenBank #CAA54060)
*Cuphea hookeriana* fatty acyl-ACP thioesterase (GenBank #AAC72882)
*Cuphea calophylla* subsp. *mesostemon* fatty acyl-ACP thioesterase (GenBank #ABB71581)
*Cuphea lanceolata* fatty acyl-ACP thioesterase (GenBank #CAC19933)
*Elaeis guineensis* fatty acyl-ACP thioesterase (GenBank #AAL15645)
*Cuphea hookeriana* fatty acyl-ACP thioesterase (GenBank #Q39513)
*Gossypium hirsutum* fatty acyl-ACP thioesterase (GenBank #AAD01982)
*Vitis vinifera* fatty acyl-ACP thioesterase (GenBank #CAN81819)
*Garcinia mangostana* fatty acyl-ACP thioesterase (GenBank #AAB51525)
*Brassica juncea* fatty acyl-ACP thioesterase (GenBank #ABI18986)
*Madhuca longifolia* fatty acyl-ACP thioesterase (GenBank #AAX51637)
*Brassica napus* fatty acyl-ACP thioesterase (GenBank #ABH11710)
*Oryza sativa* (*indica* cultivar-group) fatty acyl-ACP thioesterase (GenBank #EAY86877)
*Oryza sativa* (*japonica* cultivar-group) fatty acyl-ACP thioesterase (GenBank #NP_001068400)
*Oryza sativa* (*indica* cultivar-group) fatty acyl-ACP thioesterase (GenBank #EAY99617)
*Cuphea hookeriana* fatty acyl-ACP thioesterase (GenBank #AAC49269)

Other suitable enzymes for use with the microbes and the methods of the invention include those that have at least 70% amino acid identity with one of the proteins listed in Table 4, and that exhibit the corresponding desired enzymatic activity (i.e., cleavage of a fatty acid from an acyl carrier protein. In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference.

The lipid pathway enzymes described above are useful in the production of various lipids from a microbe (e.g., a microalgae, an oleaginous yeast, or a fungus) or population of microbes, whereby a fatty acyl-ACP thioesterase cleaves a fatty acid from an acyl carrier protein (ACP) during lipid synthesis. These lipid pathway enzymes can have a specificity for acting on a substrate which includes a specific number of carbon atoms. For example, a fatty acyl-ACP thioesterase may have a specificity for cleaving a fatty acid having 16 carbon atoms from the ACP. Therefore, in various embodiments, the microbe can contain an exogenous gene that encodes a protein with specificity for catalyzing an enzymatic activity (e.g., cleavage of a fatty acid from an ACP) with regard to the number of carbon atoms contained in the substrate. The enzymatic specificity can, in various embodiments, be for a substrate having from 8 to 34 carbon atoms, preferably from 8 to 18 carbon atoms, and more preferably from 14 to 18 carbon atoms.

By selecting the desired combination of exogenous genes to be expressed, one can tailor the lipid components generated by the microbe. The microbe, when cultured as described above, synthesizes a fatty acid linked to an ACP and the fatty acyl-ACP thioesterase catalyzes the cleavage of the fatty acid from the ACP to yield, through further enzymatic processing, a TAG incorporating the fatty acid molecule.

2. Increased Carbon Flux into Lipid Pathway

Some microalgae produce significant quantities of non-lipid metabolites, such as, for example, polysaccharides. Because polysaccharide biosynthesis can use a significant proportion of the total metabolic energy available to cells, mutagenesis of lipid-producing cells followed by screening for reduced or eliminated polysaccharide production generates strains that are capable of producing higher yields of lipids.

Examples of expression of transgenes in *Chlorella* can be found in the literature (see, for example, *Current Microbiology* Vol. 35 (1997), pp. 356-362; Sheng Wu Gong Cheng Xue Bao. 2000 July; 16(4):443-6; *Current Microbiology* Vol. 38 (1999), pp. 335-341; *Appl Microbiol Biotechnol* (2006) 72: 197-205; *Marine Biotechnology* 4, 63-73, 2002; *Current Genetics* 39:5, 365-370 (2001); *Plant Cell Reports* 18:9, 778-780, (1999); *Biologia Plantarium* 42(2): 209-216, (1999); *Plant Pathol. J* 21(1): 13-20, (2005)). Any convenient technique for introducing a transgene into *Chorella* can be employed for purposes of the present invention.

Examples of expression of transgenes in oleaginous yeast (e.g., *Yarrowia lipolytica*) can be found in the literature (see, for example, Bordes et al., *J Microbiol Methods*, June 27 (2007)). Examples of expression of transgenes in fungi (e.g., *Mortierella alpine*, *Mucor circinelloides*, and *Aspergillus ochraceus*) can also be found in the literature (see, for example, *Microbiology*, July; 153(Pt. 7):2013-25 (2007); *Mol Genet Genomics*, June; 271(5):595-602 (2004); *Curr Genet*, March; 21(3):215-23 (1992); *Current Microbiology*, 30(2):83-86 (1995); Sakuradani, NISR Research Grant, "Studies of Metabolic Engineering of Useful Lipid-producing Microorganisms" (2004); and PCT/JP2004/012021). Examples of expression of exogenous genes in bacteria such as *E. coli* are well known; see, for example, Molecular Cloning: A Laboratory Manual, Sambrook et al. (3d edition, 2001, Cold Spring Harbor Press.

IV. Methods of In Situ Transesterification

In situ transesterification of TAGs to fatty acid alkyl esters in accordance with the methods of the present invention can be performed on biomass generated from the microbial cultures described above. In some embodiments, the biomass may comprise biomass combined from two or more cultures of distinct strains or species of microorganisms. In some embodiments, the distinct stains or species have different glycerolipid profiles, as illustrated in Examples 22 and 24.

In some methods of the invention, the microbial biomass is first harvested from the culture medium and dried, and then subjected to an optional biomass disruption process prior to transesterification. In other methods of the invention, the microbial biomass is subjected to a biomass disruption process prior to drying and transesterification. In some methods, harvesting the biomass comprises separating the cellular components of the biomass from the water and cell culture media by, for example, passing the contents of the cell culture bioreactor through a screen or similar filtering apparatus. In some embodiments, harvesting the biomass comprises processing the cellular components of the cell culture into a paste or low moisture-content composition.

A. Drying Methods

Drying the biomass generated from the cultured microorganisms described herein removes water that would otherwise be available as a substrate during the transesterification reaction, described in greater detail below, leading to the formation of free fatty acids, rather than the desired fatty acid alkyl esters. The extent to which biomass used in the in situ transesterification methods of the present invention must be dried depends on the alcohol:biomass ratio used in the transesterification process, the cost of the alcohol, and the cost or other volume constraints placed on the size of the reaction vessel in which the transesterfication is to be performed. As will be appreciated, these factors, balanced against the costs of drying the biomass, determine an "acceptable dryness" for the biomass.

In some embodiments, the biomass can be dried using a drum dryer in which the biomass is rotated in a drum and dried with the application of air, which may be heated to expedite the drying process. In other embodiments, an oven or spray dryer can be used to facilitate drying of the biomass. Alternatively, the biomass may be dried via a lyophilization process. The lyophilization process may summarily be described as a "freeze-drying" process, in which the biomass is frozen in a freeze-drying chamber. The application of a vacuum to the freeze-drying chamber results in sublimation (primary drying) and desorption (secondary drying) of the water from the biomass, resulting in a product suitable for further processing as described below. In still other embodiments a combination of the foregoing may be utilized to appropriately dry the biomass for further processing in accordance with the methods described herein.

B. Biomass Disruption Methods

In some embodiments it may be desirable to disrupt the biomass prior to in situ transesterification to make the intracellular contents of the microorganisms more readily accessible to the alcohol and catalyst transesterification reagents. This can help to facilitate the conversion of TAGs to fatty acid alkyl esters or other molecules in accordance with the methods of the invention.

In some methods of the invention, disruption of the biomass can be accomplished prior to subjecting the biomass to one or more of the drying processes described above. In other methods, disruption of the biomass can follow such a drying process. In some methods, water is removed from the biomass prior to or after disruption of the biomass, with or without subjecting the biomass to a drying process. Following growth, the microorganisms are optionally isolated by centrifuging the culture medium to generate a concentrated microbial biomass. Disruption of the biomass can be accomplished by lysing the microbial cells to produce a lysate. Cell lysis can be achieved by any convenient means including heat-induced lysis, addition of a base, addition of an acid, via the use of enzymes such as proteases or polysaccharide degradation enzymes such as amylases, via the use of ultrasound, mechanical lysis, via the use of osmotic shock, infection with a lytic virus, and/or expression of one or more lytic genes.

Lysis is performed to release intracellular molecules which have been produced by the microorganism. Each of these methods for lysing a microorganism can be used as a single method or in combination.

The extent of cell disruption can be observed by microscopic analysis. Using one or more of the methods described herein, typically more than 70% cell breakage is observed. Preferably, cell breakage is more than 80%, more preferably more than 90% and most preferably about 100%.

In particular embodiments, the microorganism is lysed after growth, for example to increase the exposure of cellular lipid to a catalyst for transesterification such as a lipase or a chemical catalyst, expressed as described below. The timing of lipase expression (e.g., via an inducible promoter), cell lysis, and the adjustment of transesterification reaction conditions (e.g., removal of water, addition of alcohol, etc.) can be adjusted to optimize the yield of fatty acid esters from lipase-mediated transesterification.

In one embodiment of the present invention, the process of lysing a microorganism comprises heating a cellular suspension containing the microorganisms. In this embodiment, the culture medium containing the microorganisms (or a suspension of microorganisms isolated from the culture medium) is heated until the microorganisms, i.e., the cell walls and membranes of microorganisms, degrade or breakdown. Typically, temperatures applied are at least 50° C. Higher temperatures, such as, at least 60° C., at least 70° C., at least 80° C., at least 90° C., at least 100° C., at least 110° C., at least 120° C., at least 130° C. or higher are used for more efficient cell lysis.

In another embodiment of the present invention, the process of lysing a microorganism comprises adding a base to a cellular suspension containing the microorganism. The base should be strong enough to hydrolyze at least a portion of the proteinaceous compounds of the microorganisms used. Bases which are useful for solubilizing proteins are known in the art of chemistry. Exemplary bases which are useful in these methods include, but are not limited to, hydroxides, carbonates and bicarbonates of lithium, sodium, potassium, calcium, and mixtures thereof. A preferred base is KOH. In another embodiment of the present invention, the process of lysing a microorganism comprises adding an acid to a cellular suspension containing the microorganism.

In another embodiment of the present invention, the process of lysing a microorganism comprises lysing the microorganism with an enzyme. Enzymes for lysing a microorganism include proteases and polysaccharide-degrading enzymes such as hemicellulase, pectinase, cellulase, and driselase. A polysaccharide-degrading enzyme, optionally from *Chlorella* or a *Chlorella* virus, is preferred. A preferred pair of enzymes for lysing oil bearing biomass are alcalase and mannaway (Novozymes).

In another embodiment of the present invention, the process of lysing a microorganism is performed using ultrasound, i.e., sonication. Cells can also by lysed with high frequency sound. The sound can be produced electronically and transported through a metallic tip to an appropriately concentrated cellular suspension. This sonication (or ultrasonication) disrupts cellular integrity based on the creation of cavities in the cell suspension.

In another embodiment of the present invention, the process of lysing a microorganism is performed by mechanical means. Cells can be lysed mechanically and optionally homogenized to facilitate lipid transesterification. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules. Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (e.g., with a high speed or Waring blender), the french press, or even centrifugation in case of weak cell walls.

In another embodiment of the present invention, the process of lysing a microorganism is performed by applying an osmotic shock.

In another embodiment of the present invention, the process of lysing a microorganism is performed by steam treatment, i.e., through addition of pressurized steam. Steam treatment of microalgae for cell disruption is described, for example, in U.S. Pat. No. 6,750,048.

In another embodiment of the present invention, the process of lysing a microorganism comprises infection of the microorganism with a lytic virus. A wide variety of viruses are known to lyse microorganisms suitable for use in the methods of the present invention, and the selection and use of a particular lytic virus for a particular microorganism is within the level of skill in the art. For example, *paramecium bursaria chlorella* virus (PBCV-1) is the prototype of a group (family Phycodnaviridae, genus *Chlorovirus*) of large, icosahedral, plaque-forming, double-stranded DNA viruses that replicate in, and lyse, certain unicellular, eukaryotic *chlorella*-like green algae. Accordingly, any susceptible microalgae, such as *C. protothecoides*, can be lysed by infecting the culture with a suitable *chlorella* virus. Methods of infecting species of *Chlorella* with a *chlorella* virus are known. See for example *Adv. Virus Res.* 2006; 66:293-336; *Virology*, 1999 Apr. 25; 257(1):15-23; *Virology*, 2004 Jan. 5; 318(1):214-23; *Nucleic Acids Symp. Ser.* 2000; (44):161-2; *J. Virol.* 2006 March; 80(5):2437-44; and *Annu. Rev. Microbiol.* 1999; 53:447-94.

In another embodiment of the present invention, the process of lysing a microorganism comprises autolysis. In this embodiment, a microorganism useful in the methods of the invention is genetically engineered to produce a lytic gene that will lyse the microorganism. This lytic gene can be expressed using an inducible promoter, so that the cells can first be grown to a desirable density in a culture medium and then harvested, followed by induction of the promoter to express the lytic gene to lyse the cells. In one embodiment, the lytic gene encodes a polysaccharide-degrading enzyme. In certain other embodiments, the lytic gene is a gene from a lytic virus. Thus, for example, a lytic gene from a *Chlorella* virus can be expressed in a *Chlorella* such as *C. protothecoides*.

Expression of lytic genes is preferably done using an inducible promoter, such as a promoter active in microalgae that is induced by a stimulus such as the presence of a small molecule, light, heat, and other stimuli. Lytic genes from *chlorella* viruses are known. For example, see *Virology* 260, 308-315 (1999); *FEMS Microbiology Letters* 180 (1999) 45-53; *Virology* 263, 376-387 (1999); and *Virology* 230, 361-368 (1997).

In particular embodiments, the microorganisms are lysed after growth, for example to increase the exposure of cellular lipid to a catalyst for transesterification such as a lipase, discussed below, or a chemical catalyst. The timing of lipase expression (e.g., via an inducible promoter), cell lysis, and the modification of transesterification reaction conditions (e.g., removal of water, addition of alcohol, etc.) can be adjusted to optimize the yield of fatty acid esters from lipase-mediated transesterification.

C. Transesterification

Lipids produced by microorganisms as described above are subjected to a process of transesterification in accordance with the methods of the invention to generate a lipophilic phase containing fatty acid alkyl esters and a hydrophilic phase comprising cell material and glycerol. In some methods of the invention, the lipophilic phase is then separated from the hydrophilic cell material.

1. General Chemical Process

Animal and plant oils are typically made of triacylglycerols (TAGs), which are esters of free fatty acids with the trihydric alcohol, glycerol. In transesterification, the glycerol in a TAG is replaced with a lower alkyl alcohol such as methanol, ethanol or isopropanol. A typical reaction scheme is as follows:

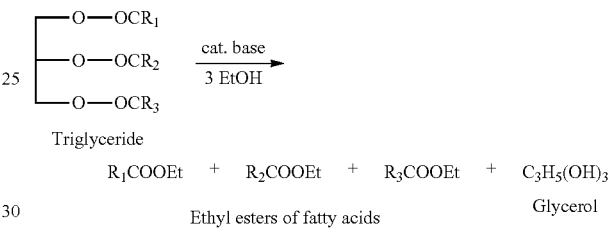

In this scheme, the alcohol is deprotonated with a base to make it a stronger nucleophile. Commonly, ethanol or methanol is used in vast excess (up to 50-fold). Normally, this reaction will proceed either exceedingly slowly or not at all. Heat, as well as an acid or base, can be used to help speed the reaction. The acid or base is not consumed by the transesterification reaction; thus, they are not reactants but catalysts. Almost all biodiesel has traditionally been produced using the base-catalyzed technique, as it requires only low temperatures and pressures and produces over 98% conversion yield (provided the starting oil is low in moisture and free fatty acids).

A special case of transesterification is glycerolysis or the use of glycerol(glycerin) to break chemical bonds. The glycerolysis reaction is usually catalyzed by the addition of an acid or a base. Glycerolysis can be performed on simple esters, fats, free fatty acids or TAGs, wherein the methyl esters react with excess glycerol to form mono- and/or diglycerides, producing methanol as a by-product. Mono- and diglycerides are useful as emulsifiers and are commonly added to food products.

2. Using Recombinant Lipases for Transesterification

Transesterification has also been carried out experimentally using an enzyme, such as a lipase, instead of a base. Lipase-catalyzed transesterification can be carried out, for example, at a temperature between the room temperature and 80° C., and a molar ratio of the TAG to the lower alcohol of greater than 1:1, preferably about 3:1. Lipases suitable for use in transesterification in accordance with the methods of the present invention include, but are not limited to, those listed in Table 5. Other examples of lipases useful for transesterification are found in, e.g. U.S. Pat. Nos. 4,798,793; 4,940,845 5,156,963; 5,342,768; 5,776,741 and WO89/01032, each of which is incorporated herein by reference.

TABLE 5

Lipases for use in transesterification.

*Aspergillus niger* lipase ABG73614, *Candida antarctica* lipase B (novozym-435) CAA83122, *Candida cylindracea* lipase AAR24090, *Candida lipolytica* lipase (Lipase L; Amano Pharmaceutical Co., Ltd.), *Candida rugosa* lipase (e.g., Lipase-OF; Meito Sangyo Co., Ltd.), *Mucor miehei* lipase (Lipozyme IM 20), *Pseudomonas fluorescens* lipase AAA25882, *Rhizopus japonicas* lipase (Lilipase A-10FG) Q7M4U7_1, *Rhizomucor miehei* lipase B34959, *Rhizopus oryzae* lipase (Lipase F) AAF32408, *Serratia marcescens* lipase (SM Enzyme) ABI13521, *Thermomyces lanuginosa* lipase CAB58509, Lipase P (Nagase ChemteX Corporation), and Lipase QLM (Meito Sangyo Co., Ltd., Nagoya, Japan)

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost. Immobilized lipases are subject to poisoning by the lower alcohols typically used in transesterification. U.S. Pat. No. 6,398,707 (issued Jun. 4, 2002 to Wu et al.), incorporated herein by reference, describes methods for enhancing the activity of immobilized lipases and regenerating immobilized lipases having reduced activity.

In particular embodiments, a recombinant lipase is expressed in the same microorganisms that produce the lipid on which the lipase acts. Suitable recombinant lipases include those listed above in Table 5 and/or those described under the GenBank Accession numbers listed above in Table 5, or a polypeptide that has at least 70% amino acid identity with one of the lipases listed above in Table 5 and that exhibits lipase activity. In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference.

An exemplary vector design for expression of a lipase gene in a microorganism such as a microalgae contains a gene encoding a lipase in operable linkage with a promoter active in microalgae. Alternatively, if the vector does not contain a promoter in operable linkage with the lipase gene, the lipase gene can be transformed into the cells such that it becomes operably linked to an endogenous promoter at the point of vector integration. The promoterless method of transformation has been demonstrated in microalgae (see, for example, *Plant Journal* 14:4, (1998), pp. 441-447). The vector can also contain a second gene that encodes a protein that imparts resistance to an antibiotic or herbicide, i.e., a selectable marker. Optionally, one or both gene(s) is/are followed by a 3' untranslated sequence containing a polyadenylation signal. Expression cassettes encoding the two genes can be physically linked in the vector or on separate vectors. Co-transformation of microalgae can also be used, in which distinct vector molecules are simultaneously used to transform cells (see, for example, *Protist* 2004 December; 155(4):381-93). The transformed cells can be optionally selected based upon the ability to grow in the presence of the antibiotic or other selectable marker under conditions in which cells lacking the resistance cassette would not grow. DNA encoding the lipase and selectable marker can be codon-optimized cDNA. Methods of recoding genes for expression in microalgae are described in U.S. Pat. No. 7,135,290. Additional information is available at the web address www.kazusa.or.jp/codon.

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Exogenous and/or endogenous promoters that are active in microalgae, and antibiotic resistance genes functional in microalgae are known in the art. The promoter used to express an exogenous gene can be the promoter naturally linked to that gene or can be a heterologous gene. Some promoters are active in more than one species of microalgae. Other promoters are species-specific. Preferred promoters include promoters such as RBCS2 from *Chlamydomonas reinhardtii* and viral promoters, such as cauliflower mosaic virus (CMV) and *chlorella* virus, which have been shown to be active in multiple species of microalgae (see, for example, *Plant Cell Rep.* 2005 March; 23(10-11):727-35; *J Microbiol.* 2005 August; 43(4):361-5; *Mar Biotechnol* (NY), 2002 January; 4(1):63-73).

Promoters, cDNAs, and 3'UTRs, as well as other elements of the vectors, can be generated through cloning techniques using fragments isolated from native sources (see, for example, Molecular Cloning: A Laboratory Manual, Sambrook et al. (3d edition, 2001, Cold Spring Harbor Press; and U.S. Pat. No. 4,683,202). Alternatively, elements can be generated synthetically using known methods (see, for example, *Gene* 1995 Oct. 16; 164(1):49-53).

Cells can be transformed by any suitable technique including, e.g., biolistics, electroporation, glass bead transformation and silicon carbide whisker transformation.

In particular embodiments, the lipase is expressed in an inducible and/or targeted manner. The use of an inducible promoter to express a lipase gene permits production of the lipase after growth of the microorganism when conditions have been adjusted, if necessary, to enhance transesterification, for example, after disruption of the cells, reduction of the water content of the reaction mixture, and/or addition sufficient alcohol to drive conversion of TAGs to fatty acid esters. Inducible promoters useful in the invention include those that mediate transcription of an operably linked gene in response to a stimulus, such as an exogenously provided small molecule, temperature (heat or cold), light, etc. Suitable promoters can activate transcription of an essentially silent gene or upregulate, preferably substantially, transcription of an operably linked gene that is transcribed at a low level. In the latter case, the level of transcription of the lipase preferably does not significantly interfere with the growth of the microorganism in which it is expressed.

It can be advantageous, in particular embodiments, to target expression of the lipase to one or more cellular compartments, where it is sequestered from the majority of cellular lipids until initiation of the transesterification reaction.

3. Advantages of Biomass with Higher Oil:Non-Oil Ratio

Direct transesterification of agricultural products has been performed as reported in US Patent Application Publication Nos. 20030229237 (published Dec. 11, 2003) and 20050020842 (published Jan. 27, 2005). These processes employ materials such as soy, coconut, palm, corn, cotton, flax, rapeseed/canola, safflower, sunflower or other seed-oil feedstocks or animal fats as the substrate for a transesterification process to produce fatty acid alkyl esters.

A particular advantage of using microorganisms, as described herein, for the generation of TAGs useful in the transesterification methods of the present invention, is the ability to modulate the ratio of oil to non-oil in the biomass, which has been unexpectedly found to impart two advantageous characteristics. First, as shown in the examples below, transesterification of biomass having a higher oil:non-oil ratio leads to an increased efficiency in the conversion of TAGs to fatty acid alkyl esters. Second, as also shown in the examples below, transesterification of biomass having a higher oil:non-oil ratio produces a biodiesel product with reduced proportions of undesirable heteroatoms. In the latter case, the lipophilic phase generated by the transesterification comprises phosphorous in an amount, by weight, no greater than 60 parts per million. In some embodiments, the amount of phosphorous by weight in the lipophilic phase is no greater than 25 parts per million. In some embodiments, the amount of phosphorous by weight in the lipophilic phase is no greater than 10 parts per million. In other embodiments, the amount of sulfur by weight in the lipophilic phase is no greater than 80 parts per million, and in still other embodiments, the amount of sulfur by weight in the lipophilic phase is no greater than 60 parts per million. In some embodiments, the amount of sulfur by weight in the lipophilic phase is no greater than 15 parts per million. In some embodiments, the amount of iron by weight in the lipophilic phase is no greater than 2 parts per million. In some embodiments, the amount of zinc by weight in the lipophilic phase is no greater than 40 parts per million. In some embodiments, the amount of zinc by weight in the lipophilic phase is no greater than 12 parts per million. In some embodiments, the combined amount of magnesium and calcium by weight in the lipophilic phase is no greater than 5 parts per million. In some embodiments, the combined amount of sodium and potassium by weight in the lipophilic phase is no greater than 50 parts per million. In some embodiments, the combined amount of sodium and potassium by weight in the lipophilic phase is no greater than 15 parts per million. Some methods of the invention yield a product in which two or more of the following heteroatoms or combinations of heteroatoms are limited in concentration in the lipophilic phase of the transesterified material to the following concentrations: sulfur is less than 15 parts per million; phosphorous is less than 2 0.001% total mass; the combined amount of magnesium and calcium is no greater than 5 parts per million; and the combined amount of sodium and potassium is no greater than 15 parts per million.

Another aspect of high oil biomass grown heterotrophically, particularly microalgae, is the amount of carotenoids resulting in the lipophilic phase after transesterification. In some embodiments of the present invention, the amount of lutein is no greater than 400 migrograms per gram of lipophilic phase. In some embodiments, the amount of lutein is no greater than 200 micrograms per gram of lipophilic phase. In some embodiments, the amount of lutein is no greater than 100 micrograms per gram of lipophilic phase. In some embodiments, the amount of lutein is no greater than 40 micrograms per gram of lipophilic phase. In some embodiments, the amount of lutein is no less than 5 micrograms per gram of lipophilic phase. In some embodiments, the amount of lutein is no less than 10 micrograms per gram of lipophilic phase. In some embodiments, the amount of lutein is no less than 30 micrograms per gram of lipophilic phase. In some embodiments, the lipophilic phase contains an amount of lutein at between any combination of the maximum and minimum levels recited above, such as below 400 and at least 5 micrograms per gram of lipophilic phase. In some embodiments, the amount of lutein is approximately 35 micrograms per gram of lipophilic phase.

In some embodiments, the amount of zeaxanthin is no greater than 275 micrograms per gram of lipophilic phase. In some embodiments, the amount of zeaxanthin is no greater than 150 micrograms per gram of lipophilic phase. In some embodiments, the amount of zeaxanthin is no greater than 75 micrograms per gram of lipophilic phase. In some embodiments, the amount of zeaxanthin is no greater than 25 micrograms per gram of lipophilic phase. In some embodiments, the amount of zeaxanthin is no less than 0.5 micrograms per gram of lipophilic phase. In some embodiments, the amount of zeaxanthin is no less than 10 micrograms per gram of lipophilic phase. In some embodiments, the amount of zeaxanthin is no less than 20 micrograms per gram of lipophilic phase. In some embodiments, the lipophilic phase contains an amount of zeaxanthin at between any combination of the maximum and minimum levels recited above, such as below 275 and at least 0.5 micrograms per gram of lipophilic phase. In some embodiments, the amount of zeaxanthin is approximately 23 micrograms per gram of lipophilic phase.

In some embodiments, the amount of $\alpha$-Cryptoxanthin is no greater than 8 migrograms per gram of lipophilic phase. In some embodiments, the amount of $\alpha$-Cryptoxanthin is no greater than 5 micrograms per gram of lipophilic phase. In some embodiments, the amount of $\alpha$-Cryptoxanthin is no greater than 2 micrograms per gram of lipophilic phase. In some embodiments, the amount of $\alpha$-Cryptoxanthin is no greater than 0.1 micrograms per gram of lipophilic phase. In some embodiments, the amount of $\alpha$-Cryptoxanthin is no less than 0.001 micrograms per gram of lipophilic phase. In some embodiments, the amount of $\alpha$-Cryptoxanthin is no less than 0.01 micrograms per gram of lipophilic phase. In some embodiments, the amount of $\alpha$-Cryptoxanthin is no less than 0.05 micrograms per gram of lipophilic phase. In some embodiments, the lipophilic phase contains an amount of $\alpha$-Cryptoxanthin at between any combination of the maximum and minimum levels recited above, such as below 8 and at least 0.01 micrograms per gram of lipophilic phase. In some embodiments, the amount of $\alpha$-Cryptoxanthin is approximately 0.06 micrograms per gram of lipophilic phase.

In some embodiments, the amount of $\beta$-Cryptoxanthin is no greater than 18 migrograms per gram of lipophilic phase. In some embodiments, the amount of $\beta$-Cryptoxanthin is no greater than 8 micrograms per gram of lipophilic phase. In some embodiments, the amount of $\beta$-Cryptoxanthin is no greater than 4 micrograms per gram of lipophilic phase. In some embodiments, the amount of $\beta$-Cryptoxanthin is no greater than 2 micrograms per gram of lipophilic phase. In some embodiments, the amount of $\beta$-Cryptoxanthin is no less than 0.1 micrograms per gram of lipophilic phase. In some embodiments, the amount of $\beta$-Cryptoxanthin is no less than 1 micrograms per gram of lipophilic phase. In some embodiments, the amount of $\beta$-Cryptoxanthin is no less than 1.5 micrograms per gram of lipophilic phase. In some embodiments, the lipophilic phase contains an amount of $\beta$-Cryptoxanthin at between any combination of the maximum and minimum levels recited above, such as below 18 and at least 0.1 micrograms per gram of lipophilic phase. In some embodiments, the amount of $\beta$-Cryptoxanthin is approximately 1.8 micrograms per gram of lipophilic phase.

In some embodiments, the amount of $\alpha$-Carotene is no greater than 1.9 migrograms per gram of lipophilic phase. In some embodiments, the amount of $\alpha$-Carotene is no greater than 1 micrograms per gram of lipophilic phase. In some embodiments, the amount of $\alpha$-Carotene is no greater than 0.1 micrograms per gram of lipophilic phase. In some embodiments, the amount of $\alpha$-Carotene is no greater than 0.09 micrograms per gram of lipophilic phase. In some embodiments, the amount of $\alpha$-Carotene is no less than 0.0005 micrograms per gram of lipophilic phase. In some embodiments, the amount of $\alpha$-Carotene is no less than 0.01 micrograms per gram of lipophilic phase. In some embodiments, the amount of α-Carotene is no less than 0.05 micrograms per gram of lipophilic phase. In some embodiments, the lipophilic phase contains an amount of α-Carotene at between any combination of the maximum and minimum levels recited above, such as below 1.9 and at least 0.0005 micrograms per gram of lipophilic phase. In some embodiments, the amount of α-Carotene is approximately 0.08 micrograms per gram of lipophilic phase.

In some embodiments, the amount of β-Carotene is no greater than 14 migrograms per gram of lipophilic phase. In some embodiments, the amount of β-Carotene is no greater than 10 micrograms per gram of lipophilic phase. In some embodiments, the amount of β-Carotene is no greater than 4 micrograms per gram of lipophilic phase. In some embodiments, the amount of β-Carotene is no greater than 1.5 micrograms per gram of lipophilic phase. In some embodiments, the amount of β-Carotene is no less than 0.1 micrograms per gram of lipophilic phase. In some embodiments, the amount of β-Carotene is no less than 0.9 micrograms per gram of lipophilic phase. In some embodiments, the amount of β-Carotene is no less than 1 microgram per gram of lipophilic phase. In some embodiments, the lipophilic phase contains an amount of β-Carotene at between any combination of the maximum and minimum levels recited above, such as below 14 and at least 0.1 micrograms per gram of lipophilic phase. In some embodiments, the amount of β-Carotene is approximately 1.2 micrograms per gram of lipophilic phase.

The increased efficiency with which TAGs are converted to fatty acid alkyl esters, and the reduced proportion of heteroatoms introduced into the lipophilic phase, via application of the methods of the present invention to biomass comprising a high oil:non-oil ratio are unexpected advantages. Examples showing the improved efficiency with which oil can be transesterified, and the reduced proportion of heteroatoms in the transesterified product, are described below.

In some embodiments, the oil:non-oil ratio of the dried biomass subjected to transesterification or other methods of chemical modification is at least 1:20, at least 1:19, at least 1:18, at least 1:17, at least 1:16, at least 1:15, at least 1:14, at least 1:13, at least 1:12, at least 1:11, at least 1:10, at least 1:9, at least 1:8, at least 1:7, at least 1:6, at least 1:5, at least 1:4, at least 1:3, at least 1:2, or at least 1:1. In other embodiments, the oil:non-oil ratio of the dried biomass subjected to transesterification is at least 1.1:1, at least 1.2:1, at least 1.3:1, at least 1.4:1, at least 1.5:1, at least 1.6:1, at least 1.7:1, at least 1.8:1, at least 1.9:1, at least 2:1, at least 3:1, at least 4:1, at least 5:1, at least 6:1, at least 7:1, at least 8:1, at least 9:1, or at least 10:1.

V. Other Methods of Chemical Modification of Lipid-Containing Biomass

The present invention provides methods of chemical modification other than transesterification that yield products useful in a variety of industrial and other applications, including hydrogenation, interesterification, hydroxylation, and hydrolysis plus derivatization. In a manner similar to that described above with reference to transesterification, these chemical modifications can also be performed on biomass generated from the microbial cultures described herein. In some embodiments, the biomass may comprise biomass combined from two or more cultures of distinct strains or species of microorganisms. In some embodiments, the distinct strains or species have different glycerolipid profiles, as illustrated in Example 22. In some methods of the invention, the microbial biomass is first harvested from the culture medium, and then subjected to a chemical reaction that covalently modifies at least 1% of the lipid. In some embodiments, at least 2%, at least 3%, at least 4%, at least 5%, at least 10%, at least 20%, at least 30%, at least 40%, at least 50%, at least 60%, at least 70%, at least 80%, or at least 90% of the lipid is modified by the chemical process.

A. Hydrogenation: Saturation of Double Bonds

Hydrogenation is the addition of hydrogen to double bonds in the fatty acid constituents of glycerolipids or of free fatty acids. The hydrogenation process permits the transformation of liquid oils into semi-solid or solid fats, which may be more suitable for specific applications. Hydrogenation is a well-known chemical process, and generally comprises contacting an oil mixture with a finely divided transition metal (e.g., nickel, palladium, platinum, or rhodium) catalyst at an elevated temperature (e.g., 140-225° C.) in the presence of hydrogen.

Hydrogenation of biomass produced by the methods described herein can be performed in conjunction with one or more of the methods and/or materials provided herein, including microbial biomass with a percentage of DCW as lipid at least 20%, or to produce products, as reported in the following: U.S. Pat. No. 7,288,278 (food additives or medicaments); U.S. Pat. No. 5,346,724 (lubrication products); U.S. Pat. No. 5,475,160 (fatty alcohols); U.S. Pat. No. 5,091,116 (edible oils); U.S. Pat. No. 6,808,737 (structural fats for margarine and spreads); U.S. Pat. No. 5,298,637 (reduced-calorie fat substitutes); U.S. Pat. No. 6,391,815 (hydrogenation catalyst and sulfur adsorbent); U.S. Pat. Nos. 5,233,099 and 5,233,100 (fatty alcohols); U.S. Pat. No. 4,584,139 (hydrogenation catalysts); U.S. Pat. No. 6,057,375 (foam suppressing agents); and U.S. Pat. No. 7,118,773 (edible emulsion spreads), each of which is incorporated herein by reference.

B. Interesterification: Interchanging Fatty Acid Components of Glycerolipids

Naturally produced glycerolipids typically do not have a uniform distribution of fatty acid constituents. In the context of oils, interesterification refers to the exchange of acyl radicals between two esters of different glycerolipids. The interesterification process provides a mechanism by which the fatty acid constituents of a mixture of glycerolipids can be rearranged to modify the distribution pattern. Interesterification is a well-known chemical process, and generally comprises heating (to about 200° C.) a mixture of oils for a period (e.g, 30 minutes) in the presence of a catalyst, such as an alkali metal or alkali metal alkylate (e.g., sodium methoxide). This process can be used to randomize the distribution pattern of the fatty acid constituents of an oil mixture, or can be directed to produce a desired distribution pattern. This method of chemical modification of lipids can be performed on materials provided herein, such as microbial biomass with a lipid percentage of DCW of at least 20%.

Directed interesterification, in which a specific distribution pattern of fatty acids is sought, can be performed by maintaining the oil mixture at a temperature below the melting point of some TAGs that might be present. This results in selective crystallization of these TAGs, which effectively removes them from the reaction mixture as they crystallize. The process can be continued until most of the fatty acids in the oil have precipitated. A directed interesterification process can be used to produce, for example, a product with a lower calorie content via the substitution of longer-chain fatty acids with shorter-chain counterparts. Directed interesterification can also be used to produce a product with a mixture of fats that can provide desired melting characteristics and structural features sought in food additives or food products (e.g., margarine) without resorting to hydrogenation, which can produce unwanted trans isomers.

Interesterification of biomass produced by the methods described herein can be performed in conjuction with one or more of the methods and/or materials, or to produce products, as reported in the following: U.S. Pat. No. 6,080,853 (nondigestible fat substitutes); U.S. Pat. No. 4,288,378 (peanut butter stabilizer); U.S. Pat. No. 5,391,383 (edible spray oil); U.S. Pat. No. 6,022,577 (edible fats for food products); U.S. Pat. No. 5,434,278 (edible fats for food products); U.S. Pat. No. 5,268,192 (low calorie nut products); U.S. Pat. No. 5,258,197 (reduced calorie edible compositions); U.S. Pat. No. 4,335,156 (edible fat product); U.S. Pat. No. 7,288,278 (food additives or medicaments); U.S. Pat. No. 7,115,760 (fractionation process); U.S. Pat. No. 6,808,737 (structural fats); U.S. Pat. No. 5,888,947 (engine lubricants); U.S. Pat. No. 5,686,131 (edible oil mixtures); and U.S. Pat. No. 4,603,188 (curable urethane compositions), each of which is incorporated herein by reference.

In one embodiment of the invention, transesterification of the biomass, as described above, is followed by reaction of the transesterified product with polyol, as reported in U.S. Pat. No. 6,465,642, incorporated herein by reference, to produce polyol fatty acid polyesters. Transesterification can also be performed on microbial biomass with short chain fatty acid esters, as reported in U.S. Pat. No. 6,278,006, incorporated herein by reference.

C. Hydroxylation: Saturation Via the Addition of Water to Double Bonds

Hydroxylation involves the addition of water to a double bond resulting in saturation and the incorporation of a hydroxyl moiety. The hydroxylation process provides a mechanism for converting one or more fatty acid constituents of a glycerolipid to a hydroxy fatty acid. Hydroxylation can be performed, for example, via the method reported in U.S. Pat. No. 5,576,027, incorporated herein by reference. Hydroxylated fatty acids, including castor oil and its derivatives, are useful as components in several industrial applications, including as food additives, surfactants, pigment wetting agents, defoaming agents, water proofing additives, plasticizing agents, cosmetic emulsifying and/or deodorant agents, as well as in electronics, pharmaceuticals, paints, inks, adhesives, and lubricants.

Hydroxylation of microbial biomass produced by the methods described herein can be performed in conjunction with one or more of the methods and/or materials, or to produce products, as reported in the following: U.S. Pat. No. 6,590,113 (oil-based coatings and ink); U.S. Pat. No. 4,049,724 (hydroxylation process); U.S. Pat. No. 6,113,971 (olive oil butter); U.S. Pat. No. 4,992,189 (lubricants and lube additives); U.S. Pat. No. 5,576,027 (hydroxylated milk); and U.S. Pat. No. 6,869,597 (cosmetics), each of which is incorporated herein by reference.

Hydroxylated glycerolipids can be converted to estolides. Estolides consist of a glycerolipid in which a hydroxylated fatty acid constituent has been esterified to another fatty acid molecule. Conversion of hydroxylated glycerolipids to estolides can be carried out by warming a mixture of glycerolipids and fatty acids and contacting the mixture with a mineral acid, as described by Isbell et al., *JAOCS* 71(2):169-174 (1994), incorporated herein by reference. Estolides are useful in a variety of applications, including without limitation those reported in the following: U.S. Pat. No. 7,196,124 (elastomeric materials and floor coverings); U.S. Pat. No. 5,458,795 (thickened oils for high-temperature applications); U.S. Pat. No. 5,451,332 (fluids for industrial applications); U.S. Pat. No. 5,427,704 (fuel additives); and U.S. Pat. No. 5,380,894 (lubricants, greases, plasticizers, and printing inks), each of which is incorporated herein by reference.

D. Hydrolysis Plus Derivatization: Cleavage and Modification of Free Fatty Acids Hydrolysis of the fatty acid constituents from the glycerolipids produced by the methods of the invention yields free fatty acids that can be derivatized to produce other useful chemical entities. Hydrolysis occurs in the presence of water and an acid or base catalyst. The liberated free fatty acids can be derivatized to yield a variety of products, as reported in the following: U.S. Pat. No. 5,304,664 (highly sulfated fatty acids); U.S. Pat. No. 7,262,158 (cleansing compositions); U.S. Pat. No. 7,115,173 (fabric softener compositions); U.S. Pat. No. 6,342,208 (emulsions for treating skin); U.S. Pat. No. 7,264,886 (water repellant compositions); U.S. Pat. No. 6,924,333 (paint additives); U.S. Pat. No. 6,596,768 (lipid-enriched ruminant feedstock); and U.S. Pat. No. 6,380,410 (surfactants for detergents and cleaners), each of which is incorporated herein by reference.

E. Additional Chemical Reactions to Modify Lipid-Containing Microbial Biomass

Other chemical reactions that can be performed on lipid-containing microbial biomass include reacting triacylglycerols with a cyclopropanating agent to enhance fluidity and/or oxidative stability, as reported in U.S. Pat. No. 6,051,539; manufacturing of waxes from triacylglycerols, as reported in U.S. Pat. No. 6,770,104; and epoxidation of triacylglycerols, as reported in "The effect of fatty acid composition on the acrylation kinetics of epoxidized triacylglycerols", Journal of the American Oil Chemists' Society, 79:1, 59-63, (2001) and Free Radical Biology and Medicine, 37:1, 104-114 (2004), each of which is incorporated herein by reference.

In some methods, the first step of modification is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization), each of which is incorporated herein by reference.

F. Saponification of Oil-Bearing Microbial Biomass and Extracted Oil

1. Basic Chemistry of Saponification

Animal and plant oils are typically made of triacylglycerols (TAGs), which are esters of fatty acids with the trihydric alcohol, glycerol. In an alkaline hydrolysis reaction, the glycerol in a TAG is removed, leaving three carboxylic acid anions that can associate with alkali metal cations such as sodium or potassium to produce fatty acid salts. A typical reaction scheme is as follows:

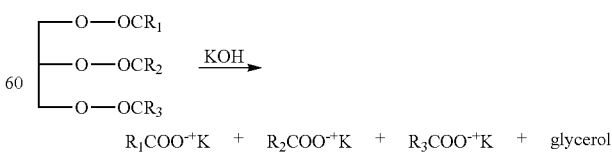

In this scheme, the carboxylic acid constituents are cleaved from the glycerol moiety and replaced with hydroxyl groups. The quantity of base (e.g., KOH) that is used in the reaction is determined by the desired degree of saponifiction. If the objective is, for example, to produce a soap product that comprises some of the oils originally present in the TAG composition, an amount of base insufficient to convert all of the TAGs to fatty acid salts is introduced into the reaction mixture. Normally, this reaction is performed in an aqueous solution and proceeds slowly, but may be expedited by the addition of heat. Precipitation of the fatty acid salts can be facilitated by addition of salts, such as water-soluble alkali metal halides (e.g., NaCl or KCl), to the reaction mixture. Preferably, the base is an alkali metal hydroxide, such as NaOH or KOH. Alternatively, other bases, such as alkanolamines, including for example triethanolamine and aminomethylpropanol, can be used in the reaction scheme. In some embodiments, these alternatives may be preferred to produce a clear soap product.

2. Saponification of Oil Bearing Biomass

Saponification of oil bearing microbial biomass can be performed in accordance with the methods of the invention on intact biomass or biomass that has been disrupted prior to being subjected to the alkaline hydrolysis reaction. In the former case, intact microbial biomass generated via the culturing of microorganisms as described herein can be directly contacted with a base to convert ester-containing lipid components of the biomass to fatty acid salts. In some embodiments, all or a portion of the water in which the microbes have been cultured is removed and the biomass is resuspended in an aqueous solution containing an amount of base sufficient to saponify the desired portion of the glycerolipid and fatty acid ester components of the biomass. In some embodiments, less than 100% of the glycerolipids and fatty acid esters in the biomass are converted to fatty acid salts.

In some methods of the invention, the biomass is disrupted prior to being subjected to the alkaline hydrolysis reaction. Disruption of the biomass can be accomplished via any one or more of the methods described above for lysing cells, including heat-induced lysis, mechanical lysis, or the like, to make the intracellular contents of the microorganisms more readily accessible to the base. This can help to facilitate the conversion of TAGs or fatty acid esters to fatty acid salts. Although acid-induced lysis can be used to disrupt the biomass prior to saponification, other methods may be more desirable to reduce the possibility that additional base will be consumed to neutralize any remaining acid during the alkaline hydrolysis reaction, which may impact the conversion efficiency to fatty acid salts. Because the application of heat can expedite the alkaline hydrolysis reaction, heat-induced lysis can be used prior to or during the saponification reaction to produce the fatty acid salts.

In some embodiments of the invention, the biomass is not subjected to any treatment, or any treatment other than disruption, prior to being subjected to the alkaline hydrolysis reaction. In some embodiments, prior enrichment of the biomass to increase the ratio of lipid to non-lipid material in the biomass to more than 50% (or by more than 50%) by weight, is performed as described herein. In other embodiments, the biomass is subjected to the alkaline hydrolysis reaction without a step of prior enrichment. In some embodiments, the biomass subjected to the alkaline hydrolysis reaction contains components other than water in the same relative proportions as the biomass at the point of harvesting. In those embodiments in which substantially all of the water has been removed, the biomass comprises a cellular emulsion or substantially-dried emulsion concentrate.

Any of the microorganisms described herein can be used to produce lipid-containing biomass for the production of saponified oils. In some embodiments, the microorganisms can also impart other characteristics to the saponified-oil compositions produced from the methods described herein. For example, microalgae of different species, as well as microalgae grown under different conditions, vary in color, including green, yellow, orange, red, and the like. Small quantities of the compounds that impart these colors to the microalgae can be purposefully retained so that the resulting saponified-oil compositions and thereby provide natural colorants. In some embodiments, other constituents of the biomass, including carotenoids and xanthophylls, can also be retained in small quantities in the saponified-oil compositions.

The extent of saponification of the biomass can vary in the methods of the invention. In some embodiments, it is desirable to produce a saponified-oil composition that also includes glycerolipid constituents of the biomass. The appropriate quantity of base (e.g., NaOH) for use in the alkaline hydrolysis reaction can be determined based on an analysis of the glycerolipid and fatty acid ester content of the biomass. In some embodiments, it is preferable to use an excess of base to saponify lipid-containing biomass directly, because some of the base may be consumed by reaction with other constituents of the biomass. In some embodiments, the use of excess quantities of base to saponify the ester-containing lipid constituents of the biomass results in a saponified oil composition that is undesirably alkaline. In these instances, the composition can be purified to reduce the alkalinity of the composition by boiling the saponified oil composition in water and re-precipitating the fatty acid salts via addition of salts such as NaCl, KCl, or the like. The purified soap composition can then be subjected to further processing, such as removing excess water, introducing various additives into the soap composition, molding the soap into bars or other shapes, and the like.

In some embodiments, the fatty acid salts (also referred to as saponified oils) generated from the methods described herein can be combined with one or more additives selected from essential oils, fragrance oils, flavor oils, botanicals, extracts, $CO_2$ extracts, clays, colorants, titanium dioxide, micas, tinting herbs, glitters, exfoliants, fruit seeds, fibers, grain powders, nut meals, seed meals, oil beads, wax beads, herbs, hydrosols, vitamins, milk powders, preservatives, antioxidants, tocopherols, salts, sugars, vegetable oils, waxes, glycerin, sea vegetables, nutritive oils, moisturizing oils, vegetable butters, propylene glycol, parabens, honey, bees wax, aloe, polysorbate, cornstarch, cocoa powder, coral powder, humectants, gums, emulsifying agents, and thickeners, or any other additives described herein.

3. Saponification of Extracted Oil

The degree of saponification of extracted lipid constituents of the biomass can be more readily controlled because of a reduced probability that the base will be consumed through interaction with components other than glycerolipids or fatty acid esters present in the extracted oil. Extraction of the lipid constituents can be performed via conventional hexane-extraction procedures, or via an oil-extraction or solventless-extraction procedure.

Conventional hexane-extraction (other suitable organic solvents can also be used) generally comprises contacting the biomass or lysate with hexane in an amount and for a period of time sufficient to allow the lipid to form a solution with the hexane. The mixture can then be filtered and the hexane removed by, for example, rotoevaporation. Hexane extraction methods are well known in the art.

Oil extraction includes the addition of an oil directly to a lysate without prior separation of the lysate components. After addition of the oil, the lysate separates either of its own accord or as a result of centrifugation or the like into different layers. The layers can include in order of decreasing density: a pellet of heavy solids, an aqueous phase, an emulsion phase, and an oil phase. The emulsion phase is an emulsion of lipids and aqueous phase. Depending on the percentage of oil added with respect to the lysate (w/w or v/v), the force of centrifugation, if any, volume of aqueous media and other factors, either or both of the emulsion and oil phases can be present. Incubation or treatment of the cell lysate or the emulsion phase with the oil is performed for a time sufficient to allow the lipid produced by the microorganism to become solubilized in the oil to form a heterogeneous mixture.

In various embodiments, the oil used in the extraction process is selected from the group consisting of oil from soy, rapeseed, canola, palm, palm kernel, coconut, corn, waste vegetable oil, Chinese tallow, olive, sunflower, cotton seed, chicken fat, beef tallow, porcine tallow, microalgae, macroalgae, *Cuphea*, flax, peanut, choice white grease (lard), *Camelina sativa*, mustard seed, cashew nut, oats, lupine, kenaf, *calendula*, hemp, coffee, linseed, hazelnut, *euphorbia*, pumpkin seed, coriander, camellia, sesame, safflower, rice, tung oil tree, cocoa, copra, pium poppy, castor beans, pecan, jojoba, jatropha, *macadamia*, Brazil nuts, and avocado. The amount of oil added to the lysate is typically greater than 5% (measured by v/v and/or w/w) of the lysate with which the oil is being combined. Thus, a preferred v/v or w/w of the oil is greater than 5%, or at least 6%, at least 7%, at least 10%, at least 20%, at least 25%, at least 30%. at least 40%, at least 50%, at least 60%, at least 70%, at least 80%, at least 90%, and at least 95% of the cell lysate.

Lipids can also be extracted from a lysate via a solventless extraction procedure without substantial or any use of organic solvents or oils by cooling the lysate. In such methods, the lysate is preferably produced by acid treatment in combination with above room temperature. Sonication can also be used, particularly if the temperature is between room temperature and 65° C. Such a lysate on centrifugation or settling can be separated into layers, one of which is an aqueous:lipid layer (the "emulsion" layer). Other layers can include a solid pellet, an aqueous layer, and a lipid layer. Lipid can be extracted from the emulsion layer by freeze thawing or otherwise cooling the emulsion. In such methods, it is not necessary to add any organic solvent or oil. If any solvent or oil is added, it can be below 5% v/v or w/w of the lysate.

The separated or extracted lipids are then subjected to an alkaline hydrolysis reaction as described above, in which the amount of base added to the reaction mixture can be tailored to saponify a desired amount of the glycerolipid and fatty acid ester constituents of the lipid composition. A close approximation or quantification of the amount of esterified lipid in the composition can be used to tailor the amount of base needed to saponify a specified portion of the oil, thereby providing an opportunity to modulate the amount of unsaponified oil remaining in the resulting composition. In some embodiments, at least 1%, at least 2%, at least 3%, at least 4%, at least 5%, at least 6%, at least 7%, at least 8%, at least 9%, or at least 10% of the oil, by weight, remains unsaponified in the resulting composition. In other embodiments, it may be desirable to saponify all or substantially all of the oil, such that the resulting composition contains no more than 10%, no more than 9%, no more than 8%, no more than 7%, no more than 6%, no more than 5%, no more than 4%, no more than 3%, no more than 2%, no more than 1%, or no more than 0.5% unsaponified oil by weight.

In various embodiments of the invention, the microbial biomass or oil can contain lipids with varying carbon chain lengths, and with varying levels of saturation. The characteristics of the lipids can result from the natural glycerolipid profiles of the one or more microorganism populations used to generate the biomass or oil subjected to the saponification reaction, or can be the result of lipid pathway engineering, as described herein, in which transgenic strains of microorganisms that produce particular lipids in greater proportions are produced.

The microbial biomass subjected to transesterification or other chemical modification, as described herein, can optionally be subjected to a process of prior enrichment that increases the ratio of the lipids to the dry weight of the microbes. In some embodiments, the ratio of lipids to non-lipid materials in the biomass is increased by more than 10%, by more than 20%, by more than 30%, by more than 40%, by more than 50%, by more than 60%, by more than 70%, by more than 80%, by more than 90%, or by more than 100% by weight. In some methods of the invention, the biomass is subjected to the chemical reaction without a step of prior enrichment, or, in some embodiments, without a step of prior enrichment that increases the ratio by more than 50%. Enrichment of the ratio of lipids to non-lipid material can be accomplished by, for example, the addition of lipids obtained from a source other than the microbial biomass (e.g., from a second microbial biomass culture, from a plant or seed-oil source, or the like). Whether or not subjected to optional enrichment, the lipid component comprises no more than 50%, no more than 60%, no more than 70%, no more than 80%, no more than 90%, or no more than 95% of the biomass subjected to the chemical reaction, and preferably the lipid component comprises no less than 15%, no less than 20%, no less than 30%, no less than 35%, no less than 40%, or no less than 45% of the biomass. In some embodiments, the harvested biomass comprises a lipid content of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% by DCW.

In some embodiments, water is removed from the biomass prior to subjecting the biomass to the saponification (or other chemical modification) reaction. In some embodiments of the invention, the microbial biomass is not subjected to any treatment, other than removing water and/or lysis, prior to subjecting the biomass to the saponification (or other chemical modification) reaction. In some embodiments, the biomass subjected to the chemical reaction contains components other than water in the same relative proportions as the biomass at the point of harvesting from the fermentation. In this context, "the same relative proportions" means that the proportions of the components remain substantially the same after having accounted for changes associated with the cells' use or metabolic conversion of some components following harvesting of the biomass, chemical conversion of some components within the harvested biomass (without the application of exogenous reagents or catalysts), the escape of gases from the harvested biomass, and/or similar modifications of the relative proportions that are not readily controllable. The phrase "the same relative proportions" is also meant to account for some level of experimental variability, e.g, ±5%.

In some methods of the invention, the covalently modified lipid is separated from other components of the biomass following chemical modification of the lipid. In some embodiments, separating the lipid comprises a phase separation whereby the covalently modified lipids form a lighter non-aqueous phase and components of the biomass form one or more heavier phases. The lighter non-aqueous phase can then be removed to isolate the covalently modified lipid components. In some embodiments, separation of a lipophilic phase containing the covalently modified lipids from hydrophilic cell material of the biomass can be facilitated by centrifugation or other techniques. The ratio of the covalently modified lipid to the biomass from which it is separated can be between 10% lipid to 90% biomass and 90% lipid to 10% biomass by dry weight.

4. Advantages of Biomass with Higher Saturated Oil Content and Fewer Colored Impurities Although biomass and/or extracted oil for use in the saponification methods described herein can be derived from any one of a number of microorganisms with varying glycerolipid profiles and varying ratios of other constituents such as pigments, in a preferred embodiment, the biomass and/or the extracted oil comprises a relatively high ratio of saturated fatty acids within the TAGs and a relatively low ratio of constituents that impart a color to the oil (e.g., pigments). In one embodiment, the biomass and/or extracted oil is derived from microalgae of the genus *Prototheca*.

The saturation characteristics of the fatty acid constituents of a saponified oil, as well as the presence of colored constituents, impact the shelf-life of compositions comprising the saponified oil, as well as their aesthetic qualities. Saturated fatty acids are less prone to oxidation than their unsaturated counterparts. Thus, use of saponified oils with a relatively higher ratio of saturated:unsaturated fatty acid constituents in the preparation of saponified oil products results in a longer overall shelf-life and minimizes the development of oxidation products, which often have an unpleasant odor. Similarly, the relative absence of colored impurities, which, upon oxidation tend to change the appearance of the saponified oil composition in which they are incorporated, improves the aesthetic qualities of the composition and consumer satisfaction with such products, particularly over an extended shelf-life. Consumers of the resulting soap tend to associate a particular color or lack of color with a brand of soap and come to expect the same color of product every time. The lack of color in the saponified oil allows for more consistency in the resulting saponified oil.

Higher ratios of saturated fatty acids are particularly advantageous in the preparation of saponified compositions, discussed below, in which a portion of the glycerolipids within the biomass (or the extracted oil) remains unsaponified. As discussed previously, a percentage of the glycerolipids can remain unmodified (unsaponified) by adjusting the quantity of base used in the saponification reaction, thus producing a soap product that retains some proportion of the originally present glycerolipids. The presence of an excess of glycerolipids in a saponification reaction is commonly referred to as "superfatting." The extra oils remaining in the product following the saponification reaction impart moisturizing properties to the composition, but like any oil, are subject to oxidation, which can lead to the development of an unpleasant-smelling composition. Use of a higher ratio of saturated:unsaturated fatty acid constituents as the "superfatting" components of the reaction mixture results in a product with a relatively longer shelf-life and minimizes the production of malodorous oxidative products.

In various embodiments, saturated fatty acid constituents comprise from 1-100% of the ester-containing lipid components of the microbial biomass or extracted oil subjected to an alkaline hydrolysis reaction in accordance with the methods of the present invention. In preferred embodiments, saturated fatty acid constituents comprise at least 50%, at least 60%, at least 70%, at least 80%, at least 90%, at least 95%, or at least 99% of the ester-containing lipid components in the alkaline hydrolysis reaction.

In some embodiments, color-generating impurities (e.g., carotenoids) are present in the microbial biomass or the extracted oil at a concentration of no more than 500 ppm, no more than 250 ppm, no more than 100 ppm, no more than 75 ppm, or no more than 25 ppm. Color-generating impurities include carotenoids such as lutein, beta carotene, zeaxanthin, astaxanthin and chlorophyll. In other embodiments, the amount of chlorophyll that is present in the microbial biomass or the extracted oil is less than 0.1 mg/kg, less than 0.05 mg/kg, or less than 0.01 mg/kg.

In some embodiments, the microbial oil or soap, before or after saponification, respectively, contains less than 60 micrograms, less than 59 micrograms, less than 58 micrograms, less than 57 micrograms, less than 56 micrograms, less than 55 micrograms, less than 54 micrograms, less than 53 micrograms, less than 52 micrograms, less than 51 micrograms, less than 50 micrograms, less than 49 micrograms, less than 48 micrograms, less than 47 micrograms, less than 46 micrograms, less than 45 micrograms, less than 44 micrograms, less than 43 micrograms, less than 42 micrograms, less than 41 micrograms, less than 40 micrograms, less than 39 micrograms, less than 38 micrograms, less than 37 micrograms, less than 36 micrograms, less than 35 micrograms, less than 34 micrograms, less than 33 micrograms, less than 32 micrograms, less than 31 micrograms, less than 30 micrograms, less than 29 micrograms, less than 28 micrograms, less than 27 micrograms, less than 26 micrograms, less than 25 micrograms, less than 24 micrograms, less than 23 micrograms, less than 22 micrograms, less than 21 micrograms, less than 20 micrograms, less than 19 micrograms, less than 18 micrograms, less than 17 micrograms, less than 16 micrograms, less than 15 micrograms, less than 14 micrograms, less than 13 micrograms, less than 12 micrograms, less than 11 micrograms, less than 10 micrograms, less than 9 micrograms, less than 8 micrograms, less than 7 micrograms, less than 6 micrograms, less than 5 micrograms or less than 4 micrograms carotenoids per gram of saponified oil.

Microalgae of the genus *Prototheca*, including without limitation, *Prototheca wickerhamii*, *Prototheca stagnora*, *Prototheca portoricensis*, *Prototheca moriformis*, and *Prototheca zopfii* naturally produce higher ratios of saturated lipid constituents, as illustrated in Example 28. Moreover, oils extracted from microalgae of the genus *Prototheca* generally include fewer color-generating impurities, allowing for the production of colorless compositions comprising the saponified oils. Thus, use of such microorganisms as the source of biomass or oil for practicing saponification methods in accordance with the present invention is preferred.

VI. Compositions

The present invention also provides compositions that can be prepared by the methods described herein. In each of the various compositions of the present invention, the microbial biomass is selected from the group consisting of bacteria, cyanobacteria, eukaryotic microalgae, oleaginous yeast, and fungi. In some embodiments, the microbial biomass is selected from biomass derived from microbes in the group consisting of the eukaryotic microalgae listed in Table 1. In some embodiments, the microbial biomass is a species of the genus *Chlorella*, and in some embodiments, the species is selected from the group consisting of *Chlorella fusca*, *Chlorella protothecoides*, *Chlorella pyrenoidosa*, *Chlorella kessleri*, *Chlorella vulgaris*, *Chlorella saccharophila*, *Chlorella sorokiniana* and *Chlorella ellipsoidea*. In one embodiment, the species is *Chlorella protothecoides*. In some embodiments, the microbial biomass is derived from a yeast selected from the group consisting of the oleaginous yeast listed in Table 2, or is derived from a fungus selected from the group consisting of the fungi listed in Table 3.

In one embodiment, the present invention is directed to a composition comprising a lighter phase containing fatty acid alkyl esters and at least one heavier phase containing microbial biomass.

In various embodiments of the composition, at least 20% of the fatty acid alkyl esters are C18. In other embodiments, at least 30%, at least 40%, or at least 50% of the fatty acid alkyl esters are C18. In some embodiments, at least 50% of the fatty acid alkyl esters are C16 or longer chain lengths. In some embodiments, at least 10% of the fatty acid alkyl esters are C14 or shorter chain lengths. In some embodiments, at least 20% of the fatty acid alkyl esters are C14 or shorter chain lengths.

In some embodiments, the composition comprises heteroatoms in varying amounts. In some embodiments, the amount of calcium and magnesium combined by weight in the lighter phase is no greater than 5 parts per million. In some embodiments, the amount of phosphorous in the lighter phase is no greater than 0.001%, by mass. In some embodiments, the amount of sulfur in the lighter phase is no greater than 15 parts per million. In some embodiments, the amount of potassium and sodium combined by weight in the lighter phase is no greater than 5 parts per million. In some embodiments, the total carotenoid content of the lighter phase is no greater than 100 micrograms of carotenoid per gram.

In another embodiment, the present invention provides a composition comprising a lightest phase containing completely saturated lipids, and at least one heavier phase containing microbial biomass.

In still another embodiment, the present invention provides a composition comprising a lighter phase containing lipids and at least one heavier phase containing microbial biomass from more than one species or strain. In yet another embodiment, the present invention provides a composition comprising a lighter phase containing hydroxylated lipids and at least one heavier phase containing microbial biomass. In another embodiment, the present invention provides a composition comprising a lighter phase containing free fatty acids and at least one heavier phase containing microbial biomass.

In still another embodiment, the present invention provides a composition comprising saponified oils derived from the alkaline hydrolysis of biomass produced by culturing a population of microbes, as described above. In some embodiments, the biomass from which the saponified oils are derived comprises a mixture of biomass from two or more distinct strains or species of microbes that have been separately cultured. In one embodiment, at least two of the distinct strains or species of microbes, the biomass from which is combined, comprise different glycerolipid profiles. In different embodiments, the composition can be a solid (including a powder) or a liquid.

Saponified oil compositions of the invention can include fatty acid salts derived from one or more species of microorganisms, as described herein, and may include carotenoids or other components derived directly from the biomass from which saponified oils were prepared. In some embodiments, the saponified oil compositions include, without limitation, β-carotene, α-carotene, astaxanthin, α-cryptoxanthin, β-cryptoxanthin, lutein, lycopene, phytoene, phytofluene, and/or zeaxanthin. In some embodiments, the saponified oil compositions include an algal polysaccharide, such as those described in international publication number WO/2007/084769, incorporated herein by reference.

In some embodiments, the saponified oil compositions comprise various proportions of unsaponified glycerolipids derived from the biomass. In various embodiments, the unsaponified glycerolipids derived from the biomass comprise at least 2%, at least 3%, at least 4%, at least 5%, at least 10%, at least 20%, at least 30%, at least 40%, or at least 50% of the saponified oil composition. In other embodiments, the unsaponified glycerolipids comprise no more than 25%, no more than 20%, no more than 15%, no more than 10%, no more than 9%, no more than 8%, no more than 7%, no more than 6%, no more than 5%, no more than 4%, no more than 3%, no more than 2%, or no more than 1% of the saponified oil composition.

In various embodiments of the saponified oil compositions in accordance with the invention, the saponified oil comprises at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the composition's total mass. In some embodiments, the saponified oil comprises no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% of the composition's total mass. In some embodiments, components derived from the biomass, including without limitation, saponified oils, unsaponified oils, carotenoids, and the like, constitute at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the composition's total mass. In other embodiments, components derived from the biomass constitute no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% of the composition's total mass.

In some embodiments of the saponified oil composition, the composition further includes at least one oil selected from soy, rapeseed, canola, palm, palm kernel, coconut, corn, waste vegetable, Chinese tallow, olive, sunflower, cotton seed, chicken fat, beef tallow, porcine tallow, microalgae, macroalgae, *Cuphea*, flax, peanut, choice white grease, lard, *Camelina sativa*, mustard seed, cashew nut, oats, lupine, kenaf, *calendula*, hemp, coffee, linseed (flax), hazelnut, *euphorbia*, pumpkin seed, coriander, camellia, sesame, safflower, rice, tung oil tree, cocoa, copra, opium poppy, castor beans, pecan, jojoba, jatropha, *macadamia*, Brazil nuts, or avocado.

In some embodiments of the saponified oil composition, one or more additives are combined with the fatty acid salts. In some embodiments, the additives are selected to optimize the cleansing efficiency of the composition when used, for example, as a skin cleanser. In other embodiments, the additives are selected with regard to a characteristic imparted by the additive to the composition that appeals to a consumer. In some embodiments, additives are selected for both optimization of cleansing efficiency and for consumer appeal. In the various embodiments, the additives are selected from essential oils, fragrance oils, flavor oils, botanicals, extracts, $CO_2$ extracts, clays, colorants, titanium dioxide, micas, tinting herbs, glitters, exfoliants, fruit seeds, fibers, grain powders, nut meals, seed meals, oil beads, wax beads, herbs, hydrosols, vitamins, milk powders, preservatives, antioxidants, tocopherols, salts, sugars, vegetable oils, waxes, glycerin, sea vegetables, nutritive oils, moisturizing oils, vegetable butters, propylene glycol, parabens, honey, bees wax, aloe, polysorbate, cornstarch, cocoa powder, coral powder, humectants, gums, emulsifying agents, and thickeners. These additives are commercially available from a number of skin care ingredient and bath accessory suppliers.

Essential oils include allspice, amyris, angelica root, anise seed, basil, bay, bergamot, black pepper, cajeput, camphor, cananga, cardamom, carrot seed, *cassia*, catnip, cedarwood, chamomile, cinnamon bark, cinnamon leaf, citronella java, clary sage, clovebud, coriander, cornmint, cypress, davana, dill seed, elemi, eucalyptus, fennel, fir, frankincense, geranium bourbon, geranium roast, geranium, ginger, grapefruit pink, grapefruit, gurjum balsam, hyssop, juniper berry, lavandin, *lavandula*, lavender, lemon myrtle, lemon tea tree, lemon, lemongrass, lime, litsea cubeba, mandarin, marjoram, mullein, myrrh, neroli, nerolina, niaouli, nutmeg, orange, palmarosa, patchouli, peppermint, petitgrain, pine needle, ravensara, ravintsara, rosalina, rose, rosemary, rosewood, sage, sandalwood, spearmint, spikenard, star anise, tangerine, tea tree, thyme, tulsi, verbena, vetiver, ylang ylang, and zdravetz, or combinations thereof.

Fragrance and flavor oils include absolute tulip, almond, amaretto, amber, anais, apple, apple cinnamon, apple spice, apricot, apricot crème, arabian musk, asian pear, asian plum blossom, autumn woods, banana, basil, basil nectarine, bay rum, bayberry, bergamot, berries and cream, birthday cake, black cherry, black tea, blackberry tea, blackcurrent, blue nile, blueberry delight, brambleberry preserves, brown sugar, bubble gum, buttercream, butterscotch, calla lily, cantaloupe, caramel apple, carnation, carrot cake, chai tea, chamomile, china musk, china rain, chinese peony, chrysanthemum, cinnamon, coconut, coconut cream, cotton candy, cranberry, cucumber, cucumber melon, daffodil, dandelion, delphinium, dewberry, dulce de leche, earl grey tea, easter cookie, egg nog, eqyptian musk, enchanted forest, english lavender, english pear, evergreen, fig, frangipani, frankincense, french vanilla, fresh apple, fresh brewed coffee, fruit punch, gardenia, geranium, ginger lily, gingerbread, grape, grapefruit, green apple, green grass, green tea, guava, guava flower, hawaiian white ginger, heliotrope, hemp, herbaceous, holiday fruitcake, hollyberry, honey ginger, honey, honeysuckle, jasmine, jasmine tea, juniper berries, kiwi, lavender, leather, lemon, lemon parsley, lilac, lime, loganberry, lotus blossom, magnolia, mandarin, mango, mango and kiwi, maple, milk chocolate, mimosa, minty lime, mulberry, myrrh, neroli, oakmoss, oatmeal, ocean rain, orange blossom, orange sherbet, orange vanilla, papaya, passion fruit, patchouli, peach, peaches and cream, pearberry, peppermint, pikaki, pina colada, pineapple, pomegranate, pumpkin pie, raisins and almonds, raspberry, roasted nuts, rosewood, sage, sandalwood, sassafras, sea moss, sesame, siberian pine, snowberry, spanish moss, spice, strawberry, sugar plum, suntan lotion, sweet clove, sweet grass, sweet pea, tangerine, that coconut, timber, tomato leaf, vanilla, watermelon, white chocolate, wild cherry, wisteria, witches brew, and ylang ylang, or combinations thereof.

Exfoliants include particles that can be used to dislodge dead skin cells, dirt, or other materials from the surface of the skin, and include without limitation, fruit seeds and fibers, grain powders, nut and seed meals, and oil or wax beads. Fruit fibers include blueberry, cranberry, grape, kiwi, raspberry, blackberry, strawberry, and the like. Grain powders include oat powder, and almond powder, or the like, milled to varying degrees of courseness. Polymer beads, such as those made from polyethylene, or the like, can also be used. The removal of dead skin cells and/or the outer most layer of skin can provide an opportunity for bioactive agents, such as carotenoids, which can also be present in the compositions of the invention, to have greater access to deeper layers of the skin.

Extracts and $CO_2$ extracts include herbal extracts derived from conventional extraction procedures, or via the use of liquified carbon dioxide. Herbs include aloe vera leaf, alfalfa leaf, alkanet root, annatto seed, arrowroot, burdock root, *calendula* petals, carrot root, chamomile flower, comfrey leaf, cornsilk, dutch blue poppies, fennel seed, ginger root, ginseng, green tea leaf, jasmine flower, juniper berries, lavender buds, lemon peel, lemongrass, marshmallow root, nettles, oat straw, orange peel, paprika, parsley, peppermint leaf, rose buds, rose petals, rosehip, rosemary leaf, shavegrass, spearmint leaf, and St. john's wort, and combinations thereof.

Colorants and glitters include green #5, green #8, orange #4, red #22, red #33, violet #2, blue #1, green #3, red #40, yellow #5, yellow #6, green #6, red #17, as well as pearlescent micas and tinting herbs such as henna leaf, sandalwood, turmeric, cranberry, kiwi, raspberry, alkanet, annatto, carrot root, nettles, paprika, and parsley.

In various embodiments, the saponified oil composition containing one or more additives, as described above, is formulated for use as a cosmetic product. In some embodiments, the cosmetic product is a personal hygiene product, such as a cleansing composition for use on an individual's body or parts thereof (e.g., face, legs, etc.).

In one aspect, the invention is directed to a kit comprising a saponified oil composition, as described herein, and an oral supplement. In one embodiment, the oral supplement is a vitamin. In another embodiment, the oral supplement is an herb.

In another aspect, the invention is directed to a method of using saponified oil derived from the alkaline hydrolysis of biomass, produced as described herein, for admixture with one or more additives, as described above, and packaging the mixture as a cosmetic product. In one embodiment, the cosmetic product comprises a cleansing composition (e.g., a facial cleanser).

Conventional DNA analysis methods can be used to detect the presence of components derived from microbial biomass in accordance with the present invention.

All references cited herein, including patents, patent applications, and publications, are hereby incorporated by reference in their entireties, regardless of whether previously specifically incorporated. The publications mentioned herein are cited for the purpose of describing and disclosing reagents, methodologies and concepts that may be used in connection with the present invention. Nothing herein is to be construed as an admission that these references are prior art in relation to the inventions described herein. In particular, the following patent applications are hereby incorporated by reference in their entireties for all purposes: U.S. Provisional Application No. 61/043,620 filed Apr. 9, 2008, entitled "Direct Chemical Modification of Microbial Biomass"; U.S. Provisional Application No. 61/074,610, filed Jun. 20, 2008, entitled "Soaps and Cosmetic Products Produced from Oil-Bearing Microbial Biomass and Oils"; International publication number WO 2008/151149; and U.S. Provisional Application No. 61/112,464 filed Nov. 7, 2008, entitled "Cosmetic Compositions Comprising Microalgal Components".

Although this invention has been described in connection with specific embodiments thereof, it will be understood that it is capable of further modifications. Variations, uses, or adaptations of the invention following, in general, the principles of the invention and including such departures from the present disclosure as come within known or customary practice within the art to which the invention pertains and as may be applied to the essential features hereinbefore set forth, are included in the scope of the claims below. The following examples are offered to illustrate, but not to limit, the claimed invention.

VII. EXAMPLES

Example 1

Unless otherwise noted, all strains described in this and the following Examples were obtained from the University of Texas Culture Collection of Algae (Austin, Tex.). In this example, *Chlorella* strains were tested for growth on glycerol and glucose. The following *Chlorella* species and strains were cultured: *Chlorella kessleri* (strains 263, 397, 398, 2228); *Chlorella sorokiniana* (strains 1663, 1665, 1669, 1671, 1810); *Chlorella saccharophila* (2911; 2469); *Chlorella protothecoides* (31, 249, 250, 264). Each strain was inoculated from solid media into 25 ml liquid base media (2 g/L yeast extract, 2.94 mM $NaNO_3$, 0.17 mM $CaCl_2.2H_2O$, 0.3 mM $MgSO_4.7H_2O$, 0.4 mM $K_2HPO_4$, 1.28 mM $KH_2PO_4$, 0.43 mM NaCl) and grown shaking at 27° C. for 72 hours under a light intensity of 75 $\mu Em^{-2}s^{-1}$. These cultures were used to inoculate each strain to a final density of $1\times10^5$ cells per ml into 24-well plates containing 2 ml of (a) base media only; (b) base media plus 0.1% glucose; and (c) base media plus 0.5% reagent grade glycerol (EM Science, catalog #GX0185-6). Plates were placed in the dark and grown for 72 hours shaking at 27° C. Samples of each strain grown in the three conditions were diluted 1.9:1 in distilled $H_2O$ and absorbance was read at 600 nm in a Molecular Devices SpectraMax 340PC. All strains exhibited growth in the presence of glucose and glycerol compared to only base media.

Example 2

Strains and Media:
*Chlorella protothecoides* #1 (STRAIN 250), #2 (STRAIN 264) and *Chlorella kessleri* #1 (STRAIN 398) stock cultures were maintained on modified Proteose medium. Modified Proteose medium consisted (g/L) of 0.25 g $NaNO_3$, 0.09 g $K_2HPO_4$, 0.175 g $KH_2PO_4$ 0.025 g, 0.025 g $CaCl_2.2H_2O$, 0.075 g $MgSO_4.7H_2O$, and 2 g yeast extract per liter. Glycerol wastes from biodiesel production (acidulated glycerol (AG) and non-acidulated glycerol (NAG)) were obtained from Imperial Western Products (Selma, Calif., USA). "Pure" or "reagent grade" glycerol was from EM Science (a division of Merck KGA), catalog #GX0185-6. For each strain, 1 ml of the following different media was prepared in 24-well plates.
1. Proteose+1% pure glycerol
2. Proteose+1% acidulated glycerol
3. Proteose+1% non-acidulated glycerol
4. Proteose+1% pure glycerol+1% glucose (added after 72 hr)
5. Proteose+1% acidulated glycerol+1% glucose (added after 72 hr)
6. Proteose+1% non-acidulated glycerol+1% glucose (added after 72 hr)

Each strain was inoculated to different media to $5\times10^5$ cells/ml concentration. The cultures were kept in the dark and were agitated by orbital shaker from Labnet (Berkshire, UK) at 430 rpm. After 72 hr of initial growth, 1% (w/v) glucose was added to samples #4, 5, and 6 and the cells cultured another 24 hr. To measure DCW, 1 ml of each culture was pelleted by centrifugation at 5,000 rpm for 5 min in an Eppendorf 5415C centrifuge. After removing supernatant, cell pellets were frozen at −80° C. and lyophilized in a lab scale freeze dryer (Labconco, Mo., USA). Results are shown in FIG. 1.

Example 3

Strains and Media: *Chlorella protothecoides* #1 (STRAIN 250), #3 (STRAIN 249) and *Chlorella kessleri* #2 (strain 397) stock cultures were maintained on modified Proteose medium (see EXAMPLE 2). For each strain, 1 ml of the following different media was prepared in 24-well plates.
1. Proteose+1% pure glycerol+1% glucose
2. Proteose+1% acidulated glycerol+1% glucose
3. Proteose+1% non-acidulated glycerol+1% glucose Each strain was inoculated to different media to $5\times10^5$ cells/ml concentration. The cultures were kept in the dark and agitated by orbital shaker from Labnet (Berkshire, UK) at 430 rpm. After 96 hr, cell growth was measured for DCW (see EXAMPLE 2). Results are shown in FIG. 2.

Example 4

Strains and Media: *Chlorella protothecoides* #3 (STRAIN 249), #4 (STRAIN 31), and *Chlorella kessleri* #2 (STRAIN 397) stock cultures were maintained on modified Proteose medium (see EXAMPLE 2). For each strain, 1 ml of the following different media was prepared in 24-well plates.
1. Proteose+1% pure glycerol+1% glucose
2. Proteose+1% acidulated glycerol+1% glucose
3. Proteose+1% non-acidulated glycerol+1% glucose Each strain was inoculated to media containing different glycerols (pure, acidulated, or non-acidulated) to $5\times10^5$ cells/ml concentration. The cultures were kept in the dark and agitated by orbital shaker from Labnet (Berkshire, UK) at 430 rpm. After 96 hr, lipid contents were measured. To measure the amount of lipid content in cells, 100 µl of cultures were collected and washed once with same volume of media. To each tube, 5 µl of washed cells and 200 µl of sulfuric acid (18 M) were added. The tubes were incubated at 90° C. in a water bath for 30 min, and 1 ml of phosphoric acid-vanillin reagent was added to the tubes and incubated at 37° C. for 15 min. To prepare the phosphoric acid-vanillin reagent, 0.12 g of vanillin was added to 20 ml of water, and the volume adjusted to 100 ml with 85% phosphoric acid. The optical density at 530 nm was read in a glass cuvette against a reference tube with 5 µl water as sample. Results are shown in FIG. 3.

Example 5

Strains and Media: *Chlorella protothecoides* #2 (STRAIN 264) and *Chlorella kessleri* #1 (STRAIN 398) stock cultures were maintained on modified Proteose medium (see EXAMPLE 2). For each strain, 1 ml of the following different media was prepared in 24-well plates.
1. Proteose+1% pure glycerol
2. Proteose+1% non-acidulated glycerol
3. Proteose+1% pure glycerol+1% glucose (added after 72 hr)
4. Proteose+1% non-acidulated glycerol+1% glucose (added after 72 hr)

Each strain was inoculated to media containing different glycerols (pure or non-acidulated) to $5\times10^5$ cells/ml concentration. The cultures were kept in the dark and agitated by orbital shaker from Labnet (Berkshire, UK) at 430 rpm. After 72 hr of initial growth, 1% glucose was added to sample #3 and #4 and the cells cultured another 24 hr. Lipid contents were measured in all samples (see EXAMPLE 4). The optical density at 600 nm was also measured to check for non-specific absorbance and subtracted from O.D. 530 nm to calculate the amount of lipid. The reference curve is composed of Triolein dissolved in chloroform ranging from 1 to 10 µg. Results are shown in FIG. 4.

Example 6

Strains and Media: *Chlorella protothecoides* #3 (STRAIN 249) and *Chlorella kessleri* #2 (STRAIN 397) stock cultures were maintained on modified Proteose medium (see EXAMPLE 2). For each strain, 1 ml of the following different media was prepared in 24-well plates.
1. Proteose+1% pure glycerol+1% glucose (added after 72 hr)
2. Proteose+1% acidulated glycerol+1% glucose (added after 72 hr)
3. Proteose+1% non-acidulated glycerol+1% glucose (added after 72 hr)

Each strain was inoculated to media containing different glycerols (pure, acidulated, or non-acidulated) to $5\times10^5$ cells/ml concentration. The cultures were kept in the dark and agitated by orbital shaker from Labnet (Berkshire, UK) at 430 rpm. After 72 hr of initial growth, 1% glucose was added and the cells cultured another 24 hr. DCW and lipid content were measured in all samples (see EXAMPLES 2 and 5). The lipid percentage was calculated from total lipid amount divided by DCW. Results are shown in FIG. 5.

Example 7

Strains and Media: *Chlorella protothecoides* #2 (STRAIN 264) and *Chlorella kessleri* #1 (STRAIN 398) stock cultures were maintained on modified Proteose medium (see EXAMPLE 2). For each strain, 1 ml of the following different media was prepared in 24-well plates.
1. Proteose+1% pure glycerol+1% glucose (added after 72 hr)
2. Proteose+1% non-acidulated glycerol+1% glucose (added after 72 hr)

Each strain was inoculated to media containing either 1% pure or 1% non-acidulated glycerol to $5\times10^5$ cells/ml concentration. The cultures were kept in the dark and agitated by orbital shaker from Labnet (Berkshire, UK) at 430 rpm. After 72 hr of initial growth, 1% glucose was added and the cells cultured another 24 hr. DCW and lipid content were measured in all samples (see EXAMPLE 1 and 4). The lipid percentage was calculated from total lipid amount divided by dried cell weight. Results are shown in FIG. 6.

Example 8

Figure 7:
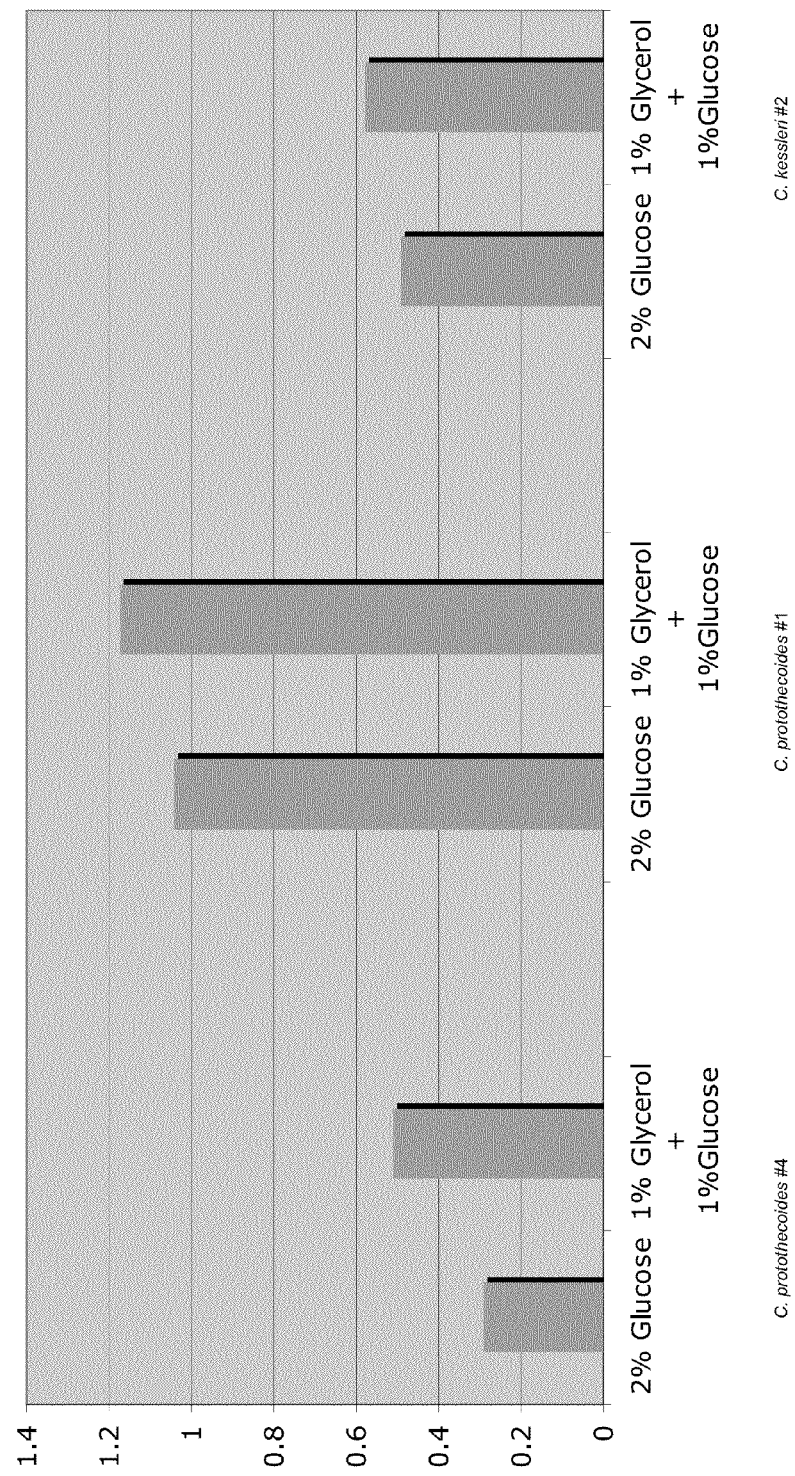
FIG. 7 shows relative lipid concentration of cultures of multiple species and strains of *Chlorella* when cultured in the presence of 2% glucose and 1% glucose+1% reagent grade glycerol.

Strains and Media: *Chlorella protothecoides* #1 (STRAIN 250), #4 (STRAIN 31) and *Chlorella kessleri* #2 (STRAIN 397) stock cultures were maintained on modified Proteose medium (see EXAMPLE 2) For each strain, 1 ml of the following different media was prepared in 24-well plates.
1. Proteose+2% glucose
2. Proteose+1% glycerol+1% glucose Each strain was inoculated to different media to $5\times10^5$ cells/ml concentration. The cultures were kept in the dark and agitated by orbital shaker from Labnet (Berkshire, UK) at 430 rpm. After 96 hr of initial growth, lipid contents were measured (see EXAMPLE 5). Results are shown in FIG. 7.

Example 9

Strains and Media: *Chlorella protothecoides* #3 (STRAIN 249), #4 (STRAIN 31) and *Chlorella kessleri* #1 (STRAIN 398) stock cultures were maintained on modified Proteose medium (see EXAMPLE 2). For each strain, 1 ml of the following different media was prepared in 24-well plates.
1. Proteose+2% glucose
2. Proteose+1% glycerol+1% glucose
3. Proteose+1% glycerol+1% glucose (added after 72 hr)

Each strain was inoculated to different media to $5\times10^5$ cells/ml concentration. The cultures were kept in the dark and agitated by orbital shaker from Labnet (Berkshire, UK) at 430 rpm. After 72 hr of initial growth, 1% (w/v) glucose was added to #3 media and the cells cultured another 24 hr. DCW and lipid contents were measured in all samples (see EXAMPLES 2 and 5). The lipid percentage was calculated from total lipid amount divided by dried cell weight. Results are shown in FIG. 8.

Example 10

Strains and Media: *Chlorella protothecoides* #1 (STRAIN 250), #3 (STRAIN 249), and *Chlorella kessleri* #2 (STRAIN 397) stock cultures were maintained on modified Proteose medium (see EXAMPLE 2). For each strain, 1 ml of the following different media was prepared in 24-well plates.
1. Proteose+1% pure glycerol+1% glucose
2. Proteose+1% pure glycerol+1% glucose (added after 72 hr)
3. Proteose+1% acidulated glycerol+1% glucose
4. Proteose+1% acidulated glycerol+1% glucose (added after 72 hr)
5. Proteose+1% non-acidulated glycerol+1% glucose
6. Proteose+1% non-acidulated glycerol+1% glucose (added after 72 hr)

Each strain was inoculated to different media to $5\times10^5$ cells/ml concentration. The cultures were kept in the dark and agitated by orbital shaker from Labnet (Berkshire, UK) at 430 rpm. After 72 hr of initial growth, 1% (w/v) glucose was added to #2, #4, and #6 media and the cells cultured another 24 hr. Lipid contents were measured in all samples (see EXAMPLE 4). Results are shown in FIG. 9.

Example 11

Strains and Media: *Chlorella protothecoides* #1 (STRAIN 250), #3 (STRAIN 249), #4 (STRAIN 31) and *Chlorella kessleri* #2 (STRAIN 397) stock cultures were maintained on modified Proteose medium (see EXAMPLE 2). For each strain, 1 ml of the following different media was prepared in 24-well plates.
1. Proteose+1% pure glycerol+1% glucose
2. Proteose+1% pure glycerol+1% glucose (added after 72 hr)
3. Proteose+1% acidulated glycerol+1% glucose
4. Proteose+1% acidulated glycerol+1% glucose (added after 72 hr)
5. Proteose+1% non acidulated glycerol+1% glucose
6. Proteose+1% non acidulated glycerol+1% glucose (added after 72 hr)

Each strain was inoculated to different media to $5\times10^5$ cells/ml concentration. The cultures were kept in the dark and agitated by orbital shaker from Labnet (Berkshire, UK) at 430 rpm. After 72 hr of initial growth, 1% (w/v) glucose was added to #2, #4, and #6 media and the cells cultured another 24 hr. DCW was measured in all samples (see EXAMPLE 2). Results are shown in FIG. 10.

Example 12

Strains and Media: (a) *Spirulina platensis* (UTEX 2340) and (b) *Navicula pelliculosa* (UTEX 667) stock culture of Spirulina was maintained in Spirulina medium and Navicula was maintained in soil extract medium (SEM). Spirulina medium consisted of 162 mM NaHCO$_3$, 38 mM Na$_2$CO$_3$, 1.9 mM K$_2$HPO$_4$, 29 mM NaNO$_3$, 5.75 mM K$_2$SO$_4$, 17.1 mM NaCl, 0.8 mM MgSO$_4$.7H$_2$O, 0.25 mM CaCl$_2$.2H$_2$O, 2 mM Na$_2$EDTA, 0.36 mM FeCl$_3$.6H$_2$O, 0.21 mM MnCl$_2$.4H$_2$O, 0.037 mM ZnCl$_2$, 0.0085 mM CoCl$_2$.6H$_2$O, 0.017 mM NaMoO$_4$.2H$_2$O, 0.78 µM CuSO$_4$.5H$_2$O, 0.15 µM ZnSO$_4$.7H$_2$O, 10 µM H$_3$BO$_3$, and 0.001 mM Vitamin B$_{12}$. Soil extract medium consisted of 2.94 mM NaNO$_3$, 0.17 mMCaCl$_2$.2H$_2$O, 0.3 mM MgSO$_4$.7H$_2$O, 0.43 mM K$_2$HPO$_4$, 1.29 mM KH$_2$PO$_4$, 0.43 mM NaCl, and soil extract. Glycerol wastes from biodiesel production (acidulated glycerol (AG) and non-acidulated glycerol (NAG)) were obtained from Imperial Western Products (Selma, Calif., USA). For each strain, 1 ml of the following different media was prepared in 24-well plates.

(a)
7. Spirulina medium+2% glucose
8. Spirulina medium+2% reagent grade glycerol
9. Spirulina medium+2% non-acidulated glycerol
10. Spirulina medium+1% non-acidulated glycerol+1% glucose (b)
1. SEM+2% glucose
2. SEM+2% reagent grade glycerol
3. SEM+1% reagent grade glycerol+1% glucose
4. SEM+2% acidulated glycerol
5. SEM+1% acidulated glycerol+1% glucose
6. SEM+2% non-acidulated glycerol
7. SEM+1% non-acidulated glycerol+1% glucose Each strain was inoculated to different media to 5×10$^5$ cells/ml concentration. The cultures were kept in the dark and agitated by orbital shaker from Labnet (Berkshire, UK) at 430 rpm. After 96 hr, lipid contents were measured. To measure the amount of lipid content in cells, 100 µl of cultures were collected and washed once with same volume of media. To each tube, 5 µl of washed cells and 200 µl of sulfuric acid 18 M were added. The tubes were incubated at 90° C. water bath for 30 min, and 1 ml of phosphoric acid-vanillin reagent were added to the tubes and incubated at 37° C. for 15 min. To prepare the phosphoric acid-vanillin reagent, 0.12 g of vanillin was added to 20 ml of water, and the volume adjusted to 100 ml with 85% phosphoric acid. The optical density at 530 nm was read in a glass cuvette against a reference tube with 5 µl water as sample. The reference curve is composed of Triolein dissolved in chloroform ranging from 1 to 10 µg.

To measure DCW, 0.5 ml of each culture was pelleted by centrifugation at 5000 rpm for 5 min. After removing supernatant, cell pellets were frozen at −80° C. and dried overnight in a Freeze Dry system (Labconco, Mo., USA). The lipid percentage was calculated from total lipid amount divided by dried cell weight. Results are shown in FIG. 11.

Example 13

Strains and Media: *Scenedesmus armatus* (UTEX 2552) stock cultures were maintained on modified Proteose medium. Modified Proteose medium consisted (g/L) of 0.25 g NaNO$_3$, 0.09 g K$_2$HPO$_4$, 0.175 g KH$_2$PO$_4$ 0.025 g, 0.025 g CaCl$_2$.2H$_2$O, 0.075 g MgSO$_4$.7H$_2$O, and 2 g yeast extract per liter. For each growth condition, 1 ml of the following different media was prepared in 24-well plates.

(a), (b)
1. Proteose+2% glucose
2. Proteose+2% glycerol
3. Proteose+2% acidulated glycerol
4. Proteose+2% non-acidulated glycerol
5. Proteose+1% non-acidulated glycerol+1% glucose

*Scenedesmus armatus* (UTEX 2552) was inoculated to different media to 5×10$^5$ cells/ml concentration. The cultures were kept in the dark and agitated by orbital shaker from Labnet (Berkshire, UK) at 430 rpm. After 96 hr, cell growth was measured by DCW, and lipid content was measured by phosphor-vanillin assay (see EXAMPLE 12). The lipid percentage was calculated from total lipid amount divided by dried cell weight. Results are shown in FIG. 12.

Example 14

Strains and Media: *Navicula pelliculosa* (UTEX 667) stock cultures were maintained on soil extract medium (see EXAMPLE 12). For each growth condition, 1 ml of the following different media was prepared in 24-well plates.
1. SEM+2% glucose
2. SEM+2% glycerol
3. SEM+2% acidulated glycerol
4. SEM+1% acidulated glycerol+1% glucose
5. SEM+2% non-acidulated glycerol
6. SEM+1% non-acidulated glycerol+1% glucose

*Navicula pelliculosa* (UTEX 667) was inoculated to media containing glucose or different glycerols (pure, acidulated, or non-acidulated) to 5×10$^5$ cells/ml concentration. The cultures were kept in the dark and agitated by orbital shaker from Labnet (Berkshire, UK) at 430 rpm. After 96 hr, cell growth was measured by DCW (see EXAMPLE 12). Results are shown in FIG. 13.

Example 15

Strains and Media: *Scenedesmus armatus* (UTEX 2552) and *Navicula pelliculosa* (UTEX 667) stock cultures were maintained on modified Proteose medium for *Scenedesmus armatus* and soil extract medium for *Navicula pelliculosa* (see EXAMPLE 1). For each strain, 1 ml of the following different media was prepared in 24-well plates.

*Scenedesmus armatus*
5. Proteose+1% acidulated glycerol+1% glucose
6. Proteose+1% acidulated glycerol+1% glucose (added after 72 hr)

*Navicula pelliculosa*
1. SEM+1% acidulated glycerol+1% glucose
2. SEM+1% acidulated glycerol+1% glucose (added after 72 hr)

Figure 14:
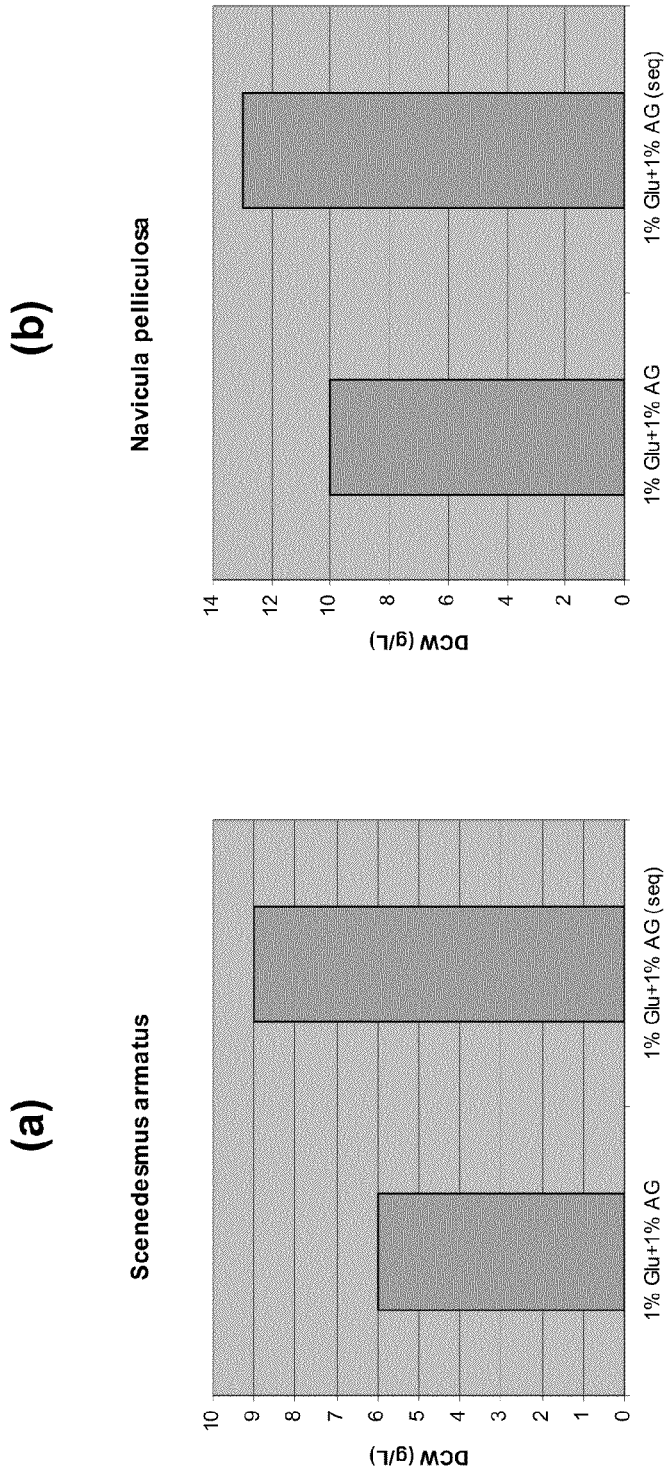
FIGS. 14(*a*) and (*b*) shows DCW per liter of *Scenedesmus armatus* and *Navicula pelliculosa* when cultured in the presence of acidulated and non-acidulated biodiesel byproduct glycerol with additional glucose, wherein glycerol is added sequentially or in combination with glucose.

Each strain was inoculated to media to 5×10$^5$ cells/ml concentration. The cultures were kept in the dark and agitated by orbital shaker from Labnet (Berkshire, UK) at 430 rpm. After 72 hr of initial growth, 1% glucose was added to sample #2 and the cells cultured another 24 hr. Cell growth was measured by DCW (see EXAMPLE 12). Results are shown in FIGS. 14 (*a*) and (*b*).

Example 16

Strains and Media: *Chlorella protothecoides* (UTEX 31) stock cultures were maintained on modified Proteose medium (see EXAMPLE 1). For each condition, 1 ml of the following different media was prepared in 24-well plates.
4. Proteose
5. Proteose+0.5% glucose
6. Proteose+0.5% xylose
7. Proteose+0.25% glucose+0.25% xylose

*Chlorella protothecoides* #4 (UTEX 31) was inoculated to media containing different sugars (glucose, or xylose) to 3×10⁵ cells/ml concentration. The cultures were kept in the dark and agitated by orbital shaker from Labnet (Berkshire, UK) at 430 rpm. After 72 hr of growth, cell growth was measured by counting cell numbers of each culture. Results are shown in FIG. 15.

Example 17

Figure 16:
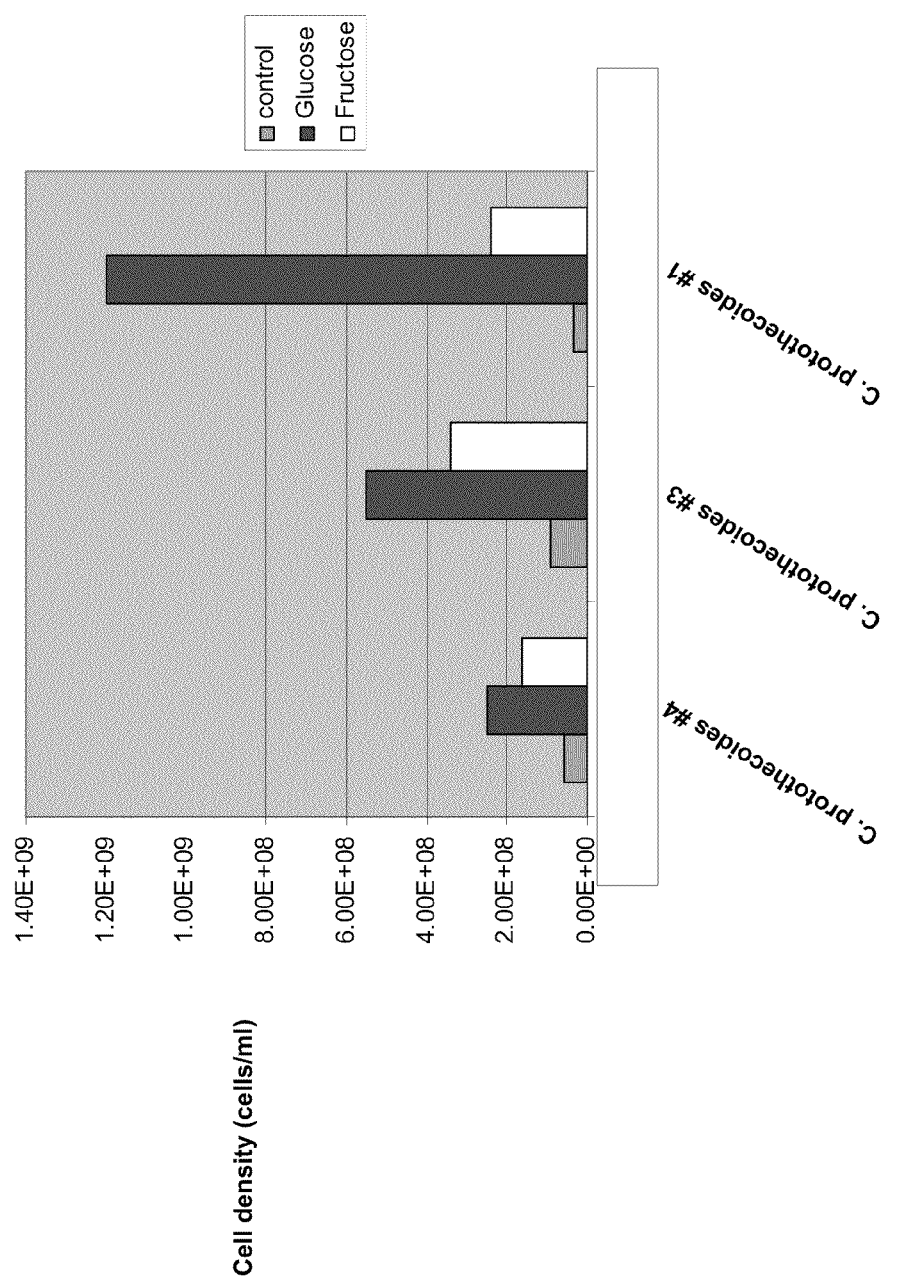
FIG. 16 shows growth of *Chlorella protothecoides* on glucose and fructose.
Figure 17:
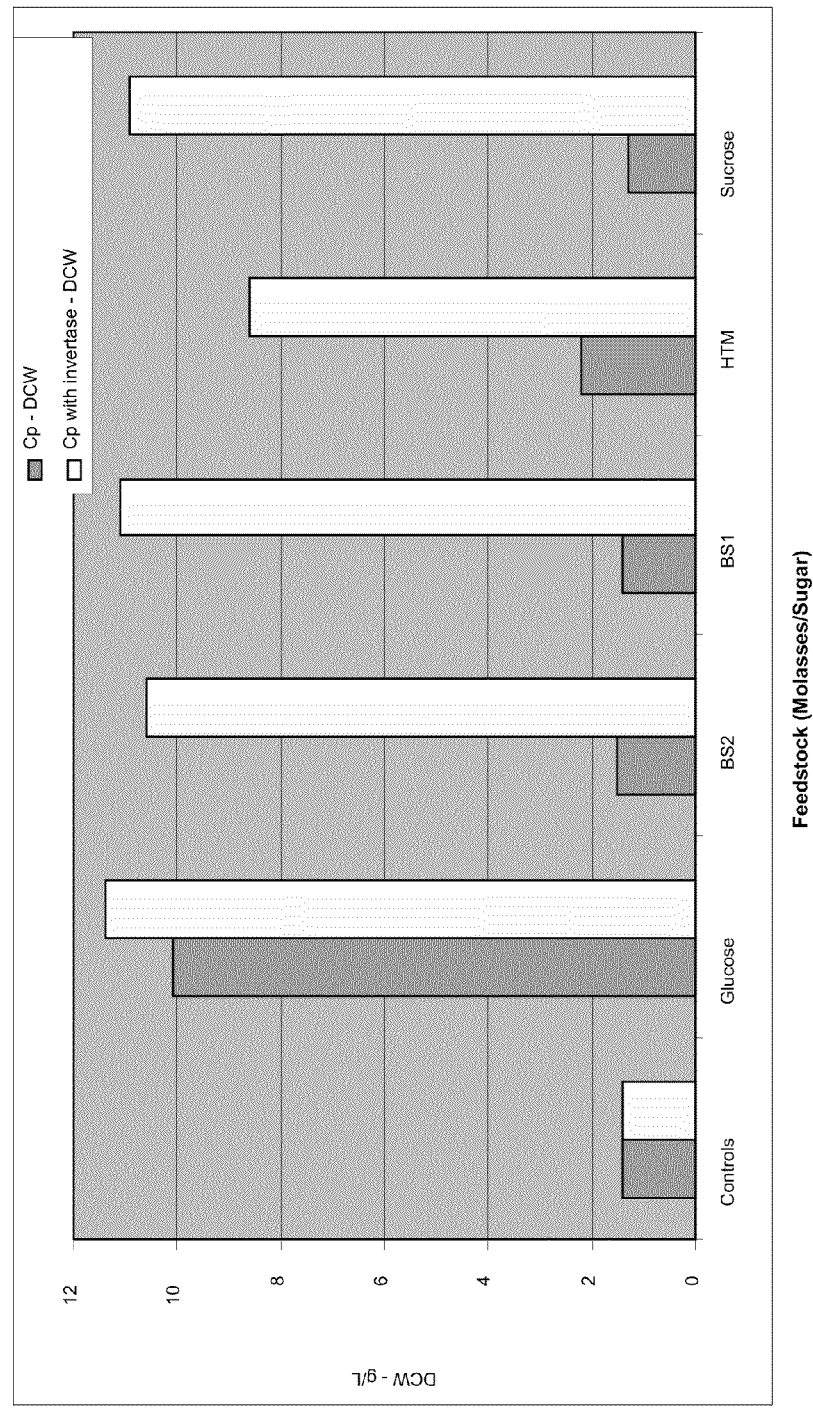
FIG. 17 shows DCW per liter of *Chlorella protothecoides* when cultured in the presence of glucose, sucrose, or one of several molasses samples (designated BS1, BS2 and HTM) in the presence or absence of a sucrose invertase.
Figure 18:
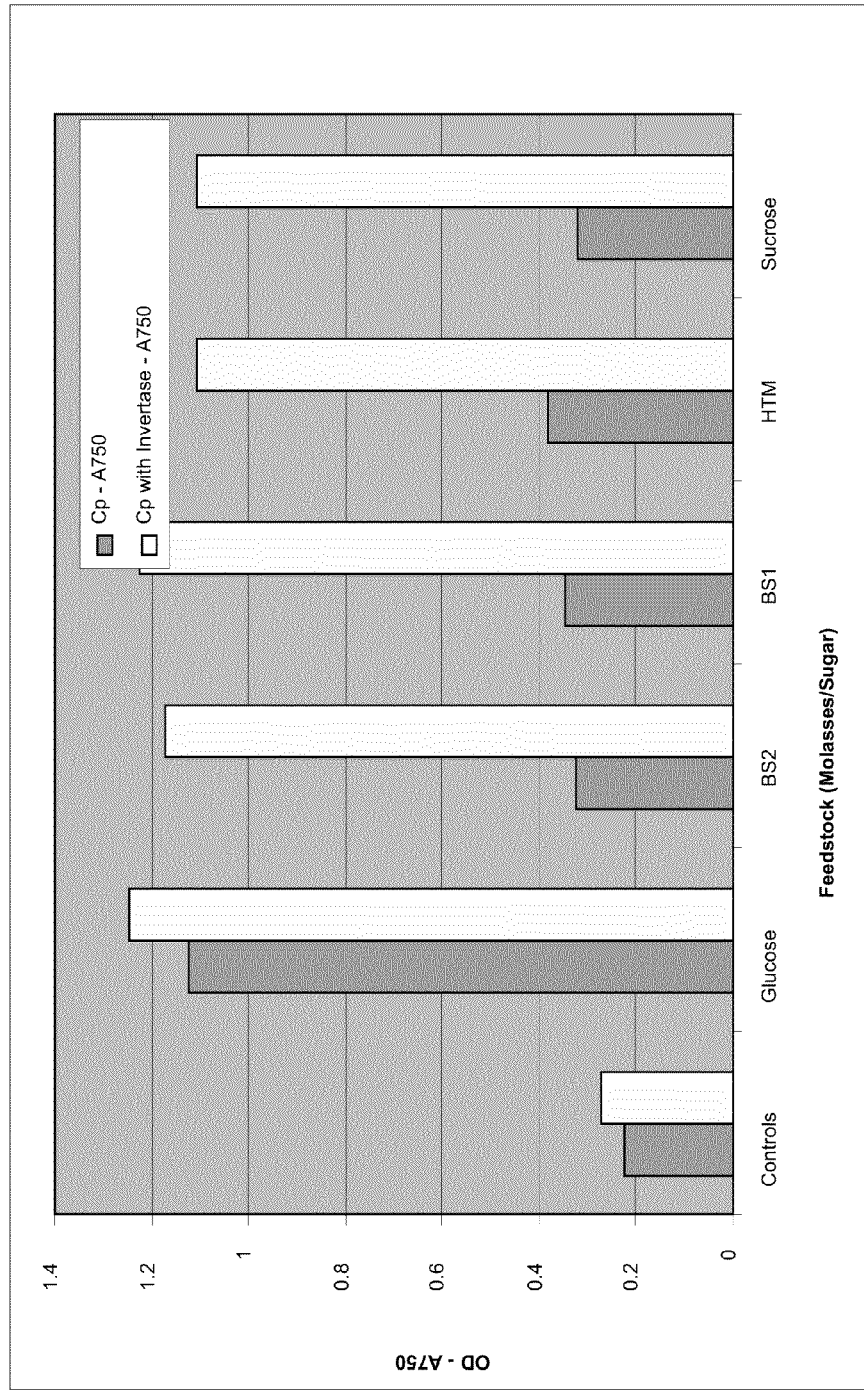
FIG. 18 shows growth of *Chlorella protothecoides* when cultured in the presence of glucose, sucrose, or one of several molasses samples (designated BS1, BS2 and HTM) in the presence or absence of a sucrose invertase as measured by relative cell density.

*Chlorella protothecoides* strains #1, #3, and #4 stock cultures were maintained on modified Proteose medium (see EXAMPLE 1). For each condition, 1 ml of the following different media was prepared in 24-well plates.
 1. Proteose
 2. Proteose+1% glucose
 3. Proteose+1% fructose Each strain was inoculated to media containing different sugars (glucose, or fructose) to 1×10⁶ cells/ml concentration. The cultures were kept in the dark and agitated by orbital shaker from Labnet (Berkshire, UK) at 430 rpm. After 96 hr of growth, cell density was measured by counting cell numbers of each culture. Results are shown in FIG. 16.

Example 18

*Chlorella* on Sucrose

*Chlorella protothecoides* (UTEX 249) was inoculated into three 50 ml flasks of Proteose media with 1% sucrose (2.94 mM NaNO₃, 0.428 mM K₂HPO₄, 1.28 mM KH₂PO₄, 0.427 mM NaCl, 0.17 mM CaCl₂-2H₂O, 0.3 mM MgSO₄.7H₂O, proteose peptone 1 g/L) to a final cell density of 4×10⁵ cells per ml. Invertase (Sigma #14504) was added to two of the cultures at 0.01 U/ml and 0.05 U/ml. All three cultures were grown in the dark for ~60 hrs shaking at 150 rpm. Final cell counts were performed on all three cultures after ~60 hrs of shaking in the dark. The control flask reached 4.4×10⁵ cells per ml while the 0.01 U/ml and 0.05 U/ml flasks reached cell densities of 1×10⁸ and 3×10⁸, respectively. Each flask was checked for contamination at the end of the experiment by microscopic analysis and all were clean.

Example 19

*Chlorella protothecoides* Growth on Molasses with a Sucrose Invertase

Preparation of *Chlorella* Cells for Inoculation:

A 10 ml liquid culture of *Chlorella* was started taking the inoculum from a solid Proteose plate. The cultures were grown in light for approximately 2 days at 26° C. Growth was measured using an optical densitomer (OD) at 750 nm and by determining DCWs.

Preparation of Molasses and Sugar Stock Solutions: A 5% stock solution was prepared with glucose, sucrose and three different molasses samples (labeled BS1, BS2 and HTM) obtained from the commercial processing of sugarcane into sugar, as shown in the following Table 6. The pH of all stocks was verified to be in the range of 6-6.6, and the stocks were then autoclaved.

TABLE 6

Molasses and sugar solutions.

| Molasses | % Sugar | 5% sugar dil.in 100 mls Grams or mls |
|---|---|---|
| HTM | 78.72 | 6.4 |
| BS1 (FL) | 44.25 | 11.3 |
| BS2 (AU) | 51.55 | 9.7 |

TABLE 6-continued

Molasses and sugar solutions.

| Molasses | % Sugar | 5% sugar dil.in 100 mls Grams or mls |
|---|---|---|
| Sucrose | 100 | 5 |
| Glucose | 100 | 5 |

Preparation of Invertase Solution: A 40 units/ml stock solution of invertase was prepared by reconstituting 1 mg of a 400 unit/mg Invertase (Sigma) in 10 milliliters of distilled water.

Experimental Conditions and Setup:10 ml cultures were prepared, each consisting of 1% final molasses/sugar concentration, 0.05 units/ml Invertase, and 1.0e6 cells per ml of *Chlorella protothecoides* in a base Proteose media. The cultures were numbered as follows: (1) media only control; (2) 1% HTM; (3) 1% BS1; (4) 1% BS2; (5) 1% glucose; and (6) 1% sucrose. A similar control set was also prepared without the addition of invertase. The cultures were grown in darkness for five days shaking at 250 rpm at 28° C.

Results: Growth of the *Chlorella protothecoides* cells was evaluated following the five days of incubation on the respective feedstock in darkness. As shown in FIGS. 19-20, the cells can be grown on molasses in the presence of a sucrose invertase with yields comparable to that of growth on pure glucose.

Example 20

Generation of High-Oil and Low-Oil Biomass

Materials and Methods: *Chlorella protothecoides* #1 (STRAIN 250) biomass for transesterification was grown heterotrophically in the presence of glucose as a fixed carbon source as a fed-batch fermentation, essentially as described in *Appl Microbiol Biotechnol* 78:29-36 (2008). Sample "LO-1" was taken during exponential growth (at 60 hours) and contains an oil content similar to that obtained with photosynthetic growth. Sample "080020-1" was taken at 115 hours, after all nitrogen in the culture had been consumed and the culture had entered a steady state phase of lipid accumulation.

Lipid Content: Total lipid content of oil (pre-transesterification) was determined by HPLC analysis. Approximately 10 mg of dried biomass were mixed with 1 ml of isopropanol saturated with KOH and incubated at 80° C. for 4 hours. Lipids from cell pellets were extracted and hydrolyzed using an isopropanol potassium hydroxide solution heated to 80° C. for four hours. The extract samples were analyzed with an Aglient 1100 HPLC using the following method. The samples were derivatized with bromophenacyl bromide (60 mg/ml) and loaded onto a Luna 5u C8(2) 100 A 150×2 mm column (Phenomenex). The samples were eluted from the column using a gradient of water to 100% acetonitrile:tetrahydrofuran (95:5). Signals were detected using a DAD array detector at a wavelength of 254 nm.

Sample "LO-1" contained 8.6% oil, and sample "080020-1" contained 28% oil.

Example 21

Direct Transesterification of Microbial Biomass

Sample Preparation: Wet pellets of biomass comprising low-oil content and high-oil content, respectively, prepared as described above, were lyophilized. Dried biomass from samples was ground to a coarse powder and dried again overnight at 55° C. under vacuum. Percent moisture was determined to be <3% for each sample using a Mettler Toledo Moisture analyzer.

Transesterification: Anhydrous methanol/1N NaOH was added to dried biomass (<3% moisture) at a ratio of 1:5 in a screw cap glass bottle 4 times the volume of the biomass. A stir bar was placed in the bottle, which was then sealed tightly. The mixture was stirred vigorously at 55° C. for 7 hours. The biomass was filtered through Whatmann filter paper and washed with methanol until filtrate was clear. All washes were combined in a balloon flask with original filtrate, and methanol was distilled off using a rotovap. Chloroform (1 part) was added and mixed well, and then poured into a separatory funnel. Methanol (2 parts) was then added to the flask, mixed well, and added to the separatory funnel. DI water (0.8 volume) was added to the flask, mixed, and added to the separatory funnel. The contents of the separatory funnel were shaken vigorously (with venting) and allowed to separate. The lower layer (chloroform/oil) was collected into a pre-weighed flask and fresh chloroform was added back to the funnel for a secondary extraction. The chloroform was then distilled off using the rotovap. Re-weighing the flask provided the yield determination. Lipid content was again determined by HPLC, as described above. Analytical measurements of the carotenoid constituents of the transesterified compositions were made using an HPLC method, as described by Schmid et al., *J of Applied Phycology* 7:487-494 (1995). Elemental analysis was performed by inductively coupled plasma mass spectrometry.

Results: Table 7 shows the results of the transesterified product from low-oil (LO-1-8.6% lipid) and high-oil (080020-1-28% lipid) biomass. All carotenoids are in mcg/g of lipophilic phase containing fatty acid methyl esters.

TABLE 7

Composition of transesterified low-oil and high-oil biomass.

|  | LO-1 | 080020-1 | ASTM D6751 Specification |
|---|---|---|---|
| % oil of biomass | 8.6 | 28 |  |
| % of oil converted to FAME (gram oil/gram dry cell wgt.) | 9.3 | 30.5 |  |
| Element (ppm) |  |  |  |
| Sulfur | 121 | 52 | 15 ppm max |
| Phosphorus | 784 | <2 | 0.001% mass max |
| Magnesium | 2 | 3 | Ca + Mg: 5 ppm max |
| Calcium | 4 | <2 | Ca + Mg: 5 ppm max |
| Iron | 3 | <2 |  |
| Zinc | 40 | 12 |  |
| Sodium | 190 | 15 | Na + K: 15 ppm max |
| Potassium | 72 | <2 | Na + K: 15 ppm max |
| Lutein (mcg/g) | 469 | 35.5 |  |
| Zeaxanthin (mcg/g) | 288 | 23.5 |  |
| α-Cryptoxanthin (mcg/g) | 8.45 | 0.06 |  |
| β-Cryptoxanthin (mcg/g) | 19.2 | 1.80 |  |
| α-Carotene (mcg/g) | 1.96 | 0.08 |  |
| β-Carotene (mcg/g) | 15.0 | 1.20 |  |
| Total Identified Carotenoids (mcg/g) | 801 | 62.2 |  |
| Total Carotenoids (mcg/g) | 1006 | 79.3 |  |

Example 22

Cultivation of Microalgae to Achieve High Oil Content

Microalgae strains were cultivated (cultured) to achieve a high percentage of oil by DCW. Cryopreserved cells were thawed at room temperature and 500 μl of cells were added to 4.5 ml of medium (4.2 g/L $K_2HPO_4$, 3.1 g/L $NaH_2PO_4$, 0.24 g/L $MgSO_4 \cdot 7H_2O$, 0.25 g/L Citric Acid monohydrate, 0.025 g/L $CaCl_2$ $2H_2O$, 2 g/L yeast extract) plus 2% glucose and grown for 7 days at 28° C. with agitation (200 rpm) in a 6-well plate. DCWs were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hrs and DCWs calculated. For determination of total lipid in cultures, 3 ml of culture were removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil DCW measurements are shown in Table 8.

TABLE 8

Cultivation of microalgae to achieve high oil content.

| Species | Strain | % Oil | Strain # (FIGS. 28 and 29a-i) |
|---|---|---|---|
| Chlorella kessleri | UTEX 397 | 39.42 | 4 |
| Chlorella kessleri | UTEX 2229 | 54.07 | 5 |
| Chlorella kessleri | UTEX 398 | 41.67 | 6 |
| Parachlorella kessleri | SAG 11.80 | 37.78 | 7 |
| Parachlorella kessleri | SAG 14.82 | 50.70 | 8 |
| Parachlorella kessleri | SAG 21.11 H9 | 37.92 | 9 |
| Prototheca stagnora | UTEX 327 | 13.14 | 10 |
| Prototheca moriformis | UTEX 1441 | 18.02 | 11 |
| Prototheca moriformis | UTEX 1435 | 27.17 | 12 |
| Chlorella minutissima | UTEX 2341 | 31.39 | 13 |
| Chlorella protothecoides | UTEX 250 | 34.24 | 1 |
| Chlorella protothecoides | UTEX 25 | 40.00 | 2 |
| Chlorella protothecoides | CCAP 211/8D | 47.56 | 3 |
| Chlorella sp. | UTEX 2068 | 45.32 | 14 |
| Chlorella sp. | CCAP 211/92 | 46.51 | 15 |
| Chlorella sorokiniana | SAG 211.40B | 46.67 | 16 |
| Parachlorella beijerinkii | SAG 2046 | 30.98 | 17 |
| Chlorella luteoviridis | SAG 2203 | 37.88 | 18 |
| Chlorella vulgaris | CCAP 211/11K | 35.85 | 19 |
| Chlorella reisiglii | CCAP 11/8 | 31.17 | 20 |
| Chlorella ellipsoidea | CCAP 211/42 | 32.93 | 21 |
| Chlorella saccharophila | CCAP 211/31 | 34.84 | 22 |
| Chlorella saccharophila | CCAP 211/32 | 30.51 | 23 |

Example 23

Genotyping of Microalgae with High Oil Content

Microalgae samples from the 23 strains listed in Table 8 above were genotyped. Genomic DNA was isolated from algal biomass as follows. Cells (approximately 200 mg) were centrifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 μl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 μl of 5 M NaCl. Samples were vortexed briefly, followed by the addition of 66 μl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 μl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 μl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 μl of 10 mM TrisCl, 1 mM EDTA (pH 8.0).

Five μl of total algal DNA, prepared as described above, were diluted 1:50 in 10 mM Tris, pH 8.0. PCR reactions, final volume 20 were set up as follows. Ten μl of 2× iProof HF master mix (BIO-RAD) was added to 0.4 μl primer SZ02613 (5'-TGTTGAAGAATGAGCCGGCGAC-3' (SEQ ID NO:1) at 10 mM stock concentration). This primer sequence runs from position 567-588 in Gen Bank accession no. L43357 and is highly conserved in higher plants and algal plastid genomes. This was followed by the addition of 0.4 μl primer SZ02615 (5'-CAGTGAGCTATTACGCACTC-3' (SEQ ID NO:2) at 10 mM stock concentration). This primer sequence is complementary to position 1112-1093 in Gen Bank accession no. L43357 and is highly conserved in higher plants and algal plastid genomes. Next, 5 μl of diluted total DNA and 3.2 μl dH$_2$O were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 μl of 10 mM Tris, pH 8.0, was added to each reaction, followed by extraction with 40 μl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. Sequence alignments and unrooted trees, were generated using Geneious DNA analysis software, are shown in FIGS. 29a-29i. Sequences from strains 1-23 (designated in Example 22, Table 8) are listed as SEQ ID NOs:7-29 in the attached Sequence Listing.

Example 24

Diversity of Lipid Chains in Algal Species

Cultures of various species of algae were maintained, and all experiments were carried out in Modified Protease media, as described above in EXAMPLE 2. For each strain, 10 ml cultures were setup in 50 ml flasks as follows:
1. Proteose growth media with no carbon addition;
2. Proteose growth media with 1% glucose.

Each strain was grown in the two conditions described above, at an initial seeding density of 1.0×10$^6$ cells/ml. The cultures were kept in the dark and agitated at 250 rpm for 7 days. The cells were harvested after a 7 day growth period, and assessed for growth in the dark relative to the control by measuring dried cell weight. DCWs were determined as follows: One ml of culture was centrifuged and the resulting pellet was rinsed with water to remove any salt or residual media; the final, rinsed pellet was frozen at −80 degree C.; and subjected to freeze drying overnight in a Freeze Dry System (Labconco, Mo., USA). All species listed in Table 9 below grew on glucose as a carbon source in the dark. No cells grew in the absence of glucose (condition 1). Glycerolipid profile was determined as described in Example 20.

TABLE 9

Glycerolipid profiles of various algal species.

| Species | C12:0 | C18:3 | C14:0 | C18:2 | C16 | C18:1 | C18:0 |
|---|---|---|---|---|---|---|---|
| Chlorella protothecoides | 0.0% | 4.0% | 1.1% | 24.1% | 11.3% | 54.9% | 4.6% |
| Chlorella kessleri | 15.6% | 0.0% | 4.0% | 26.2% | 26.6% | 23.0% | 4.6% |
| Chlorella trebouxiodes | 27.0% | 0.0% | 10.7% | 0.0% | 43.1% | 19.3% | 0.0% |
| Chlorella sorokiniana | 34.8% | 0.0% | 0.0% | 0.0% | 46.2% | 19.1% | 0.0% |
| Prototheca kruegani | 1.5% | 0.0% | 1.2% | 12.9% | 15.1% | 66.0% | 3.3% |
| Prototheca stagnora | 0.8% | 0.0% | 0.9% | 15.6% | 17.1% | 61.5% | 4.1% |

Lipid samples from a subset of strains grown as described in Example 22, and shown in Table 8, were also analyzed for lipid profile using HPLC. Results are shown in FIG. 29.

Example 25

Saponification of High-Oil *Chlorella protothecoides* Biomass

Biomass having a high-oil content is generated and analyzed according to the method described in Example 20. The biomass comprises 45% lipid, 20% carbohydrates, 10% protein, 10% other cellular constituents, 10% water, and 5% salts. In an embodiment, the biomass can comprise dried whole algal cells comprising lipid globules suspended in a partially dehydrated cell mass.

Preparation of a Liquid Cellular Soap:

The biomass identified above is dispersed in water to form an oil-in-cell emulsion concentrate. An excess of KOH sufficient to convert the desired amount of glycerolipids and fatty acid esters to fatty acid salts is then dissolved in the aqueous solution comprising the biomass. The mixture is then stirred to facilitate completion of the alkaline hydrolysis reaction, and heated to a temperature between 80-90° C. for from 30 minutes to 12 hours to complete the conversion of lipids to fatty acid salts. Water lost to evaporation is replaced as necessary throughout the reaction process. Various additives can be combined with the saponified composition, including glycerin (for clarity and to impart a moisturizing characteristic), ethylenediamine (EDTA, a chelating agent to enhance performance when used in hard water conditions), cocoamidopropyl betaine (an amphoteric surfactant used to impart cleansing and rinsing properties), and a fragrance to produce a soap product. In some embodiments, the soap product comprises a cellular soap with components as shown in Table 10 below.

TABLE 10

Components of cellular soap made directly from biomass.

| Component | Quantity |
| --- | --- |
| Biomass (Whole Cells) | 10-60% |
| KOH | 1-5% |
| Glycerin | 5-25% |
| Fragrance | 1-2% |
| EDTA | 1-5% |
| Water | to 100% |

The cellular soaps described in this example include natural hydrating and skin softening characteristics imparted by the presence of carbohydrates and proteins from the algal cells, as well as antioxidant properties derived from the incorporation of algal carotenoids and other compounds into the composition.

Alternatively, an organic base such as triethanolamine can be used in the alkaline hydrolysis reaction to produce a clearer product. The use of triethanolamine or another organic base will also generally produce a milder product, less likely to cause irritation to skin when used as a cleanser.

Optionally, the fatty acid salts can be precipitated from the mixture by addition of NaCl or KCl salts, and separated for use in compositions in combination with various additives as described herein.

FIG. 20 shows a micrograph of soap made with 48% oil DCW *Chlorella protothecoides* biomass. The soap contained 10% w/w algal biomass.

Example 26

Saponification of Hexane-Extracted Oil from *Chlorella protothecoides* Biomass

Biomass is generated according to the method described in Example 20. Conventional hexane extraction of the lipids from the biomass is performed. The hexane extracted lipids are then saponified by mixing the lipids with an aqueous solution of NaOH or KOH containing an amount of base sufficient to convert the desired amount of lipid to fatty acid salts, and optionally heating the mixture to expedite the reaction. The fatty acid salts are then precipitated by addition of NaCl or KCl. Compositions of saponified oils derived from hexane-extracted biomass contain higher proportions of contaminating carotenoids due to the efficiency with which hexane extracts such compounds from the microbial biomass.

Example 27

Saponification of Solventless-Extracted Oil from *Chlorella protothecoides* Biomass Biomass is generated according to the method described in Example 20. A solventless extraction of the lipids from the biomass is performed by lysis and pressing of the biomass through the use of physical pressure. The extracted lipids are then saponified by mixing the lipids with an aqueous solution of NaOH or KOH containing an amount of base sufficient to convert the desired amount of lipid to fatty acid salts, and optionally heating the mixture to expedite the reaction. The fatty acid salts are then precipitated by addition of NaCl or KCl. Compositions of saponified oils derived from hexane-extracted biomass contain relatively lower proportions of contaminating carotenoids, as compared to hexane-extracted lipids, due to the decreased efficiency with which such compounds are extracted from the microbial biomass using the solventless procedure.

Example 28

Glycerolipid Profile of *Prototheca* Strains

Five *Prototheca* strains were cultivated in media with 2% glucose and grown for 7 days at 28° C. with agitation (200 rpm) in a 6-well plate. Lipid profiles were determined using standard HPLC methods. The lipid profile for a particular strain did not change significantly when grown in different culture media. The results are shown in Table 11, below.

TABLE 11

Glycerolipid profile of *Prototheca* strains.

| Origin | Species | C:12:0 | C:13:0 | C:14:0 | C:16:0 | C16:1 | C:18:0 | C:18:1 | C:18:2 | C:18:3 |
| --- | --- | --- | --- | --- | --- | --- | --- | --- | --- | --- |
| UTEX 327 | *Prototheca stagnora* | 0% | 0% | 0% | 15% | 0% | 0% | 63% | 22% | 0% |
| UTEX 1439 | *Prototheca moriformis* | 0% | 0% | 0% | 27% | 0% | 3% | 57% | 13% | 0% |
| UTEX 1441 | *Prototheca moriformis* | 0% | 0% | 1% | 28% | 1% | 3% | 54% | 12% | 1% |
| UTEX 1435 | *Prototheca moriformis* | 0% | 0% | 1% | 26% | 0% | 3% | 55% | 12% | 2% |
| UTEX 1437 | *Prototheca moriformis* | 0% | 0% | 0% | 25% | 0% | 2% | 57% | 12% | 3% |

Biomass from UTEX 1435 was subjected to hexane extraction. The extracted oil contained very little coloration. FIG. 19 shows a sample of the UTEX 1435 oil in comparison to oil from *Chlorella protothecoides* UTEX 250.

Example 29

Carotenoid and Chlorophyll Analysis of Oil Extracted from *Prototheca moriformis* UTEX 1435

Hexane extracted oil from *Prototheca moriformis* (UTEX 1435) biomass was generated according to methods described in Example 26 above and was analyzed for carotenoids and chlorophyll using HPLC. Overall, the carotenoid levels were much lower than the carotenoid levels in oils described in Table 7 above. Additionally, the chlorophyll content of the oil was less than 0.01 mg/kg. This result is consistent with the results shown in FIG. 19, with the extracted oil from UTEX 1435 biomass having very little coloration. The carotenoid and chlorophyll analysis for oil extracted from UTEX 1435 biomass is summarized in Table 12, below.

TABLE 12

Carotenoid analysis of oil extracted from *Prototheca moriformis* UTEX 1435.

| | |
| --- | --- |
| Lutein | 0.382 mcg/g |
| Zeaxanthin | 1.23 mcg/g |
| cis-Lutein/Zeaxanthin | 0.446 mcg/g |
| alpha-Cryptoxanthin | none detected |
| beta-Cryptoxanthin | none detected |
| Lycopene | none detected |
| alpha-Carotene | 0.057 mcg/g |

TABLE 12-continued

Carotenoid analysis of oil extracted from *Prototheca moriformis* UTEX 1435.

| | |
|---|---|
| beta-Carotene | 0.127 mcg/g |
| cis-beta-Carotene | 0.069 mcg/g |
| Phytofluene | 0.696 mcg/g |
| Phytoene | 0.689 mcg/g |
| Total Identified Carotenoids | 3.70 mcg/g |
| Chlorophyll | <0.01 mg/kg |

Example 30

Genomic DNA Analysis of 23S rRNA from 8 Strains of *Chlorella protothecoides*

Genomic DNA from 8 strains of *Chlorella protothecoides* (UTEX 25, UTEX 249, UTEX 250, UTEX 256, UTEX 264, UTEX 411, CCAP 211/17, and CCAP 211/8d) was isolated and genomic DNA analysis of 23S rRNA was performed according to the methods described in Example 23, above.

Figure 21A:
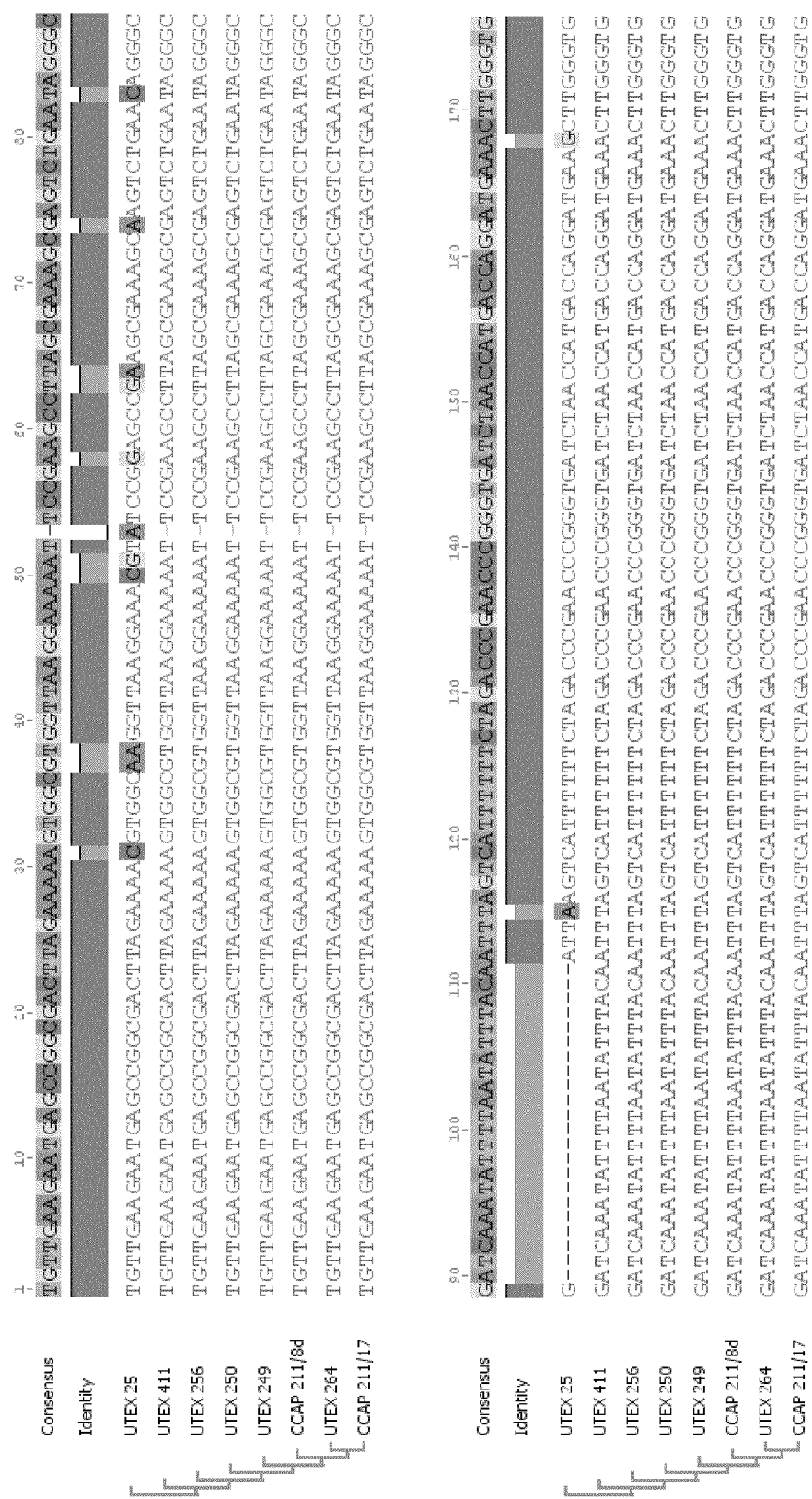
FIGS. 21*a-c* show a Cladogram comparing the genomic DNA sequences of 23s rRNA from 8 different strains of *Chlorella protothecoides.*
Figure 21B:
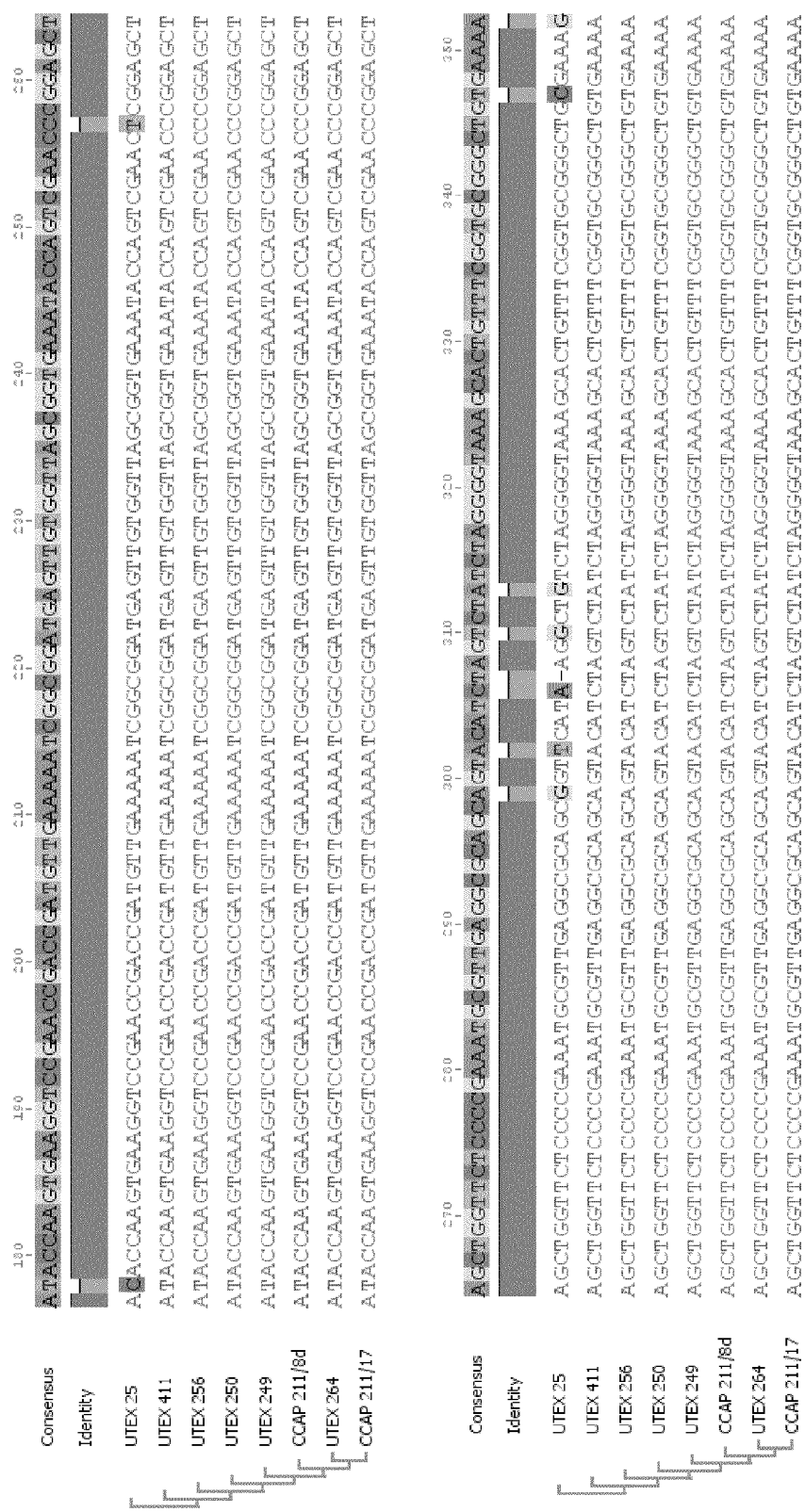
Figure 21C:
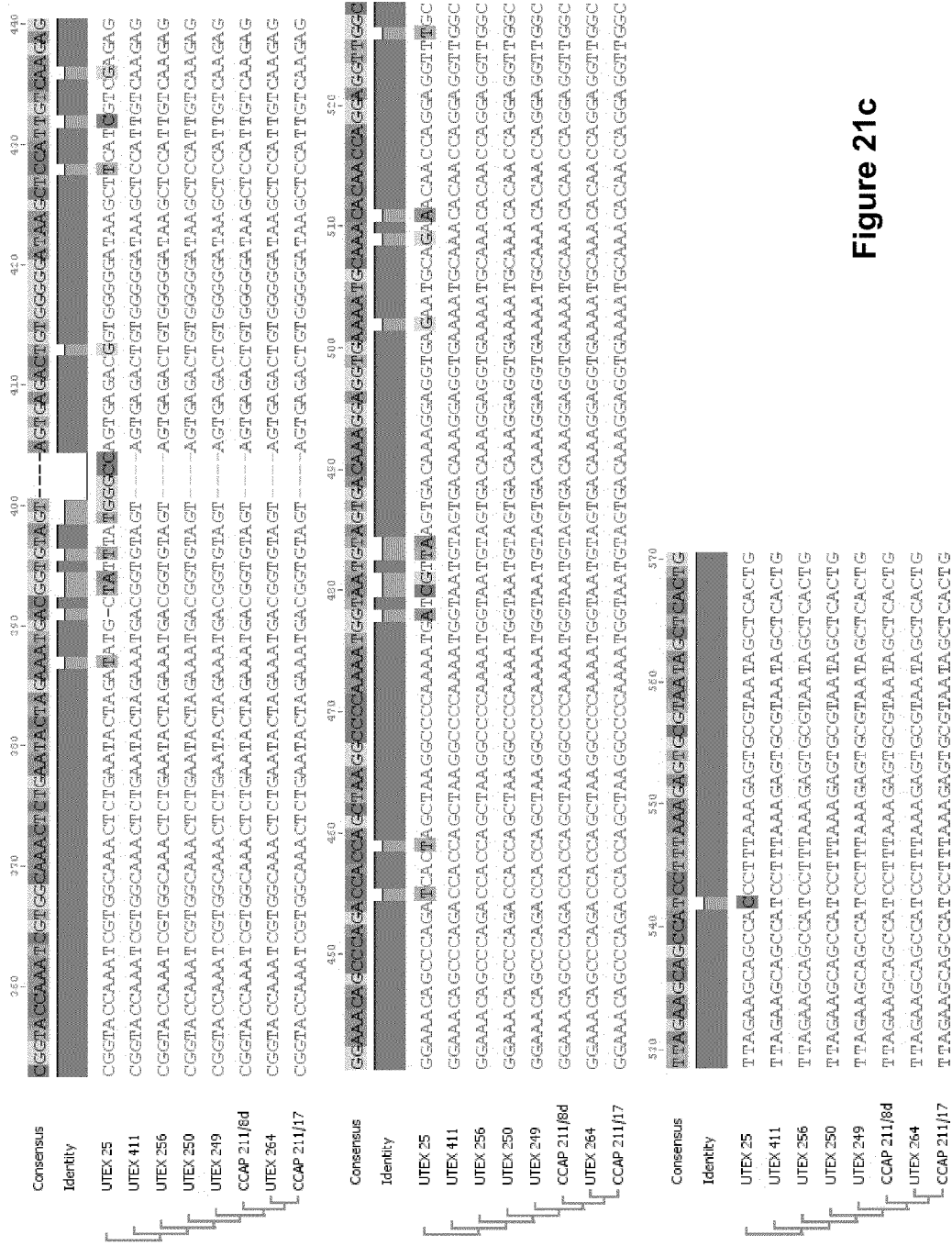
Figure 22:
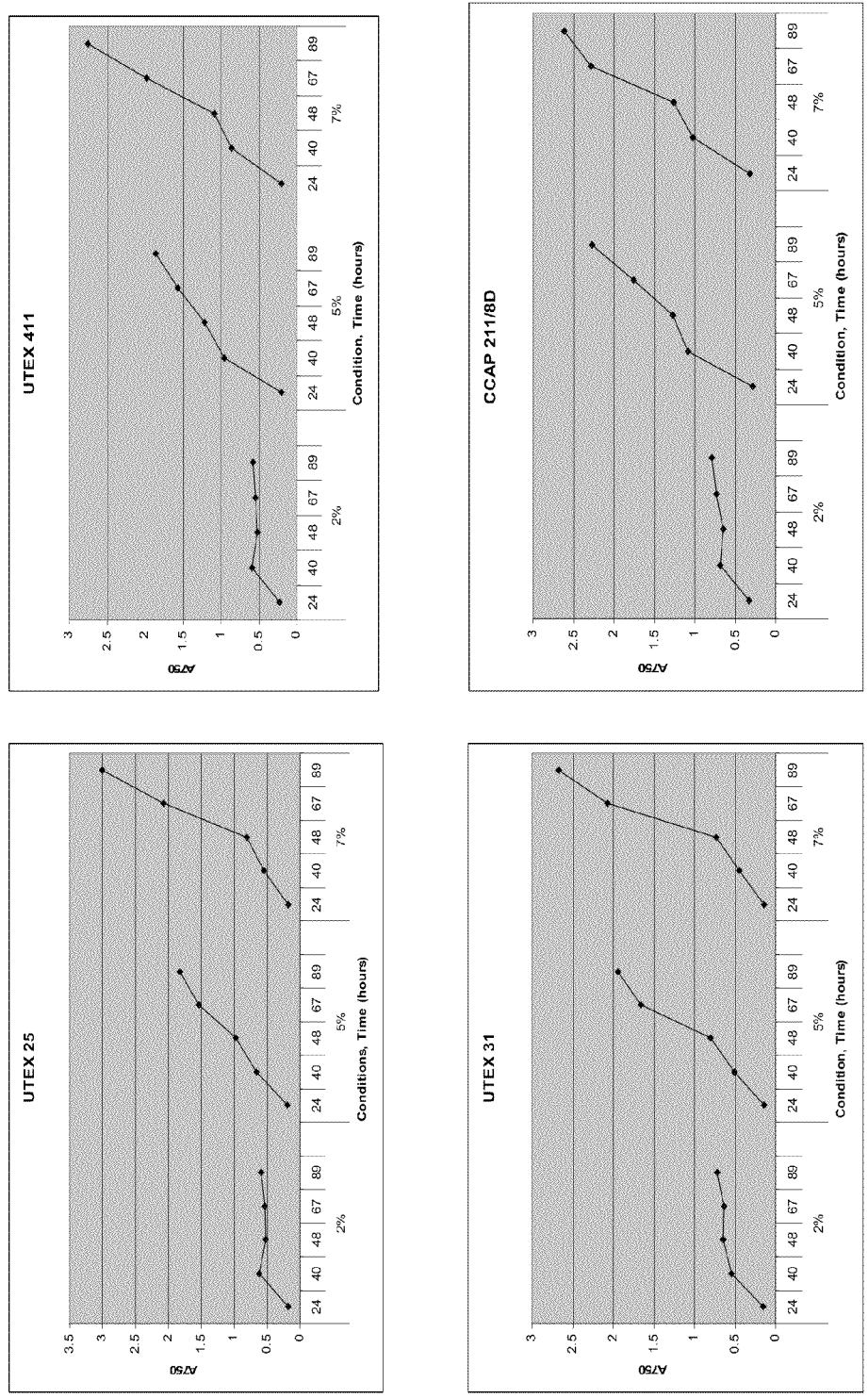
FIGS. 22-27 show the growth curve of different strains of microalgae grown on three different concentrations of pure *sorghum* as the sole carbon source.
Figure 23:
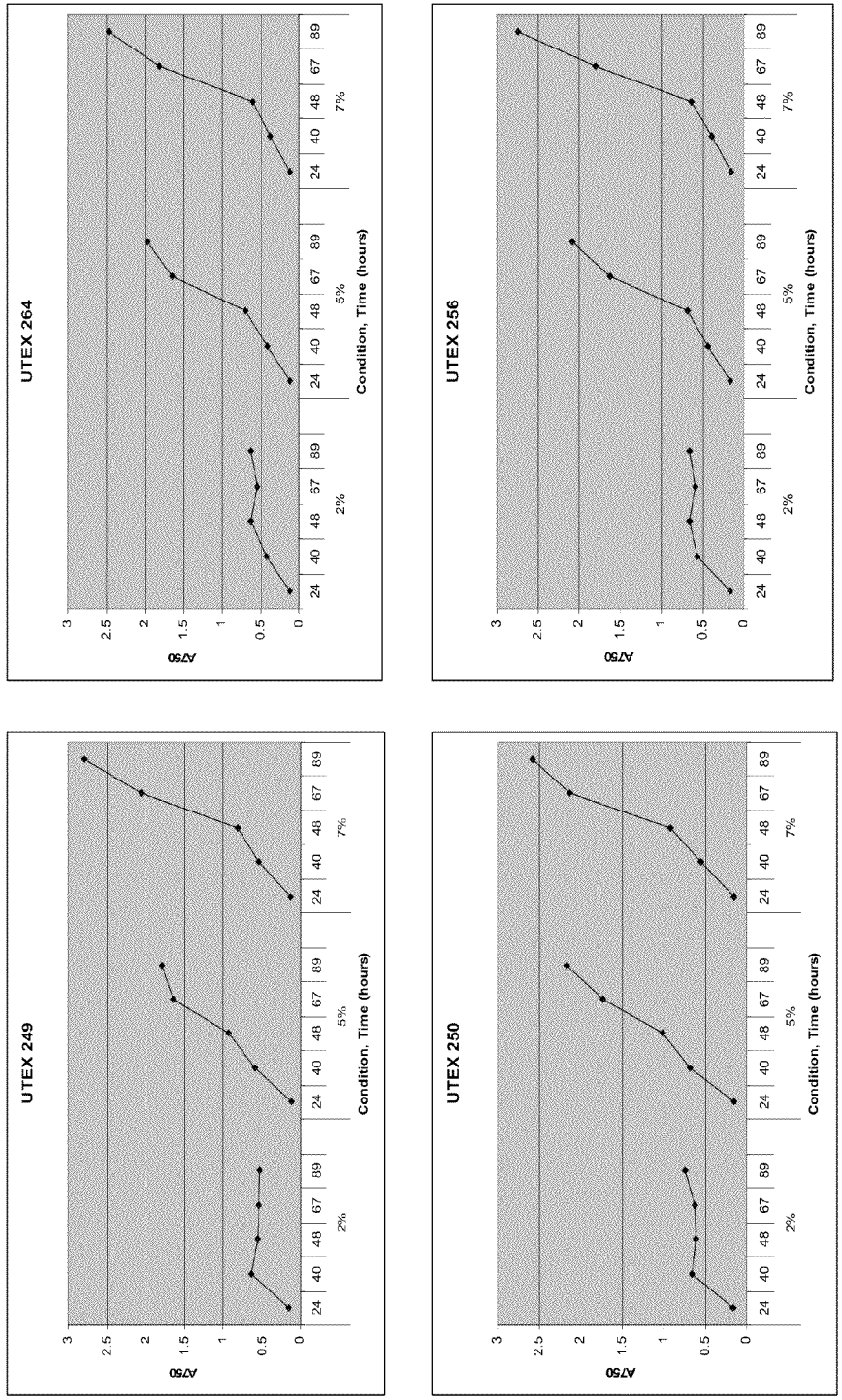
Figure 24:
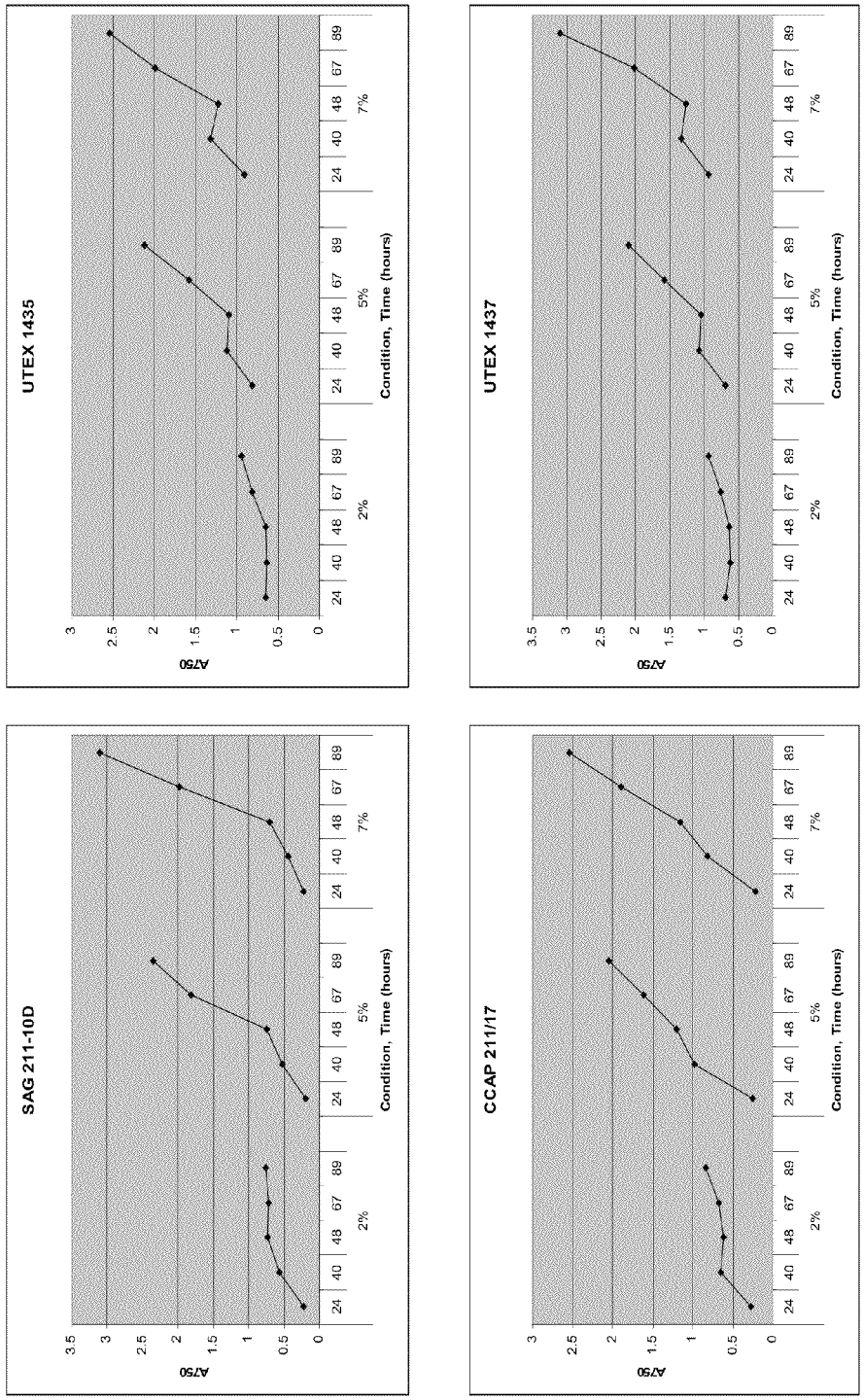
Figure 25:
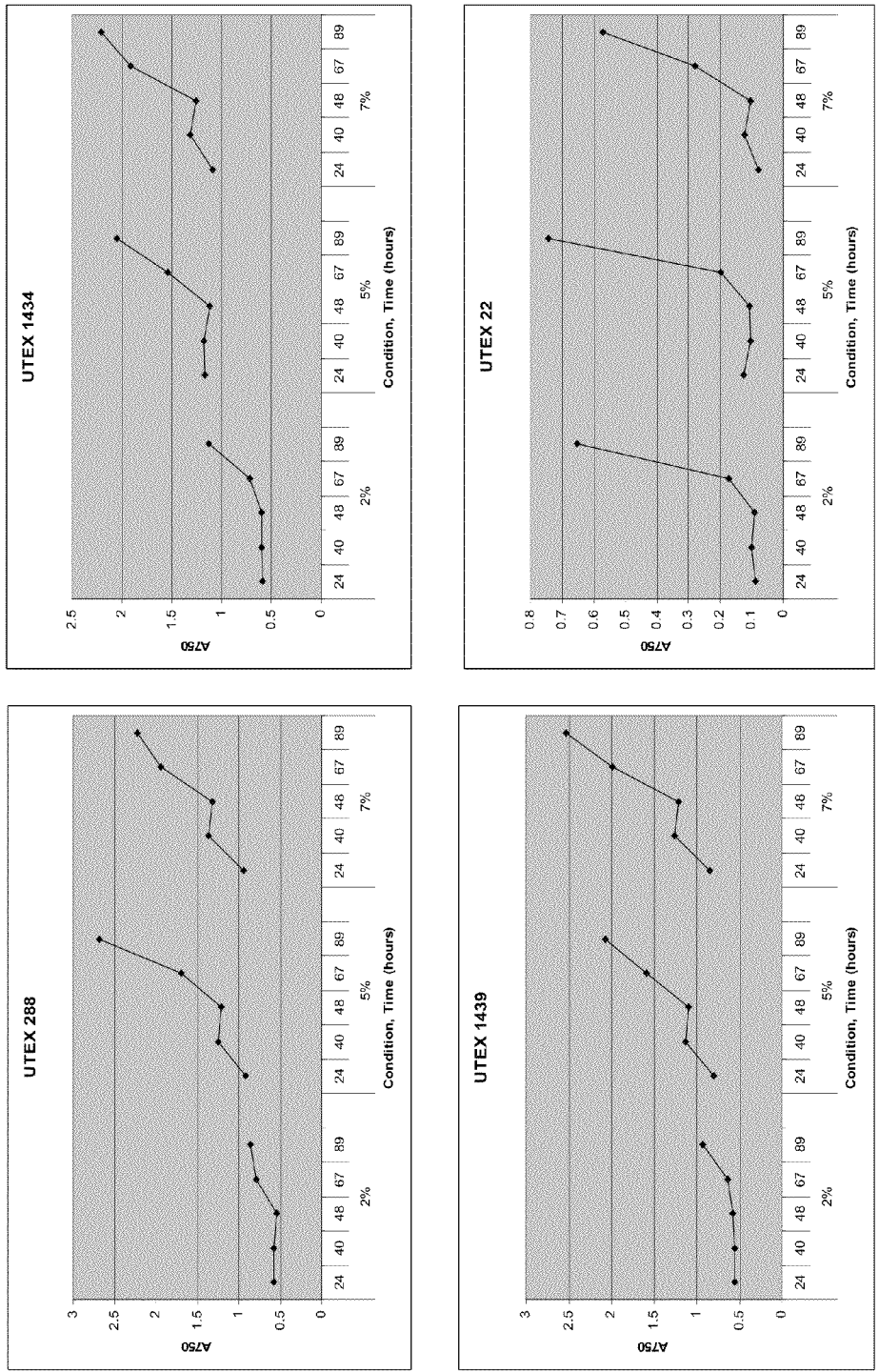
Figure 26:
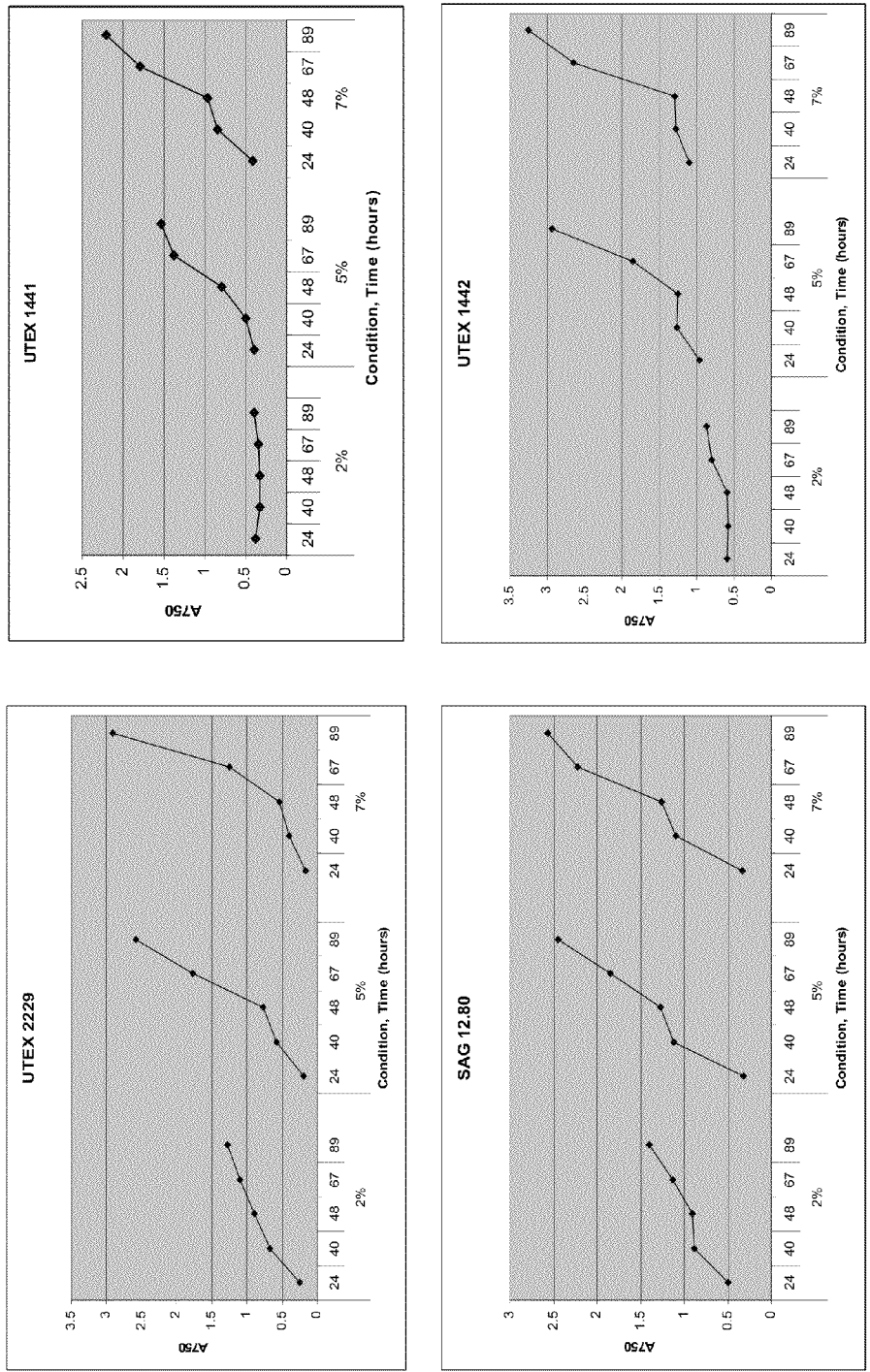
Figures 27, 28:
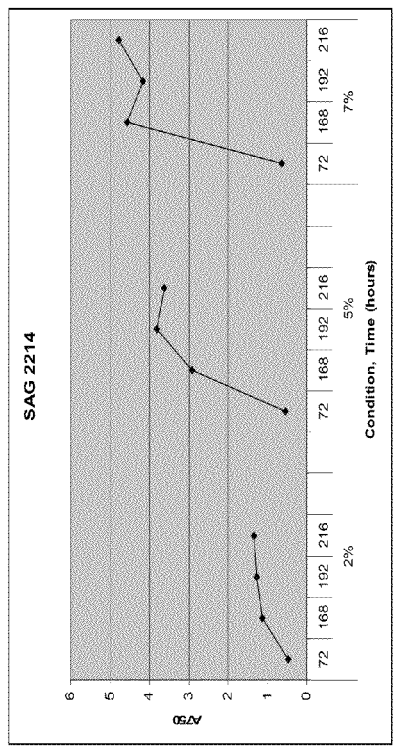
FIG. 28 shows a summary of diversity of lipid chains in microalgal species.
Figure 29A:
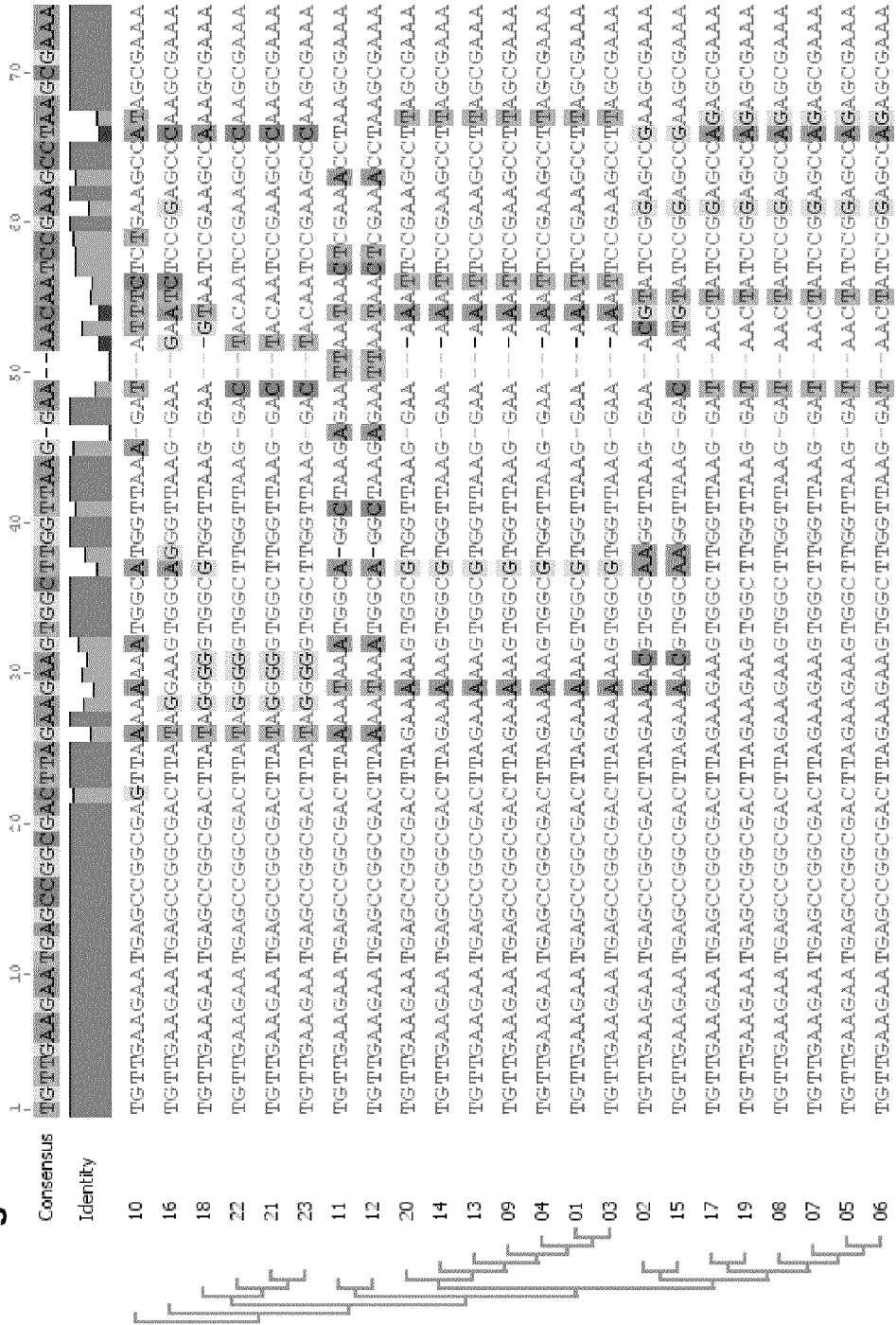
FIGS. 29*a-i* show a Cladogram comparing the genomic DNA sequences of 23S rRNA from 23 strains of microalgae.
Figure 29B:
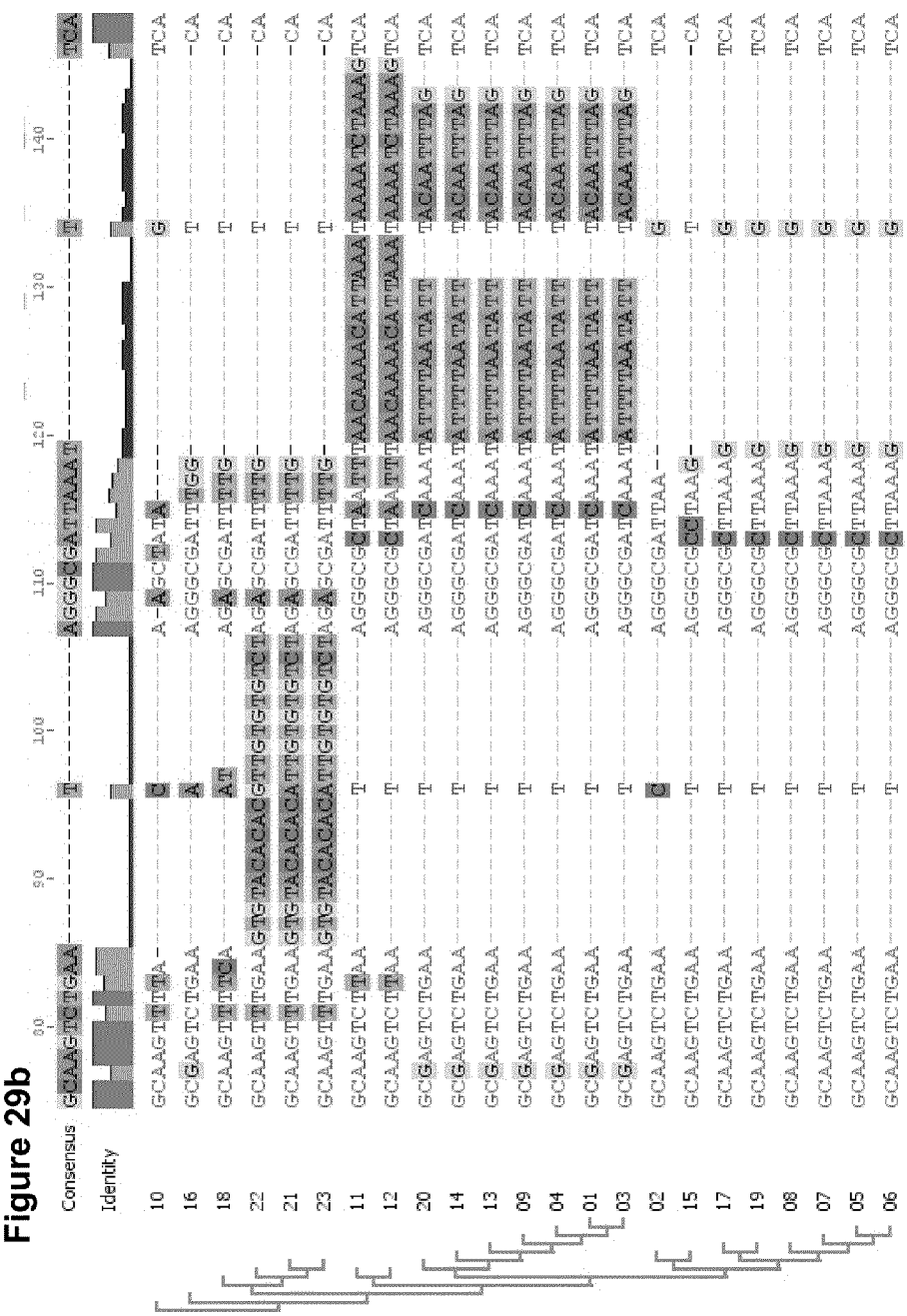
Figure 29C:
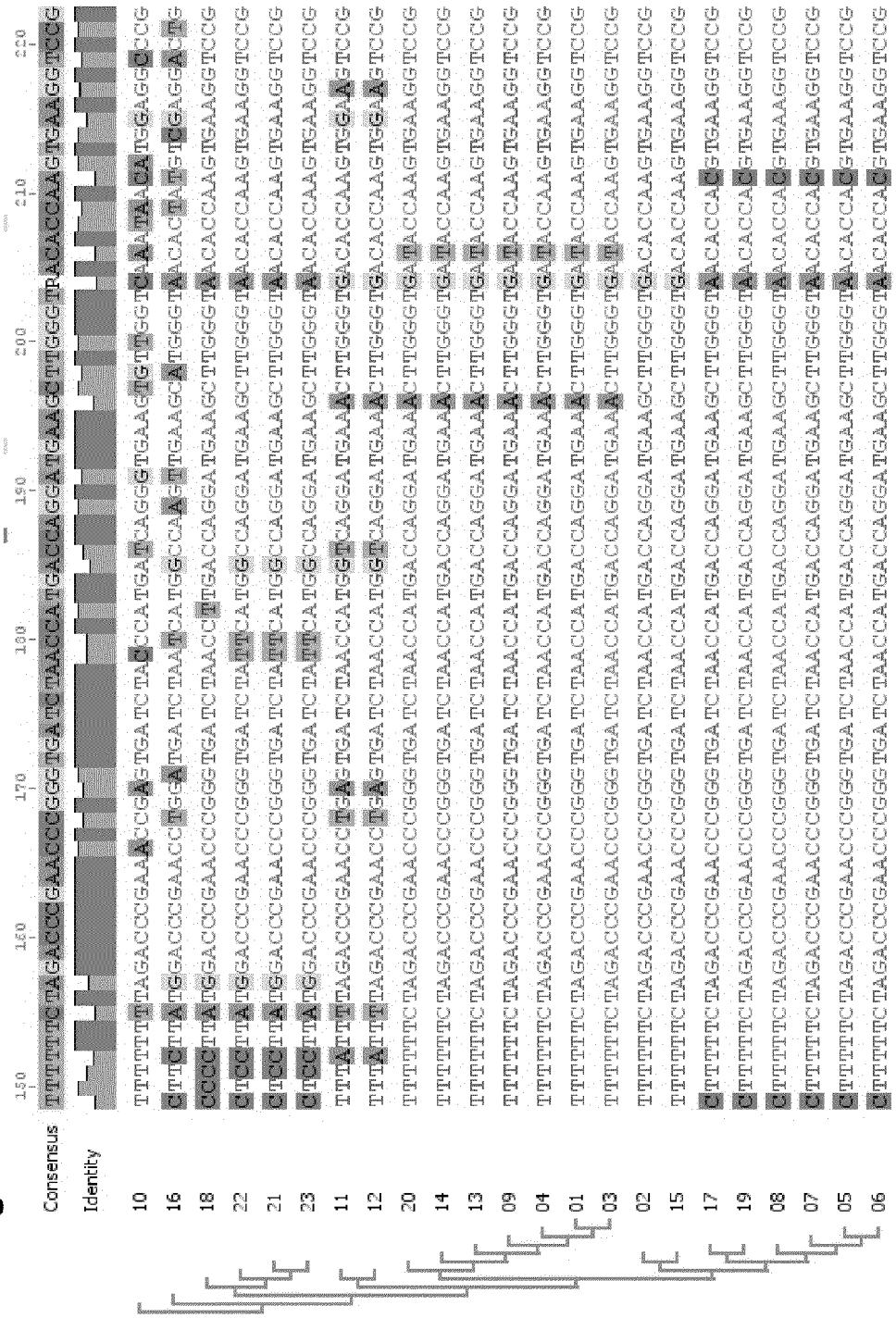
Figure 29D:
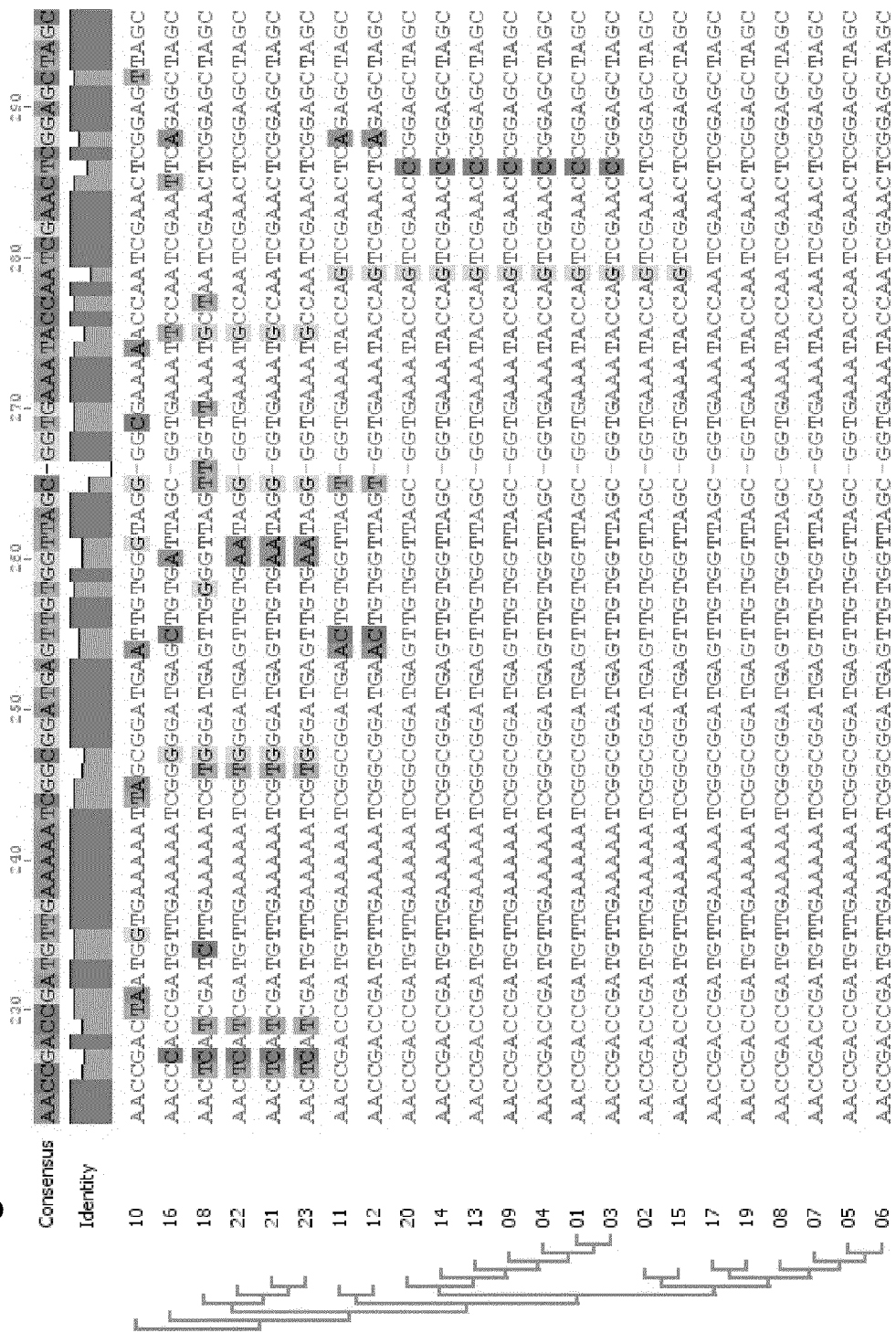
Figure 29E:
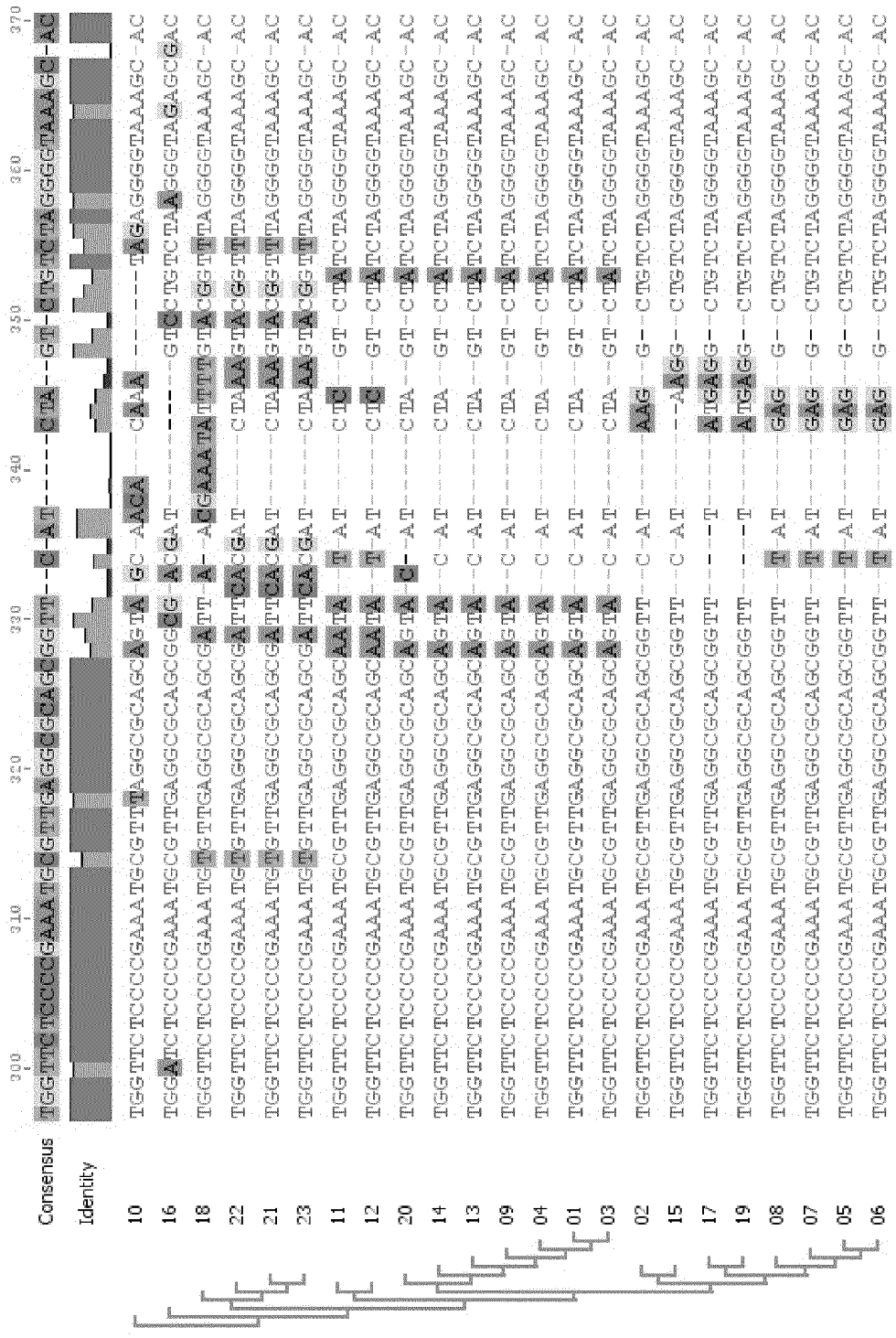
Figure 29F:
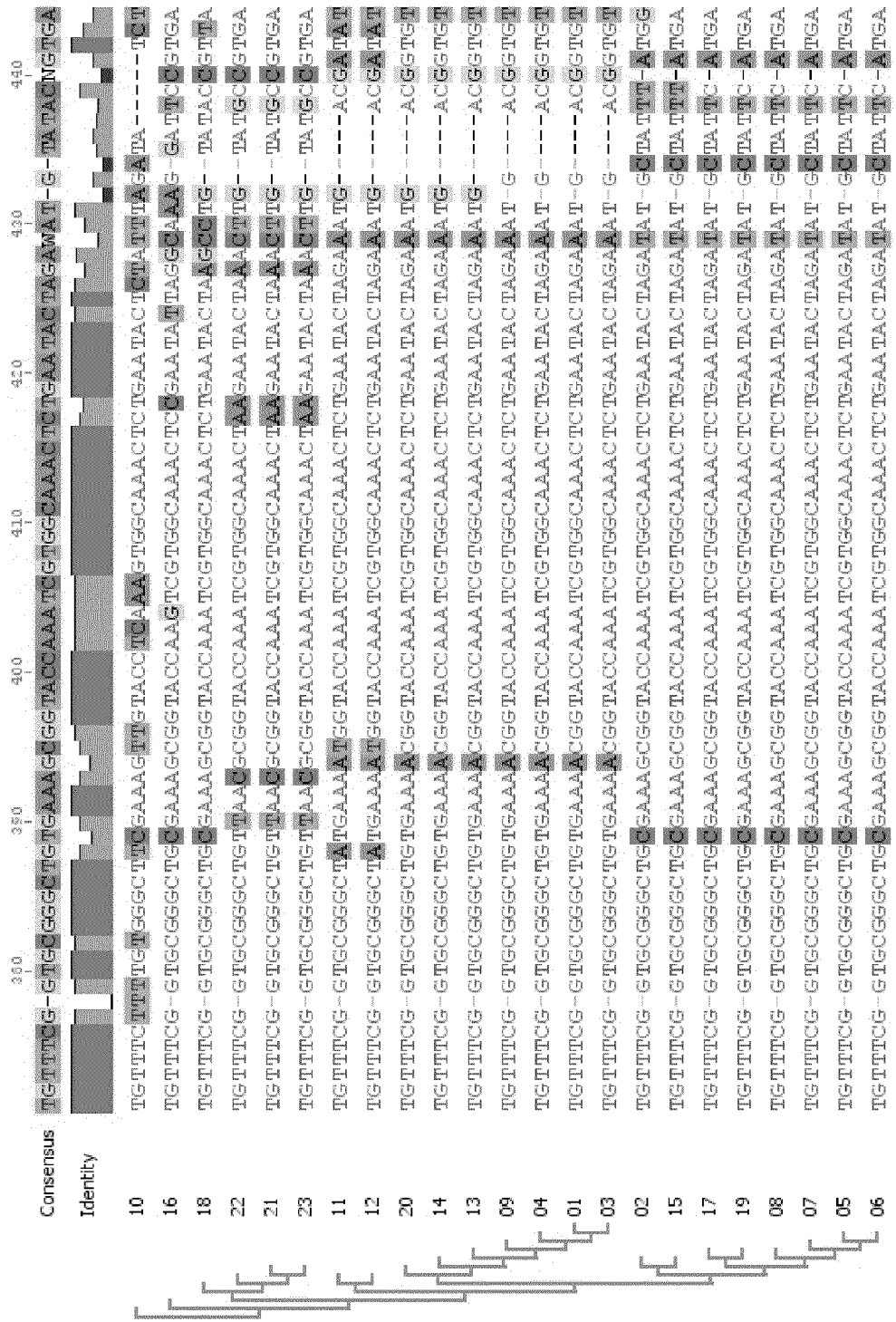
Figure 29G:
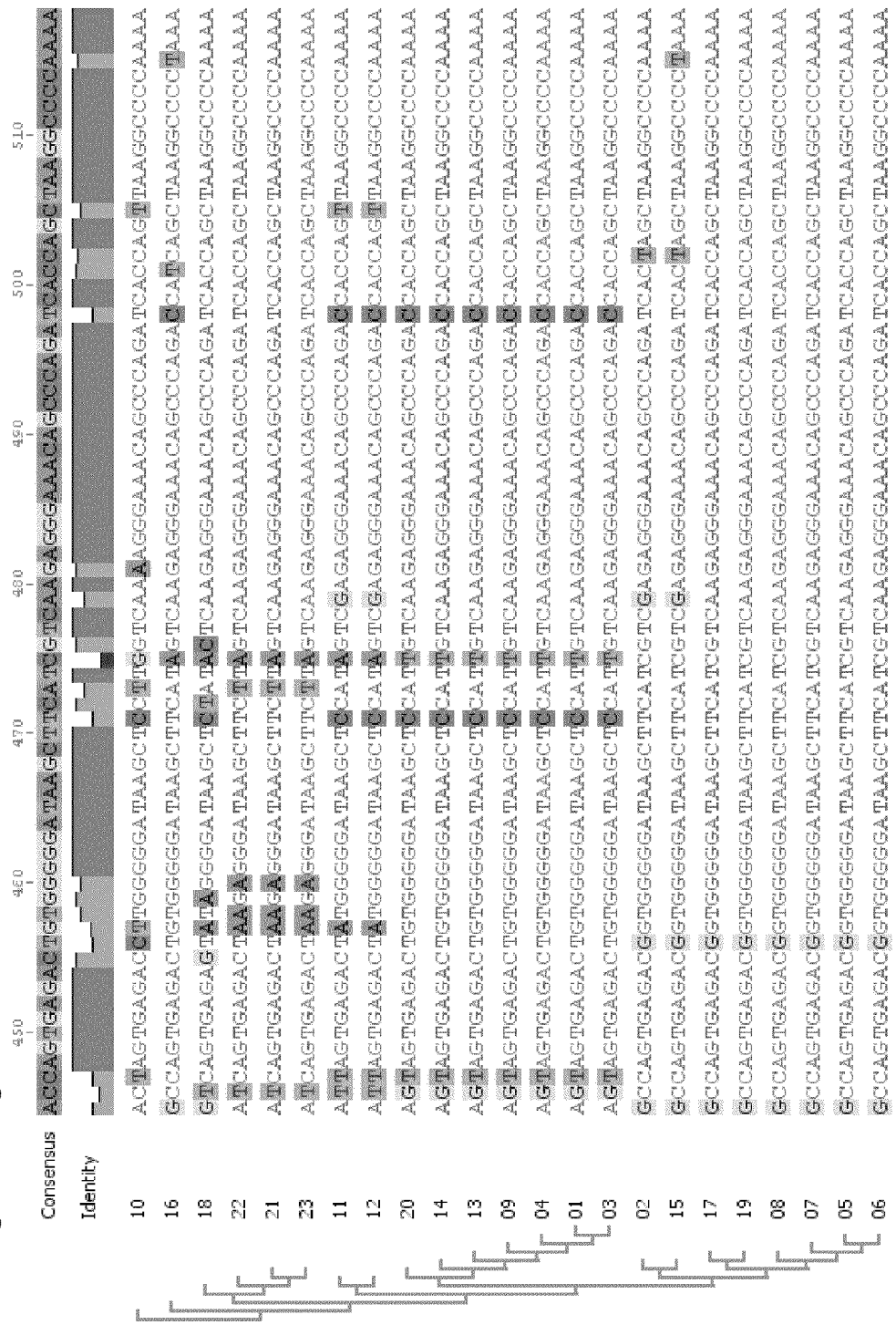
Figure 29H:
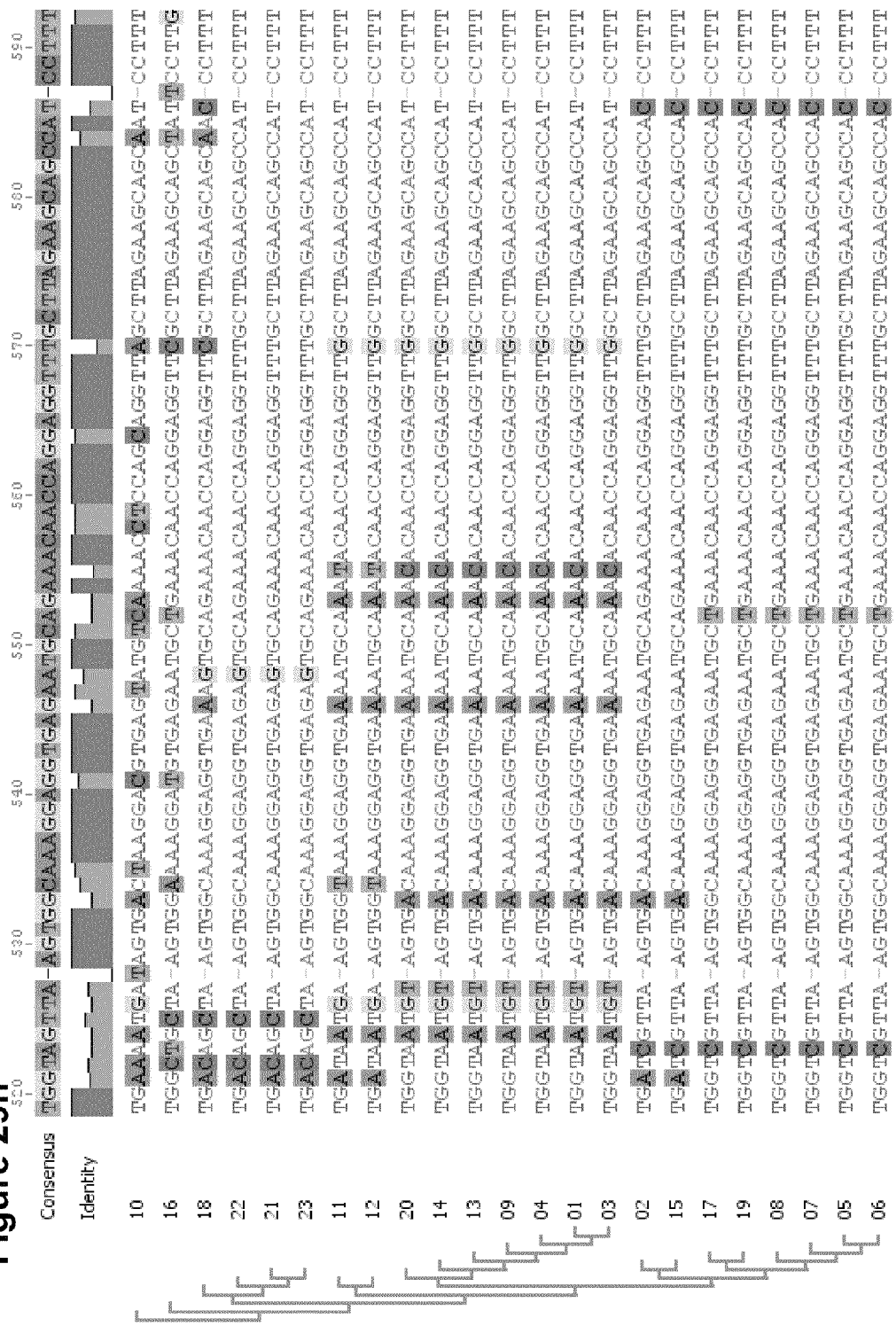
Figure 29I:
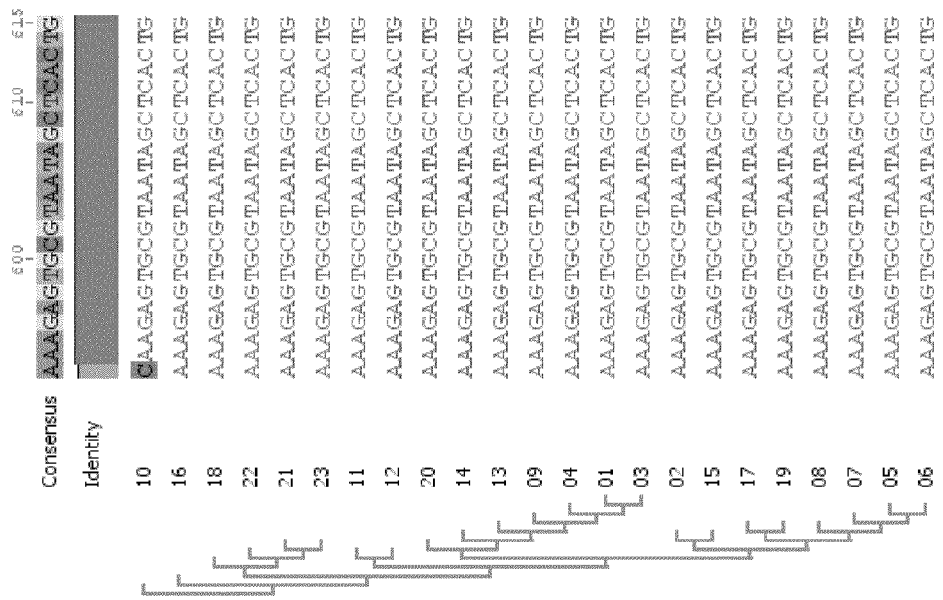

All strains of *Chlorella protothecoides* tested were identical in sequence except for UTEX 25. Results are summarized in the Cladogram shown in FIGS. 21a-21c. Sequences for all eight strains are listed as SEQ ID NOs:3-4 in the attached Sequence Listing.

The 23s rRNA genomic sequence for *Prototheca moriformis* UTEX 1436 (SEQ ID NO:5) was also compared to other *Prototheca* species and *Chlorella protothecoides*. The comparison showed that the 23s rRNA genomic sequence for *Prototheca moriformis* UTEX 1436 was dissimilar to the other *Prototheca* genotypes (SEQ ID NO:6).

Example 31

*Sorghum* Utilization Screen

Strains:

The following strains were used in the screen for identifying microalgae strains capable of utilizing *sorghum* as a sole carbon source: 10 strains were *Chlorella protothecoides* (UTEX 25, UTEX 31, UTEX 411, CCAP 221/8D, UTEX 249, UTEX 250, UTEX 256, UTEX 264, SAG 211-10D, and CCAP 211/17). 6 strains were *Prototheca moriformis* (UTEX 1435, UTEX 1437, UTEX 288, UTEX 1439, UTEX 1441 and UTEX 1434. Other strains included *Chlorella luteoviridis* (UTEX 22 and SAG 2214), *Chlorella kessleri* (UTEX 2229), *Parachlorella kessleri* (SAG 12.80) and *Prototheca stagnora* (UTEX 1442).

Culture Conditions:

Seed cultures of the microalgal strains (identified above) were started as 1 ml liquid cultures in 24 well plates and were grown autotrophically for 48 hours in light, agitating at ~350 rpm. Pure *sorghum* was purchased from Maasdam *Sorghum* Mills (Lynnville, Iowa) with a sugar profile of fructose 21.0% w/w, dextrose 28.0% w/w, sucrose 16.0% w/w and maltose<0.5% w/w. The cultures were then transferred to liquid medium containing 2%, 5% or 7% (v/v) pure *sorghum* (diluted from the pure stock) as the sole carbon source and the cultures were then grown heterotrophically in the dark, agitating at ~350 rpm. Samples from the cultures were pulled at 24, 40, 48, 67 and 89 hours and growth was measured using A750 readings on a spectrophotometer. Growth was observed for each of the strains tested, as shown in FIGS. 22-27.

What is claimed is:

1. A method of making a chemically modified lipid, comprising:
   (a) providing a microalgal lipid comprising no more than 500 ppm color-generating impurities, wherein the lipid is obtained from microalgae cultured under heterotrophic growth conditions in a bioreactor substantially in the absence of light; and
   (b) subjecting the microalgal lipid to an epoxidation reaction to produce the modified lipid,
   wherein the microalgae are selected from strains *Parachlorella*, *Prototheca*, *Chlorella* and strains having at least 85% nucleotide sequence identity in 23S rRNA sequences to a *Parachlorella*, *Prototheca*, or *Chlorella* strain.

2. The method of claim 1, wherein the microalgal lipid is obtained from microalgae cultured on sucrose.

3. The method of claim 2, wherein the microalgal lipid is obtained from microalgae cultured on sorghum, sugar cane, sugar beet, or molasses.

4. The method of claim 1, wherein the microalgal lipid is obtained from microalgae cultured on glucose.

5. The method of claim 2, wherein at least 50% of the microalgal or modified lipid is C16 or a lipid of longer chain lengths.

6. The method of claim 2, wherein at least 20% of the microalgal or modified lipid is C18.

7. The method of claim 2, wherein at least 30% of the microalgal or modified lipid is C18.

8. The method of claim 2, wherein at least 40% of the microalgal or modified lipid is C18.

9. The method of claim 2, wherein at least 50% of the microalgal or modified lipid is C18.

10. The method of claim 2, wherein the microalgae are *Chlorella*.

11. The method of claim 2, wherein the microalgae are *Parachlorella*.

12. The method of claim 2, wherein the microalgae are incapable of performing photosynthesis.

13. The method of claim 12, wherein the microalgae are *Prototheca*.

14. The method of claim 13, wherein the microalgae are selected from the group consisting of *Prototheca wickerhamii*, *Prototheca stagnora*, *Prototheca portoricensis*, *Prototheca moriformis*, and *Prototheca zopfii*.

15. The method of claim 14, wherein the microalgae are *Prototheca moriformis*.

* * * * *